US012622932B2

(12) United States Patent
Nagy et al.

(10) Patent No.: US 12,622,932 B2
(45) Date of Patent: May 12, 2026

(54) IMMUNOMODULATORY CELLS AND USES THEREOF

(71) Applicant: Sinai Health System, Toronto (CA)

(72) Inventors: Andras Nagy, Toronto (CA); Jeffrey Harding, Toronto (CA); Kristina Nagy, Toronto (CA)

(73) Assignee: Sinai Health System, Toronto (CA)

( * ) Notice: Subject to any disclaimer, the term of this patent is extended or adjusted under 35 U.S.C. 154(b) by 1028 days.

(21) Appl. No.: 17/413,314

(22) PCT Filed: Dec. 13, 2019

(86) PCT No.: PCT/CA2019/051808
§ 371 (c)(1),
(2) Date: Jun. 11, 2021

(87) PCT Pub. No.: WO2020/118447
PCT Pub. Date: Jun. 18, 2020

(65) Prior Publication Data

US 2022/0016181 A1 Jan. 20, 2022

Related U.S. Application Data

(60) Provisional application No. 62/779,449, filed on Dec. 13, 2018.

(51) Int. Cl.

| | |
|---|---|
| ***A61K 39/00*** | (2006.01) |
| ***A61K 35/545*** | (2015.01) |
| ***A61K 40/10*** | (2025.01) |
| ***A61K 40/22*** | (2025.01) |
| ***A61K 40/41*** | (2025.01) |
| ***A61K 40/42*** | (2025.01) |
| ***A61K 45/06*** | (2006.01) |
| ***A61P 37/06*** | (2006.01) |
| ***C07K 14/47*** | (2006.01) |
| ***C07K 14/52*** | (2006.01) |
| ***C07K 14/705*** | (2006.01) |
| ***C07K 14/81*** | (2006.01) |
| *A61K 40/50* | (2025.01) |

(52) U.S. Cl.
CPC ............ *A61K 35/545* (2013.01); *A61K 40/10* (2025.01); *A61K 40/22* (2025.01); *A61K 40/416* (2025.01); *A61K 40/418* (2025.01); *A61K 40/428* (2025.01); *A61K 45/06* (2013.01); *A61P 37/06* (2018.01); *C07K 14/47* (2013.01); *C07K 14/521* (2013.01); *C07K 14/70503* (2013.01); *C07K 14/70532* (2013.01); *C07K 14/70575* (2013.01); *C07K 14/811* (2013.01); *A61K 40/50* (2025.01)

(58) Field of Classification Search
CPC ....... A61K 35/545; A61K 45/06; A61P 37/06; C07K 14/47; C07K 14/521; C07K 14/70503; C07K 14/70532; C07K 14/70575; C07K 14/811
See application file for complete search history.

(56) References Cited

U.S. PATENT DOCUMENTS

| | | | | |
|---|---|---|---|---|
| 10,968,426 | B2 | 4/2021 | Meissner et al. | |
| 2017/0058015 | A1* | 3/2017 | Seidel, III | A61P 31/12 |
| 2018/0044686 | A1 | 2/2018 | Nagy et al. | |
| 2019/0376045 | A1 | 12/2019 | Schrepfer et al. | |
| 2021/0161971 | A1 | 6/2021 | Nagy et al. | |

FOREIGN PATENT DOCUMENTS

| | | | |
|---|---|---|---|
| CN | 104619722 | | 5/2015 |
| JP | 2006091773 | A | 4/2006 |
| JP | 2007047468 | A | 2/2007 |
| JP | 2015009948 | A | 1/2015 |
| JP | 2016089692 | A | 5/2016 |
| JP | 2016160622 | A | 9/2016 |
| WO | WO2002072798 | A1 | 9/2002 |
| WO | WO2006091773 | A2 | 8/2006 |
| WO | WO2007047468 | A2 | 4/2007 |
| WO | WO-2009/139921 | A2 | 11/2009 |
| WO | WO2011100460 | A2 | 8/2011 |
| WO | WO-2014/022423 | A2 | 2/2014 |
| WO | WO2015009948 | A1 | 1/2015 |
| WO | WO2015195531 | A2 | 12/2015 |
| WO | WO-2016/081924 | A1 | 5/2016 |
| WO | WO2016089692 | A1 | 6/2016 |
| WO | WO-2016/141480 | A1 | 9/2016 |
| WO | WO2016160622 | A2 | 10/2016 |

(Continued)

OTHER PUBLICATIONS

Rong et al., Cell Stem Cell (2014) 14, 121-130 (Year: 2014).*

(Continued)

*Primary Examiner* — Evelyn Y Pyla
*Assistant Examiner* — Katherine R Small
(74) *Attorney, Agent, or Firm* — C. Rachal Winger; Chrystal Quisenberry; Lee & Hayes PC

(57) ABSTRACT

Featured are cells and methods of use thereof for modulating an antigen-specific immune response in a subject. The cells comprise a set of transgenes comprising two or more of PD-L1, HLA-G or H2-M3, Cd47, Cd200, FASG or FasL, Ccl21 or Ccl21b, MfgeS and Serpin B9 or Spi6, that shield the cells from immune surveillance (ie. "cloaking genes"). The cells can be used to induce immune tolerance to an antigen (e.g., a donor alloantigen or a self-antigen), or to induce an immune response to (e.g., induce the production of antibodies directed against) a non-self antigen.

17 Claims, 1 Drawing Sheet

Specification includes a Sequence Listing.

(56) References Cited

FOREIGN PATENT DOCUMENTS

| | | | |
|---|---|---|---|
| WO | WO2017066561 | A2 | 4/2017 |
| WO | WO-2018/227286 | A1 | 12/2018 |
| WO | WO2021041316 | A1 | 3/2021 |

OTHER PUBLICATIONS

Zhao et al., Stem Cell Research (2014) 13, 342-354 (Year: 2014).*
Habicht, et al., J Immunol (2007) 179 (8): 5211-5219 (Year: 2007).*
Houlihan, et al., J Immunol (1992) 149(2): 668-75 (Year: 1992).*
Lindberg, et al., Science (1996) 274: 795-798 (Year: 1996).*
Chen et al., BBA—Molecular Basis of Disease (1997) 1362(1): 6-10 (Year: 1997).*
Boldin, et al., J Biol Chem (1995) 270 (14): 7795-8 (Year: 1995).*
Yang et al., J of Leukocyte Biology (2003) 74: 448-455 (Year: 2003).*
Aoki, et al., BBA—General Subjects (1997) 1334(2-3): 182-190 (Year: 1997).*
Kanamori, et al., J. of Biological Chemistry (2000) 275(8): 5867-5873 (Year: 2000).*
Pugliese et al., J. Clin. Invest. (2001) 107: 555-564 (Year: 2001).*
Office Action for Korean Application No. 10-2020-7000550, Dated May 22, 2024, 5 pages.
Abdullah et al., "Serpin-6 Expression Protects Embryonic Stem Cells From Lysis by Antigen-Specific CTL," J Immunol. 178(6):3390-9 (2007).
Adhikari et al., "Inhibitory phosphorylation of Cdk1 mediates prolonged prophase I arrest in female germ cells and is essential for female reproductive lifespan," Cell Res. 26:1212-1225 (2016).
Blomen et al., "Gene essentiality and synthetic lethality in haploid human cells," Science. 350(6264):1092-96 (2015) (6 pages).
Boone et al., "Human Genome. The indispensable genome," Science. 350(6264):1028-9 (2015) (3 pages).
Chan et al., "Transgenic Monkeys Produced by Retroviral Gene Transfer into Mature Oocytes," Science. 291(5502):309-312 (2001) (5 pages).
Chen et al., "OGEE v2: an update of the online gene essentiality database with special focus on differentially essential genes in human cancer cell lines," Nucleic Acids Res. 45(D1):D940-D944 (2017).
Communication pursuant to Article 94(3) EPC for European Application No. 16760977.5, dated Feb. 27, 2019 (5 pages).
Dai et al., "Targeted disruption of the alpha1,3-galactosyltransferase gene in cloned pigs," Nat Biotechnol. 20(3):251-255 (2002) (5 pages).
Di Stasi et al., "Inducible Apoptosis as a Safety Switch for Adoptive Cell Therapy," available in PMC May 3, 2012, published in final edited form as: N Engl J Med. 365(18):1673-1683 (2011) (16 pages).
Diril et al., "Cyclin-dependent kinase 1 (Cdk1) is essential for cell division and suppression of DNA re-replication but not for liver regeneration," Proc Natl Acad Sci U S A. 109(10):3826-31 (2012).
Extended European Search Report for European Application No. 16760977.5, mailed Jun. 5, 2018 (9 pages).
Gorczynski et al., "Long-Term Tolerance and Skin Allograft Survival in CD200tg Mice After Autologous Marrow Transplantation," Transplantation. 98(12):1271-1278 (2014).
Guo et al., "Oct 4 is Critical for Survival/Antiapoptosis of Murine Embryonic Stem Cells Subjected to Stress. Effects Associated with STAT3/Survivin," available in PMC Feb. 10, 2010, published in final edited form as: Stem Cells. 26(1):30 (2008) (15 pages).
Hara et al., "Neuron-like differentiation and selective ablation of undifferentiated embryonic stem cells containing suicide gene with Oct-4 promoter," Stem Cells Dev. 17(4):619-627 (2008) (9 Pages).
Harding et al., "Induction of long-term allogenic cell acceptance and formation of immune priveleged tissue in immunocompetent hosts." BIORXIV. <https://www.biorxiv.org/content/10.1101/716571v1>, dated Jul. 30, 2019.
International Preliminary Report on Patentability for International Application No. PCT/CA2016/050256, issued Sep. 12, 2017 (10 pages).
International Search Report and Written Opinion for International Application No. PCT/CA2016/050256, mailed Jul. 13, 2016 (14 pages).
International Search Report and Written Opinion for International Application No. PCT/CA2018/050706, mailed Sep. 13, 2018 (16 pages).
International Search Report and Written Opinion for International Patent Application No. PCT/CA2019/051808, dated Mar. 19, 2020 (18 pages).
Jung et al., "Ablation of tumor-derived stem cells transplanted to the central nervous system by genetic modification of embryonic stem cells with a suicide gene," Hum Gene Ther. 18(12):1182-92 (2007).
Kyba et al., "Enhanced hematopoietic differentiation of embryonic stem cells conditionally expressing Stat5," Proc Natl Acad Sci USA. 100(Suppl 1):11904-10 (2003).
Lai et al., "Production of alpha-1,3-Galactosyltransferase Knockout Pigs by Nuclear Transfer Cloning," Science. 295(5557):1089-1092 (2002) (5 pages).
Lanza et al., "Engineering Universal Cells that Evade Immune Detection," Nat Rev Immunol. 19(12):723-733 (2019).
Lee et al., "Induced pluripotent stem cells in regenerative medicine: an argument for continued research on human embryonic stem cells," Regen Med. 4(5):759-69 (2009).
Li et al., "Safeguarding clinical translation of pluripotent stem cells with suicide genes," Organogenesis. 9(1):34-9 (2013) (7 pages).
Liang et al., "Linking a cell-division gene and a suicide gene to define and improve cell therapy safety," Nature. 563(7733):701-4 (including supplement) (2018) (20 pages).
Lim et al., "Lentiviral vector mediated thymidine kinase expression in pluripotent stem cells enables removal of tumorigenic cells," PLoS One. 8(7):e70543 (2013) (16 pages).
Liu et al., "A Highly Efficient Recombineering-Based Method for Generating Conditional Knockout Mutations," Genome Res. 13(3):476-484 (2003).
Liu, "PL253 Map," <https://www.med.upenn.edu/robertsonlab/assets/user-content/documents/PL253_map.pdf>, retrieved on Oct. 20, 2020 (1 page).
Malecki, "'Above all, do no harm': safeguarding pluripotent stem cell therapy against iatrogenic tumorigenesis," Stem Cell Res Ther. 5(3): 73 (2014) (10 pages).
Mansour et al., "Disruption of the proto-oncogene int-2 in mouse embryo-derived stem cells: a general strategy for targeting mutations to non-selectable genes," Nature. 336(6197):348-352 (1988).
Mitsui et al., "The homeoprotein Nanog is required for maintenance of pluripotency in mouse epiblast and ES cells," Cell. 113(5):631-42 (2003).
Rong et al., "A scalable approach to prevent teratoma formation of human embryonic stem cells," J Biol Chem. 287(39):32338-45 (2012).
Rong et al., "An effective approach to prevent immune rejection of human ESC-derived allografts," Cell Stem Cell. 14(1):121-30 (2014).
Sarin et al., "Conditional telomerase induction causes proliferation of hair follicle stem cells," Nature. 436(7053):1048-52 (2005).
Schwarz et al., "Nanog is Dispensable for the Generation of Induced Pluripotent Stem Cells," available in PMC Aug. 3, 2014, published in final edited form as: Curr Biol. 24(3):347-350 (2014) (9 pages).
Shields et al., "Induction of Lymphoidlike Stroma and Immune Escape by Tumors That Express the Chemokine CCL21," Science. 328(5979):749-52 (2010).
Straathof et al., "An inducible caspase 9 safety switch for T-cell therapy," Blood. 105(11):4247-54 (2005) (9 pages).
Tan et al., "MFG-E8 Is Critical for Embryonic Stem Cell-Mediated T Cell Immunomodulation," Stem Cell Reports. 5(5):741-752 (2015).
Tena et al., "Transgenic Expression of Human CD47 Markedly Increases Engraftment in a Murine Model of Pig-to-Human Hematopoietic Cell Transplantation," Am J Transplant. 14(12):2713-22 (2014).
Wang et al., "Identification and characterization of essential genes in the human genome," Science. 350(6264):1096-1101 (2015) (7 pages).

(56) References Cited

OTHER PUBLICATIONS

Wang et al., "One-Step Generation of Mice Carrying Mutations in Multiple Genes by CRISPR/Cas-Mediated Genome Engineering," available in PMC Mar. 30, 2014, published in final edited form as: Cell. 153(4):910-918 (2013) (17 pages).
Warming et al., "Zfp423 Is Required for Normal Cerebellar Development," Mol Cell Biol. 26(18):6913-6922 (2006).
Webb, "No role for Oct4 in regenerating adult tissues," Nat Rep Stem Cells. doi: https://doi.org/10.1038/stemcells.2007.103, retrieved from <https://www.nature.com/articles/stemcells.2007.103> on May 2, 2019 (2007) (3 pages).
Yang et al., "Effective gene targeting in rabbits using RNA-guided Cas9 nucleases," J Mol Cell Biol. 6(1):97-99 (2014) (3 pages).
Yolcu et al., "Induction of tolerance to cardiac allografts using donor splenocytes engineered to display on their surface an exogenous fas ligand protein," J Immunol. 181(2):931-9 (2008).
Zhao et al., "Heterologous expression of mutated HLA-G decreases immunogenicity of human embryonic stem cells and their epidermal derivatives," Stem Cell Res. 13(2):342-54 (2014).
Chinese Office Action mailed Sep. 29, 2023 for Chinese Application No. 201880038734.5, a foreign counterpart to U.S. Appl. No. 16/621,490, 9 pages.
Canadian Office Action mailed Jul. 13, 2023 for Canadian Patent Application No. 3,064,297, a foreign counterpart to U.S. Appl. No. 16/621,490, 4 pages.
Canadian Office Action mailed Aug. 21, 2023 for Canadian patent application No. 3123102, a counterpart foreign application of U.S. Appl. No. 17/413,314 , #6 pages.
Israeli Office Action mailed Jul. 11, 2023 for Israeli Patent Application No. 270835, a foreign counterpart to U.S. Appl. No. 16/621,490, 2 pages.
Korean Office Action mailed Aug. 30, 2023 for Korean Patent Application No. 10-2020-7000550, a foreign counterpart to U.S. Appl. No. 16/621,490, 8 pages.
Examination Report Dated Apr. 6, 2023 in Australian Application No. 2018285972, 3 pages.
Examination Report Dated Jul. 27, 2022 in Australian Application No. 2018285972, 4 pages.
Bhattacharya, et al., "Impact of Genetic Variation on Three Dimensional Structure and Function of Proteins," PLoS One, vol. 12, No. 3, 2017, 22 pgs.
Office Action Dated Marcy 1, 2023 in Chinese Application No. 201880038734.5, 10 pages.
Deuse, et al., "Hypoimmunogenic Derivatives of Induced Pluripotent Stem Cells Evade Immune Rejection in Fully Immunocompetent Allogeneic Recipients," Nat. Biotechnol., vol. 37, No. 3, 2019, pp. 252-258.
Extended European Search Report Dated Aug. 9, 2021 in European Application No. 18818206.7, 14 pages.
Fenton, et al., "Rheostat Positions: A New Classification of Protein Positions Relevant to Pharmacogenomics," Medicinal Chemistry Research, vol. 29, 2020, pp. 1133-1146.
Gorczynski, et al., "Regulation of Transplantation Tolerance by Antigen-Preesenting Cells," Transplantation Reviews, vol. 19, No. 3, 2005, pp. 123-137.
Han, et al., "Generation of Hypoimmunogenic Human Pluripotent Stem Cells," PNAS, vol. 116, No. 21, 2019, pp. 10441-10446.
Notice of Reasons for Refusal Dated Aug. 2, 2022 in Japanese Application No. 2020-518110, 9 pages.
McDonald, et al., "An Amyloid-Like C-Terminal Domain of Thrombospondin-1 Displays CD47 Agonist Activity Requiring Both VVM Motifs," Biochemistry, vol. 42, 2003, pp. 10001-10011.
Office Action Dated Oct. 26, 2022 in U.S. Appl. No. 16/621,490, 17 pages.
Tokuriki & Tawfik, "Stability Effects of Mutations and Protein Evolvability," Curr. Opin. Struc. Biol., vol. 19, 2009, pp. 596-604.
The Japanese Office Action mailed May 9, 2023 for Japanese patent application No. 2020-518110, a foreign counterpart of U.S. Appl. No. 16/621,490, 5 pages.
Chinese Office Action Dated Feb. 27, 2024 for Chinese Application No. 201880038734.5, a foreign counterpart to U.S. Appl. No. 16/621,490, 16 pages.
El Haddad, et al., "The Novel Role of SERPINB9 in Cytotoxic Protection of Human Mesenchymal Stem Cells", J. Immunol., vol. 187, No. 5, 2011, pp. 2252-2260.
Harding et al. , "Immune-privileged tissues formed from immunologically cloaked mouse embryonic stem cells survive long term in allogeneic hosts", (2023, Nature Biomedical Engineering, https://doi.org/10.1038/s41551-023-01133-y, pp. 1-33).
Office Action Dated Apr. 24, 2024 for U.S. Appl. No. 18/175,409, 15 pages.
Office Action for Chinese Application No. 201880038734.5, Dated Sep. 2, 2024, 13 pages.

* cited by examiner

H&E stain, teratoma section

IMMUNOMODULATORY CELLS AND USES THEREOF

CROSS-REFERENCE TO RELATED APPLICATIONS

This application is a U.S. National Stage Application of PCT/CA2019/051808, filed Dec. 13, 2019, which claims the benefit of the earlier filing date of U.S. Provisional Application Ser. No. 62/779,449, filed Dec. 13, 2018, each of which is incorporated herein by reference its entirety as if fully set forth herein.

BACKGROUND OF THE DISCLOSURE

The immune system is essential for the maintenance of health and protection against disease. The immune system is also capable of causing harm or impeding therapeutic treatment. For example, although the immune system is designed to detect and attack foreign antigens from bacteria, viruses, and other pathogens, an immune response can be mistakenly mounted against endogenous "self" antigens, which may lead to autoimmune disease. In addition, immune system activation against foreign antigens can make treatments, such as organ and tissue transplants, challenging and uncertain due a possibility that the immune system of a recipient will reject the organ or tissue transplant as foreign. Both transplant recipients and subjects with an autoimmune disease may be treated with immunosuppressive medication to dampen the response of the immune system, but this approach is accompanied by undesirable side effects and an increased risk of infection.

The adaptive immune response to foreign antigens involves the generation of antibodies, which leads to immunity against such antigens given that the antibodies can be rapidly generated by the immune system upon detection of the same antigen in the future. This feature of the immune response can be harnessed by vaccine technology, and a number of vaccines have been created using antigens from common viruses to produce widespread immunity. There is interest in using vaccines to treat a variety of different diseases and conditions, but the development of vaccines is a long and complex process that often lasts 10-15 years. For this reason, some have turned to other approaches to induce antibody-based immunity in a subject. One approach involves cell-based immunization, in which a cell is used to present an antigen to the immune system. This approach can be unreliable and cumbersome and may lead to the production of multiple non-specific antibodies against various proteins contained in the cell rather than production of a specific therapeutic antibody against the target antigen.

There is a need for targeted immunomodulatory therapies that can be used to generate a desired immune response to an antigen without off target effects or the need for widespread suppression of the immune system.

SUMMARY OF THE DISCLOSURE

Featured are cells and methods of use thereof for modulating an antigen-specific immune response in a subject. The cells contain a set of transgenes that shield the cells from immune surveillance. The cells may further contain a polypeptide containing a donor alloantigen or a polypeptide containing a self-antigen. The cells can be used to induce immune tolerance to an antigen (e.g., a donor alloantigen or a self-antigen). The cells can also be used to induce immune tolerance in a subject in a method of inducing an immune response to (e.g., induce the production of antibodies directed against) a non-self antigen.

In a first aspect, the invention features a cell genetically modified to contain at least one mechanism for inducing immune tolerance to an antigen when administered to a subject, the genetically modified cell containing a transgene selected from one or more (e.g., one, two, three, four, five, six, seven, or all eight, e.g., a set of transgenes containing two, three, four, five, six, seven, or all eight) of the following genes: PD-L1, HLA-G or H2-M3, Cd47, Cd200, FASLG or FasL, Ccl21 or Ccl21b, Mfge8, and Serpin B9 or Spi6 or a gene encoding a biologic that acts as an agonist of PD-L1, HLA-G or H2-M3, Cd47, Cd200, FASLG or FasL, Ccl21 or Ccl21b, Mfge8, or Serpin B9 or Spi6; and a transgene encoding a polypeptide containing an antigen.

In some embodiments, each transgene of the set of transgenes encodes a gene product that is cytoplasmic, membrane bound, or local acting, and that has one or more of the following functions: a) to mitigate antigen presenting cell activation and function; b) to mitigate graft attacking leukocyte activity or cytolytic function; c) to mitigate macrophage cytolytic function and phagocytosis of allograft cells; d) to induce apoptosis in graft attacking leukocytes; e) to mitigate local inflammatory proteins; and f) to protect against leukocyte-mediated apoptosis.

In some embodiments, the cell contains a transgene selected from two or more (e.g., a set of transgenes containing two, three, four, five, six, seven, or all eight) of the following genes: PD-L1, HLA-G or H2-M3, Cd47, Cd200, FASLG or FasL, Ccl21 or Ccl21b, Mfge8, and Serpin B9 or Spi6 or a gene encoding a biologic that acts as an agonist of PD-L1, HLA-G or H2-M3, Cd47, Cd200, FASLG or FasL, Ccl21 or Ccl21b, Mfge8, or Serpin B9 or Spi6.

In some embodiments, the antigen is a donor alloantigen.

In some embodiments, the antigen is an antigen associated with an autoimmune disease or condition.

In some embodiments, the antigen is a self-antigen to which the subject's immune system mounts an aberrant immune response.

In some embodiments, the antigen is selected from an antigen listed in Table 2.

In some embodiments, the antigen is a food antigen or an allergen antigen.

In some embodiments, the antigen is not endogenous to the cell.

In some embodiments, the transgene encoding the polypeptide containing the antigen is incorporated into the genome of the cell at a non-endogenous locus.

In some embodiments, the polypeptide containing the antigen is expressed at a level that corresponds to the expression level of the polypeptide in a target cell. In some embodiments, the antigen is a donor alloantigen and the target cell is a donor cell. In some embodiments, the antigen is a self-antigen to which the subject's immune system mounts an aberrant immune response and the target cell is a cell from the subject that endogenously expresses the polypeptide.

In some embodiments, the polypeptide containing the antigen is expressed at a level that corresponds to the expression level of a polypeptide encoded by a housekeeping gene. In some embodiments, the polypeptide encoded by the housekeeping gene is β-actin, GAPDH, or Rosa26.

In another aspect, the invention features a method of inducing immune tolerance in a subject to a donor alloantigen, including the steps of: (i) providing a donor cell expressing a polypeptide containing the donor alloantigen; (ii) expressing in the cell a set of transgenes containing two or more (e.g., two, three, four, five, six, seven, or all eight) of the following genes: PD-L1, HLA-G or H2-M3, Cd47, Cd200, FASLG or FasL, Ccl21 or Ccl21b, Mfge8, and Serpin B9 or Spi6 or a gene encoding a biologic that acts as an agonist of PD-L1, HLA-G or H2-M3, Cd47, Cd200, FASLG or FasL, Ccl21 or Ccl21b, Mfge8, or Serpin B9 or Spi6; and (iii) administering the cell to the subject to induce immune tolerance to the donor alloantigen.

In another aspect, the invention features a method of inducing immune tolerance in a subject to a donor alloantigen, including the steps of: (i) providing a cell; (ii) expressing in the cell a set of transgenes containing two or more (e.g., two, three, four, five, six, seven, or all eight) of the following genes: PD-L1, HLAG or H2-M3, Cd47, Cd200, FASLG or FasL, Ccl21 or Ccl21b, Mfge8, and Serpin B9 or Spi6 or a gene encoding a biologic that acts as an agonist of PD-L1, HLA-G or H2-M3, Cd47, Cd200, FASLG or FasL, Ccl21 or Ccl21b, Mfge8, or Serpin B9 or Spi6; (iii) modifying the cell to express a transgene encoding a polypeptide containing the donor alloantigen; and (iv) administering the cell to the subject to induce immune tolerance to the donor alloantigen.

In some embodiments of any of the foregoing aspects, the donor alloantigen is a blood group antigen or a histocompatibility antigen.

In some embodiments, the polypeptide containing the donor alloantigen is expressed at a level corresponding to the expression level of the polypeptide containing the donor alloantigen in a donor cell.

In some embodiments, the cell is administered to or near a body site that will receive an organ or tissue transplant from the donor, or the cell is administered to a subcutaneous site.

In some embodiments, the method further includes measuring a response of an immune cell from the subject (e.g., immune cell activation, differentiation, polarization, proliferation, migration, pro-inflammatory cytokine production, degranulation, phagocytosis, or cytotoxicity) to the donor alloantigen after administration of the cell.

In some embodiments, the method prepares the subject to receive an organ or tissue transplant from the donor.

In some embodiments, the method further includes transplanting an organ or tissue from the donor into the subject after inducing immune tolerance to the donor alloantigen.

In some embodiments, the subject does not require treatment with an immunosuppressive medication.

In some embodiments, the method further includes administering to the subject an immunosuppressive medication. In some embodiments, the immunosuppressive medication is administered at a dose that is reduced relative to a standard dose of the immunosuppressive medication administered to a recipient of an organ or tissue transplant.

In another aspect, the invention features a cell of any of the foregoing aspects or embodiments for use in a method of inducing immune tolerance in a subject to an antigen.

In another aspect, the invention features a cell of any of the foregoing aspects or embodiments for use in a method of treating a subject having or at risk of developing an autoimmune disease or condition.

In another aspect, the invention features the use of the cell of any of the foregoing aspects or embodiments in the manufacture of a medicament for inducing immune tolerance in a subject to an antigen.

In another aspect, the invention features the use of the cell of any of the foregoing aspects or embodiments in the manufacture of a medicament for treating a subject having or at risk of developing an autoimmune disease or condition.

In another aspect, the invention features the use of the cell of any of the foregoing aspects or embodiments in the manufacture of a medicament for preparing a subject to receive an organ or tissue transplant.

In another aspect, the invention features a method of inducing immune tolerance in a subject to an antigen, including the steps of: (i) providing a cell; and (ii) expressing in the cell a set of transgenes containing two or more (e.g., two, three, four, five, six, seven, or all eight) of the following genes: PD-L1, HLAG or H2-M3, Cd47, Cd200, FASLG or FasL, Ccl21 or Ccl21b, Mfge8, and Serpin B9 or Spi6 or a gene encoding a biologic that acts as an agonist of PD-L1, HLA-G or H2-M3, Cd47, Cd200, FASLG or FasL, Ccl21 or Ccl21b, Mfge8, or Serpin B9 or Spi6; (iii) expressing in the cell a transgene encoding a polypeptide containing the antigen; and (iv) administering the cell to the subject to induce immune tolerance to the antigen.

In some embodiments, the antigen is an antigen associated with an autoimmune disease or condition.

In another aspect, the invention features a method of treating a subject having or at risk of developing an autoimmune disease or condition by administering to the subject a cell modified to express a transgene encoding a polypeptide containing an antigen associated with the autoimmune disease or condition and a set of transgenes including two or more (e.g., two, three, four, five, six, seven, or all eight) of the following genes: PD-L1, HLAG or H2-M3, Cd47, Cd200, FASLG or FasL, Ccl21 or Ccl21b, Mfge8, and Serpin B9 or Spi6 or a gene encoding a biologic that acts as an agonist of PD-L1, HLA-G or H2-M3, Cd47, Cd200, FASLG or FasL, Ccl21 or Ccl21b, Mfge8, or Serpin B9 or Spi6.

In some embodiments of any of the foregoing aspects, the antigen is a self-antigen to which the subject's immune system mounts an aberrant immune response. In some embodiments, the polypeptide containing the self-antigen is expressed at a level that corresponds to the endogenous expression level of the polypeptide in a cell of the subject.

In some embodiments of any of the foregoing aspects, the antigen is selected from an antigen listed in Table 2.

In some embodiments of any of the foregoing aspects, the antigen is a food antigen or an allergen antigen.

In some embodiments, the cell is administered to or near a body site associated with an autoimmune disease or condition, or the cell is administered to a subcutaneous site.

In some embodiments, the method or use further includes measuring a response of an immune cell from the subject (e.g., immune cell activation, differentiation, polarization, proliferation, migration, pro-inflammatory cytokine production, degranulation, phagocytosis, or cytotoxicity) to the antigen after administration of the cell.

In some embodiments, the autoimmune disease or condition is multiple sclerosis (MS) and the polypeptide containing the antigen is myelin oligodendrocyte glycoprotein (MOG).

In some embodiments, the autoimmune disease or condition is type 1 diabetes and the polypeptide containing the antigen is insulin or glutamic acid decarboxylase 65 (GAD65).

In another aspect, the invention features a method of inducing an immune response in a subject to an antigen, including the steps of: (i) administering to the subject a first cell expressing a set of transgenes including two or more (e.g., two, three, four, five, six, seven, or all eight) of the following genes: PD-L1, HLAG or H2-M3, Cd47, Cd200, FASLG or FasL, Ccl21 or Ccl21b, Mfge8, and Serpin B9 or Spi6 or a gene encoding a biologic that acts as an agonist of PD-L1, HLA-G or H2-M3, Cd47, Cd200, FASLG or FasL, Ccl21 or Ccl21b, Mfge8, or Serpin B9 or Spi6; and (ii) administering to the subject a second cell of the same type as the first cell that is modified to express a transgene encoding a polypeptide comprising the antigen and that does not express the set of transgenes.

In another aspect, the invention features the use of a combination of a first cell and a second cell for inducing an immune response in a subject to an antigen, the use including the steps of (i) administering to the subject a first cell expressing a set of transgenes containing two or more of the following genes: PD-L1, HLAG or H2-M3, Cd47, Cd200, FASLG or FasL, Ccl21 or Ccl21b, Mfge8, and Serpin B9 or Spi6 or a gene encoding a biologic that acts as an agonist of PD-L1, HLA-G or H2-M3, Cd47, Cd200, FASLG or FasL, Ccl21 or Ccl21b, Mfge8, or Serpin B9 or Spi6; and (ii) administering to the subject a second cell of the same type as the first cell that is modified to express a transgene encoding a polypeptide containing the antigen and that does not express the set of transgenes.

In another aspect, the invention features the use of a first cell in the manufacture of a medicament for inducing an immune response in a subject to an antigen, characterized in that the medicament is for administration in a treatment regimen with a second cell, in which the first cell expresses a set of transgenes containing two or more of the following genes: PD-L1, HLAG or H2-M3, Cd47, Cd200, FASLG or FasL, Ccl21 or Ccl21b, Mfge8, and Serpin B9 or Spi6 or a gene encoding a biologic that acts as an agonist of PD-L1, HLA-G or H2-M3, Cd47, Cd200, FASLG or FasL, Ccl21 or Ccl21b, Mfge8, or Serpin B9 or Spi6; and in which the second cell is a cell of the same type as the first cell that does not express the set of transgenes and that is modified to express a transgene encoding a polypeptide containing the antigen.

In some embodiments, the method or use further includes measuring a response of an immune cell from the subject (e.g., immune cell activation, differentiation, polarization, proliferation, migration, pro-inflammatory cytokine production, degranulation, phagocytosis, or cytotoxicity) to the first cell before administration of the second cell.

In some embodiments, the second cell is administered after inducing immune tolerance in the subject to the first cell.

In some embodiments, the antigen is a non-self antigen. In some embodiments, the non-self antigen is a cancer antigen, a viral antigen, a bacterial antigen, a fungal antigen, or a parasitic antigen.

In some embodiments, the cancer antigen is derived from a leukemia, lymphoma, sarcoma, carcinoma, blastoma, myeloma, melanoma, neuroma, glioma, liver cancer, bone cancer, lung cancer, brain cancer, bladder cancer, gastrointestinal cancer, urogenital cancer, breast cancer cardiac cancer, gynecological cancer, uterine cancer, head and neck cancer, gallbladder cancer, laryngeal cancer, lip and oral cavity cancer, ocular cancer, melanoma, pancreatic cancer, prostate cancer, colorectal cancer, testicular cancer, throat cancer, skin cancer, thyroid cancer, bone and soft tissue sarcoma, anal cancer, appendix cancer, astrocytoma, atypical teratoid/rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, langerhans cell histiocytosis, Hodgkin lymphoma, hypopharyngeal cancer, islet cell tumors, pancreatic neuroendocrine tumors, Wilms tumor and other childhood kidney tumors, langerhans cell histiocytosis, small cell lung cancer, cutaneous T cell lymphoma, intraocular melanoma, merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, non-Hodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, stomach cancer, renal cancer, pelvic cancer, bronchus cancer, oropharyngeal cancer, larynx cancer, biliary tract cancer, a cancer of the central nervous system, a cancer of the respiratory system, and a cancer of the urinary system, cancer of the peritoneum, hepatocellular cancer, hepatoma, endometrial or uterine carcinoma, salivary gland carcinoma, hepatic carcinoma, anal carcinoma, penile carcinoma, post-transplant lymphoproliferative disorder (PTLD), bladder carcinoma, a pharynx cancer, a tumor of the tongue, a synovial cell sarcoma, a neuroblastoma, pheochromocytoma, pituitary tumor, pleuropulmonary blastoma, primary peritoneal cancer, rectal cancer, retinoblastoma, rhabdomyosarcoma, salivary gland cancer, Kaposi sarcoma, rhabdomyosarcoma, Sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, Waldenström macroglobulinemia, meningioma, malignant mesothelioma, or a virally induced cancer.

In some embodiments, the viral antigen is derived from a virus of a viral family selected from the group consisting of Retroviridae, Flaviviridae, Arenaviridae, Bunyaviridae, Filoviridae, Togaviridae, Poxviridae, Herpesviridae, Orthomyxoviridae, Coronaviridae, Rhabdoviridae, Paramyxoviridae, Picornaviridae, Hepadnaviridae, Papillomaviridae, Parvoviridae, Astroviridae, Polyomaviridae, Caliciviridae, and Reoviridae. In some embodiments, the viral antigen is derived from human immunodeficiency virus (HIV), human papillomavirus (HPV), hepatitis A virus (Hep A), hepatitis B virus (HBV), hepatitis C virus (HCV), *Variola major, Variola minor*, monkeypox virus, measles virus, rubella virus, mumps virus, varicella zoster virus (VZV), poliovirus, rabies virus, Japanese encephalitis virus, herpes simplex virus (HSV), cytomegalovirus (CMV), rotavirus, influenza, Ebola virus, yellow fever virus, Zika virus, or Marburg virus. In some embodiments, the polypeptide containing the viral antigen is Gag, Pol, Nef, Tat, Rev, Vif, Vpr, Vpu, 9D antigen, or Env.

In some embodiments, the bacterial antigen is derived from *Acinetobacter* spp., *Bacteroides distasonis, Bacteroides fragilis, Bacteroides ovatus, Bacteroides thetaiotaomicron, Bacteroides uniformis, Bacteroides vulgatus, B. cepacia, Citrobacter freundii, Citrobacter koseri, Clostridium*

*clostridioforme, Clostridium perfringens, C. sordellii, Enterobacter aerogenes, Enterobacter cloacae, Enterococcus faecalis, Enterococcus* spp. *Escherichia coli, Eubacterium lentum, Fusobacterium* spp., *Haemophilus influenza, Haemophilus parainfluenzae, Klebsiella pneumoniae, Klebsiella oxytoca, Legionella pneumophilia, Moraxella catarrhalis, Morganella morganii, Mycoplasma* spp., *Peptostreptococcus* spp., *Porphyromonas saccharolytica, Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus, Staphylococcus epidermidis, Stenotrophomonas maltophilia, Streptococcus agalactiae, Streptococcus constellatus, Streptococcus pneumoniae, Streptococcus pyogenes, Streptococcus pyogenes, Mycobacterium tuberculosis, Mycobacterium bovis, Mycobacterium africanum, Mycobacterium microti, Mycobacterium leprae, Salmonella typhimurium, Francisella tularensis, Brucella, Burkholderia mallei, Yersinia pestis, Corynebacterium diphtheria, Neisseria meningitidis, Bordetella pertussis, Clostridium tetani*, or *Bacillus anthracis*. In some embodiments, the polypeptide containing the bacterial antigen is 10.4, 85A, 85B, 86C, CFP-10, Rv3871, ESAT-6, O antigen, H antigen, K antigen, or protective antigen (PA).

In some embodiments, the parasitic antigen is derived from *Toxoplasma Plasmodium falciparum, Plasmodium vivax, Plasmodium ovale, Plasmodium malariae, Trypanosoma* spp., or *Legionella* spp. In some embodiments, the polypeptide containing the parasitic antigen is circumsporozoite (CS) protein, gamete surface protein Pfs230 or Pfs48/45, or Liver Specific Antigen 1 or 3 (LSA-1 or LSA-3).

In some embodiments, the fungal antigen is derived from a mold pathogen from phylum Ascomycota, phylum Basidomycota, phylum Chytridiomycota, phylum, or phylum Oomycota in the Stramenopila kingdom. In some embodiments, the fungal antigen is derived from *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus*, or *Rhizopus arrhizus*. In some embodiments, the polypeptide containing the fungal antigen is a cell wall mannoprotein or a surface-expressed glycoprotein.

In some embodiments of any of the foregoing aspects, the polypeptide containing the antigen is expressed at a level that corresponds to the expression level of a polypeptide encoded by a housekeeping gene. In some embodiments, the polypeptide encoded by the housekeeping gene is β-actin, GAPDH, or Rosa26.

In some embodiments, the first cell and/or the second cell is administered to a subcutaneous site.

In some embodiments, the method or use further includes assessing a blood sample from the subject for antibodies directed against the antigen.

In some embodiments, the method or use immunizes the subject to the antigen.

In some embodiments, the method or use induces the production of antibodies directed against the antigen by the immune system of the subject.

In some embodiments of any of the foregoing aspects, the set of transgenes includes three, four, five, six, seven, or all eight of the following genes: PD-L1, HLA-G or H2-M3, Cd47, Cd200, FASLG or FasL, Ccl21 or Ccl21b, Mfge8, and Serpin B9 or Spi6 or a gene encoding a biologic that acts as an agonist of PD-L1, HLA-G or H2-M3, Cd47, Cd200, FASLG or FasL, Ccl21 or Ccl21b, Mfge8, or Serpin B9 or Spi6.

In some embodiments of any of the foregoing aspects, the set of transgenes includes PD-L1, HLA-G or H2-M3, Cd47, Cd200, FASLG or FasL, Ccl21 or Ccl21b, Mfge8, and Serpin B9 or Spi6 or a gene encoding a biologic that acts as an agonist of PD-L1, HLA-G or H2-M3, Cd47, Cd200, FASLG or FasL, Ccl21 or Ccl21b, Mfge8, and Serpin B9 or Spi6.

In some embodiments of any of the foregoing aspects, the cell further contains one or more (e.g., one, two, three, four, five, six, seven, eight, nine, ten, or all eleven) of the following transgenes: TGF-β, Cd73, Cd39, Lag3, Il1r2, Ackr2, Tnfrsf22, Tnfrs23, Tnfrsf10, Dad1, and IFNγR1 d39 or a gene encoding a biologic that acts as an agonist of TGF-β, Cd73, Cd39, Lag3, Il1r2, Ackr2, Tnfrsf22, Tnfrs23, Tnfrsf10, Dad1, or IFNγR1 d39. In some embodiments, the TGF-β or biologic is local acting in the graft environment.

In some embodiments of any of the foregoing aspects, the cell is a stem cell, an autologous cell, a somatic cell, a germ cell, a syngeneic cell, or a cell amenable for genome editing.

In some embodiments of any of the foregoing aspects, the cell is an embryonic stem cell, a pluripotent stem cell, an induced pluripotent stem cell (iPSC), a hematopoietic stem cell, a mesenchymal stem cell, an endothelial stem cell, an epithelial stem cell, an adipose stem or progenitor cell, a germline stem cell, a lung stem or progenitor cells, a mammary stem cell, an olfactory adult stem cell, a hair follicle stem cell, an intestinal stem or progenitor cell, a multipotent stem cell, an amniotic stem cell, a cord blood stem cell, a neural stem or progenitor cell, an adult stem cell, a somatic stem cell, a tissue-specific stem cell, a totipotent stem cell, a fibroblast, a monocytic precursor, a B cell, an exocrine cell, a pancreatic progenitor, an endocrine progenitor, a hepatoblast, a myoblast, a preadipocyte, a hepatocyte, a chondrocyte, a smooth muscle cell, a K562 human erythroid leukemia cell line, a bone cell, a synovial cell, a tendon cell, a ligament cell, a meniscus cell, an adipose cell, a dendritic cell, a neutrophil, a basophil, a mast cell, a monocyte, an innate lymphoid cell, a natural killer cell, a skeletal muscle cell, a cardiac muscle cell, an erythroid-megakaryocytic cell, an eosinophil, a macrophage, a T cell, an islet beta-cell, a neuron, a cardiomyocyte, a blood cell, an exocrine progenitor, a ductal cell, an acinar cell, an alpha cell, a beta cell, a delta cell, a PP cell, a cholangiocyte, a white or brown adipocyte, a hormone-secreting cell, an epidermal keratinocyte, an epithelial cell, a kidney cell, a skeletal joint synovium cell, a periosteum cell, a perichondrium cell, a cartilage cell, an endothelial cell, a pericardium cell, a meningeal cell, a keratinocyte precursor cell, a keratinocyte stem cell, a pericyte, a glial cell, an ependymal cell, a cell isolated from an amniotic or placental membrane, a serosal cell, or a cell derived from skin, heart, brain or spinal cord, liver, lung, kidney, pancreas, bladder, bone marrow, spleen, intestine, or stomach.

In some embodiments of any of the foregoing aspects, the cell is an autologous cell.

In some embodiments of any of the foregoing aspects, the cell further includes at least one mechanism for controlling cell proliferation (e.g., reducing or inhibiting proliferation of a cell or ablating (e.g., killing) a cell), including: a genetic modification of one or more (e.g., one, two, three, or more) cell division locus/loci (CDL), the CDL being one or more endogenous or exogenous genetic loci encoding a transcription product(s) (e.g., a product resulting from transcription of a gene, the loss of expression of which would result in cell death or the inability of a cell to proliferate) that is expressed by dividing cells (e.g., cells actively undergoing cell division), cells capable of dividing but not currently undergoing cell division, or non-dividing cells (e.g., post-mitotic cells, such as a neuron). The genetic modification includes the incorporation at the CDL of one or more of: i) an ablation link (ALINK) system that includes a DNA sequence encoding a negative selectable marker that is transcriptionally linked to a DNA sequence of the CDL (e.g., the DNA sequence encoding the negative selectable marker is inserted into the CDL such that expression of the negative selectable marker is linked to expression of the transcription product of the CDL, e.g., such that the negative selectable marker and the transcription product of the CDL are co-expressed); and ii) an exogenous activator of regulation of a CDL (EARC) system that includes an inducible activator-based gene expression system that is operably linked to the CDL. In some embodiments, the genetic modification of the CDL includes performing targeted replacement of the CDL with one or more of: a) a DNA vector containing the ALINK system; b) a DNA vector containing the EARC system; and c) a DNA vector containing the ALINK system and the EARC system; wherein the ALINK and/or EARC systems are each operably linked to the CDL. In some embodiments, the genetic modification of the CDL includes performing targeted insertion into a coding or non-coding region of the CDL with one or more of a) a DNA sequence encoding the negative selectable marker; b) a DNA sequence encoding the inducible activator-based gene expression system; or c) a DNA sequence encoding the negative selectable marker and a DNA sequence encoding the inducible activator-based gene expression system. In some embodiments, the genetic modification of the CDL including the ALINK system is homozygous, heterozygous, hemizygous or compound heterozygous and/or wherein the genetic modification of the CDL including the EARC system results in activation of the CDL solely by an inducer of the inducible activator-based gene expression system. In some embodiments, the CDL encodes a gene product that functions in one or more of: cell cycle, DNA replication, RNA transcription, protein translation, and metabolism. In some embodiments, the CDL is a gene that is required for cell viability (e.g., cell survival, e.g., a gene without which the cell dies). In some embodiments, the CDL is a gene that is required for cell proliferation (e.g., a gene without which the cell cannot proliferate). In some embodiments, the CDL is one or more of Cdk1/CDK1, Top2A/TOP2A, Cenpa/CENPA, Birc5/BIRC5, and Eef2/EEF2, preferably wherein the CDL is Cdk1 or CDK1. In some embodiments, the CDL is two or more of Cdk1/CDK1, Top2A/TOP2A, Cenpa/CENPA, Birc5/BIRC5, and Eef2/EEF2, preferably wherein the CDL is Cdk1/CDK1 and Top2A/TOP2A or Cdk1/CDK1 and Eef2/EEF2. In some embodiments, the ALINK system includes a herpes simplex virus-thymidine kinase/ganciclovir system, a cytosine deaminase/5-fluorocytosine system, a carboxyl esterase/irinotecan system or an iCasp9/AP1903 system, preferably wherein the ALINK system is a herpes simplex virus-thymidine kinase/ganciclovir system. In some embodiments, the EARC system is a dox-bridge system, a cumate switch inducible system, an ecdysone inducible system, a radio wave inducible system, or a ligand-reversible dimerization system, preferably wherein the EARC system is a dox-bridge system.

In some embodiments of any of the foregoing aspects, the method or use further includes: i) permitting proliferation of the cell containing the ALINK system by maintaining the cell containing the ALINK system in the absence of an inducer of the negative selectable marker or ablating (e.g., killing) and/or inhibiting proliferation of the cell containing the ALINK system by exposing the cell containing the ALINK system to the inducer of the negative selectable marker; and/or ii) permitting proliferation of the cell containing the EARC system by exposing the cell containing the EARC system to an inducer of the inducible activator-based gene expression system or preventing or inhibiting proliferation of the cell containing the EARC system by maintaining the cell containing the EARC system in the absence of the inducer of the inducible activator-based gene expression system.

In some embodiments of any of the foregoing aspects, the method or use further includes removing the cell expressing the polypeptide containing the antigen after the immune system of the subject has responded to the antigen. In some embodiments, the cell is removed surgically. In some embodiments, the cell is removed by the use of the ALINK and/or EARC systems. In some embodiments, one or more (e.g., one, two, three, four, or more) ALINK and/or EARC systems are used to eliminate all of the cloaked cells and/or all of the cells expressing the polypeptide containing the antigen.

In some embodiments of any of the foregoing aspects, one or more (e.g., one, two, three, four, five, six, seven, or all eight) of PD-L1, HLA-G or H2-M3, Cd47, Cd200, FASLG or FasL, Ccl21 or Ccl21b, Mfge8, and Serpin B9 or Spi6 is expressed at a level that is equal to or greater than the expression level of the corresponding endogenous gene in an activated leukocyte (e.g., a T cell, e.g., the expression level of the cloaking transgene is equal to the level of expression of the endogenous gene in activated leukocytes, or is 1.5, 2, 3, 4, 5, 6, 7, 8, 9, 10-fold or more higher than the level of expression of the endogenous gene in activated leukocytes). In some embodiments, all eight of PD-L1, HLA-G or H2-M3, Cd47, Cd200, FASLG or FasL, Ccl21 or Ccl21b, Mfge8, and Serpin B9 or Spi6 are expressed at a level that is equal to or greater than the expression level of the corresponding endogenous gene in an activated leukocyte.

In some embodiments of any of the foregoing aspects, one or more (e.g., one, two, three, four, five, six, seven, or all eight) of PD-L1, HLA-G or H2-M3, Cd47, Cd200, FASLG or FasL, Ccl21 or Ccl21b, Mfge8, and Serpin B9 or Spi6 is expressed at a level that is in the top 5% of gene expression for all genes in the genome of the cell. In some embodiments, all eight of PD-L1, HLA-G or H2-M3, Cd47, Cd200, FASLG or FasL, Ccl21 or Ccl21b, Mfge8, and Serpin B9 or Spi6 are expressed at a level that is in the top 5% of gene expression for all genes in the genome of the cell.

In some embodiments of any of the foregoing aspects, one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) is expressed at a level that is greater than the expression level of the corresponding endogenous gene in a wild-type stem cell (e.g., a wild-type ES cell from the same species, e.g., the expression level of the cloaking transgene is at least 2, 3, 4, 5, 6, 7, 8, 9, 10, 20, 30, 40, 50, 100, 500, 1,000-fold or more higher in cloaked cells compared to expression of the endogenous gene in unmodified wild-type ES cells from the same species). In some embodiments, all 8 of PD-L1, HLA-G (H2-M3), Cd47, Cd200, FASLG (FasL), Ccl21 (Ccl21b), Mfge8, and Serpin B9 (Spi6) are expressed at a level that is greater (e.g., 2, 3, 4, 5, 6, 7, 8, 9, 10, 20, 30, 40, 50, or 100-fold higher or more) than the expression level of the endogenous gene in a wild-type stem cell (e.g., an embryonic stem cell from the same species as the cloaked cell). In some embodiments, one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) is expressed at a level that is in the top 5% of gene expression for all genes in the ES cell genome. In some embodiments, one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) is expressed at a level that is in the top 1% of gene expression for all genes in the ES cell genome. In some embodiments, all of PD-L1, HLA-G (H2-M3), Cd47, Cd200, FASLG (FasL), Ccl21 (Ccl21b), Mfge8, and Serpin B9 (Spi6) are expressed at a level that is in the top 5% of gene expression for all genes in the ES cell genome.

In some embodiments of any of the foregoing aspects, the PD-L1 transgene encodes a protein having at least 85% identity (e.g., 85%, 90%, 95%, 96%, 97%, 98%, 99% sequence identity or more) to the amino acid sequence of SEQ ID NO: 11 or SEQ ID NO: 12.

In some embodiments of any of the foregoing aspects, the HLA-G or H2-M3 transgene encodes a protein having at least 85% identity (e.g., 85%, 90%, 95%, 96%, 97%, 98%, 99% sequence identity or more) to the amino acid sequence of SEQ ID NO: 16 or SEQ ID NO: 15.

In some embodiments of any of the foregoing aspects, the Cd47 transgene encodes a protein having at least 85% identity (e.g., 85%, 90%, 95%, 96%, 97%, 98%, 99% sequence identity or more) to the amino acid sequence of SEQ ID NO: 3 or SEQ ID NO: 4.

In some embodiments of any of the foregoing aspects, the CD200 transgene encodes a protein having at least 85% identity (e.g., 85%, 90%, 95%, 96%, 97%, 98%, 99% sequence identity or more) to the amino acid sequence of SEQ ID NO: 5 or SEQ ID NO: 6.

In some embodiments of any of the foregoing aspects, the FASLG or FasL transgene encodes a protein having at least 85% identity (e.g., 85%, 90%, 95%, 96%, 97%, 98%, 99% sequence identity or more) to the amino acid sequence of SEQ ID NO: 10 or SEQ ID NO: 9.

In some embodiments of any of the foregoing aspects, the Ccl21 or Ccl21b transgene encodes a protein having at least 85% identity (e.g., 85%, 90%, 95%, 96%, 97%, 98%, 99% sequence identity or more) to the amino acid sequence of SEQ ID NO: 2 or SEQ ID NO: 1.

In some embodiments of any of the foregoing aspects, the Mfge8 transgene encodes a protein having at least 85% identity (e.g., 85%, 90%, 95%, 96%, 97%, 98%, 99% sequence identity or more) to the amino acid sequence of SEQ ID NO: 13 or SEQ ID NO: 14.

In some embodiments of any of the foregoing aspects, the Serpin B9 or Spi6 transgene encodes a protein having at least 85% identity (e.g., 85%, 90%, 95%, 96%, 97%, 98%, 99% sequence identity or more) to the amino acid sequence of SEQ ID NO: 8 or SEQ ID NO: 7.

In some embodiments of any of the foregoing aspects, the IFNγR1 d39 transgene encodes a protein having at least 85% identity (e.g., 85%, 90%, 95%, 96%, 97%, 98%, 99% sequence identity or more) to the amino acid sequence of SEQ ID NO: 17.

In some embodiments of any of the foregoing aspects, the two or more transgenes (e.g., of the set of PD-L1, HLA-G or H2-M3, Cd47, Cd200, FASLG or FasL, Ccl21 or Ccl21b, Mfge8, and Serpin B9 or Spi6) are operably linked to a constitutive promoter.

In some embodiments of any of the foregoing aspects, the transgene encoding the polypeptide containing the antigen is operably linked to a constitutive promoter.

In some embodiments of any of the foregoing aspects, the constitutive promoter is selected from the group consisting of the CAG promoter, the cytomegalovirus (CMV) promoter, the EF1α promoter, the PGK promoter, adenovirus late promoter, vaccinia virus 7.5K promoter, SV40 promoter, tk promoter of HSV, mouse mammary tumor virus (MMTV) promoter, LTR promoter of HIV, promoter of moloney virus, Epstein barr virus (EBV) promoter, and the Rous sarcoma virus (RSV) promoter.

In some embodiments of any of the foregoing aspects, the polypeptide containing the antigen is expressed using an inducible expression system selected from the group consisting of a tetracycline response element, a light inducible system, a radiogenetic system, a cumate switch inducible system, an ecdysone inducible system, a destabilization domain system, or a ligand-reversible dimerization system.

In some embodiments of any of the foregoing aspects, the cell includes an EARC system, and wherein expression of the EARC system and the polypeptide containing the antigen is controlled by two different inducible expression systems.

In some embodiments of any of the foregoing aspects, the cells are administered intravenously, subcutaneously, intramuscularly, percutaneously, intradermally, parenterally, intraarterially, intravascularly, or by perfusion.

In some embodiments, the cells are administered as a tissue. In some embodiments, the tissue is administered with a gel, biocompatible matrix, or cellular scaffold.

In some embodiments of any of the foregoing aspects, the cells are administered in an amount of 25,000 to 5,000,000,000 cells (e.g., $2.5\times10^4$, $5\times10^4$, $7.5\times10^4$, $1\times10^5$, $2\times10^5$, $3\times10^5$, $4\times10^5$, $6\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, or $5\times10^9$ cells).

In some embodiments of any of the foregoing aspects, the cells are administered in an amount of 800,000,000 to 100,000,000,000 cells (e.g., $8\times10^8$, $9\times10^8$, $1\times10^9$, $2\times10^9$, or $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ cells).

In some embodiments of any of the foregoing aspects, the method further includes administering an additional therapeutic agent. In some embodiments, the additional therapeutic agent is administered after administration of the cells. In some embodiments, the additional therapeutic agent is administered concurrently with administration of the cells. In some embodiments, the additional therapeutic agent is an immunosuppressive agent, a disease-modifying anti-rheumatic drug (DMARD), a biologic response modifier (a type of DMARD), a corticosteroid, or a nonsteroidal anti-inflammatory medication (NSAID), prednisone, prednisolone, methylprednisolone, methotrexate, hydroxychloroquine, sulfasalazine, leflunomide, cyclophosphamide, azathioprine, tofacitinib, adalimumab, abatacept, anakinra, kineret, certolizumab, etanercept, golimumab, infliximab, rituximab or tocilizumab, 6-mercaptopurine, 6-thioguanine, abatacept, adalimumab, alemtuzumab, an aminosalicylate, an antibiotic, an anti-histamine, Anti-TNFα, azathioprine, belimumab, beta interferon, a calcineurin inhibitor, certolizumab, a corticosteroid, cromolyn, cyclosporin A, cyclosporine, dimethyl fumarate, etanercept, fingolimod, fumaric acid esters, glatiramer acetate, golimumab, hydroxyurea, IFNγ, IL-11, leflunomide, leukotriene receptor antagonist, long-acting beta2 agonist, mitoxantrone, mycophenolate mofetil, natalizumab, ocrelizumab, pimecrolimus, a probiotic, a retinoid, salicylic acid, short-acting beta2 agonist, sulfasalazine, tacrolimus, teriflunomide, theophylline, tocilizumab, ustekinumab, vedolizumab, interferon beta-1b, gliatrimer acetate, daclizumab, teriflunomide, fingolimod, dimethyl fumarate, alemtuzumab, mitoxantrone, ocrelizumab, natalizumab, an antiviral compound, a nucleoside-analog reverse transcriptase inhibitor (NRTI), a non-nucleoside reverse transcriptase inhibitor (NNRTI), a protease inhibitor, an antibacterial compound, an antifungal compound, an anti-parasitic compound, insulin, a sulfonylurea, a biguanide, a meglitinide, a thiazolidinedione, a DPP-4 inhibitor, an SGLT2 inhibitor, an alpha-glucosidase inhibitor, a bile acid sequestrant, aspirin, a dietary regimen, an immunosuppressive agent, a checkpoint inhibitor, a chemotherapeutic drug, a biologic drug, radiation therapy, cryotherapy, hyperthermia, surgical excision or tumor tissue, or an anti-cancer vaccine.

In some embodiments of any of the foregoing aspects, the subject is a mammal. In some embodiments, the mammal is a mouse. In some embodiments, the mammal is a human.

In some embodiments of any of the foregoing aspects, the cell includes two of the set of transgenes PD-L1, HLA-G (H2-M3), Cd47, Cd200, FASLG (FasL), Ccl21 (Ccl21b), Mfge8, and Serpin B9 (Spi6) (e.g., PD-L1 and HLA-G (H2-M3); PD-L1 and Cd47; PD-L1 and Cd200; PD-L1 and FASLG (FasL); PD-L1 and Ccl21 (Ccl21b); PD-L1 and Mfge8; PD-L1 and Serpin B9 (Spi6); HLA-G (H2-M3) and Cd47; HLA-G (H2-M3) and Cd200; HLA-G (H2-M3) and FASLG (FasL); HLA-G (H2-M3) and Ccl21 (Ccl21b); HLA-G (H2-M3) and Mfge8; HLA-G (H2-M3) and Serpin B9 (Spi6); Cd47 and Cd200; Cd47 and FASLG (FasL); Cd47 and Ccl21 (Ccl21b); Cd47 and Mfge8; Cd47 and Serpin B9 (Spi6); Cd200 and FASLG (FasL); Cd200 and Ccl21 (Ccl21b); Cd200 and Mfge8; Cd200 and Serpin B9 (Spi6); FASLG (FasL) and Ccl21 (Ccl21b); FASLG (FasL) and Mfge8; FASLG (FasL) and Serpin B9 (Spi6); Ccl21 (Ccl21b) and Mfge8; Ccl21 (Ccl21b) and Serpin B9 (Spi6); or Mfge8 and Serpin B9 (Spi6)).

In some embodiments of any of the foregoing aspects, the cell includes three of the set of transgenes PD-L1, HLA-G (H2-M3), Cd47, Cd200, FASLG (FasL), Ccl21 (Ccl21b), Mfge8, and Serpin B9 (Spi6) (e.g., PD-L1, HLA-G (H2-M3), and Cd47; PD-L1, HLA-G (H2-M3), and Cd200; PD-L1, HLA-G (H2-M3), and FASLG (FasL); PD-L1, HLA-G (H2-M3), and Ccl21 (Ccl21b); PD-L1, HLA-G (H2-M3), and Mfge8; PD-L1, HLA-G (H2-M3), and Serpin B9 (Spi6); PD-L1, Cd47, and Cd200; PD-L1, Cd47, and FASLG (FasL); PD-L1, Cd47, and Ccl21 (Ccl21b); PD-L1, Cd47, and Mfge8; PD-L1, Cd47, and Serpin B9; PD-L1, Cd200, and FASLG (FasL); PD-L1, Cd200, and Ccl21 (Ccl21b); PD-L1, Cd200, and Mfge8; PD-L1, Cd200, and Serpin B9 (Spi6); PD-L1, FASLG (FasL), and Ccl21 (Ccl21b); PD-L1, FASLG (FasL), and Mfge8; PD-L1, FASLG (FasL), and Serpin B9 (Spi6); PD-L1, Ccl21 (Ccl21b), and Mfge8; PD-L1, Ccl21 (Ccl21b), and Serpin B9 (Spi6); PD-L1, Mfge8, and Serpin B9 (Spi6); HLA-G (H2-M3), Cd47, and Cd200; HLA-G (H2-M3), Cd47, and FASLG (FasL); HLA-G (H2-M3), Cd47, and Ccl21 (Ccl21b); HLA-G (H2-M3), Cd47, and Mfge8; HLA-G (H2-M3), Cd47, and Serpin B9; HLA-G (H2-M3), Cd200, and FASLG (FasL); HLA-G (H2-M3), Cd200, and Ccl21 (Ccl21b); HLA-G (H2-M3), Cd200, and Mfge8; HLA-G (H2-M3), Cd200, and Serpin B9; HLA-G (H2-M3), FASLG (FasL), and Ccl21 (Ccl21b); HLA-G (H2-M3), FASLG (FasL), and Mfge8; HLA-G (H2-M3), FASLG (FasL), and Serpin B9 (Spi6); HLA-G (H2-M3), Ccl21 (Ccl21b), and Mfge8; HLA-G (H2-M3), Ccl21 (Ccl21b), and Serpin B9 (Spi6); HLA-G (H2-M3), Mfge8, and Serpin B9 (Spi6); Cd47, Cd200, and FASLG (FasL); Cd47, Cd200, and Ccl21 (Ccl21b); Cd47, Cd200, and Mfge8; Cd47, Cd200, and Serpin B9 (Spi6); Cd47, FASLG (FasL), and Ccl21 (Ccl21b); Cd47, FASLG (FasL), and Mfge8; Cd47, FASLG (FasL), and Serpin B9 (Spi6); Cd47, Ccl21 (Ccl21b), and Mfge8; Cd47, Ccl21 (Ccl21b), and Serpin B9 (Spi6); Cd47, Mfge8, and Serpin B9 (Spi6); Cd200, FASLG (FasL), and Ccl21 (Ccl21b); Cd200, FASLG (FasL), and Mfge8; Cd200, FASLG (FasL), and Serpin B9 (Spi6); Cd200, Ccl21 (Ccl21b), and Mfge8; Cd200, Ccl21 (Ccl21b), and Serpin B9 (Spi6); Cd200, Mfge8, and Serpin B9 (Spi6); FASLG (FasL), Ccl21 (Ccl21b), and Mfge8; FASLG (FasL), Ccl21 (Ccl21b), and Serpin B9 (Spi6); Ccl21 (Ccl21b), Mfge8, and Serpin B9 (Spi6)).

In some embodiments of any of the foregoing aspects, the cell includes four of the set of transgenes PD-L1, HLA-G (H2-M3), Cd47, Cd200, FASLG (FasL), Ccl21 (Ccl21b), Mfge8, and Serpin B9 (Spi6) (e.g., PD-L1, HLA-G (H2-M3), Cd47, and Cd200; PD-L1, HLA-G (H2-M3), Cd47, and FASLG (FasL); PD-L1, HLA-G (H2-M3), Cd47, and Ccl21 (Ccl21b); PD-L1, HLA-G (H2-M3), Cd47, and Mfge8; PD-L1, HLA-G (H2-M3), Cd47, and Serpin B9 (Spi6); PD-L1, HLA-G (H2-M3), Cd200, and FASLG (FasL); PD-L1, HLA-G (H2-M3), Cd200, and Ccl21 (Ccl21b); PD-L1, HLA-G (H2-M3), Cd200, and Mfge8; PD-L1, HLA-G (H2-M3), Cd200, and Serpin B9 (Spi6); PD-L1, HLA-G (H2-M3), FASLG (FasL), and Ccl21 (Ccl21b); PD-L1, HLA-G (H2-M3), FASLG (FasL), and Mfge8; PD-L1, HLA-G (H2-M3), FASLG (FasL), and Serpin B9 (Spi6); PD-L1, HLA-G (H2-M3), Ccl21(Ccl21b), and Mfge8; PD-L1, HLA-G (H2-M3), Ccl21(Ccl21b), and Serpin B9 (Spi6); PD-L1, HLA-G (H2-M3), Mfge8, and Serpin B9 (Spi6); PD-L1, Cd47, Cd200, and FASLG (FasL); PD-L1, Cd47, Cd200, and Ccl21 (Ccl21b); PD-L1, Cd47, Cd200, and Mfge8; PD-L1, Cd47, Cd200, and Serpin B9 (Spi6); PD-L1, Cd47, FASLG (FasL), and Ccl21 (Ccl21b); PD-L1, Cd47, FASLG (FasL), and Mfge8; PD-L1, Cd47, FASLG (FasL), and Serpin B9 (Spi6); PD-L1, Cd47, Ccl21 (Ccl21b), and Mfge8; PD-L1, Cd47, Ccl21 (Ccl21b), and Serpin B9 (Spi6); PD-L1, Cd47, Mfge8, and Serpin B9 (Spi6); PD-L1, Cd200, FASLG (FasL), and Ccl21 (Ccl21b); PD-L1, Cd200, FASLG (FasL), and Mfge8; PD-L1, Cd200, FASLG (FasL), and Serpin B9 (Spi6); PD-L1, Cd200, Ccl21 (Ccl21b), and Mfge8; PD-L1, Cd200, Ccl21 (Ccl21b), and Serpin B9 (Spi6); PD-L1, Cd200, Mfge8, and Serpin B9 (Spi6); PD-L1, FASLG (FasL), Ccl21 (Ccl21b), and Mfge8; PD-L1, FASLG (FasL), Ccl21 (Ccl21b), and Serpin B9 (Spi6); PD-L1, FASLG (FasL), Mfge8, and Serpin B9 (Spi6); PD-L1, Ccl21 (Ccl21b), Mfge8, and Serpin B9 (Spi6); HLA-G (H2-M3), Cd47, Cd200, and FASLG (FasL); HLA-G (H2-M3), Cd47, Cd200, and Ccl21 (Ccl21b); HLA-G (H2-M3), Cd47, Cd200, and Mfge8; HLA-G (H2-M3), Cd47, Cd200, and Serpin B9 (Spi6); HLA-G (H2-M3), Cd47, FASLG (FasL), and Ccl21 (Ccl21b); HLA-G (H2-M3), Cd47, FASLG (FasL), and Mfge8; HLA-G (H2-M3), Cd47, FASLG (FasL), and Serpin B9 (Spi6); HLA-G (H2-M3), Cd47, Ccl21 (Ccl21b), and Mfge8; HLA-G (H2-M3), Cd47, Ccl21 (Ccl21b), and Serpin B9 (Spi6); HLA-G (H2-M3), Cd47, Mfge8, and Serpin B9 (Spi6); HLA-G (H2-M3), Cd200, FASLG (FasL), and Ccl21 (Ccl21b); HLA-G (H2-M3), Cd200, FASLG (FasL), and Mfge8; HLA-G (H2-M3), Cd200, FASLG (FasL), and Serpin B9 (Spi6); HLA-G (H2-M3), Cd200, Ccl21 (Ccl21b), and Mfge8; HLA-G (H2-M3), Cd200, Ccl21 (Ccl21b), and Serpin B9 (Spi6); HLA-G (H2-M3), Cd200, Mfge8, and Serpin B9 (Spi6); HLA-G (H2-M3), FASLG (FasL), Ccl21 (Ccl21b), and Mfge8; HLA-G (H2-M3), FASLG (FasL), Ccl21 (Ccl21b), and Serpin B9 (Spi6); HLA-G (H2-M3), FASLG (FasL), Mfge8, and Serpin B9 (Spi6); HLA-G (H2-M3), Ccl21 (Ccl21b), Mfge8, and Serpin B9 (Spi6); Cd47, Cd200, FASLG (FasL), and Ccl21 (Ccl21b); Cd47, Cd200, FASLG (FasL), and Mfge8; Cd47, Cd200, FASLG (FasL), and Serpin B9 (Spi6); Cd47, Cd200, Ccl21 (Ccl21b), and Mfge8; Cd47, Cd200, Ccl21 (Ccl21b), and Serpin B9 (Spi6); Cd47, Cd200, Mfge8, and Serpin B9 (Spi6); Cd47, FASLG (FasL), Ccl21 (Ccl21b), and Mfge8; Cd47, FASLG (FasL), Ccl21 (Ccl21b), and Serpin B9 (Spi6); Cd47, Ccl21 (Ccl21b), Mfge8, and Serpin B9 (Spi6); Cd200, FASLG (FasL), Ccl21 (Ccl21b), and Mfge8; Cd200, FASLG (FasL), Ccl21 (Ccl21b), and Serpin B9 (Spi6); Cd200, Ccl21 (Ccl21b), Mfge8, and Serpin B9 (Spi6); or FASLG (FasL), Ccl21 (Ccl21b), Mfge8, and Serpin B9 (Spi6)).

In some embodiments of any of the foregoing aspects, the cell includes five of the set of transgenes PD-L1, HLA-G (H2-M3), Cd47, Cd200, FASLG (FasL), Ccl21 (Ccl21b), Mfge8, and Serpin B9 (Spi6) (e.g., PD-L1, HLA-G (H2-M3), Cd47, Cd200, and FASLG (FasL); PD-L1, HLA-G (H2-M3), Cd47, Cd200, and Ccl21 (Ccl21b); PD-L1, HLA-G (H2-M3), Cd47, Cd200, and Mfge8; PD-L1, HLA-G (H2-M3), Cd47, Cd200, and Serpin B9 (Spi6); PD-L1, HLA-G (H2-M3), Cd47, FASLG (FasL), and Ccl21 (Ccl21b); PD-L1, HLA-G (H2-M3), Cd47, FASLG (FasL), and Mfge8; PD-L1, HLA-G (H2-M3), Cd47, FASLG (FasL), and Serpin B9 (Spi6); PD-L1, HLA-G (H2-M3), Cd47, Ccl21 (Ccl21b), and Mfge8; PD-L1, HLA-G (H2-M3), Cd47, Ccl21 (Ccl21b), and Serpin B9 (Spi6); PD-L1, HLA-G (H2-M3), Cd47, Mfge8, and Serpin B9 (Spi6); PD-L1, HLA-G (H2-M3), Cd200, FASLG (FasL), and Ccl21 (Ccl21b); PD-L1, HLA-G (H2-M3), Cd200, FASLG (FasL), and Mfge8, PD-L1, HLA-G (H2-M3), Cd200, FASLG (FasL), and Serpin B9 (Spi6); PD-L1, HLA-G (H2-M3), Cd200, Ccl21 (Ccl21b), and Mfge8; PD-L1, HLA-G (H2-M3), Cd200, Ccl21 (Ccl21b), and Serpin B9 (Spi6); PD-L1, HLA-G (H2-M3), Cd200, Mfge8, and Serpin B9 (Spi6); PD-L1, HLA-G (H2-M3), FASLG (FasL), Ccl21 (Ccl21b), and Mfge8; PD-L1, HLA-G (H2-M3), FASLG (FasL), Ccl21 (Ccl21b), and Serpin B9 (Spi6); PD-L1, HLA-G (H2-M3), FASLG (FasL), Mfge8, and Serpin B9 (Spi6); PD-L1, HLA-G (H2-M3), Ccl21 (Ccl21b), Mfge8, and Serpin B9 (Spi6); PD-L1, Cd47, Cd200, FASLG (FasL), and Ccl21 (Ccl21b); PD-L1, Cd47, Cd200, FASLG (FasL), and Mfge8, PD-L1, Cd47, Cd200, FASLG (FasL), and Serpin B9 (Spi6); PD-L1, Cd47, Cd200, Ccl21 (Ccl21b), and Mfge8; PD-L1, Cd47, Cd200, Ccl21 (Ccl21b), and Serpin B9 (Spi6); PD-L1, Cd47, Cd200, Mfge8, and Serpin B9 (Spi6); PD-L1, Cd47, FASLG (FasL), Ccl21 (Ccl21b), and Mfge8; PD-L1, Cd47, FASLG (FasL), Ccl21 (Ccl21b), and Serpin B9 (Spi6); PD-L1, Cd47, FASLG (FasL), Mfge8, and Serpin B9 (Spi6); PD-L1, Cd47, Ccl21 (Ccl21b), Mfge8, and Serpin B9 (Spi6); PD-L1, Cd200, FASLG (FasL), Ccl21 (Ccl21b), and Mfge8; PD-L1, Cd200, FASLG (FasL), Ccl21 (Ccl21b), and Serpin B9 (Spi6); PD-L1, Cd200, FASLG (FasL), Mfge8, and Serpin B9 (Spi6); PD-L1, Cd200, Ccl21 (Ccl21b), Mfge8, and Serpin B9 (Spi6); PD-L1, FASLG (FasL), Ccl21 (Ccl21b), Mfge8, and Serpin B9 (Spi6); HLA-G (H2-M3), Cd47, Cd200, FASLG (FasL), and Ccl21 (Ccl21b); HLA-G (H2-M3), Cd47, Cd200, FASLG (FasL), and Mfge8; HLA-G (H2-M3), Cd47, Cd200, FASLG (FasL), and Serpin B9 (Spi6); HLA-G (H2-M3), Cd47, Cd200, Ccl21 (Ccl21b), and Mfge8; HLA-G (H2-M3), Cd47, Cd200, Ccl21 (Ccl21b), and Serpin B9 (Spi6); HLA-G (H2-M3), Cd47, Cd200, Mfge8, and Serpin B9 (Spi6); HLA-G (H2-M3), Cd47, FASLG (FasL), Ccl21 (Ccl21b), and Mfge8; HLA-G (H2-M3), Cd47, FASLG (FasL), Ccl21 (Ccl21b), and Serpin B9 (Spi6); HLA-G (H2-M3), Cd47, FASLG (FasL), Mfge8, and Serpin B9 (Spi6); HLA-G (H2-M3), Cd47, Ccl21 (Ccl21b), Mfge8, and Serpin B9 (Spi6); HLA-G (H2-M3), Cd200, FASLG (FasL), Ccl21 (Ccl21b), and Mfge8; HLA-G (H2-M3), Cd200, FASLG (FasL), Ccl21 (Ccl21b), and Serpin B9 (Spi6); HLA-G (H2-M3), Cd200, FASLG (FasL), Mfge8, and Serpin B9 (Spi6); HLA-G (H2-M3), Cd200, Ccl21 (Ccl21b), Mfge8, and Serpin B9 (Spi6); HLA-G (H2-M3), FASLG (FasL), Ccl21 (Ccl21b), Mfge8, and Serpin B9 (Spi6); Cd47, Cd200, FASLG (FasL), Ccl21 (Ccl21b), and Mfge8; Cd47, Cd200, FASLG (FasL), Ccl21 (Ccl21b), and Serpin B9 (Spi6); Cd47, Cd200, FASLG (FasL), Mfge8, and Serpin B9 (Spi6); Cd47, Cd200, Ccl21 (Ccl21b), Mfge8, and Serpin B9 (Spi6); Cd47, FASLG (FasL), Ccl21 (Ccl21b), Mfge8, and Serpin B9 (Spi6); or Cd200, FASLG (FasL), Ccl21 (Ccl21b), Mfge8, and Serpin B9 (Spi6)).

In some embodiments of any of the foregoing aspects, the cell includes six of the set of transgenes PD-L1, HLA-G (H2-M3), Cd47, Cd200, FASLG (FasL), Ccl21 (Ccl21b), Mfge8, and Serpin B9 (Spi6) (e.g., PD-L1, HLA-G (H2-M3), Cd47, Cd200, FASLG (FasL), and Ccl21 (Ccl21b); PD-L1, HLA-G (H2-M3), Cd47, Cd200, FASLG (FasL), and Mfge8; PD-L1, HLA-G (H2-M3), Cd47, Cd200, FASLG (FasL), and Serpin B9 (Spi6); PD-L1, HLA-G (H2-M3), Cd47, Cd200, Ccl21 (Ccl21b), and Mfge8; PD-L1, HLA-G (H2-M3), Cd47, Cd200, Ccl21 (Ccl21b), and Serpin B9 (Spi6); PD-L1, HLA-G (H2-M3), Cd47, Cd200, Mfge8, and Serpin B9 (Spi6); PD-L1, HLA-G (H2-M3), Cd47, FASLG (FasL), Ccl21 (Ccl21b), and Mfge8; PD-L1, HLA-G (H2-M3), Cd47, FASLG (FasL), Ccl21 (Ccl21b), and Serpin B9 (Spi6); PD-L1, HLA-G (H2-M3), Cd47, FASLG (FasL), Mfge8, and Serpin B9 (Spi6); PD-L1, HLA-G (H2-M3), Cd200, FASLG (FasL), Ccl21 (Ccl21b), and Mfge8; PD-L1, HLA-G (H2-M3), Cd200, FASLG (FasL), Ccl21 (Ccl21b), and Serpin B9 (Spi6); PD-L1, HLA-G (H2-M3), Cd200, FASLG (FasL), Mfge8, and Serpin B9 (Spi6); PD-L1, HLA-G (H2-M3), Cd200, Ccl21 (Ccl21b), Mfge8, and Serpin B9 (Spi6); PD-L1, Cd47, Cd200, FASLG (FasL), Ccl21 (Ccl21b), and Mfge8; PD-L1, Cd47, Cd200, FASLG (FasL), Ccl21 (Ccl21b), and Serpin B9 (Spi6); PD-L1, Cd47, Cd200, FASLG (FasL), Mfge8, and Serpin B9 (Spi6); PD-L1, Cd47, Cd200, Ccl21 (Ccl21b), Mfge8, and Serpin B9 (Spi6); PD-L1, Cd47, FASLG (FasL), Ccl21 (Ccl21b), Mfge8, and Serpin B9 (Spi6); PD-L1, Cd200, FASLG (FasL), Ccl21 (Ccl21b), Mfge8, and Serpin B9 (Spi6); HLA-G (H2-M3), Cd47, Cd200, FASLG (FasL), Ccl21 (Ccl21b), and Mfge8; HLA-G (H2-M3), Cd47, Cd200, FASLG (FasL), Ccl21 (Ccl21b), and Serpin B9 (Spi6); HLA-G (H2-M3), Cd47, Cd200, FASLG (FasL), Mfge8, and Serpin B9 (Spi6); HLA-G (H2-M3), Cd47, Cd200, Ccl21 (Ccl21b), Mfge8, and Serpin B9 (Spi6); HLA-G (H2-M3), Cd47, FASLG (FasL), Ccl21 (Ccl21b), Mfge8, and Serpin B9 (Spi6); HLA-G (H2-M3), Cd200, FASLG (FasL), Ccl21 (Ccl21b), Mfge8, and Serpin B9 (Spi6); or Cd47, Cd200, FASLG (FasL), Ccl21 (Ccl21b), Mfge8, and Serpin B9 (Spi6)).

In some embodiments of any of the foregoing aspects, the cell includes seven of the set of transgenes PD-L1, HLA-G (H2-M3), Cd47, Cd200, FASLG (FasL), Ccl21 (Ccl21b), Mfge8, and Serpin B9 (Spi6) (e.g., PD-L1, HLA-G (H2-M3), Cd47, Cd200, FASLG (FasL), Ccl21 (Ccl21b), and Mfge8; PD-L1, HLA-G (H2-M3), Cd47, Cd200, FASLG (FasL), Ccl21 (Ccl21b), and Serpin B9 (Spi6); PD-L1, HLA-G (H2-M3), Cd47, Cd200, FASLG (FasL), Mfge8, and Serpin B9 (Spi6); PD-L1, HLA-G (H2-M3), Cd47, Cd200, Ccl21 (Ccl21b), Mfge8, and Serpin B9 (Spi6); PD-L1, HLA-G (H2-M3), Cd47, FASLG (FasL), Ccl21 (Ccl21b), Mfge8, and Serpin B9 (Spi6); PD-L1, HLA-G (H2-M3), Cd200, FASLG (FasL), Ccl21 (Ccl21b), Mfge8, and Serpin B9 (Spi6); PD-L1, Cd47, Cd200, FASLG (FasL), Ccl21 (Ccl21b), Mfge8, and Serpin B9 (Spi6); or HLA-G (H2-M3), Cd47, Cd200, FASLG (FasL), Ccl21 (Ccl21b), Mfge8, and Serpin B9 (Spi6)).

In some embodiments of any of the foregoing aspects, the cell includes all eight of the set of transgenes PD-L1, HLA-G (H2-M3), Cd47, Cd200, FASLG (FasL), Ccl21 (Ccl21b), Mfge8, and Serpin B9 (Spi6).

In some embodiments of any of the foregoing aspects, the cell includes one or more (e.g., one, two, three, four, five, six, or all seven) of the set of transgenes HLA-G (H2-M3), Cd47, Cd200, FASLG (FasL), Ccl21 (Ccl21b), Mfge8, and Serpin B9 (Spi6).

In some embodiments of any of the foregoing aspects, the cell includes one or more (e.g., one, two, three, four, five, six, or all seven) of the set of transgenes PD-L1, HLA-G (H2-M3), Cd47, Cd200, Ccl21 (Ccl21b), Mfge8, and Serpin B9 (Spi6).

In some embodiments of any of the foregoing aspects, the cell includes one or more (e.g., one, two, three, four, five, or all six) of the set of transgenes HLA-G (H2-M3), Cd47, Cd200, Ccl21 (Ccl21b), Mfge8, and Serpin B9 (Spi6).

In some embodiments of any of the foregoing aspects, the cell is not modified to express PD-L1.

In some embodiments of any of the foregoing aspects, the cell is not modified to express FasL.

In some embodiments of any of the foregoing aspects, the cell is not modified to express TGF-β. In some embodiments of any of the foregoing aspects, the cell is not modified to express CTLA4 or CLTA4-Ig. In some embodiments of any of the foregoing aspects, the cell is not modified to express IDO. In some embodiments of any of the foregoing aspects, the cell is not modified to express IL-35. In some embodiments of any of the foregoing aspects, the cell is not modified to express IL-10. In some embodiments of any of the foregoing aspects, the cell is not modified to express VEGF. In some embodiments of any of the foregoing aspects, the cell is not modified to express an NFκb decoy receptor. In some embodiments of any of the foregoing aspects, the cell is not modified to express soluble TNFR. In some embodiments of any of the foregoing aspects, the cell is not modified to express CCR7. In some embodiments of any of the foregoing aspects, the cell is not modified to express SOCS1. In some embodiments of any of the foregoing aspects, the cell is not modified to express HLA-E. In some embodiments of any of the foregoing aspects, the cell is not modified to express siRNA directed to IL-12.

In another aspect, the invention features a population of cells described herein.

In another aspect, the invention features composition including a cell described herein.

In another aspect, the invention features a composition including a population of cells described herein.

In some embodiments of any of the foregoing aspects, the composition further includes a pharmaceutically acceptable excipient.

In another aspect, the invention features a kit containing a cell described herein or a composition described herein.

Definitions

Unless defined otherwise, all technical and scientific terms used herein have the same meaning as commonly understood by one of ordinary skill in the art to which this disclosure belongs. Terms such as "a", "an," and "the" are not intended to refer to only a singular entity, but include plural referents unless context clearly indicates otherwise.

As used herein, the term "about" refers to a value that is no more than 10% above or below the value being described. For example, the term "about 5 nM" indicates a range of from 4.5 nM to 5.5 nM.

As used herein, the term "activated leukocyte" refers to the state of a leukocyte (e.g., a granulocyte, such as a neutrophil, eosinophil, or basophil; a monocyte, or a lymphocyte, such as a B or T cell) caused by response to a perceived insult. When leukocytes become activated, they can proliferate, secrete cytokines, differentiate, present antigens, become more polarized, become more phagocytic, and/or become more cytotoxic. Factors that stimulate immune cell activation include pro-inflammatory cytokines, pathogens, and non-self antigen presentation. Activated leukocytes can be isolated from lymphoid organs. Leukocytes, such as T cells, can also be activated in vitro using anti-CD3/CD28 beads or other methods employed by those of skill in the art (see, e.g., Frauwith and Thompson, *J. Clin Invest* 109:295-299 (2002); and Trickett and Kwan, *J Immunol Methods* 275:251-255 (2003)).

As used herein, "allogeneic" means cells, tissue, DNA, or factors taken or derived from a different subject of the same species.

As used herein, the term "alloantigen" refers to a non-self antigen from a member of the same species. Two major types of alloantigens are blood group antigens (e.g., Antigen A, Antigen B, or an Rh antigen) and histocompatibility antigens (e.g., human leukocyte antigens (HLA), such as class I antigens (e.g., HLA-A, HLA-B, and HLA-C) and class II antigens (e.g., HLA-DR, HLA-DQ, and HLA-DP)).

As used herein, the term "antigen" refers to a substance (e.g., a protein, peptide, or polysaccharide) that can bind to (e.g., can be bound by) Ag-specific receptors, antibodies, and/or T lymphocyte receptors. The term "antigen" is used herein to refer to a polypeptide or a portion of a polypeptide (e.g., a full-length protein) that can stimulate an immune response. The antigen can be produced in vivo by proteolytic processing of the polypeptide (e.g., fragments of 10-20 amino acids in length may be produced that may be recognized by the immune system). Antigens can be classified as self or non-self antigens based on their relationship to a subject.

As used herein, the term "autologous" refers to cells, tissue, DNA, or factors taken or derived from a subject that can be modified and used to treat the same subject.

As used herein, the term "immune tolerance" refers to the failure to mount an immune response (e.g., unresponsiveness) to an antigen that has the capacity to elicit an immune response in a subject.

As used herein, the term "stem cell" refers to a cell that can differentiate into one or more specialized cells and has the capacity for self-renewal. Stem cells include pluripotent stem cells (PSCs), such as embryonic stem cells (ESCs) and induced pluripotent stem cells (iPSCs), and multipotent stem cells, such as cord blood stem cells, mesenchymal stromal cells and adult stem cells, which are found in various tissues. The term "stem cell" also includes cells amenable for genome editing, cells that can serve as a source of a therapeutic cell type (e.g., cells that can be directed to differentiate into a lineage restricted or terminally differentiated cell that is used for cell therapy, or cells of a desired target tissue), and cells with "artificial" cell acquired stem cell properties (e.g., pluripotency or multipotency or self-renewal).

As used herein, the terms "embryonic stem cell" and "ES cell" refer to an embryo-derived totipotent or pluripotent stem cell, derived from the inner cell mass of a blastocyst that can be maintained in an in vitro culture under suitable conditions. ES cells are capable of differentiating into cells of any of the three vertebrate germ layers, e.g., the endoderm, the ectoderm, or the mesoderm. ES cells are also characterized by their ability propagate indefinitely under suitable in vitro culture conditions. See, for example, Thomson et al., Science 282:1145 (1998).

As used herein, the terms "induced pluripotent stem cell," "iPS cell," and "iPSC" refer to a pluripotent stem cell that can be derived directly from a differentiated somatic cell. Human iPS cells can be generated by introducing specific sets of reprogramming factors into a non-pluripotent cell that can include, for example, Oct3/4, Sox family transcription factors (e.g., Sox1, Sox2, Sox3, Sox15), Myc family transcription factors (e.g., c-Myc, 1-Myc, n-Myc), Kruppel-like family (KLF) transcription factors (e.g., KLF1, KLF2, KLF4, KLF5), and/or related transcription factors, such as NANOG, LIN28, and/or Glis1. Human iPS cells can also be generated, for example, by the use of miRNAs, small molecules that mimic the actions of transcription factors, or lineage specifiers. Human iPS cells are characterized by their ability to differentiate into any cell of the three vertebrate germ layers, e.g., the endoderm, the ectoderm, or the mesoderm. Human iPS cells are also characterized by their ability propagate indefinitely under suitable in vitro culture conditions. See, for example, Takahashi and Yamanaka, Cell 126:663 (2006).

As used herein, the term "mitigate antigen presenting cell activation and function" refers to a transgene that encodes a gene product whose function is to inhibit antigen presenting cell activation or the ability of an antigen presenting cell to promote the activation of graft attacking leukocytes (Fiorentino et al., *J Immunol.* 146:3444-51 (1991); Salio et al., *Eur J Immunol.* 29:3245-53 (1999)). In an embodiment, mitigation of antigen presenting cell activation and function refers to a decrease in APC activation and function of at least about 10%, 20%, 30%, 40%, 50%, 60%, 70%, 80%, 90%, 95% or 100%, relative to a control (e.g., as determined using an assay for antigen presenting cell activation, such as reduced proliferation, reduced secretion of pro-inflammatory cytokines (e.g., interleukin-1 (IL-1, e.g., IL-1β), IL-5, IL-6, IL-8, IL-10, IL-12, IL-13, IL-18, tumor necrosis factor (TNF, e.g., TNFα), interferon gamma (IFNγ), and granulocyte macrophage colony stimulating factor (GMCSF), which can be measured using an ELISA or Western Blot analysis of culture media or a patient sample, such as a blood sample), or reduced levels of cell surface markers (e.g., CD11c, CD11 b, HLA molecules (e.g., MHC-II), CD40, B7, IL-2, CD80 or CD86, which can be assessed using flow cytometry, immunohistochemistry, in situ hybridization, and other assays that allow for measurement of cell surface markers)). Antigen presenting cells include dendritic cells, B cells, and macrophages. Mast cells and neutrophils can also be induced to present antigens. Methods for determining mitigation of antigen presenting cell activation and function are known in the art. Examples of gene products that mitigate antigen presenting cell activation and function include, but are not limited to: Ccl21 (Ccl21b) and PD-L1. Such transgenes may be referred herein to "cloaking" or "cloaked" genes.

As used herein, the term "mitigate graft attacking leukocyte activity or cytolytic function" refers to a transgene that encodes a gene product whose function is to inhibit or prevent graft attacking leukocyte activity or cytolytic function near allograft cells (MacDonald et al., *J Immunol.* 126:1671-5 (1981); Bongrand et al., *Eur J Immunol.* 13:424-9 (1983); MacDonald et al., *Eur J Immunol.* 9:466-70 (1979)). In an embodiment, mitigation of graft attacking leukocyte activity or cytolytic function refers to a decrease in leukocyte activity or cytolytic function of at least about 10%, 20%, 30%, 40%, 50%, 60%, 70%, 80%, 90%, 95% or 100%, relative to a control (e.g., as determined using an assay for leukocyte activation, such as reduced proliferation, reduced secretion of pro-inflammatory cytokines (e.g., interleukin-1 (IL-1, e.g., IL-1β), IL-5, IL-6, IL-8, IL-10, IL-12, IL-13, IL-18, tumor necrosis factor (TNF, e.g., TNFα), interferon gamma (IFNγ), and granulocyte macrophage colony stimulating factor (GMCSF), which can be measured using an ELISA or Western Blot analysis of culture media or a patient sample, such as a blood sample), or reduced polarization (e.g., a reduction in the level of IL-12, TNF, IL-1p, IL-6, IL-23, MARCO, MHC-II, CD86, iNOS, CXCL9, and CXCL10 in a macrophage or monocyte, or a reduction in the level of a Th1-specific marker (e.g., T-bet, IL-12R, STAT4), a chemokine receptor (e.g., CCR5, CXCR6, or CXCR3); or a Th2-specific marker: (e.g., CCR3, CXCR4, STATE, GATA3, or IL-4Rα) in a T cell, which can be assessed using flow cytometry, immunohistochemistry, situ hybridization, qPCR, or western blot analysis for cell surface markers or intracellular proteins, and ELISA or western blot analysis for secreted proteins); or as determined using an assay for cytolytic function (e.g., by incubating leukocytes with a target cell line that has been pre-coated with antibodies to a surface antigen expressed by the target cell line and measuring the number of surviving target cells with a fluorescent viability stain, or by measuring the secretion of cytolytic granules (e.g., perforin, granzymes, or other cytolytic proteins released from immune cells) from the leukocytes). Methods for determining mitigation of graft attacking leukocyte activity or cytolytic function are known in the art. Examples of gene products that mitigate graft attacking leukocyte activity or cytolytic function include, but are not limited to: PD-L1, HLA-G (H2-M3), Cd39, Cd73, and Lag3. Such transgenes may be referred herein to "cloaking" or "cloaked" genes.

As used herein, the term "mitigate macrophage cytolytic function and phagocytosis of allograft cells" refers to a transgene that encodes a gene product whose function is to inhibit or prevent macrophage cytolytic function and/or phagocytosis of allograft cells (Fish et al., Toxicology. 19:127-38. (1981); Sung et al., *J Biol Chem.* 260:546-54 (1985); Amash et al., *J Immunol.* 196:3331-40 (2016)). In an embodiment, mitigation of macrophage cytolytic function and phagocytosis of allograft cells refers to a decrease in macrophage cytolytic function and/or phagocytosis of allograft cells of at least about 10%, 20%, 30%, 40%, 50%, 60%, 70%, 80%, 90%, 95% or 100%, relative to a control (e.g., as determined using an assay for macrophage cytolytic function (e.g., by incubating macrophages with a target cell line that has been pre-coated with antibodies to a surface antigen expressed by the target cell line and measuring the number of surviving target cells with a fluorescent viability stain, or by measuring the secretion of cytolytic granules (e.g., perforin, granzymes, or other cytolytic proteins released from immune cells) released from the macrophages; or as determined using an assay for macrophage phagocytosis (e.g., culturing macrophages with fluorescent beads or a target cell line that has been pre-coated with antibodies to a surface antigen expressed by the target cell line and measuring fluorescence inside the immune cell or quantifying the number of beads or cells engulfed)). Methods for determining mitigation of macrophage cytolytic function and phagocytosis of allograft cells are known in the art. Examples of gene products that mitigate macrophage cytolytic function include, but are not limited to: Cd47, Cd200, Mfge8, and Il1r2. Such transgenes may be referred herein to "cloaking" or "cloaked" genes.

As used herein, the term "induce apoptosis in graft attacking leukocytes" refers to a transgene that encodes a gene product whose function is to kill graft attacking leukocytes near allograft cells (Huang et al., *Proc Natl Acad Sci USA.* 96:14871-6 (1999); Suzuki et al., *Proc Natl Acad Sci USA.* 97:1707-12 (2000); Simon et al., *Proc Natl Acad Sci USA.* 98:5158-63 (2001)). In an embodiment, induction of apoptosis in graft attacking leukocytes refers to an increase in apoptosis in graft attacking leukocytes of at least about 10%, 20%, 30%, 40%, 50%, 60%, 70%, 80%, 90%, 95% or 100%, relative to a control (e.g., as determined using an assay for apoptosis, such as TUNEL staining, caspase staining, or Annexin-V staining, or use of fluorescent viability stains). Methods for determining induction of apoptosis in graft attacking leukocytes are known in the art. Examples of gene products that can induce apoptosis in graft attacking leukocytes include, but are not limited to: FASLG (FasL) and Tnfsf10. Such transgenes may be referred herein to "cloaking" or "cloaked" genes.

As used herein, the term "mitigate local inflammatory proteins" refers to a transgene that encodes a gene product whose function is to inhibit the activity of local proteins, where the function of said proteins is to promote graft attacking leukocyte accumulation, and/or their cytolytic function (Felix et al., *Nat Rev Immunol.* 17:112-29 (2017)). In an embodiment, mitigation of local inflammatory proteins refers to a reduction in local inflammatory proteins of at least about 10%, 20%, 30%, 40%, 50%, 60%, 70%, 80%, 90%, 95% or 100%, relative to a control (e.g., as determined using an assay for inflammatory proteins that promote leukocyte activation or migration to a site of inflammation (e.g., a chemokine, such as CCL2, CCL3, CCLS, CXCL1, CXCL2, and CXCL8, or a pro-inflammatory cytokine, such as IL-1β, IL-5, IL-6, IL-8, IL-10, IL-12, IL-13, IL-18, TNFα, IFNγ, or GMCSF, which can be measured using an ELISA, Western blot analysis, or other techniques known in the art for measuring secreted proteins)). Methods for determining mitigation of local inflammatory proteins are known in the art. Examples of gene products that mitigate local inflammatory proteins include, but are not limited to: PD-L1, Il1r2, and Ackr2. Such transgenes may be referred herein to "cloaking" or "cloaked" genes.

As used herein, the term "protect against leukocyte-mediated apoptosis" refers to a transgene that encodes a gene product whose function is to inhibit any cell component that may induce apoptosis or cytolysis of an allograft cell (Abdullah et al., *J Immunol.* 178:3390-9 (2007)). In an embodiment, protection against leukocyte-mediated apoptosis refers to a decrease in leukocyte-mediated apoptosis of at least about 10%, 20%, 30%, 40%, 50%, 60%, 70%, 80%, 90%, 95% or 100%, relative to a control (e.g., as determined using an assay for leukocyte-mediated apoptosis (e.g., by incubating leukocytes with a target cell line that has been pre-coated with antibodies to a surface antigen expressed by the target cell line and measuring the number of surviving target cells with a fluorescent viability stain, or by measuring the secretion of cytolytic granules (e.g., perforin, granzymes, or other cytolytic proteins released from immune cells) released from the leukocyte). Methods for determining protection against leukocyte-mediated apoptosis are known in the art. Examples of gene products that protect against leukocyte-mediated apoptosis include, but are not limited to: Serpin B9 (Spi6) and Dad1. Such transgenes may be referred herein to "cloaking" or "cloaked" genes.

As used herein, the term "activation" refers to the response of an immune cell to a perceived insult. When immune cells become activated, they proliferate, secrete pro-inflammatory cytokines, differentiate, present antigens, become more polarized, and become more phagocytic and cytotoxic. Factors that stimulate immune cell activation include pro-inflammatory cytokines, pathogens, and non-self antigen presentation (e.g., antigens from pathogens presented by dendritic cells, macrophages, or B cells).

As used herein, the term "antigen presentation" refers to a process in which fragments of antigens are displayed on the cell surface of immune cells. Antigens are presented to T cells and B cells to stimulate an immune response. Antigen presenting cells include dendritic cells, B cells, and macrophages. Mast cells and neutrophils can also be induced to present antigens.

As used herein, the term "cytokine" refers to a small protein involved in cell signaling. Cytokines can be produced and secreted by immune cells, such as T cells, B cells, macrophages, and mast cells, and include chemokines, interferons, interleukins, lymphokines, and tumor necrosis factors.

As used herein, the term "cytokine production" refers to the expression, synthesis, and secretion (e.g., release) of cytokines by an immune cell.

As used herein, the term "cytotoxicity" refers to the ability of immune cells to kill other cells. Immune cells with cytotoxic functions release toxic proteins (e.g., perforin and granzymes) capable of killing nearby cells. Natural killer cells and cytotoxic T cells (e.g., CD8+ T cells) are the primary cytotoxic effector cells of the immune system, although dendritic cells, neutrophils, eosinophils, mast cells, basophils, macrophages, and monocytes have been shown to have cytotoxic activity.

As used herein, the term "degranulation" refers to a cellular process in which molecules, including antimicrobial and cytotoxic molecules, are released from intracellular secretory vesicles called granules. Degranulation is part of the immune response to pathogens and invading microorganisms by immune cells such as granulocytes (e.g., neutrophils, basophils, and eosinophils), mast cells, and lymphocytes (e.g., natural killer cells and cytotoxic T cells). The molecules released during degranulation vary by cell type and can include molecules designed to kill the invading pathogens and microorganisms or to promote an immune response, such as inflammation.

As used herein, the term "phagocytosis" refers to the process in which a cell engulfs or ingests material, such as other cells or parts of cells (e.g., bacteria), particles, or dead or dying cells. A cell that is capable of performing this function is called a phagocyte. Immune phagocytes include neutrophils, monocytes, macrophages, mast cells, B cells, eosinophils, and dendritic cells.

As used herein, the term "polarization" refers to the ability of an immune cell to shift between different functional states. A cell that is moving toward one of two functional extremes is said to be in the process of becoming more polarized. The term polarization is often used to refer to macrophages, which can shift between states known as M1 and M2. M1, or classically activated, macrophages secrete pro-inflammatory cytokines (e.g., IL-12, TNF, IL-6, IL-8, IL-1B, MCP-1, and CCL2), are highly phagocytic, and respond to pathogens and other environmental insults. M1 macrophages can also be detected by expression of Nos2. M2, or alternatively activated, macrophages secrete a different set of cytokines (e.g., IL-10) and are less phagocytic. M2 macrophages can detected by expression of Arg1, IDO, PF4, CCL24, IL10, and IL4Rα. Cells become polarized in response to external cues such as cytokines, pathogens, injury, and other signals in the tissue microenvironment.

As used herein, the term "pro-inflammatory cytokine" refers to a cytokine secreted from immune cells that promotes inflammation. Immune cells that produce and secrete pro-inflammatory cytokines include T cells (e.g., Th cells) macrophages, B cells, and mast cells. Pro-inflammatory cytokines include interleukin-1 (IL-1, e.g., IL-1β), IL-5, IL-6, IL-8, IL-10, IL-12, IL-13, IL-18, tumor necrosis factor (TNF, e.g., TNFα), interferon gamma (IFNγ), and granulocyte macrophage colony stimulating factor (GMCSF).

As used herein, the term "biologic" refers to a designed polypeptide and corresponding encoding DNA, which can be expressed as a transgene. The polypeptide may agonize or inhibit the function of an endogenous gene or inhibit or activate a biological process. Methods for determining whether a polypeptide has agonist or antagonist activity or function are generally known in the art. In an embodiment, the agonist function is at least about 10%, 20%, 30%, 40%, 50%, 60%, 70%, 80%, 90, 95% or 100% of the function, relative to the function of a control. In an embodiment, the antagonist function is at least about 10%, 20%, 30%, 40%, 50%, 60%, 70%, 80%, 90, 95% or 100% of the function, relative to the function of a control.

As used herein, the term "operably linked" refers to a first molecule joined to a second molecule, wherein the molecules are so arranged that the first molecule affects the function or expression of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. Additionally, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

As used herein, the term "promoter" refers to a recognition site on DNA that is bound by an RNA polymerase. The polymerase drives transcription of the transgene.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction X/Y)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

As used herein, the term "pharmaceutical composition" refers to a mixture containing a therapeutic agent, optionally in combination with one or more pharmaceutically acceptable excipients, diluents, and/or carriers, to be administered to a subject, such as a mammal, e.g., a human, in order to prevent, treat or control a particular disease or condition affecting or that may affect the subject.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and/or other problem complications commensurate with a reasonable benefit/risk ratio.

As used herein, the term "wild-type" refers to a genotype with the highest frequency for a particular gene in a given organism.

The terms "cell division locus", "cell division loci", and "CDL" as used herein, refer to a genomic locus (or loci) whose transcription product(s) is required to maintain cell viability (which means that loss of such a gene leads to cell death) or cell proliferative ability (which means that loss of such a gene impairs or prevents cell proliferation). The gene can be expressed by dividing cells (e.g., cells actively undergoing cell division), cells capable of cell division (e.g., cells that are not currently undergoing cell division but that are capable of proliferating), and/or by non-diving cells (e.g., post-mitotic cells such as neurons). When a CDL comprises a single locus, absence of CDL expression in a cell (or its derivatives) means that tumor initiation and/or formation is prohibited either because the cell(s) will be ablated (e.g., killed) in the absence of CDL expression (e.g., the CDL is required for cell viability, which means that cells die in the absence of CDL expression) or because proliferation of the cell(s) will be blocked or compromised in the absence of CDL expression (e.g., the CDL is required for cell proliferation, which means that cells fail to proliferate in the absence of CDL expression). When a CDL comprises multiple loci, absence of expression by all or subsets of the loci in a cell (or its derivatives) means that tumor initiation and/or formation is prohibited either because the cell(s) will be ablated in the absence of CDL expression or because proliferation of the cell(s) will be blocked or compromised in the absence of CDL expression. A CDL may or may not be expressed in non-dividing and/or non-proliferating cells. A CDL may be endogenous to a host cell or it may be a transgene. If a CDL is a transgene, it may be from the same or different species as a host cell or it may be of synthetic origin. In an embodiment, a CDL is a single locus that is transcribed during cell division. For example, in an embodiment, a single locus CDL is CDK1. In an embodiment, a CDL comprises two or more loci that are transcribed during cell division. For example, in an embodiment, a multi-locus CDL comprises two MYC genes (c-Myc and N-myc) (Scognamiglio et al., 2016). In an embodiment, a multi-locus CDL comprises AURORA B and C kinases, which may have overlapping functions (Fernandez-Miranda et al., 2011). Cell division and cell proliferation are terms that may be used interchangeably herein.

The terms "normal rate of cell division", "normal cell division rate", "normal rate of cell proliferation", and "normal cell proliferation rate" as used herein, refer to a rate of cell division and/or proliferation that is typical of a non-cancerous healthy cell. A normal rate of cell division and/or proliferation may be specific to cell type. For example, it is widely accepted that the number of cells in the epidermis, intestine, lung, blood, bone marrow, thymus, testis, uterus and mammary gland is maintained by a high rate of cell division and a high rate of cell death. In contrast, the number of cells in the pancreas, kidney, cornea, prostate, bone, heart and brain is maintained by a low rate of cell division and a low rate of cell death (Pellettieri and Sanchez Alvarado, 2007).

The terms "inducible negative effector of proliferation" and "iNEP" as used herein, refer to a genetic modification that facilitates use of CDL expression to control cell division and/or proliferation by: i) inducibly stopping or blocking CDL expression, thereby prohibiting cell division and proliferation; ii) inducibly ablating at least a portion of CDL-expressing cells (i.e., killing at least a portion of proliferating cells); or iii) inducibly slowing the rate of cell division relative to a cell's normal cell division rate, such that the rate of cell division would not be fast enough to contribute to tumor formation.

The terms "ablation link" and "ALINK" as used herein, refer to an example of an iNEP, which comprises a transcriptional link between a CDL and a sequence encoding a negative selectable marker (e.g., a modification of a coding or non-coding region of the CDL such that the negative selectable marker is co-expressed with the gene product of the CDL). The ALINK modification allows a user to inducibly kill proliferating host cells containing the ALINK or inhibit the host cell's proliferation by killing at least a portion of proliferating cells by exposing the ALINK-modified cells to an inducer of the negative selectable marker. For example, a cell modified to comprise an ALINK at a CDL may be treated with an inducer (e.g., a prodrug) of the negative selectable marker in order to ablate proliferating cells or to inhibit cell proliferation by killing at least a portion of proliferating cells.

The terms "exogenous activator of regulation of CDL" and "EARC" as used herein, refer to an example of an iNEP, which comprises a mechanism or system that facilitates exogenous alteration of non-coding or coding DNA transcription or corresponding translation via an activator. An EARC modification allows a user to inducibly stop or inhibit division of cells containing the EARC by removing from the EARC-modified cells an inducer that permits transcription and/or translation of the EARC-modified CDL. For example, an inducible activator-based gene expression system may be operably linked to a CDL and used to exogenously control expression of a CDL or CDL translation, such that the presence of a drug inducible activator and corresponding inducer drug are required for CDL transcription and/or translation. In the absence of the inducer drug, cell division and/or proliferation would be stopped or inhibited (e.g., slowed to a normal cell division rate). For example, the CDL Cdk1/CDK1 may be modified to comprise a dox-bridge, such that expression of Cdk1/CDK1 and cell division and proliferation are only possible in the presence of an inducer (e.g., doxycycline).

The term "proliferation antagonist system" as used herein, refers to a natural or engineered compound(s) whose presence inhibits (completely or partially) proliferation of a cell.

The term "dox-bridge" as used herein, refers to a mechanism for separating activity of a promoter from a target transcribed region by expressing rtTA (Gossen et al., 1995) by the endogenous or exogenous promoter and rendering the transcription of target region under the control of TRE. As used herein, "rtTA" refers to the reverse tetracycline transactivator elements of the tetracycline inducible system (Gossen et al., 1995) and "TRE" refers to a promoter consisting of TetO operator sequences upstream of a minimal promoter. Upon binding of rtTA to the TRE promoter in the presence of doxycycline, transcription of loci downstream of the TRE promoter increases. The rtTA sequence may be inserted in the same transcriptional unit as the CDL or in a different location of the genome, so long as the transcriptional expression's permissive or non-permissive status of the target region is controlled by doxycycline. A dox-bridge is an example of an EARC.

As used herein, the term "fail-safe cell" refers to a cell that contains one or more homozygous, heterozygous, hemizygous or compound heterozygous ALINKs or EARCs in one or more CDLs (e.g., at least two, three, four, or five CDLs). Fail-safe cells may contain either ALINKs or EARCs or both ALINK and EARC modifications (e.g., ALINK and EARC modifications in different CDLs or in a single CDL).

As used herein, the term "fail-safe" refers to a property of a cell that is unlikely to exhibit uncontrolled (e.g., tumorigenic) proliferation. A cell can be considered "fail safe" when cell proliferation is under the control of a negative regulator or inducer, and the possibility of the cell losing the activity of the system that controls proliferation due to genetic mutation is low. The fail-safe volume will depend on the number of ALINKs and the number of ALINK-targeted CDLs (e.g., a cell with homozygous modifications of two different CDLs has a higher fail safe volume (e.g., it is less likely to lose all systems that control proliferation through genetic mutation) than a cell with a heterozygous modification of a single CDL). The fail-safe property is further described in Table 3.

DESCRIPTION OF THE DRAWINGS

FIG. 1A shows a C3H mouse that received an initial subcutaneous injection of allogenic C57BL/6 cloaked embryonic stem cells (ESCs) (boxes near the flanks, "B"), and, approximately two months later, received a subcutaneous injection of uncloaked allogeneic cells of the same type as the cloaked cells (boxes near the shoulders, "A"). The uncloaked cells were not rejected by the immune system of the mouse, indicating that the cloaked cells induced immune tolerance (FIG. 1A). FIGS. 1B and 1C show H&E staining of the teratomas formed by both the cloaked (FIG. 1C) and uncloaked (FIG. 1B) allogeneic cells showing that the teratomas are well differentiated tissues with no sign of excessive lymphocyte infiltration or necrosis.

DETAILED DESCRIPTION OF THE DISCLOSURE

Figure 1B:
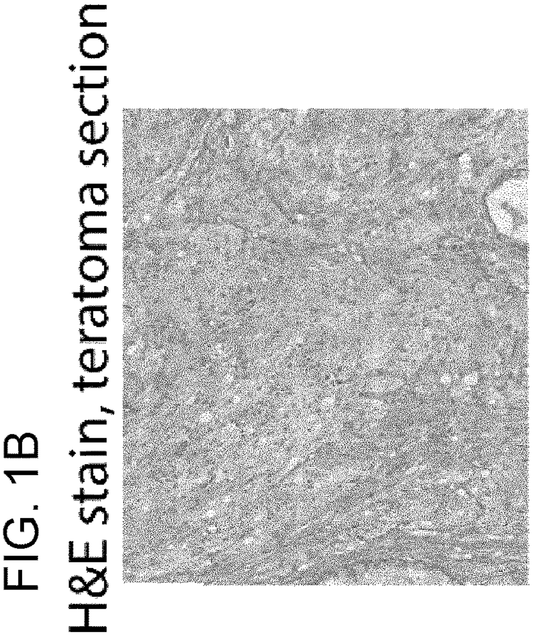
FIGS. 1A-1C are images showing that administration of cloaked allogeneic cells induces immune tolerance to the cells.

Described herein are compositions and methods for modulating the immune system to produce an antigen-specific immune response in a subject (e.g., a human subject). The invention features cells that express one or more cloaking transgenes in addition to a polypeptide containing a donor alloantigen, and methods of using such cells to induce immune tolerance to the donor alloantigen in a subject prior to transplantation of an organ or tissue from the donor into the subject. The invention also features cells that express one or more cloaking transgenes in addition to a polypeptide containing an endogenous or "self" antigen, which can be used to induce tolerance to the antigen in a subject with an autoimmune disease or condition (e.g., a subject whose immune system aberrantly mounts an immune response against the antigen). Finally, the invention features a method of using cloaked cells (e.g., cells that express one or more cloaking transgenes) to induce the production of antibodies against an antigen (e.g., a disease-related antigen) in a subject (e.g., a human subject). The methods and compositions described herein provide targeted, longer lasting, and lower risk therapeutic approaches compared to the current standard of care.

Cloaked Cells for Antigen-Specific Modulation of the Immune System

Self versus non-self discrimination is a feature of a properly functioning immune system, as the immune system must detect and mount an immune response against non-self or foreign antigens from viruses, bacteria, and other pathogens, while recognizing and not responding to endogenous "self" antigens. The adaptive immune system responds to foreign antigens by producing antibodies, which promotes long lasting immunity and a rapid response to the same antigen should the immune system encounter it again. The ability to detect and mount an immune response against foreign antigens is a characteristic of the immune system. Yet, this function can pose a challenge for cell-based therapies and transplantation, as the immune system may attack any foreign cell or tissue that contains non-self proteins, including intentionally transplanted cells, tissues, and organs. Therefore, cell-based therapies and transplantation are often accompanied by administration of immunosuppressive medications that limit the immune system from mounting an immune response. Unfortunately, administration of immunosuppressive medications carries a number of risks.

The present invention is based, in part, on the discovery that one can suppress the immune response to a non-self cell by modifying the cell to express one or more cloaking transgenes, which encode proteins that inhibit or negatively regulate an immune response (e.g., a response of macrophages, T cells, NK cells, or other antigen presenting cells), or induce cell death of an immune cell (e.g., a T cell or macrophage). The cloaking transgenes are listed below in Table 1, and cells that express one or more (e.g., one, two, three, four, five, six, seven, or all eight) of PD-L1, H2-M3, Cd47, Cd200, FasL, Ccl21b, Mfge8, and Spi6 are referred to herein as cloaked cells.

In addition to suppressing the immune response of a subject to the cloaked cell, the present inventors have also discovered that administration of a cell modified to express one or more cloaking transgenes (e.g., one, two, three, four, five, six, seven, or all eight of PD-L1, H2-M3, Cd47, Cd200, FasL, Ccl21b, Mfge8, and Spi6) induces immune tolerance to an uncloaked cell of the same type (e.g., the same type of cell from the same source that is not modified to express any of the cloaking transgenes). These findings indicate that the immune system of a subject treated with a cloaked cell learns to treat all of the proteins expressed by the cloaked cell as "self" proteins. In view of this discovery, cells can be modified to express one or more cloaking transgenes (e.g., cloaked) and one or more polypeptides containing one or more antigens, and then administered to a subject to induce immune tolerance to the one or more antigens. In other embodiments, the ability to induce immune tolerance to a cloaked cell can be harnessed to promote an immune response to (e.g., produce antibodies directed against) a specific antigen. The cloaking transgenes used in the compositions and methods described herein are characterized in more detail below and in International Patent Application No. PCT/CA2018/050706, which is incorporated herein by reference in its entirety.

TABLE 1

Genes that can be expressed to promote immune tolerance

| Gene | Function |
|---|---|
| PD-L1 | Induces cell death in PD-L1 expressing T cells and macrophages |
| HLA-G (mouse gene: H2-M3) | Inhibits NK cells from attacking cells lacking MHC molecules |
| Cd47 | Negative regulator of macrophages and killer T cells |
| Cd200 | Inhibits macrophage activation |
| FASLG (mouse gene: FasL) | Induces apoptosis in Fas expressing CD8 + T cells |
| Clc21 (mouse gene: Ccl21b) | Chemo-attractant for antigen presenting cells (APCs) |
| Mfge8 | Inhibition of macrophage phagocytosis |
| Serpin B9 (mouse gene: Spi6) | Inhibition of granzyme/perforin attack |
| Dad1 | Negative regulator of programmed cell death |
| Tnfrsf10 | Induces apoptosis in leukocytes expressing the TRAIL receptor |
| Cd39 | Converts ATP to AMP, inhibits T-cells |
| Cd73 | Converts AMP to adenosine, inhibits T-cells, suppresses dendritic cells |

TABLE 1-continued

| Genes that can be expressed to promote immune tolerance | |
|---|---|
| Gene | Function |
| Lag3 | Inhibits T-cell activation, proliferation, function |
| Il1r2 | Blocks IL-1B activity, blocks inflammation and innate cell activation |
| Ackr2 | Decoy receptor for chemokines, prevents leukocyte accumulation |
| Tnfrsf22 | Decoy receptor, blocks TRAIL-induced apoptosis from T-cells |
| Tnfrsf23 | Decoy receptor, blocks TRAIL-induced apoptosis from T-cells |
| IFNγR1 d39 | Dominant negative interferon gamma receptor 1, prevents IFNγ-mediated upregulation of MHCs in ES cells |

C-C motif chemokine ligand 21(Ccl21) is expressed by local lymph nodes where it acts to attract activated antigen presenting cells (APCs). This key function offers an opportunity to "reverse" the migration of APCs by overexpressing this gene on grafted cells. Indeed, some melanomas express Ccl21 and recruit $CCR7^+$ cells that, in turn, can reorganize portions of their tumor stroma as "self". This leads to a stromal reconstruction that directs the recruitment and maintenance of $Cd4^+$ Tregs (Zindl et al., Science. 328:697-8 (2010)). In fact, the expression of Ccl21 on tumors can protect co-implanted Ccl21 deficient tumor cells from rejection in a syngeneic allograft setting (Shields et al., Science. 328:749-52(2010)). Ccl21b is the mouse ortholog of human Ccl21.

The amino acid sequences of mouse and human Ccl21 are:

```
Mouse Ccl21
                                              (SEQ ID NO: 1)
MAQMMTLSLLSLVLALCIPWTQGSDGGGQDCCLKYSQKKIPYSIVRGYRK

QEPSLGCPIPAILFLPRKHSKPELCANPEEGWVQNLMRRLDQPPAPGKQS

PGCRKNRGTSKSGKKGKGSKGCKRTEQTQPSRG

Human Ccl21
                                              (SEQ ID NO: 2)
MAQSLALSLLILVLAFGIPRTQGSDGGAQDCCLKYSQRKIPAKVVRSYRK

QEPSLGCSIPAILFLPRKRSQAELCADPKELWVQQLMQHLDKTPSPQKPA

QGCRKDRGASKTGKKGKGSKGCKRTERSQTPKGP
```

Expression of Cd47 in umbilical cord blood can promote the development of hyporesponsive T-cells (Avice et al., *J Immunol.* 167:2459-68 (2001)). Erythrocytes also up-regulate Cd47 to avoid dendritic cell activation due to their lack of "self" presentation (van den Berg et al., *Immunity.* 43:622-4 (2015)). More recently, it was shown that expression of human Cd47 increases engraftment in a mouse model of pig-to-human hematopoietic cell transplantation (Tena et al., *Am J Transplant.* 14:2713-22 (2014)).

The amino acid sequences of mouse and human Cd47 are:

```
Mouse Cd47
                                              (SEQ ID NO: 3)
MWPLAAALLLGSCCCGSAQLLFSNVNSIEFTSCNETVVIPCIVRNVEAQS

TEEMFVKWKLNKSYIFIYDGNKNSTTTDQNFTSAKISVSDLINGIASLKM

DKRDAMVGNYTCEVTELSREGKTVIELKNRTVSWFSPNEKILIVIFPILA

ILLFWGKFGILTLKYKSSHTNKRIILLLVAGLVLTVIVVVGAILLIPGEK
```

-continued

```
PVKNASGLGLIVISTGILILLQYNVFMTAFGMTSFTIAILITQVLGYVLA

LVGLCLCIMACEPVHGPLLISGLGIIALAELLGLVYMKFVASNQRTIQPP

RNR

Human Cd47
                                              (SEQ ID NO: 4)
MWPLVAALLLGSACCGSAQLLFNKTKSVEFTFCNDTVVIPCFVTNMEAQN

TTEVYVKWKFKGRDIYTFDGALNKSTVPTDFSSAKIEVSQLLKGDASLKM

DKSDAVSHTGNYTCEVTELTREGETIIELKYRVVSWFSPNENILIVIFPI

FAILLFWGQFGIKTLKYRSGGMDEKTIALLVAGLVITVIVIVGAILFVPG

EYSLKNATGLGLIVTSTGILILLHYYVFSTAIGLTSFVIAILVIQVIAYI

LAVVGLSLCIAACIPMHGPLLISGLSILALAQLLGLVYMKFVASNQKTIQ

PPRKAVEEPLNAFKESKGMMNDE
```

Cd200 is also as an important immunoregulatory molecule; increased expression can reduce the severity of allograft rejection, autoimmunity, and allergic disease (Gorczynski et al., *J Immunol.* 172:7744-9 (2004)). It has been shown that, in vitro, APC expression of Cd200 suppresses production of interferon gamma (IFN-γ) and cytolytic granules by activated Cd8+ T-cells (Misstear et al., *J Virol.* 86:6246-57 (2012)). Most interestingly, overexpression of Cd200 increases the survival of skin and cardiac allografts in mice by promoting of Foxp3+ Treg cells (Gorczynski et al., *Transplantation.* 98:1271-8 (2014)).

The amino acid sequences of mouse and human Cd200 are:

```
Mouse Cd200
                                              (SEQ ID NO: 5)
MGSLVFRRPFCHLSTYSLIWGMAAVALSTAQVEVVTQDERKALHTTASLR

CSLKTSQEPLIVTWQKKKAVSPENMVTYSKTHGVVIQPAYKDRINVTELG

LWNSSITFWNTTLEDEGCYMCLFNTFGSQKVSGTACLTLYVQPIVHLHYN

YFEDHLNITCSATARPAPAISWKGTGTGIENSTESHFHSNGTTSVTSILR

VKDPKTQVGKEVICQVLYLGNVIDYKQSLDKGFWFSVPLLLSIVSLVILL

VLISILLYWKRHRNQERGESSQGMQRMK

Human Cd200
                                              (SEQ ID NO: 6)
MERLVIRMPFSHLSTYSLVWVMAAVVLCTAQVQVVTQDEREQLYTPASLK

CSLQNAQEALIVTWQKKKAVSPENMVTFSENHGVVIQPAYKDKINITQLG

LQNSTITFWNITLEDEGCYMCLFNTFGFGKISGTACLTVYVQPIVSLHYK

FSEDHLNITCSATARPAPMVFWKVPRSGIENSTVTLSHPNGTTSVTSILH
```

-continued

```
IKDPKNQVGKEVICQVLHLGTVTDFKQTVNKGYWFSVPLLLSIVSLVILL

VLISILLYWKRHRNQDRGELSQGVQKMT
```

Spi6 is an endogenous inhibitor of the cytotoxic effector molecule granzyme B released by activated Cd8+ T-cells (Sun et al., *J Biol Chem.* 272:15434-41 (1997)). Some data shows that Mesenchymal Stem Cells (MSCs) escape immune rejection by upregulating this molecule (El Haddad et al., *Blood.* 117:1176-83 (2011)). It has also recently been demonstrated that the ability of dendritic cells to present antigen to cytotoxic T cells without themselves being killed through contact mediated cytotoxicity is mediated by Spi6 (Lovo et al., *J Immunol.* 188:1057-63 (2012)). Spi6 is also known as Serpin B9.

The amino acid sequences of mouse Spi6 and the human counterpart, Serpin B9, are:

```
Mouse Spi6
                                          (SEQ ID NO: 7)
MNTLSEGNGTFAIHLLKMLCQSNPSKNVCYSPASISSALAMVLLGAKGQT

AVQISQALGLNKEEGIHQGFQLLLRKLNKPDRKYSLRVANRLFADKTCEV

LQTFKESSLHFYDSEMEQLSFAEEAEVSRQHINTWVSKQTEGKIPELLSG

GSVDSETRLVLINALYFKGKWHQPFNKEYTMDMPFKINKDEKRPVQMMCR

EDTYNLAYVKEVQAQVLVMPYEGMELSLVVLLPDEGVDLSKVENNLTFEK

LTAWMEADFMKSTDVEVFLPKFKLQEDYDMESLFQRLGVVDVFQEDKADL

SGMSPERNLCVSKFVHQSVVEINEEGTEAAAASAIIEFCCASSVPTFCAD

HPFLFFIRHNKANSILFCGRFSSP

Human Serpin B9
                                          (SEQ ID NO: 8)
METLSNASGTFAIRLLKILCQDNPSHNVFCSPVSISSALAMVLLGAKGNT

ATQMAQALSLNTEEDIHRAFQSLLTEVNKAGTQYLLRTANRLFGEKTCQF

LSTFKESCLQFYHAELKELSFIRAAEESRKHINTWVSKKTEGKIEELLPG

SSIDAETRLVLVNAIYFKGKWNEPFDETYTREMPFKINQEEQRPVQMMYQ

EATFKLAHVGEVRAQLLELPYARKELSLLVLLPDDGVELSTVEKSLTFEK

LTAWTKPDCMKSTEVEVLLPKFKLQEDYDMESVLRHLGIVDAFQQGKADL

SAMSAERDLCLSKFVHKSFVEVNEEGTEAAAASSCFVVAECCMESGPRFC

ADHPFLFFIRHNRANSILFCGRFSSP
```

Activated, cytotoxic, Cd8+ can kill target cells by expression of FasL, which binds to the FAS receptor and activates a caspase-mediated apoptosis in targeted cells. However, many tumors have developed a "counterattack" by upregulating FasL on their surface (Chen et al., *J Immunol.* 171: 1183-91 (2003)). Selective expression of FasL in the vasculature of human and mouse solid tumors has been associated with scarce Cd8+ T-cell infiltration and a predominance of FoxP3+ Treg cells (Motz et al. *Nat Med.* 20:607-15 (2014)). Most recently, it was shown that B-lymphocytes also use the expression of FasL to kill T helper cells at the effector stage of immune responses (Lundy et al., *Front Immunol.* 6:122 (2015)). FasL is the mouse ortholog of human FASLG.

The amino acid sequences of mouse FasL and the human counterpart, FASLG, are:

```
Mouse FasL
                                          (SEQ ID NO: 9)
MQQPMNYPCPQIFWVDSSATSSWTPPGSVFPCPSSGPRGPDQRRPPPPPP

PVSPLPPPSQPLPLPPLTPLKKKDHNTNLWLPVVFFMVLVALVGMGLGMY

QLFHLQKELAELREFTNQSLKVSSFEKQIANPSTPSEKKELRSVAHLTGN

PHSRSIPLEWEDTYGTALISGVKYKKGSLVINEAGLYFVYSKVYFRGQSC

NNQPLNHKVYMRNSKYPGDLVLMEEKRLNYCTTGQIWAHSSYLGAVFNLT

SADHLYVNISQLSLINFEESKTFFGLYKL

Human FASLG
                                          (SEQ ID NO: 10)
MQQPFNYPYPQIYWVDSSASSPWAPPGTVLPCPTSVPRRPGQRRPPPPPP

PPPLPPPPPPPPLPPLPLPPLKKRGNHSTGLCLLVMFFMVLVALVGLGLG

MFQLFHLQKELAELRESTSQMHTASSLEKQIGHPSPPPEKKELRKVAHLT

GKSNSRSMPLEWEDTYGIVLLSGVKYKKGGLVINETGLYFVYSKVYFRGQ

SCNNLPLSHKVYMRNSKYPQDLVMMEGKMMSYCTTGQMWARSSYLGAVFN

LTSADHLYVNVSELSLVNFEESQTFFGLYKL
```

PD-L1 is a critical immune modulatory molecule that binds to Programmed Cell Death 1 (PD-1). PD-1 is expressed on T-cells, and binding to PD-L1 results in T-cell anergy (MacDonald et al., *J Immunol.* 126:1671-5 (1981)).

The amino acid sequences of mouse and human PD-L1 are:

```
Mouse PD-L1
                                          (SEQ ID NO: 11)
MRIFAGIIFTACCHLLRAFTITAPKDLYVVEYGSNVTMECRFPVERELDL

LALVVYWEKEDEQVIQFVAGEEDLKPQHSNFRGRASLPKDQLLKGNAALQ

ITDVKLQDAGVYCCIISYGGADYKRITLKVNAPYRKINQRISVDPATSEH

ELICQAEGYPEAEVIWTNSDHQPVSGKRSVTTSRTEGMLLNVTSSLRVNA

TANDVFYCTFWRSQPGQNHTAELIIPELPATHPPQNRTHWVLLGSILLFL

IVVSTVLLFLRKQVRMLDVEKCGVEDTSSKNRNDTQFEET

Human PDL1 (CD274)
                                          (SEQ ID NO: 12)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET
```

Inflammatory environments, like those induced by allograft transplants, attracts macrophages and inflammatory monocytes, among many other innate immune cells. The milk fat globule epidermal growth factor-8 (Mfge-8) is expressed by many murine tumors (Neutzner et al., *Cancer Res.* 67:6777-85 (2007)) and has been shown to contribute to local immune suppression by polarizing incoming monocytes to suppressive, M2-like macrophages (Soki et al., *J Biol Chem.* 289:24560-72 (2014)).

The amino acid sequences of mouse and human MFGE-8 are:

Mouse MFGE8

(SEQ ID NO: 13)
MQVSRVLAALCGMLLCASGLFAASGDFCDSSLCLNGGTCLTGQDNDIYCL
CPEGFTGLVCNETERGPCSPNPCYNDAKCLVTLDTQRGDIFTEYICQCPV
GYSGIHCETETNYYNLDGEYMFTTAVPNTAVPTPAPTPDLSNNLASRCST
QLGMEGGAIADSQISASSVYMGFMGLQRWGPELARLYRTGIVNAWTASNY
DSKPWIQVNLLRKMRVSGVMTQGASRAGRAEYLKTFKVAYSLDGRKFEFI
QDESGGDKEFLGNLDNNSLKVNMFNPTLEAQYIKLYPVSCHRGCTLRFEL
LGCELHGCSEPLGLKNNTIPDSQMSASSSYKTWNLRAFGWYPHLGRLDNQ
GKINAWTAQSNSAKEWLQVDLGTQRQVTGIITQGARDFGHIQYVASYKVA
HSDDGVQWTVYEEQGSSKVFQGNLDNNSHKKNIFEKPFMARYVRVLPVSW
HNRITLRLELLGC

Human MFGE8

(SEQ ID NO: 14)
MPRPRLLAALCGALLCAPSLLVALDICSKNPCHNGGLCEEISQEVRGDVF
PSYTCTCLKGYAGNHCETKCVEPLGMENGNIANSQIAASSVRVTFLGLQH
WVPELARLNRAGMVNAWTPSSNDDNPWIQVNLLRRMWVTGVVTQGASRLA
SHEYLKAFKVAYSLNGHEFDFIHDVNKKHKEFVGNWNKNAVHVNLFETPV
EAQYVRLYPTSCHTACTLRFELLGCELNGCANPLGLKNNSIPDKQITASS
SYKTWGLHLFSWNPSYARLDKQGNFNAWVAGSYGNDQWLQVDLGSSKEVT
GIITQGARNFGSVQFVASYKVAYSNDSANWTEYQDPRTGSSKIFPGNWDN
HSHKKNLFETPILARYVRILPVAWHNRIALRLELLGC

The potent killing potential of NK cells is also absolutely critical in graft rejection. NK cells can kill targets cells that lack MHC class I molecules, as well as other cells within an inflammatory setting. H2-M3, the murine homologue of human HLA-G has recently been shown to have a regulatory effect on NK cells, licensing them to ignore cells that lack "self molecules" (Andrews et al., *Nat Immunol.* 13:1171-7 (2012)). This is thought to be achieved by binding of HLA-G, immunosuppressive receptors on both NK and T-cells (Carosella et al., *Adv Immunol.* 127:33-144 (2015)). H2-M3 is the mouse ortholog of human HLA-G.

The amino acid sequences of mouse H2-M3 and the human counterpart, HLA-G, are:

Mouse H2-M3

(SEQ ID NO: 15)
SIEEIPRMEPRAPWMEKERPEYWKELKLKVKNIAQSARANLRTLLRYYNQ
SEGGSHILQWMVSCEVGPDMRLLGAHYQAAYDGSDYITLNEDLSSWTAVD
MVSQITKSRLESAGTAEYFRAYVEGECLELLHRFLRNGKEILQRADPPKA
HVAHHPRPKGDVTLRCWALGFYPADITLTWQKDEEDLTQDMELVETRPSG
DGTFQKWAAVVVPSGEEQRYTCYVHHEGLTEPLALKWGRSSQSSVVIMV

Human HLA-G (SEQ ID NO: 16)
MVVMAPRTLFLLLSGALTLTETWAGSHSMRYFSAAVSRPGRGEPRFIAMG
YVDDTQFVRFDSDSACPRMEPRAPWVEQEGPEYWEEETRNTKAHAQTDRM
NLQTLRGYYNQSEASSHTLQWMIGCDLGSDGRLLRGYEQYAYDGKDYLAL
NEDLRSWTAADTAAQISKRKCEAANVAEQRRAYLEGTCVEWLHRYLENGK -continued EMLQRADPPKTHVTHHPVFDYEATLRCWALGFYPAEIILTWQRDGEDQTQ
DVELVETRPAGDGTFQKWAAVVVPSGEEQRYTCHVQHEGLPEPLMLRWKQ
SSLPTIPIMGIVAGLVVLAAVVTGAAVAAVLWRKKSSD Each of the transgenes in the set of transgenes (e.g., PD-L1, H2-M3, Cd47, Cd200, FasL, Ccl21 b, Mfge8, and Spi6) encodes a gene product that is cytoplasmic, membrane bound, or local acting, whose function is one or more of mitigating antigen presenting cell activation and function; mitigating graft attacking leukocyte activity or cytolytic function; mitigating macrophage cytolytic function and phagocytosis of allograft cells; inducing apoptosis in graft attacking leukocytes; mitigating local inflammatory proteins; and protecting against leukocyte-mediated apoptosis. These cellular functions can serve to suppress the immune response to a cell expressing one or more e.g., one, two, three, four, five, six, seven, or all eight) of the transgenes.

A set of transgenes that includes one or more (e.g., one, two, three, four, five, six, seven, or all eight) of PD-L1, H2-M3, Cd47, Cd200, FasL, Ccl21b, Mfge8, and Spi6 can be expressed in cells. The cells may be, for example, stem cells or a cell that is amenable to genome editing, such as a cell that can be used for therapy and/or differentiated into a therapeutic cell type. The stem cells may be, for example, embryonic stem (ES) cells or induced pluripotent stem (iPS) cells. The cells may be allogeneic or autologous cells. The set of transgenes may comprise 1, 2, 3, 4, 5, 6, 7, or all 8 of these genes or may comprise at least 1, at least 2, at least 3, at least 4, at least 5, at least 6, or at least 7 of these genes. The cell may be further genetically modified to express one or more of TGF-β, Cd73, Cd39, Lag3, Il1r2, Ackr2, Tnfrsf22, Tnfrs23, Tnfrsf10, Dad1, and/or IFNγR1 d39. The TGF-β transgene may be modified to express the gene product in a membrane-bound form (i.e., such that the gene product is expressed on the surface of the cell), using methods known to those skilled in the art. For example, a method for localizing TGF-β to the membrane is to co-express TGF-β with an additional transgene encoding the LRRC32 protein or any other polypeptide that results in localization of TGF-β to the cell membrane. This protein anchors TGF-β to the membrane. (Tran D Q et al., Proc Natl Acad Sci U.S.A 106:13445-50 (2009)).

The amino acid sequence of IFNγR1 d39 is:

(SEQ ID NO: 17)
MGPQAAAGRMILLVVLMLSAKVGSGALTSTEDPEPPSVPVPTNVLIKSYN
LNPVVCWEYQNMSQTPIFTVQVKVYSGSWTDSCTNISDHCCNIYGQIMYP
DVSAWARVKAKVGQKESDYARSKEFLMCLKGKVGPPGLEIRRKKEEQLSV
LVFHPEVVVNGESQGTMFGDGSTCYTFDYTVYVEHNRSGEILHTKHTVEK
EECNETLCELNISVSTLDSRYCISVDGISSFWQVRTEKSKDVCIPPFHDD
RKDSIWILVVAPLTVFTVVILVFAYWYTKKNSFKRKSIMLPKSLLSVVKS
ATLETKPESKYSLVTPHQPAVLESETVICEEPLSTVTAPDSPEAAEQEEL
SKETKALEAGGSTSAMTPDSPPTPTQRRSFSLLSSNQSGPCSLTAYHSRN
GSDSGLVGSGSSISDLESLPNNNSETKMAEHDPPPVRKA

The genes may be human genes or murine genes. In an embodiment, the gene is of the same species as the recipient in which the cell is to be transplanted. In an embodiment, the gene is of any species in which the function of the gene is conserved or in which a designed biologic has the agonist function of the endogenous counterpart. Methods for introducing and expressing these transgenes in cells are described herein and are also known to those skilled in the art. Cells expressing these transgenes may be referred to as "cloaked" due to their ability to evade allorejection without systemic immunosuppression and without the need for immunosuppressive medication.

The cloaked cells can be further modified to express one or more polypeptides or portions thereof containing one or more antigens (e.g., a non-self antigen, a self-antigen, a food antigen, or an allergen antigen). In other embodiments, an uncloaked cell of the same type as the cloaked cell (e.g., a cell of the same type derived from the same source as the cloaked cell that is not modified to express any of the cloaking transgenes) can be modified to express a polypeptide or a portion of a polypeptide containing an antigen (e.g., a disease-associated antigen). The cells may also be modified to express an antigen itself if the immunogenic fragment of the polypeptide is known.

Before or after generating the cloaked cells of the disclosure, the cells can be modified to be FAILSAFE™ cells. FAILSAFE™ cells contain one or more cell division loci (CDLs) that control cell proliferation in animal cells. CDLs, as provided herein, may be loci whose transcription product(s) are expressed during cell division. CDLs may be genetically modified, as described herein, to comprise a negative selectable marker and/or an inducible activator-based gene expression system, which allows a user to permit, ablate, and/or inhibit proliferation of the genetically modified cell(s) by adding or removing an appropriate inducer. Methods for making and using FAILSAFE™ cells are described, for example, in WO 2016/141480, the entire teachings of which are incorporated herein by reference. A cell may be made FAILSAFE™ first and then cloaked afterwards. Alternatively, a cell may be cloaked first and then made FAILSAFE™ afterwards. In another embodiment, an uncloaked cell of the same type as the cloaked cell (e.g., a cell of the same type derived from the same source as the cloaked cell that is not modified to express any of the cloaking transgenes) that is modified to express a polypeptide or a portion of a polypeptide containing an antigen (e.g., a disease-associated antigen) can be made FAILSAFE™ (e.g., either before or after it is modified to express the disease-associated antigen).

The cell may be a vertebrate cell, for example, a mammalian cell, such as a human cell or a mouse cell. The cell may also be a vertebrate stem cell, for example, a mammalian stem cell, such as a human stem cell or a mouse stem cell. Preferably, the cell or stem cell is amenable to genetic modification. Preferably, the cell or stem cell is deemed by a user to have therapeutic value, meaning that the cell or stem cell may be used to treat a disease, disorder, defect or injury in a subject in need of treatment for same.

In some embodiments, the cell is a stem cell or progenitor cell (e.g., iPSC, embryonic stem cell, hematopoietic stem cell, mesenchymal stem cell, endothelial stem cell, epithelial stem cell, adipose stem or progenitor cells, germline stem cells, lung stem or progenitor cells, mammary stem cells, olfactory adult stem cells, hair follicle stem cells, multipotent stem cells, amniotic stem cells, cord blood stem cells, or neural stem or progenitor cells). In some embodiments, the stem cells are adult stem cells (e.g., somatic stem cells or tissue specific stem cells). In some embodiments, the stem or progenitor cell is capable of being differentiated (e.g., the stem cell is totipotent, pluripotent, or multipotent). In some embodiments, the cell is isolated from embryonic or neonatal tissue. In some embodiments, the cell is a fibroblast, monocytic precursor, B cell, exocrine cell, pancreatic progenitor, endocrine progenitor, hepatoblast, myoblast, preadipocyte, progenitor cell, hepatocyte, chondrocyte, smooth muscle cell, K562 human erythroid leukemia cell line, bone cell, synovial cell, tendon cell, ligament cell, meniscus cell, adipose cell, dendritic cell, neutrophil, basophil, mast cell, monocyte, innate lymphoid cell, or natural killer cell. In some embodiments, the cell is manipulated (e.g., converted or differentiated) into a muscle cell, erythroid-megakaryocytic cell, eosinophil, iPS cell, macrophage, T cell, islet beta-cell, neuron, cardiomyocyte, blood cell (e.g., red blood cell, white blood cell, or platelet), endocrine progenitor, exocrine progenitor, ductal cell, acinar cell, alpha cell, beta cell, delta cell, PP cell, hepatocyte, cholangiocyte, or brown adipocyte. In some embodiments, the cell is a muscle cell (e.g., skeletal, smooth, or cardiac muscle cell), erythroid-megakaryocytic cell, eosinophil, iPS cell, macrophage, T cell, islet beta-cell, neuron, cardiomyocyte, blood cell (e.g., red blood cell, white blood cell, or platelet), endocrine progenitor, exocrine progenitor, ductal cell, acinar cell, alpha cell, beta cell, delta cell, PP cell, hepatocyte, cholangiocyte, or white or brown adipocyte. In some embodiments, the cell is a hormone-secreting cell (e.g., a neuroendocrine cell, e.g., a cell that secretes insulin, oxytocin, endorphin, vasopressin, serotonin, somatostatin, gastrin, secretin, glucagon, thyroid hormone, bombesin, cholecystokinin, testosterone, estrogen, or progesterone, renin, ghrelin, amylin, or pancreatic polypeptide), an epidermal keratinocyte, an epithelial cell (e.g., an exocrine secretory epithelial cell, a thyroid epithelial cell, a keratinizing epithelial cell, a gall bladder epithelial cell, or a surface epithelial cell of the cornea, tongue, oral cavity, esophagus, anal canal, distal urethra, or vagina), a kidney cell, a germ cell, a skeletal joint synovium cell, a periosteum cell, a bone cell (e.g., osteoclast or osteoblast), a perichondrium cell (e.g., a chondroblast or chondrocyte), a cartilage cell (e.g., chondrocyte), a fibroblast, an endothelial cell, a pericardium cell, a meningeal cell, a keratinocyte precursor cell, a keratinocyte stem cell, a pericyte, a glial cell (e.g., oligodendrocyte, Schwann cell, astrocyte, or microglial cell), an ependymal cell, a cell isolated from an amniotic or placental membrane, or a serosal cell (e.g., a serosal cell lining body cavities). In some embodiments, the cell is a somatic cell. In some embodiments, the cells are derived from skin or other organs, e.g., heart, brain or spinal cord, liver, lung, kidney, pancreas, bladder, bone marrow, spleen, intestine, or stomach. The cells can be from humans or other mammals (e.g., rodent, non-human primate, bovine, or porcine cells). The cells can be from a cell line (e.g., a human cell line). The cells can be allogeneic or autologous cells. The cells may be syngeneic cells.

In some embodiments, the cloaked cells described herein survive in a host without stimulating the host immune response for one week or more (e.g., one week, two weeks, one month, two months, three months, 6 months, one year, two years, three years, four years, five years or more, e.g., for the life of the cell and/or its progeny). The cells maintain expression of the cloaking transgenes for as long as they survive in the host (e.g., if cloaking transgenes are no longer expressed, the cloaked cells may be removed by the host's immune system). In some embodiments, the cloaked cells further express a transgene encoding a protein that allows the cloaked cells to be detected in vivo (e.g., a fluorescent protein, such as GFP, or other detectable marker).

It is contemplated herein that the combination of cloaked and fail-safe cells may be of use in cell-based therapies wherein it may be desirable to induce antigen-specific immune tolerance or an antigen-specific immune response, while also being able to eliminate cells exhibiting undesirable growth rates, irrespective of whether such cells are generated before or after grafting the cells into a host. The combination of the cloaking and fail-safe technologies allows for targeted modulation of the immune response while addressing the risk that the recipient will develop a malignancy due to uncontrolled proliferation of the cloaked cells or because the cells are providing local immunosuppression.

Methods of Producing Cloaked Cells

The compositions and methods described herein can be used modulate the response of the immune system to specific antigens through expression of cloaking transgenes concurrently with or prior to the expression of a polypeptide containing an antigen. A wide array of methods has been established for the delivery of proteins to mammalian cells and for the stable expression of genes encoding proteins in mammalian cells, which can be used to produce the cloaked cells described herein.

Polynucleotides Encoding Cloaking Proteins or Polypeptides Containing Antigens

One platform that can be used to achieve therapeutically effective expression of cloaking proteins and/or polypeptides containing antigens in mammalian cells is via the stable expression of a gene encoding a cloaking protein or a gene encoding a polypeptide containing an antigen (e.g., by integration into the nuclear or mitochondrial genome of a mammalian cell, or by episomal concatemer formation in the nucleus of a mammalian cell). The gene is a polynucleotide that encodes the primary amino acid sequence of the corresponding protein. In order to introduce exogenous genes into a mammalian cell, genes can be incorporated into a vector. Vectors can be introduced into a cell by a variety of methods, including transformation, transfection, transduction, direct uptake, projectile bombardment, and by encapsulation of the vector in a liposome. Examples of suitable methods of transfecting or transforming cells include calcium phosphate precipitation, electroporation, microinjection, infection, lipofection and direct uptake. Such methods are described in more detail, for example, in Green, et al., Molecular Cloning: A Laboratory Manual, Fourth Edition (Cold Spring Harbor University Press, New York 2014); and Ausubel, et al., Current Protocols in Molecular Biology (John Wiley & Sons, New York 2015), the disclosures of each of which are incorporated herein by reference.

Cloaking proteins or polypeptides containing antigens can also be introduced into a mammalian cell by targeting vectors containing portions of a gene encoding a cloaking protein or a gene encoding a polypeptide containing an antigen to cell membrane phospholipids. For example, vectors can be targeted to the phospholipids on the extracellular surface of the cell membrane by linking the vector molecule to a VSV-G protein, a viral protein with affinity for all cell membrane phospholipids. Such a construct can be produced using methods well known to those of skill in the field.

Recognition and binding of the polynucleotide encoding a cloaking protein or the polynucleotide encoding a polypeptide containing an antigen by mammalian RNA polymerase is important for gene expression. As such, one may include sequence elements within the polynucleotide that exhibit a high affinity for transcription factors that recruit RNA polymerase and promote the assembly of the transcription complex at the transcription initiation site. Such sequence elements include, e.g., a mammalian promoter, the sequence of which can be recognized and bound by specific transcription initiation factors and ultimately RNA polymerase.

Polynucleotides suitable for use in the compositions and methods described herein also include those that encode a cloaking protein or encode a polypeptide containing an antigen downstream of a mammalian promoter. Promoters that are useful for the expression of a cloaking protein or a polypeptide containing an antigen in mammalian cells include constitutive promoters. Constitutive promoters include the CAG promoter, the cytomegalovirus (CMV) promoter, the EF1α promoter, and the PGK promoter. Alternatively, promoters derived from viral genomes can also be used for the stable expression of these agents in mammalian cells. Examples of functional viral promoters that can be used to promote mammalian expression of these agents include adenovirus late promoter, vaccinia virus 7.5K promoter, SV40 promoter, tk promoter of HSV, mouse mammary tumor virus (MMTV) promoter, LTR promoter of HIV, promoter of moloney virus, Epstein barr virus (EBV) promoter, and the Rous sarcoma virus (RSV) promoter.

Once a polynucleotide encoding a cloaking protein or encoding a polypeptide containing an antigen described herein below has been incorporated into the nuclear DNA of a mammalian cell, the transcription of this polynucleotide can be induced by methods known in the art. For example expression can be induced by exposing the mammalian cell to an external chemical reagent, such as an agent that modulates the binding of a transcription factor and/or RNA polymerase to the mammalian promoter and thus regulates gene expression. The chemical reagent can serve to facilitate the binding of RNA polymerase and/or transcription factors to the mammalian promoter, e.g., by removing a repressor protein that has bound the promoter. Alternatively, the chemical reagent can serve to enhance the affinity of the mammalian promoter for RNA polymerase and/or transcription factors such that the rate of transcription of the gene located downstream of the promoter is increased in the presence of the chemical reagent. Examples of chemical reagents that potentiate polynucleotide transcription by the above mechanisms include tetracycline and doxycycline. These reagents are commercially available (Life Technologies, Carlsbad, CA) and can be administered to a mammalian cell in order to promote gene expression according to established protocols.

Other DNA sequence elements that may be included in the nucleic acid vectors for use in the compositions and methods described herein include enhancer sequences. Enhancers represent another class of regulatory elements that induce a conformational change in the polynucleotide containing the gene of interest such that the DNA adopts a three-dimensional orientation that is favorable for binding of transcription factors and RNA polymerase at the transcription initiation site. Thus, polynucleotides for use in the compositions and methods described herein include those that encode a cloaking protein or encode a polypeptide containing an antigen and additionally include a mammalian enhancer sequence. Many enhancer sequences are now known from mammalian genes, and examples include enhancers from the genes that encode mammalian globin, elastase, albumin, α-fetoprotein, and insulin. Enhancers for use in the compositions and methods described herein also include those that are derived from the genetic material of a virus capable of infecting a eukaryotic cell. Examples include the SV40 enhancer on the late side of the replication origin (bp 100-270), the cytomegalovirus early promoter enhancer, the polyoma enhancer on the late side of the replication origin, and adenovirus enhancers. Additional enhancer sequences that induce activation of eukaryotic gene transcription are disclosed in Yaniv, et al., Nature 297:17 (1982). An enhancer may be spliced into a vector containing a polynucleotide encoding a cloaking protein or a polynucleotide encoding a polypeptide containing an antigen, for example, at a position 5' or 3' to this gene. In a preferred orientation, the enhancer is positioned at the 5' side of the promoter, which in turn is located 5' relative to the polynucleotide encoding a cloaking protein or a polypeptide containing an antigen.

The nucleic acid vectors described herein may include a Woodchuck Posttranscriptional Regulatory Element (WPRE). The WPRE acts at the transcriptional level, by promoting nuclear export of transcripts and/or by increasing the efficiency of polyadenylation of the nascent transcript, thus increasing the total amount of mRNA in the cell. The addition of the WPRE to a vector can result in a substantial improvement in the level of transgene expression from several different promoters, both in vitro and in vivo.

In some embodiments, the nucleic acid vectors for use in the compositions and methods described herein include a reporter sequence, which can be useful in verifying gene expression, for example, in specific cells and tissues. Reporter sequences that may be provided in a transgene include DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements which drive their expression, the reporter sequences provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA), and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer.

Techniques for Introducing Transgenes into Cells

Transfection

Techniques that can be used to introduce a transgene, such as a cloaking transgene or a transgene encoding a polypeptide containing an antigen described herein, into a target cell (e.g., a mammalian cell) are well known in the art. For instance, electroporation can be used to permeabilize mammalian cells (e.g., human target cells) by the application of an electrostatic potential to the cell of interest. Mammalian cells, such as human cells, subjected to an external electric field in this manner are subsequently predisposed to the uptake of exogenous nucleic acids. Electroporation of mammalian cells is described in detail, e.g., in Chu et al., Nucleic Acids Research 15:1311 (1987), the disclosure of which is incorporated herein by reference. A similar technique, NUCLEOFECTION™, utilizes an applied electric field in order to stimulate the uptake of exogenous polynucleotides into the nucleus of a eukaryotic cell. NUCLEOFECTION™ and protocols useful for performing this technique are described in detail, e.g., in Distler et al., Experimental Dermatology 14:315 (2005), as well as in US 2010/0317114, the disclosures of each of which are incorporated herein by reference.

Additional techniques useful for the transfection of target cells include the squeeze-poration methodology. This technique induces the rapid mechanical deformation of cells in order to stimulate the uptake of exogenous DNA through membranous pores that form in response to the applied stress. This technology is advantageous in that a vector is not required for delivery of nucleic acids into a cell, such as a human target cell. Squeeze-poration is described in detail, e.g., in Sharei et al., Journal of Visualized Experiments 81:e50980 (2013), the disclosure of which is incorporated herein by reference.

Lipofection represents another technique useful for transfection of target cells. This method involves the loading of nucleic acids into a liposome, which often presents cationic functional groups, such as quaternary or protonated amines, towards the liposome exterior. This promotes electrostatic interactions between the liposome and a cell due to the anionic nature of the cell membrane, which ultimately leads to uptake of the exogenous nucleic acids, for instance, by direct fusion of the liposome with the cell membrane or by endocytosis of the complex. Lipofection is described in detail, for instance, in U.S. Pat. No. 7,442,386, the disclosure of which is incorporated herein by reference. Similar techniques that exploit ionic interactions with the cell membrane to provoke the uptake of foreign nucleic acids include contacting a cell with a cationic polymer-nucleic acid complex. Exemplary cationic molecules that associate with polynucleotides so as to impart a positive charge favorable for interaction with the cell membrane include activated dendrimers (described, e.g., in Dennig, Topics in Current Chemistry 228:227 (2003), the disclosure of which is incorporated herein by reference) polyethylenimine, and diethylaminoethyl (DEAE)-dextran, the use of which as a transfection agent is described in detail, for instance, in Gulick et al., Current Protocols in Molecular Biology 40:1:9.2:9.2.1 (1997), the disclosure of which is incorporated herein by reference. Magnetic beads are another tool that can be used to transfect target cells in a mild and efficient manner, as this methodology utilizes an applied magnetic field in order to direct the uptake of nucleic acids. This technology is described in detail, for instance, in US 2010/0227406, the disclosure of which is incorporated herein by reference.

Another useful tool for inducing the uptake of exogenous nucleic acids by target cells is laserfection, also called optical transfection, a technique that involves exposing a cell to electromagnetic radiation of a particular wavelength in order to gently permeabilize the cells and allow polynucleotides to penetrate the cell membrane. The bioactivity of this technique is similar to, and in some cases found superior to, electroporation.

Impalefection is another technique that can be used to deliver genetic material to target cells. It relies on the use of nanomaterials, such as carbon nanofibers, carbon nanotubes, and nanowires. Needle-like nanostructures are synthesized perpendicular to the surface of a substrate. DNA containing the gene, intended for intracellular delivery, is attached to the nanostructure surface. A chip with arrays of these needles is then pressed against cells or tissue. Cells that are impaled by nanostructures can express the delivered gene(s). An example of this technique is described in Shalek et al., PNAS 107: 1870 (2010), the disclosure of which is incorporated herein by reference.

Magnetofection can also be used to deliver nucleic acids to target cells. The magnetofection principle is to associate nucleic acids with cationic magnetic nanoparticles. The magnetic nanoparticles are made of iron oxide, which is fully biodegradable, and coated with specific cationic proprietary molecules varying upon the applications. Their association with the gene vectors (DNA, siRNA, viral vector, etc.) is achieved by salt-induced colloidal aggregation and electrostatic interaction. The magnetic particles are then concentrated on the target cells by the influence of an external magnetic field generated by magnets. This technique is described in detail in Scherer et al., Gene Therapy 9:102 (2002), the disclosure of which is incorporated herein by reference.

Another useful tool for inducing the uptake of exogenous nucleic acids by target cells is sonoporation, a technique that involves the use of sound (typically ultrasonic frequencies) for modifying the permeability of the cell plasma membrane permeabilize the cells and allow polynucleotides to penetrate the cell membrane. This technique is described in detail, e.g., in Rhodes et al., Methods in Cell Biology 82:309 (2007), the disclosure of which is incorporated herein by reference.

Microvesicles represent another potential vehicle that can be used to modify the genome of a target cell according to the methods described herein. For instance, microvesicles that have been induced by the co-overexpression of the glycoprotein VSV-G with, e.g., a genome-modifying protein, such as a nuclease, can be used to efficiently deliver proteins into a cell that subsequently catalyzes the site-specific cleavage of an endogenous polynucleotide sequence so as to prepare the genome of the cell for the covalent incorporation of a polynucleotide of interest, such as a gene or regulatory sequence. The use of such vesicles, also referred to as Gesicles, for the genetic modification of eukaryotic cells is described in detail, e.g., in Quinn et al., Genetic Modification of Target Cells by Direct Delivery of Active Protein [abstract]. In: Methylation changes in early embryonic genes in cancer [abstract], in: Proceedings of the 18th Annual Meeting of the American Society of Gene and Cell Therapy; 2015 May 13, Abstract No. 122.

Viral Infection

In addition to achieving high rates of transcription and translation, stable expression of an exogenous gene in a mammalian cell can be achieved by integration of the polynucleotide containing the gene into the nuclear genome of the mammalian cell. A variety of vectors for the delivery and integration of polynucleotides encoding exogenous proteins into the nuclear DNA of a mammalian cell have been developed. Examples of expression vectors are disclosed in, e.g., WO 1994/011026 and are incorporated herein by reference. Expression vectors for use in the compositions and methods described herein contain a cloaking transgene or a transgene encoding a polypeptide containing an antigen, as well as, e.g., additional sequence elements used for the expression of these agents and/or the integration of these polynucleotide sequences into the genome of a mammalian cell. Certain vectors that can be used for the expression of cloaking transgenes or transgenes encoding a polypeptide containing an antigen include plasmids that contain regulatory sequences, such as promoter and enhancer regions, which direct gene transcription. Other useful vectors for expression of cloaking transgenes or transgenes encoding a polypeptide containing an antigen contain polynucleotide sequences that enhance the rate of translation of these genes or improve the stability or nuclear export of the mRNA that results from gene transcription. These sequence elements include, e.g., 5' and 3' untranslated regions and a polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

Viral Vectors for Nucleic Acid Delivery

Viral genomes provide a rich source of vectors that can be used for the efficient delivery of a gene of interest into the genome of a target cell (e.g., a mammalian cell, such as a human cell). Viral genomes are particularly useful vectors for gene delivery because the polynucleotides contained within such genomes are typically incorporated into the nuclear genome of a mammalian cell by generalized or specialized transduction. These processes occur as part of the natural viral replication cycle, and do not require added proteins or reagents in order to induce gene integration. Examples of viral vectors include a retrovirus (e.g., Retroviridae family viral vector), adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, human papilloma virus, human foamy virus, and hepatitis virus, for example. Examples of retroviruses include: avian leukosis-sarcoma, avian C-type viruses, mammalian C-type, B-type viruses, D-type viruses, oncoretroviruses, HTLV-BLV group, lentivirus, alpharetrovirus, gammaretrovirus, spumavirus (Coffin, J. M., Retroviridae: The viruses and their replication, Virology, Third Edition (Lippincott-Raven, Philadelphia, 1996)). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, U.S. Pat. No. 5,801,030, the disclosure of which is incorporated herein by reference as it pertains to viral vectors for use in gene therapy.

AAV Vectors for Nucleic Acid Delivery

In some embodiments, cloaking transgenes or transgenes encoding a polypeptide containing an antigen described herein are incorporated into rAAV vectors and/or virions in order to facilitate their introduction into a cell. rAAV vectors useful in the compositions and methods described herein are recombinant nucleic acid constructs that include (1) a promoter, (2) a heterologous sequence to be expressed (e.g., a cloaking transgene or a transgene encoding a polypeptide containing an antigen described herein), and (3) viral sequences that facilitate integration and expression of the heterologous genes. The viral sequences may include those sequences of AAV that are required in cis for replication and packaging (e.g., functional ITRs) of the DNA into a virion. Such rAAV vectors may also contain marker or reporter genes. Useful rAAV vectors have one or more of the AAV WT genes deleted in whole or in part, but retain functional flanking ITR sequences. The AAV ITRs may be of any serotype suitable for a particular application. Methods for using rAAV vectors are described, for example, in Tal et al., J. Biomed. Sci. 7:279 (2000), and Monahan and Samulski, Gene Delivery 7:24 (2000), the disclosures of each of which are incorporated herein by reference as they pertain to AAV vectors for gene delivery.

The transgenes and vectors described herein (e.g., a promoter operably linked to a cloaking transgene or a transgene encoding a polypeptide containing an antigen) can be incorporated into a rAAV virion in order to facilitate introduction of the polynucleotide or vector into a cell. The capsid proteins of AAV compose the exterior, non-nucleic acid portion of the virion and are encoded by the AAV cap gene. The cap gene encodes three viral coat proteins, VP1, VP2 and VP3, which are required for virion assembly. The construction of rAAV virions has been described, for instance, in U.S. Pat. Nos. 5,173,414; 5,139,941; 5,863,541; 5,869,305; 6,057,152; and 6,376,237; as well as in Rabinowitz et al., J. Virol. 76:791 (2002) and Bowles et al., J. Virol. 77:423 (2003), the disclosures of each of which are incorporated herein by reference as they pertain to AAV vectors for gene delivery.

rAAV virions useful in conjunction with the compositions and methods described herein include those derived from a variety of AAV serotypes including AAV 1, 2, 3, 4, 5, 6, 7, 8, 9, 10, rh10, rh39, rh43, and rh74. Construction and use of AAV vectors and AAV proteins of different serotypes are described, for instance, in Chao et al., Mol. Ther. 2:619 (2000); Davidson et al., Proc. Natl. Acad. Sci. USA 97:3428 (2000); Xiao et al., J. Virol. 72:2224 (1998); Halbert et al., J. Virol. 74:1524 (2000); Halbert et al., J. Virol. 75:6615 (2001); and Auricchio et al., Hum. Molec. Genet. 10:3075 (2001), the disclosures of each of which are incorporated herein by reference as they pertain to AAV vectors for gene delivery.

Also useful in conjunction with the compositions and methods described herein are pseudotyped rAAV vectors. Pseudotyped vectors include AAV vectors of a given serotype (e.g., AAV9) pseudotyped with a capsid gene derived from a serotype other than the given serotype (e.g., AAV1, AAV2, AAV3, AAV4, AAV5, AAV6, AAV7, AAV8, etc.). Techniques involving the construction and use of pseudotyped rAAV virions are known in the art and are described, for instance, in Duan et al., J. Virol. 75:7662 (2001); Halbert et al., J. Virol. 74:1524 (2000); Zolotukhin et al., Methods, 28:158 (2002); and Auricchio et al., Hum. Molec. Genet. 10:3075 (2001).

AAV virions that have mutations within the virion capsid may be used to infect particular cell types more effectively than non-mutated capsid virions. For example, suitable AAV mutants may have ligand insertion mutations for the facilitation of targeting AAV to specific cell types. The construction and characterization of AAV capsid mutants including insertion mutants, alanine screening mutants, and epitope tag mutants is described in Wu et al., J. Virol. 74:8635 (2000). Other rAAV virions that can be used in methods described herein include those capsid hybrids that are generated by molecular breeding of viruses as well as by exon shuffling. See, e.g., Soong et al., Nat. Genet., 25:436 (2000) and Kolman and Stemmer, Nat. Biotechnol. 19:423 (2001).

Genome Editing

In addition to the above, a variety of tools have been developed that can be used for the incorporation of a gene of interest into a target cell, such as a mammalian cell. One such method that can be used for incorporating polynucleotides encoding target genes (e.g., a cloaking transgene or a transgene encoding a polypeptide containing an antigen described herein) into target cells involves the use of transposons. Transposons are polynucleotides that encode transposase enzymes and contain a polynucleotide sequence or gene of interest flanked by 5' and 3' excision sites. Once a transposon has been delivered into a cell, expression of the transposase gene commences and results in active enzymes that cleave the gene of interest from the transposon. This activity is mediated by the site-specific recognition of transposon excision sites by the transposase. In some instances, these excision sites may be terminal repeats or inverted terminal repeats. Once excised from the transposon, the gene of interest can be integrated into the genome of a mammalian cell by transposase-catalyzed cleavage of similar excision sites that exist within the nuclear genome of the cell. This allows the gene of interest to be inserted into the cleaved nuclear DNA at the complementary excision sites, and subsequent covalent ligation of the phosphodiester bonds that join the gene of interest to the DNA of the mammalian cell genome completes the incorporation process. In certain cases, the transposon may be a retrotransposon, such that the gene encoding the target gene is first transcribed to an RNA product and then reverse-transcribed to DNA before incorporation in the mammalian cell genome. Exemplary transposon systems are the piggybac transposon (described in detail in, e.g., WO 2010/085699) and the sleeping beauty transposon (described in detail in, e.g., US 2005/0112764), the disclosures of each of which are incorporated herein by reference as they pertain to transposons for use in gene delivery to a cell of interest.

Another tool for the integration of target genes into the genome of a target cell is the clustered regularly interspaced short palindromic repeats (CRISPR)/Cas system, a system that originally evolved as an adaptive defense mechanism in bacteria and archaea against viral infection. The CRISPR/Cas system includes palindromic repeat sequences within plasmid DNA and an associated Cas9 nuclease. This ensemble of DNA and protein directs site specific DNA cleavage of a target sequence by first incorporating foreign DNA into CRISPR loci. Polynucleotides containing these foreign sequences and the repeat-spacer elements of the CRISPR locus are in turn transcribed in a host cell to create a guide RNA, which can subsequently anneal to a target sequence and localize the Cas9 nuclease to this site. In this manner, highly site-specific cas9-mediated DNA cleavage can be engendered in a foreign polynucleotide because the interaction that brings cas9 within close proximity of the target DNA molecule is governed by RNA:DNA hybridization. As a result, one can design a CRISPR/Cas system to cleave any target DNA molecule of interest. This technique has been exploited in order to edit eukaryotic genomes (Hwang et al., Nature Biotechnology 31:227 (2013)) and can be used as an efficient means of site-specifically editing target cell genomes in order to cleave DNA prior to the incorporation of a gene encoding a target gene. The use of CRISPR/Cas to modulate gene expression has been described in, for example, U.S. Pat. No. 8,697,359, the disclosure of which is incorporated herein by reference as it pertains to the use of the CRISPR/Cas system for genome editing. Alternative methods for site-specifically cleaving genomic DNA prior to the incorporation of a gene of interest in a target cell include the use of zinc finger nucleases (ZFNs) and transcription activator-like effector nucleases (TALENs). Unlike the CRISPR/Cas system, these enzymes do not contain a guiding polynucleotide to localize to a specific target sequence. Target specificity is instead controlled by DNA binding domains within these enzymes. The use of ZFNs and TALENs in genome editing applications is described, e.g., in Urnov et al., Nature Reviews Genetics 11:636 (2010); and in Joung et al., Nature Reviews Molecular Cell Biology 14:49 (2013), the disclosure of each of which are incorporated herein by reference as they pertain to compositions and methods for genome editing.

Additional genome editing techniques that can be used to incorporate polynucleotides encoding target genes into the genome of a target cell include the use of ARCUS™ meganucleases that can be rationally designed so as to site-specifically cleave genomic DNA. The use of these enzymes for the incorporation of genes encoding target genes into the genome of a mammalian cell is advantageous in view of the defined structure-activity relationships that have been established for such enzymes. Single chain meganucleases can be modified at certain amino acid positions in order to create nucleases that selectively cleave DNA at desired locations, enabling the site-specific incorporation of a target gene into the nuclear DNA of a target cell. These single-chain nucleases have been described extensively in, for example, U.S. Pat. Nos. 8,021,867 and 8,445,251, the disclosures of each of which are incorporated herein by reference as they pertain to compositions and methods for genome editing.

Expression of Cloaking Transgenes

The cloaking transgenes described herein (e.g., one of, or any combination of, PD-L1, HLA-G (H2-M3), Cd47, Cd200, FASLG (FasL), Ccl21 (Ccl21b), Mfge8, and Serpin B9 (Spi6)) are expressed in an amount sufficient to produce a cloaking effect (e.g., in an amount sufficient to prevent rejection when injected into a subject, e.g., a mammalian subject, such as a mouse, rat, or human). Transgene expression can be considered to produce a cloaking effect if subcutaneous injection of cloaked cells generates a teratoma that is not removed by the subject's immune system. The cloaking transgenes are also expressed at a level that is sufficient to promote production of the proteins encoded by said transgenes. Protein production can be detected using routine methods known to those of skill in the art (e.g., immunohistochemistry, Western Blot analysis, or other methods that allow for visualization or proteins). Preferably, the expression of the cloaking transgenes is such that all 8 proteins encoded by the cloaking transgenes (PD-L1, H2-M3, Cd47, Cd200, FasL, Ccl21b, Mfge8, and Spi6) can be detected in cloaked cells (e.g., detected by immunohistochemistry using antibodies directed against the proteins encoded by the cloaking transgenes).

In some embodiments, cloaking transgenes are expressed at similar levels in cloaked cells to levels of endogenous gene expression in activated leukocytes, such as T cells (e.g., activated leukocytes from the same species, such as an activated leukocyte isolated from a lymph organ, for example expression in a cloaked mouse cell is similar to expression in an activated leukocyte isolated from a murine lymphoid organ). The expression of one or more cloaking transgenes (e.g., 1, 2, 3, 4, 5, 6, 7, or 8 of PD-L1, HLA-G (H2-M3), Cd47, Cd200, FASLG (FasL), Ccl21 (Ccl21b), Mfge8, and Serpin B9 (Spi6)) is greater than or equal to expression of the endogenous gene in activated leukocytes (e.g., T cells) from the same species (e.g., expression level of the cloaking transgene is equal to the level of expression of the endogenous gene in activated leukocytes, or is 1.5, 2, 3, 4, 5, 6, 7, 8, 9, 10-fold or more higher than the level of expression of the endogenous gene in activated leukocytes). In some embodiments, all 8 cloaking transgenes are expressed at a level that is greater than or equal to the expression level of the endogenous gene in an activated leukocyte from the same species. Activated leukocytes can be isolated from lymphoid organs, or leukocytes, such as T cells, can activated in vitro using anti-CD3/CD28 beads or other methods employed by those of skill in the art (see, e.g., Frauwith and Thompson, *J. Clin Invest* 109:295-299 (2002); and Trickett and Kwan, *J Immunol Methods* 275:251-255 (2003)). Transgene expression in cloaked cells can also be compared to gene expression levels reported in profiling studies of activated T cells (see, e.g., Palacios et al., PLOSone 2:e1222 (2007)). In some embodiments, cloaking transgene expression is compared to expression of the endogenous gene in a wild-type version of the cell (e.g., a stem cell, e.g., an embryonic stem cell from the same species as the cloaked cell). The expression of one or more cloaking transgenes (e.g., 1, 2, 3, 4, 5, 6, 7, or 8 of PD-L1, HLA-G (H2-M3), Cd47, Cd200, FASLG (FasL), Ccl21 (Ccl21b), Mfge8, and Serpin B9 (Spi6)) is at least 2, 3, 4, 5, 6, 7, 8, 9, 10, 20, 30, 40, 50, 100, 500, 1,000-fold or more higher in cloaked cells compared to expression of the endogenous gene in unmodified wild-type cells of the same cell type as the cloaked cell (e.g., stem cells, such as embryonic stem cells from the same species). In some embodiments, all 8 cloaking transgenes are expressed at a level that is greater (e.g., 2, 3, 4, 5, 6, 7, 8, 9, 10, 20, 30, 40, 50, or 100-fold higher or more) than the expression level of the endogenous gene in a wild-type version of the cell (e.g., a stem cell, e.g., an embryonic stem cell from the same species as the cloaked cell). Gene expression can be evaluated through direct comparison to isolated ES cells, or compared to stem cell expression (e.g., ES cell expression) in the Project Grandiose dataset (www.stemformatics.org/project_grandiose). Gene expression can be measured using techniques known in the art (e.g., quantitative polymerase chain reaction (qPCR)). Exemplary expression of cloaking transgenes is described in International Patent Application No. PCT/CA2018/050706, which is incorporated herein by reference in its entirety.

Cloaked Cells for the Induction of Immune Tolerance

Due to their ability to suppress the immune response, the cloaked cells of the invention can be modified for use in various cell-based therapies. In one example, the set of transgenes described herein can be used to cloak cells for the induction of immune tolerance (e.g., to prevent or reduce the response of the immune system to antigens expressed by cloaked cells). The ability to induce immune tolerance to specific antigens allows for the development of targeted therapeutics to suppress a harmful or aberrant immune response and may reduce or obviate the need for immunosuppressive medication. Immunosuppressive medication renders the body more vulnerable to infections and malignancy; therefore, cell-based therapies that can be used in place of immunosuppressive medication or reduce the dose of immunosuppressive medication that is administered to a subject may be associated with fewer risks and side effects.

Cloaked Cells for Inducing Tolerance of an Organ or Tissue Transplant

The set of transgenes described herein can be used to cloak cells to induce immune tolerance to alloantigens from a donor (e.g., a human organ or tissue donor). After organ or tissue transplantation, the immune system of the recipient often rejects the new organ or tissue, detecting it as foreign or non-self due to differences in human leukocyte antigen (HLA) between the donor and the recipient. The immune system may then attack the new tissue, which can result in damage to or death of the donated tissue or organ. Immunosuppressive medication can be given to the recipient to suppress this immune response, but it may result in deleterious side effects. The present invention provides an alternative approach, in which the recipient is administered cloaked cells (e.g., cloaked donor cells or cloaked cells expressing an alloantigen from the donor, e.g., an HLA molecule from the donor) in advance of the transplant to induce tolerance prior to the organ or tissue transplant.

In some embodiments, the cloaked cell is a cell from an organ or tissue donor (e.g., a somatic cell or stem cell (e.g., an adult stem cell, an iPSC, a tissue-specific stem cell, a hematopoietic stem cell, a mesenchymal stem cell, an endothelial stem cell, an epithelial stem cell, or a hair follicle stem cell) from an organ or tissue donor, or a cell from the tissue or organ to be donated). Cells from an organ or tissue donor carry alloantigens from the donor to which the recipient of the organ or tissue transplant can be tolerized to reduce or prevent the risk of transplant rejection. The cells from the donor can be modified to express one or more (e.g., two, three, four, five, six, seven, or all eight) of the cloaking transgenes: PD-L1, HLA-G (H2-M3), Cd47, Cd200, FASLG (FasL), Ccl21 (Ccl21b), Mfge8, and Serpin B9 (Spi6). In some embodiments, the donor cells are modified to express all eight of Pd-L1, H2-M3, Cd47, Cd200, FasL, Ccl21b, Mfge8, and Spi6. In addition to the cloaking transgenes, the cells may be further modified to express one or more of TGF-β, Cd73, Cd39, Lag3, Il1r2, Ackr2, Tnfrsf22, Tnfrs23, Tnfrsf10, Dad1, and IFNγR1 d39. The donor cells can be modified to express the one or more cloaking transgenes using the techniques described herein above (e.g., transfection, viral infection, or gene editing) or using other methods known by those of skill in the art. This approach does not require the identification of the alloantigens expressed by the donor cells prior to administration of cloaked donor cells to the recipient. Moreover, this approach allows for the induction of immune tolerance to all of the alloantigens expressed by the donor cell (e.g., the immune system of the recipient will learn to recognize all of the alloantigens expressed by the donor cell and treat them as "self" antigens, and, therefore will not mount an immune response against these antigens when they are presented again in the uncloaked organ or tissue transplant).

In some embodiments, the cloaked cell is not from the organ or tissue donor. The cell may be a stem cell (e.g., an ES cell, an adult stem cell, an iPSC, a tissue-specific stem cell, a hematopoietic stem cell, a mesenchymal stem cell, an endothelial stem cell, an epithelial stem cell, an adipose stem or progenitor cell, a germline stem cell, a lung stem or progenitor cell, a mammary stem cell, an olfactory adult stem cell, a hair follicle stem cell, a multipotent stem cell, an amniotic stem cell, a cord blood stem cell, or a neural stem or progenitor cell), a somatic cell, a cell derived from a cell line, a cell amenable to genome editing, and/or a source of therapeutic cell type (e.g., a cell that can be differentiated into a lineage restricted cell for cell therapy, or a cell of a desired target tissue). In some embodiments, the cell is a skin, heart, brain or spinal cord, liver, lung, kidney, pancreas, bladder, bone marrow, spleen, intestine, or stomach cell. In some embodiments, the cell is a fibroblast, an epithelial cell, or an endothelial cell. The cell may be a vertebrate cell, for example, a mammalian cell, such as a human or mouse cell. In some embodiments, the cell is an autologous cell (e.g., a cell isolated from the subject in need of tolerization). In some embodiments, the cell that is cloaked is of the same cell type as the tissue or organ to be transplanted (e.g., a liver cell is cloaked if the subject will receive a liver transplant). In this embodiment, the cell is modified to express one or more (e.g., two, three, four, five, six, seven, or all eight) of the cloaking transgenes: PD-L1, HLA-G (H2-M3), Cd47, Cd200, FASLG (FasL), Ccl21 (Ccl21b), Mfge8, and Serpin B9 (Spi6) and one or more alloantigen from the organ or tissue donor (e.g., an HLA molecule from the organ or tissue donor). In some embodiments, the cloaked cell is modified to express all eight of Pd-L1, H2-M3, Cd47, Cd200, FasL, Ccl21b, Mfge8, and Spi6 and one or more alloantigen from the organ or tissue donor (e.g., an HLA molecule from the organ or tissue donor). In addition to the cloaking transgenes, the cells may be further modified to express one or more of TGF-β, Cd73, Cd39, Lag3, Il1r2, Ackr2, Tnfrsf22, Tnfrs23, Tnfrsf10, Dad1, and IFNγR1 d39.

The alloantigen from the organ or tissue donor can be any alloantigen capable of stimulating an immune response in the recipient. In some embodiments, the alloantigen is a histocompatibility protein (e.g., an HLA protein), such as an HLA class I or class II protein. In some embodiments, the alloantigen is a blood group antigen. The alloantigens expressed by the organ or tissue donor may be identified using standard methods, such as molecular typing of HLA alleles (using PCR), serologic typing of HLA antigens (using the standard complement-mediated microlymphocytotoxicity technique), sequencing, or mass spectrometry analysis. The cell can be modified to express the cloaking transgenes and one or more (e.g., 1, 2, 3, 4, 5, or more) polypeptide containing an alloantigen from the organ or tissue donor using the techniques described herein above (e.g., transfection, viral infection, or gene editing) or using other methods known by those of skill in the art. To determine whether an alloantigen stimulates an immune response in a recipient (e.g., prior to the administration of a cloaked cell expressing the alloantigen), an immune cell from the recipient can be exposed to the alloantigen and the response of the immune cell can be measured (e.g., an immune cell, such as a dendritic cell, macrophage, T cell (e.g., a cytotoxic T cell/CD8+ T cell, T helper cell/CD4+ T cell, or regulatory T cell/Treg), B cell, monocyte, granulocyte (e.g., eosinophil, mast cell, neutrophil, or basophil), natural killer (NK) cell, or innate lymphoid cell isolated from the recipient can be contacted with the alloantigen in vitro, and a response of the immune cell (e.g., immune cell activation, differentiation, polarization, proliferation, migration, pro-inflammatory cytokine production, degranulation, phagocytosis, or cytotoxicity) can be measured). If the immune cell from the subject responds to the donor alloantigen (e.g., if the immune cell becomes more activated, releases pro-inflammatory cytokines, differentiates, proliferates, becomes more polarized toward an inflammatory phenotype, or exhibits degranulation, phagocytosis, or cytotoxicity), a cloaked cell can be modified to express the protein containing the donor alloantigen to induce immune tolerance to the alloantigen in the recipient and reduce or prevent rejection of an organ or tissue transplant from the donor. The cloaked cell may be modified to express the polypeptide containing the donor alloantigen at an expression level comparable to the endogenous expression level of the polypeptide containing the donor alloantigen in a cell or tissue from the donor. Alternatively, the cloaked cell may be modified to express the polypeptide containing the donor alloantigen at a level comparable to the expression level of a housekeeping polypeptide (e.g. β-actin, GAPDH, or Rosa26). Robust expression of the polypeptide can be achieved using strong promoters, such as CAGG or CMV or through the use of a doxycycline inducible system (e.g., a doxycycline inducible TRE).

The cloaked donor cell or the cloaked cell expressing a protein containing a donor alloantigen may be administered to the subject in advance of the organ or tissue transplant to induce immune tolerance (e.g., administered to induce tolerance to a future organ or tissue transplant in order to reduce or prevent transplant rejection and to reduce or obviate the need for immunosuppressive medication, e.g., to reduce the amount of immunosuppressive medication administered to a subject). The organ or tissue to be transplanted need not be cloaked, as the recipient's immune system should no longer recognize the transplant as foreign. The cloaked donor cell or the cloaked cell expressing a protein containing a donor alloantigen may be administered to the recipient prior to the organ or tissue transplant (e.g., 1 day, 2 days, 3 days, 4 days, 5 days, 6 days, 1 week, 2 weeks, 3 weeks, 1 month, 2 months, 3 months, 4 months, 5 months, 6 months, 9 months, 1 year or more before the organ or tissue transplant). The cloaked donor cell or the cloaked cell expressing a protein containing a donor alloantigen can be injected at or near the site of the future organ or tissue transplant, injected as a circulating cell, or injected subcutaneously to produce a cloaked subcutaneous tissue. In some embodiments, twenty five thousand to one hundred billion cloaked cells expressing a protein containing a donor alloantigen (e.g., $2.5\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $6\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ cloaked cells expressing a donor alloantigen) are administered to a subject to induce immune tolerance to a donor alloantigen. In some embodiments, an immune cell from the recipient can be tested to determine whether immune tolerance has been induced. For example, after administration of the cloaked donor cell or cloaked cell expressing an alloantigen (e.g., 1 day, 2 days, 3 days, 4 days, 5 days, 6 days, 1 week, 2 weeks, 3 weeks, 1 month, 2 months, 3 months, 4 months, 5 months, 6 months, 9 months, or 1 year after administration of the cloaked donor cell or cloaked cell expressing an alloantigen), an immune cell can be isolated from the recipient and exposed to an uncloaked cell from the donor (e.g., an uncloaked cell from the donor, an uncloaked cell from the organ or tissue to be donated, or an uncloaked cell that carries the donor alloantigen to which the recipient's immune system has been tolerized). The response of the recipient immune cell can be measured as described above. If the immune cell from the recipient does not mount an immune response against the uncloaked donor cell or donor alloantigen (e.g., if the immune cell does not become more activated or exhibit a cytotoxic, pro-inflammatory, or phagocytic response to the donor cell or donor alloantigen), the recipient's immune system has been successfully tolerized to the donor cell or donor alloantigen. The transplant can then be performed with minimal risk of transplant rejection and without the use of, or upon administration of a reduced dosage of, immunosuppressive medication. There is also no need to match the HLA antigens in the donor and recipient, as administration of cloaked cells carrying a donor HLA antigen can be used to induce immune tolerance to any donor HLA antigen (e.g., a 0/6 match, a 1/6 match, a 2/6 match, a 3/6 match, a 4/6 match or a 5/6 match).

In some embodiments, the organ that is transplanted after immune tolerance is induced using cloaked cells is a heart, kidney, brain, liver, lung, stomach, pancreas, intestine, testis, penis, hand, face, arm, foot, middle ear, or thymus. In some embodiments, the tissue that is transplanted after immune tolerance is induced using cloaked cells is a bone or tendon (e.g., a musculoskeletal graft), connective tissue, a cornea, skin, a heart valve, islets of Langerhans, bone marrow, or blood vessel (e.g., a nerve or a vein), blood, or a vascularized composite allograft (e.g., a transplant of several structures that may include skin, bone, muscles, blood vessels, nerves, and connective tissue).

The cloaked cells expressing the polynucleotide containing the donor alloantigen can be removed after transplantation of the donor tissue or organ (e.g., 1 week, 1 month, 2 months, 3 months, 4 months, 5 months, 6 months, 9 months, 1 year, 2 years or more after transplantation). The cloaked cells can be removed surgically (e.g., in embodiments in which the cloaked cells formed a tissue, such as a cloaked subcutaneous tissue, the tissue can be surgically removed). In embodiments in which the cloaked cells were modified to contain one or more systems for regulating cell division (e.g., modified to be FAILSAFE™ cells, e.g., by linking the expression of a CDL to an ALINK or EARC), the cloaked cells can be removed by administering an inducer of a negative selectable marker (e.g., the ALINK) or by ceasing to administer an activator of an inducible activator-based gene expression system (e.g., the EARC).

Cloaked Cells for Inducing Tolerance to an Antigen

A normal, healthy immune system will detect and mount an immune response against foreign, "non-self" antigens expressed by a pathogenic or infectious organism, such as a virus or bacterium. Another feature of a normal, healthy immune system is the ability to recognize "self" antigens, which are endogenous and naturally produced, and refrain from mounting an immune response against these antigens. The recognition of self antigens appears to be disrupted in many autoimmune diseases, which are often characterized by immune system-induced damage to body's own cells. The cloaked cells described herein can be used to treat or mitigate such diseases, as they can be modified to express a polypeptide containing an antigen that the immune system is incorrectly targeting to induce immune tolerance to the antigen.

The cell can be cloaked (e.g., modified to express one or more (e.g., two, three, four, five, six, seven, or all eight) of PD-L1, HLA-G (H2-M3), Cd47, Cd200, FASLG (FasL), Ccl21 (Ccl21b), Mfge8, and Serpin B9 (Spi6)) and further modified to express a polypeptide (e.g., one or more polypeptides, e.g., 1, 2, 3, 4, 5, or more polypeptides) containing an antigen that stimulates an aberrant immune response in a subject, such as an antigen associated with an autoimmune disease or condition or a portion thereof that stimulates an immune response in a subject. In some embodiments, the cloaked cell expresses all eight of PD-L1, HLA-G (H2-M3), Cd47, Cd200, FASLG (FasL), Ccl21 (Ccl21b), Mfge8, and Serpin B9 (Spi6) and an antigen or portion thereof. The cells may be further modified to express one or more of TGF-β, Cd73, Cd39, Lag3, Il1r2, Ackr2, Tnfrsf22, Tnfrs23, Tnfrsf10, Dad1, and IFNγR1 d39. The cloaked cells can be modified to express the cloaking transgenes and the polypeptide containing the antigen or portion thereof using the methods described herein (e.g., transfection, viral infection, or gene editing) or using other methods known by those of skill in the art. The cell may be a stem cell (e.g., an ES cell, an adult stem cell, an iPSC, a tissue-specific stem cell, a hematopoietic stem cell, a mesenchymal stem cell, an endothelial stem cell, an epithelial stem cell, an adipose stem or progenitor cell, a germline stem cell, a lung stem or progenitor cell, a mammary stem cell, an olfactory adult stem cell, a hair follicle stem cell, a multipotent stem cell, an amniotic stem cell, a cord blood stem cell, or a neural stem or progenitor cell), a somatic cell, a cell derived from a cell line, a cell amenable to genome editing, and/or a source of therapeutic cell type (e.g., a cell that can be differentiated into a lineage restricted cell for cell therapy, or a cell of a desired target tissue). In some embodiments, the cell is a skin, heart, brain or spinal cord, liver, lung, kidney, pancreas, bladder, bone marrow, spleen, intestine, or stomach cell. In some embodiments, the cell is a fibroblast, an epithelial cell, or an endothelial cell. The cell may be a vertebrate cell, for example, a mammalian cell, such as a human or mouse cell. In some embodiments, the cell is an autologous cell (e.g., a cell isolated from the subject in need of tolerization).

The antigen to be provided by the cloaked cell may be selected based on the autoimmune disease or condition with which the subject is afflicted, as many autoimmune diseases and conditions are associated with aberrant immune responses to specific antigens. A list of polypeptides containing antigens and the autoimmune disease or condition associated with each polypeptide (e.g., the autoimmune disease or condition in which autoantibodies directed against the antigen have been found, e.g., the autoimmune disease or condition that could be treated by modifying cloaked cells to express the polypeptide containing the antigen to induce immune tolerance) are provided in Table 2 below. The portion of a polypeptide containing an antigen that induces an immune response in the subject can be determined prior to producing the cloaked cells by exposing an immune cell from the subject (e.g., a dendritic cell, macrophage, T cell (e.g., a cytotoxic T cell/CD8+ T cell, T helper cell/CD4+ T cell, or regulatory T cell/Treg), B cell, monocyte, granulocyte (e.g., eosinophil, mast cell, neutrophil, or basophil), natural killer (NK) cell, or innate lymphoid cell isolated from the subject) to different portions of the polypeptide (e.g., exposing isolated immune cells from the subject to different portions of the polypeptide in vitro) and determining whether the portion of the polypeptide produces an immune response (e.g., immune cell activation, differentiation, polarization, proliferation, migration, pro-inflammatory cytokine production, degranulation, phagocytosis, or cytotoxicity). If the polypeptide containing an antigen that produces or exacerbates the autoimmune disease or condition is unknown, immune cells from the subject can be exposed to a panel of antigens (e.g., a panel of wild-type human proteins) to determine which of the proteins may be responsible for inducing the aberrant immune response.

The cloaked cell may be modified to express the polypeptide containing the antigen at an expression level comparable to the endogenous expression level of the polypeptide containing the antigen in a cell of the subject to be treated (e.g., the subject having an autoimmune disease or condition). Alternatively, the cloaked cell may be modified to express the polypeptide containing the antigen at a level comparable to the expression level of a housekeeping polypeptide (e.g., β-actin, GAPDH, or Rosa26). Robust expression of the polypeptide can be achieved using strong promoters, such as CAGG or CMV or CMV or through the use of a doxycycline inducible system (e.g., a doxycycline inducible TRE).

The cloaked cells that are modified to provide a polypeptide containing an antigen may be administered to a subject having (e.g., identified to have, or diagnosed with) an autoimmune disease or condition, to a subject in the early stages of developing an autoimmune disease or condition (e.g., a subject with an autoimmune disease or condition that was recently identified or diagnosed, or an autoimmune disease or condition that is associated with mild, but worsening, symptoms), or to a subject at risk of developing an autoimmune disease or condition (e.g., a subject carrying a genetic mutation associated with an autoimmune disease or condition, a subject having a family history of an autoimmune disease or condition, or a subject exposed to pathogens or environmental risk factors that may increase the probability of developing an autoimmune disease or condition). The cloaked cells that are modified to provide a polypeptide containing an antigen for the induction of immune tolerance may treat or alleviate some or all of the symptoms of the autoimmune disease or condition, may reduce the severity of the autoimmune disease or condition, may slow or inhibit the progression of the autoimmune disease or condition, or may prevent or delay the development of the autoimmune disease or condition. In some embodiments, the administration of cloaked cells expressing a polypeptide containing an antigen and the subsequent induction of immune tolerance to the antigen allows other treatments for the autoimmune disease or condition to be more effective. If the antigen is transmembrane or membrane bound (e.g., naturally transmembrane or membrane bound, or modified to include a sequence that localizes the antigen to the membrane, such as a transmembrane domain or linker e.g., a GPI linker), the cloaked cell expressing a polypeptide containing the antigen can be injected at or near the site of the aberrant immune response (e.g., cloaked cells expressing insulin and/or GAD65 can be injected to or near the pancreas to treat type 1 diabetes, and cloaked cells expressing melanin associated antigen (MAA), retinal arrestin, and/or interphotoreceptor retinoid binding protein (IRBP) can be injected to or near the eye to treat uveitis), or injected subcutaneously to produce a cloaked subcutaneous tissue. If the antigen is secreted (e.g., naturally secreted, or modified to remove a sequence that localizes the antigen to the membrane, such as by deletion of a transmembrane domain or linker e.g., a GPI linker), the cloaked cell expressing a polypeptide containing the antigen can be injected as a circulating cell, injected at or near the site of the aberrant immune response, or injected subcutaneously to produce a cloaked subcutaneous tissue that secretes the antigen. Twenty five thousand to one hundred billion cloaked cells expressing an antigen (e.g., $2.5\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $6\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ cloaked cells expressing an antigen) can be administered to a subject to induce immune tolerance to the antigen depending on the route of administration and the site to which the cells are administered.

In some embodiments, an immune cell from the subject can be tested after administration of the cloaked cell expressing a polypeptide containing the antigen to determine whether immune tolerance has been induced. For example, after administration of the cloaked cell expressing an antigen (e.g., 1 day, 2 days, 3 days, 4 days, 5 days, 6 days, 1 week, 2 weeks, 3 weeks, 1 month, 2 months, 3 months, 4 months, 5 months, 6 months, 9 months, or 1 year after administration of the cloaked cell expressing an antigen), an immune cell can be isolated from the subject and exposed to the antigen (e.g., the antigen or an uncloaked cell expressing the polypeptide containing the antigen to which the subject's immune system has been tolerized). The response of the immune cell isolated from the subject can be measured as described above. If the immune cell from the subject does not mount an immune response against the antigen (e.g., if the immune cell does not become more activated or exhibit a cytotoxic, pro-inflammatory, or phagocytic response to the antigen or an uncloaked cell expressing the antigen), the subject's immune system has been successfully tolerized to the antigen.

The cloaked cells expressing a polypeptide containing the antigen can be removed after the subject's immune system has been tolerized to the antigen or after symptoms of the subject's autoimmune disease or condition have improved (e.g., 1 week, 1 month, 2 months, 3 months, 4 months, 5 months, 6 months, 9 months, 1 year, 2 years or more after the subject's immune system has been tolerized to the antigen or after symptoms of the subject's autoimmune disease or condition have improved). The cloaked cells can be removed surgically (e.g., in embodiments in which the cloaked cells formed a tissue, such as a cloaked subcutaneous tissue, the tissue can be surgically removed). In embodiments in which the cloaked cells were modified to contain one or more systems for regulating cell division (e.g., modified to be FAILSAFE™ cells, e.g., by linking the expression of a CDL to an ALINK or EARC), the cloaked cells can be removed by administering an inducer of a negative selectable marker (e.g., the ALINK) or by ceasing to administer an activator of an inducible activator-based gene expression system (e.g., the EARC).

In some embodiments, the antigen is a "self" antigen (e.g., a wild-type human protein), such as an antigen associated with an autoimmune disease or condition. In some embodiments, the antigen is a food antigen (e.g., a protein found in food, or a protein produced by the normal digestive process). In some embodiments, the antigen is an allergen (e.g., an antigen that causes an allergic reaction, such as food allergy, seasonal allergy, pet allergy, hives, hay fever, allergic conjunctivitis, poison ivy allergy, oak allergy, mold allergy, drug allergy, dust allergy, cosmetic allergy, and chemical allergy).

The self-antigen expressed by a cloaked cell described herein to induce immune tolerance may be an antigen associated with the development of an autoimmune disease, such as such as Acute Disseminated Encephalomyelitis (ADEM); Acute necrotizing hemorrhagic leukoencephalitis; Addison's disease; Adjuvant-induced arthritis; Agammaglobulinemia; Alopecia areata; Amyloidosis; Ankylosing spondylitis; Anti-GBM/Anti-TBM nephritis; Antiphospholipid syndrome (APS); Autoimmune angioedema; Autoimmune aplastic anemia; Autoimmune dysautonomia; Autoimmune gastric atrophy; Autoimmune hemolytic anemia; Autoimmune hepatitis; Autoimmune hyperlipidemia; Autoimmune immunodeficiency; Autoimmune inner ear disease (AIED); Autoimmune myocarditis; Autoimmune oophoritis; Autoimmune pancreatitis; Autoimmune retinopathy; Autoimmune thrombocytopenic purpura (ATP); Autoimmune thyroid disease; Autoimmune urticaria; Axonal & neuronal neuropathies; Balo disease; Behcet's disease; Bullous pemphigoid; Cardiomyopathy; Castleman disease; Celiac disease; Celiac sprue-dermatitis; Chagas disease; Chronic fatigue immune dysfunction syndrome (CFIDS); Chronic inflammatory demyelinating polyneuropathy (CIDP); Chronic recurrent multifocal osteomyelitis (CRMO); Churg-Strauss syndrome; Cicatricial pemphigoid/benign mucosal pemphigoid; Crohn's disease; Cogans syndrome; Collagen-induced arthritis; Cold agglutinin disease; Congenital heart block; Coxsackie myocarditis; Limited scleroderma (CREST syndrome/disease); Essential mixed cryoglobulinemia; Demyelinating neuropathies; Dermatitis herpetiformis; Dermatomyositis; Devic's disease (neuromyelitis optica); Discoid lupus; Dressler's syndrome; Endometriosis; Eosinophilic esophagitis; Eosinophilic fasciitis; Erythema nodosum Experimental allergic encephalomyelitis; Experimental autoimmune encephalomyelitis; Evans syndrome; Fibromyalgia; Fibromyositis; Fibrosing alveolitis; Giant cell arteritis (temporal arteritis); Giant cell myocarditis; Glomerulonephritis; Goodpasture's syndrome; Granulomatosis with Polyangiitis (GPA) (formerly called Wegener's Granulomatosis); Graves' disease; Guillain-Barre syndrome; Hashimoto's encephalitis; Hashimoto's thyroiditis; Hemolytic anemia; Henoch-Schonlein purpura; Herpes gestationis; Hypogammaglobulinemia; Hypothyroidism; Idiopathic thrombocytopenic purpura (ITP); Idiopathic pulmonary fibrosis; IgA nephropathy; IgG4-related sclerosing disease; Immunoregulatory lipoproteins; Inclusion body myositis; Interstitial cystitis; Inflammatory bowel disease; Juvenile arthritis; Juvenile oligoarthritis; Juvenile diabetes (Type 1 diabetes); Juvenile myositis; Kawasaki syndrome; Lambert-Eaton syndrome; Leukocytoclastic vasculitis; Lichen planus; Lichen sclerosus; Ligneous conjunctivitis; Linear IgA disease (LAD); Lupus (SLE); Lyme disease, chronic; Autoimmune lymphoproliferative syndrome (ALPS); Meniere's disease; Microscopic polyangiitis; Mixed connective tissue disease (MCTD); Mooren's ulcer; Mucha-Habermann disease; Multiple sclerosis; Myasthenia gravis; Myositis; Narcolepsy; Neuromyelitis optica (Devic's); Neutropenia; Non-obese diabetes; Ocular cicatricial pemphigoid; Optic neuritis; Palindromic rheumatism; PANDAS (Pediatric Autoimmune Neuropsychiatric Disorders Associated with *Streptococcus*); Paraneoplastic cerebellar degeneration; Paroxysmal nocturnal hemoglobinuria (PNH); Parry Romberg syndrome; Parsonnage-Turner syndrome; Pars planitis (peripheral uveitis); Pemphigus; Pemphigus vulgaris; Peripheral neuropathy; Perivenous encephalomyelitis; Pernicious anemia; POEMS syndrome; Polyarteritis nodosa; Type I, II, & III autoimmune polyglandular syndromes; Polychondritis; Polymyalgia rheumatica; Polymyositis; Postmyocardial infarction syndrome; Postpericardiotomy syndrome; Progesterone dermatitis; Primary biliary cirrhosis; Primary sclerosing cholangitis; Primary agammaglobulinemia; Psoriasis; Plaque Psoriasis; Psoriatic arthritis; Idiopathic pulmonary fibrosis; Pyoderma gangrenosum; Pure red cell aplasia; Raynauds phenomenon; Reactive Arthritis; Reflex sympathetic dystrophy; Reiter's syndrome; Relapsing polychondritis; Restless legs syndrome; Retroperitoneal fibrosis; Rheumatic fever; Rheumatoid arthritis; Sarcoidosis; Schmidt syndrome; Scleritis; Scleroderma; Sclerosing cholangitis; Sclerosing sialadenitis; Sjogren's syndrome; Sperm & testicular autoimmunity; Stiff person syndrome; Subacute bacterial endocarditis (SBE); Susac's syndrome; Sympathetic ophthalmia; Systemic lupus erythematosus (SLE); Systemic sclerosis; Takayasu's arteritis; Temporal arteritis/Giant cell arteritis; Thrombocytopenic purpura (TTP); Tolosa-Hunt syndrome; Transverse myelitis; Type 1 diabetes; Ulcerative colitis; Undifferentiated connective tissue disease (UCTD); Uveitis; Vasculitis; Vesiculobullous dermatosis; Vitiligo; or Wegener's granulomatosis (now termed Granulomatosis with Polyangiitis (GPA).

Exemplary antigens associated with autoimmune diseases and conditions are provided in Table 2, below.

TABLE 2

| Autoimmune diseases and associated polypeptides containing antigens that can be expressed by cloaked cells to treat or prevent the autoimmune disease | |
|---|---|
| Autoimmune disease | Antigen |
| Achalasia | PNMA2 (Ma-2/Ta), recoverin, glutamic acid decarboxylase 65 (GAD65) |
| Addison's disease | 21-hydroxylase |
| Alopecia areata | Trichohyalin, tyrosinase-related protein 2, tyrosinase 1, tyrosinase 2, cytokeratin 16, Pro-opiomelanocortin-1 (POMC-1), tyrosine hydroxylase isoform B1, tyrosine hydroxylase isoform B2 |
| Amyloidosis | Amyloid-β, keratin, Ro/SSA, NC1 domain of Alpha-3 chain of type IV collagen, mutant transthyretin (V30M), Scl70 |
| Ankylosing spondylitis | P2RX7, chondromodulin 1, osteoglycin, melanocortin 4 receptor, osteonectin, connective tissue growth factor, glypican 3, glypican 4, Matrix Gla protein, SPARC Related Modular Calcium Binding 1 (SMOC1), interleukin 6 (IL-6), collagen I, II, III, IV, and V, Protein Phosphatase, Mg2+/Mn2+ Dependent 1A (PPM1A), 14-3-4η |
| Anti-GBM/Anti-TBM nephritis | alpha-3 chain of type IV collagen, alpha-4 chain of type IV collagen, alpha-5 chain of type IV collagen, tubulointerstitial nephritis antigen |
| Antiphospholipid syndrome | $\beta_2$-glycoprotein-I, cardiolipin phosphatidylserine |
| Autoimmune angioedema | C1 inhibitor (C1-INH) |
| Acquired hemophilia | Factor VIII |
| Autoimmune dysautonomia | Ganglionic acetylcholine receptor (α3-nicotinic AChR), M1, M2, and M3 muscarinic AChRs |
| Autoimmune encephalomyelitis | NMDA receptors, AMPA receptors, $GABA_A$ receptors, $GABA_B$ receptors, D2 receptors, Gly receptors, GAD65, Leucine Rich Glioma Inactivated 1 (LGI1), Caspr2, amphiphysin, DPPX, PCA-1, ANNA-1, Delta/Notch Like EGF Repeat Containing (DNER), mGluR1, VGCC |
| Autoimmune hepatitis | Asialoglycoprotein, asialoglycoprotein receptor, LKM-1, LKM-3, Cytochrome P450 Family 2 Subfamily D Member 6 (CYP2D6), Cytochrome P450 Family 1 Subfamily A Member 2 (CYP1A2), Cytochrome P450 Family 2 Subfamily E Member 1 (CYP2E1), Cytochrome P450 Family 3 Subfamily A Member 4 (CYP3A4), LC1, UDP-glucuronosyltransferases, formiminotransferase cyclodeaminase, actin, troponin, vimentin, tropomyosin, proteinase-3, myeloperoxidase, UGA-suppressor-tRNA-associated protein |
| Autoimmune inner ear disease (AIED) | Sulfoglucuronosyl glycolipids, HSP70, type II collagen, type IX collagen, Raf-1, major peripheral myelin protein P0, beta actin, cochlin, CTL2, cell-density enhanced protein tyrosine phosphatase-1, connexion, proteinase 3, myeloperoxidase |
| Autoimmune myocarditis | Myosin, $\beta_1$-adrendergic receptor, Muscarinic M2 acetylcholine receptor, troponin, tropomyosin, laminin. |
| Autoimmune oophoritis | Maternal antigen that embryos require (Mater/Nalp5), 21β-hydroxylase, 17α-hydroxylase, P450scc, FSH receptor, LH receptor |
| Autoimmune orchitis | Hsp60, Hsp70, hnRNP H1, Outer Dense Fiber of Sperm Tails 2 (ODF-2), phosphoglycerate kinase 1 |
| Autoimmune pancreatitis | Carbonic anhydrase-II, carbonic anhydrase-IV, lactoferrin, Hsp10, amylase-2α, plasminogen-binding protein, pancreas secretory trypsin |

TABLE 2-continued

Autoimmune diseases and associated polypeptides containing antigens that can be expressed by cloaked cells to treat or prevent the autoimmune disease

| Autoimmune disease | Antigen |
|---|---|
| | inhibitor, trypsinogen, thyroglobulin, thyroid peroxidase |
| Autoimmune retinopathy | Carbonic anhydrase II, rhodopsin, arrestin, phosphodiesterase, enolase |
| Autoimmune urticaria | FcεRIa of FCER1, IgE |
| Axonal & neuronal neuropathy (AMAN) | Gangliosides GM1, GM1b, GD1a |
| Baló's disease | Aquaporin-4 |
| Behcet's disease | Carbonic anhydrase I, carbonic anhydrase II, claudin-1, kinectin, tubulin-α-1c |
| Benign mucosal pemphigoid | Laminin-5, laminin-6, bullous pemphigoid antigen 1, bullous pemphigoid antigen 2, $\alpha_6$-integrin subunit, $\beta_4$-integrin subunit, collagen VII |
| Bullous pemphigoid | Laminin-5, laminin-6, bullous pemphigoid antigen 1, bullous pemphigoid antigen 2, $\alpha_6$-integrin subunit, $\beta_4$-integrin subunit, collagen VII |
| Castleman disease (CD) | ADAM Metallopeptidase with Thrombospondin Type 1 Motif 13 (ADAMTS13), BP180, α3 chain of type IV collagen |
| Celiac disease | Transglutaminase 2, transglutaminase 3, transglutaminase 6, actin, GM1, collagen, calreticulin, zonulin, synapsin I, ATP synthase β chain, cardiolipin, enolase α |
| Chagas disease | B1 adrenergic receptor, M2 muscarinic acetylcholine receptor |
| Chronic inflammatory demyelinating polyneuropathy (CIDP) | Contactin-1, Myelin Protein Zero (MPZ), Peripheral Myelin Protein 2 (PMP2), Peripheral Myelin Protein 22 (PMP22), gliomedin, Neural Cell Adhesion Molecule 1 (NCAM), NF140, NF186, Contactin 1 (CNTN1), CASPR1, NF155, GM1, GD1b |
| Churg-Strauss Syndrome (CSS) or Eosinophilic Granulomatosis (EGPA) | Myeloperoxidase, proteinase 3 |
| Cicatricial pemphigoid | Laminin 5, BP180, bullous pemphigoid antigen 2 |
| Cogan's syndrome | Sulfoglucuronosyl glycolipids, HSP70, type II collagen, type IX collagen, Raf-1, major peripheral myelin protein P0, beta actin, cochlin, CTL2, cell-density enhanced protein tyrosine phosphatase-1, connexion, proteinase 3, myeloperoxidase |
| Cold agglutinin disease | Cold agglutinins |
| Congenital heart block | Ro52, p200, muscarinic acetylcholine receptor, p57, α-fodrin, calreticulin, enolase α |
| Coxsackie myocarditis | Troponin, myosin, adenine nucleotide translocator |
| CREST syndrome | Scl70, Ro/SSA, La/SSb |
| Crohn's disease | Nuclear histone 1 of polymorphonuclear leukocytes, trypsin, Ompc, Cbir1, I2, major zymogen granule membrane glycoprotein 2 |
| Dermatitis herpetiformis | Epidermal transglutaminase, HLA |
| Dermatomyositis | Melanoma differentiation antigen 5, transcriptional intermediary factor 1, nuclear matrix protein 2, small ubiquitin-like modifier activating enzyme |
| Devic's disease (neuromyelitis optica) | Aquaporin-4 |
| Discoid lupus | Ro/SSA, RNP |
| Dressler's syndrome | Myosin, actin |
| Endometriosis | Alpha(2)-HSG, transferrin, carbonic anhydrase |
| Eosinophilic esophagitis (EoE) | Desmoglein 3, transglutaminase |
| Eosinophilic fasciitis | Gliadin, serum andolase |
| Erythema nodosum | Thyroglobulin, HLA-B27 |
| Essential mixed cryoglobulinemia | Rheumatoid factor, GOR |
| Evans syndrome | Glycophorin A, Kpb antigen of Kell blood group system |

TABLE 2-continued

Autoimmune diseases and associated polypeptides containing antigens that can be expressed by cloaked cells to treat or prevent the autoimmune disease

| Autoimmune disease | Antigen |
| --- | --- |
| Fibromyalgia | Thyroid peroxidase, thyroid stimulating hormone, thyroglobulin |
| Fibrosing alveolitis | DNA topoisomerase II, thyroglobulin |
| Giant cell arteritis (temporal arteritis) | Ferritin, lamin C, lamin A, vinculin, annexin 5, 14-3-3 (γ, ε and ζ), cardiolipin |
| Giant cell myocarditis | Myosin |
| Glomerulonephritis | C3 convertase, C1q, complement factors B & H |
| Goodpasture's syndrome | Alpha 3 chain of type IV collagen |
| Granulomatosis with Polyangiitis | Proteinase 3, myeloperoxidase |
| Graves' disease | Thyroid peroxidase, thyrotropin receptor, thyroglobulin |
| Guillain-Barre syndrome | Neurofascin-186 (NF186), gliomedin, contactin, neuronal cell adhesion molecule (NrCAM), ganglioside GM1, ganglioside GD1a, ganglioside GQ1b, ganglioside GT1a |
| Hashimoto's thyroiditis | Thyroid peroxidase, thyroglobulin |
| Hemolytic anemia | Red blood cell antigens |
| Henoch-Schonlein purpura (HSP) | Cardiolipin, rheumatoid factor |
| Herpes gestationis or pemphigoid gestationis (PG) | BP180 |
| IgA Nephropathy | Protein Kinase D1 (PRKD1), Matrilin 2 (MATN2), DEAD-Box Helicase 17 (DDX17), Ubiquitin Conjugating Enzyme E2 W (UBE2W), Cyclin Dependent Kinase Inhibitor 1B (CDKN1B), Superoxide dismutase 2 (SOD2), ICQK, Basic Leucine Zipper Nuclear Factor 1 (BLZF1), Ephrin A3 (EFNA3), Eukaryotic Translation Initiation Factor 4A2 (EIF4A2), FLII actin remodeling protein (FLII), LIM And Calponin Homology Domains 1 (LIMCH1), MAGE Family Member A4 (MAGEA4), Myocyte Enhancer Factor 2D (MEF2D), MLLT6, PHD Finger Containing (MLLT6), Cytokine Induced Apoptosis Inhibitor 1 (CIAPIN1), GDP Dissociation Inhibitor 2 (GDI2), Heat Shock Protein Family A (Hsp70) Member 8 (HSPA8), Serpin family A member 5 (SERPINA5), Transglutaminase 1 (TGM1) |
| IgG4-related sclerosing disease | Carbonic anhydrase II, carbonic anhydrase IV, amylase-alpha-2α lactoferrin, rheumatoid factor, pancreatic trypsinogen, pancreatic secretory trypsin inhibitor |
| Immune thrombocytopenic purpura (ITP) | Glycoprotein IIb/IIIa (GPIIb/IIIa) and GPIb/IX |
| Inclusion body myositis (IBM) | Cytosolic 5'-nucleotidase 1A |
| Interstitial cystitis (IC) | Muscarinic M3 receptor |
| Juvenile arthritis | Rheumatoid factor, Cytosolic 5'-nucleotidase 1A, transthyretin |
| Juvenile diabetes (Type 1 diabetes) | Insulin, glutamic acid decarboxylase, protein tyrosine phosphatase, insulinoma antigen 2 protein, zinc transporter 8 |
| Juvenile myositis (JM) | Cytosolic 5'-nucleotidase 1A, p155/140, signal recognition particle, Mi2, synthetase, MJ |
| Kawasaki disease | Peroxiredoxin, cardiac myosin, 4-trimethylaminobutyraldehyde dehydrogenase |
| Lambert-Eaton syndrome | α(1) or β(3) subunits of voltage gated calcium channels |
| Leukocytoclastic vasculitis | Synthetase, proteinase 3, myeloperoxidase |
| Lichen planus | Desmogleins 1 and 3, thyroglobulin, thyroid peroxidase |
| Lichen sclerosus | Extracellular matrix protein 1 |
| Linear IgA disease (LAD) | Bullous pemphigoid antigen 180 (BP180), bullous pemphigoid antigen 230 (BP230), LABD97 (97 kDa fragment of bullous pemphigoid antigen 180), |

TABLE 2-continued

Autoimmune diseases and associated polypeptides containing antigens that can be expressed by cloaked cells to treat or prevent the autoimmune disease

| Autoimmune disease | Antigen |
|---|---|
| | LAD-1 (120 kDa fragment of bullous pemphigoid antigen 180) |
| Lupus | U1A, Sm/RNP, Ro/La, thyroglobulin, Protein Tyrosine Phosphatase Non-Receptor Type 22 (PTPN22), Bruton's tyrosine kinase, Lyn tyrosine kinase, B-Cell activating factor, Ro/SSA |
| Lyme disease chronic | CK10, LFA-1, enolase, Matrix metalloproteinase 10 (MMP10), ECGF, beta-2-glycoprotein-1, cardiolipin |
| Meniere's disease | Hsp70, 68-kD inner ear protein, myelin peroxidase zero, thyroid peroxidase, Immunoglobulin Heavy Constant Gamma 1 (IGHG1), Regulator Of G Protein Signaling 10 (RGS10), C2orf34, SH3 Domain Containing GRB2 Like, Endophilin B1 (SH3GLB1), Calcium/Calmodulin Dependent Protein Kinase IV (CAMK4), GSG1 Like (GSG1L), NIMA Related Kinase 7 (NEK7), Neural Cell Adhesion Molecule 2 (NCAM2), Aminoacylase 1 (ACY1) |
| Microscopic polyangiitis (MPA) | Proteinase 3, myeloperoxidase |
| Mixed connective tissue disease (MCTD) | U1 ribonucleoprotein (U1-RNP) |
| Mooren's ulcer | Cornea-associated antigen |
| Multifocal Motor Neuropathy (MMN) or MMNCB | Neurofascin-186, gliomedin, GM1 |
| Multiple sclerosis | Myelin oligodendrocyte glycoprotein (MOG) |
| Myasthenia gravis | Nicotinic acetylcholine receptor, LDL Receptor Related Protein 4 (LRP4), Muscle Associated Receptor Tyrosine Kinase (MuSK), rapsyn, titin, myofibrillar protein, Ryanodine receptor (RyR), Kv1.4 voltage-gated potassium channel |
| Myositis | Cytosolic 5'-nucleotidase 1A, p155/140, signal recognition particle, Mi2, synthetase, MJ, TIF1-gamma, NXP-2, MDA5, SAE, 3-Hydroxy-3-Methylglutaryl-CoA Reductase (HMGCR), Pm/Sc, Ku |
| Narcolepsy | Methyltransferase-like 22, 5'-nucleotidase cytosolic I, Poly(ADP-Ribose) Polymerase Family Member 3 (PARP3), AT-Rich Interaction Domain 4B (ARID4B), Glutaminase 2 (GLS2), Cyclin Dependent Kinase Like 1 (CDKL1) |
| Neonatal Lupus | Ro/SSA, La/SSB, U1-RNP |
| Neuromyelitis optica | Aquaporin-4, thyroid peroxidase |
| Neutropenia | FcγRIIIb, gp50-64, gp70-95, Integrin Subunit Alpha M (CD11b), Integrin Subunit Alpha L (CD11a) |
| Ocular cicatricial pemphigoid | B4-integrin, laminin 5 $\alpha 3$ subunit |
| Optic neuritis | Aquaporin-4, myelin oligodendrocyte glycoprotein |
| Palindromic rheumatism (PR) | Enolase, fibrin, vimentin, keratin, filaggrin, fibrinogen |
| PANDAS | Dopamine D2 receptor, Ca2+/calmodulin-dependent protein kinase II (CamKII) |
| Paraneoplastic cerebellar degeneration (PCD) | mGluR1, DNER, Yo |
| Paroxysmal nocturnal hemoglobinuria (PNH) | P & I antigens of red blood cells |
| Parry Romberg syndrome | Histone proteins |
| Pars planitis (peripheral uveitis) | Hsp70 |
| Parsonage-Turner syndrome | GA1 |
| Pemphigus | Desmocollin 1 (DSC1), Desmocollin 3 (DSC3), ATPase Secretory Pathway Ca2 +Transporting 1 (ATP2C1), Plakophilin 3 (PKP3), Muscarinic Acetylcholine Receptor M3 (CHRM3), Collagen Type XXI Alpha 1 Chain (COL21A1), Annexin A8 Like 1 (ANXA8L1), cluster of differentiation 88 |

TABLE 2-continued

Autoimmune diseases and associated polypeptides containing antigens that can be expressed by cloaked cells to treat or prevent the autoimmune disease

| Autoimmune disease | Antigen |
| --- | --- |
| | (CD88), Cholinergic Receptor Nicotinic Epsilon Subunit (CHRNE), CD33 molecule (CD33), GP1BA, Cholinergic Receptor Nicotinic Delta Subunit (CHRND), Solute Carrier Family 36 Member 4 (SLC36A4), CD1b Molecule (CD1B), Fc Fragment Of IgG Receptor IIa (CD32), Cadherin 8 (CDH8), Cadherin 9 (CDH9), PMP22, Major Histocompatibility Complex, Class I, E (HLA-E), NADH:Ubiquinone Oxidoreductase Core Subunit S1 (NDUFS1), Cytochrome B5 Type B (CYB5B), SO2, Pyruvate Dehydrogenase E1 Alpha 1 Subunit (PDHA1), FH, ATPase Secretory Pathway Ca2+Transporting 1 (ATP2C1) |
| Peripheral neuropathy | Myelin associated glycoprotein (MAG), ganglioside GM1, Hu, ganglioside GQ1b |
| Perivenous encephalomyelitis | Myelin oligodendrocyte glycoprotein |
| Pernicious anemia (PA) | IF-R7 |
| POEMS syndrome | C3 convertase |
| Polyarteritis nodosa | Proteinase 3, phospholipid cofactor, cardiolipin, β2-glycoprotein I phosphatidylserine-prothrombin complex |
| Polyglandular syndromes type I, II, III | 17 alpha-Hydroxylase, side-chain-cleavage enzyme, GAD65, thyroperoxidase, thyroglobulin, H+/K(+)-ATPase |
| Polymyalgia rheumatica | Ferritin |
| Polymyositis | Aminoacyl-tRNA synthetase, Mi-2, Jo-1, helicase/histone deacetylase protein complex, TIF1-γ, MDA5, NXP2, SAE, HMGCR |
| Postpericardiotomy syndrome | Cardiolipin |
| Primary biliary cirrhosis | E2 subunit of pyruvate dehydrogenase |
| Primary sclerosing cholangitis | M2, M4, M8, M9, SP100, PML, NDP52, SP140, GP120, P62, laminin, laminin B receptor, CENP-A, CENP-B, CENP-C, CENP-O, Scl70, Sm, SSA, SSb, RNP, Jo-1, U1-RNP |
| Progesterone dermatitis | Progesterone |
| Psoriasis | Rheumatoid factor, calpastatin, fibrillin, desmocollin, keratin, nebulin-related anchoring protein |
| Psoriatic arthritis | Rheumatoid factor, calpastatin, fibrillin, desmocollin, keratin, nebulin-related anchoring protein |
| Pure red cell aplasia (PRCA) | Erythropoietin |
| Raynaud's phenomenon | Synthetase, cytokeratin 10 |
| Reactive Arthritis | Human leukocyte antigen B27 (HLA B27) |
| Reflex sympathetic dystrophy | α1-adrenaline receptor |
| Relapsing polychondritis | Collagens II, IX, XI |
| Rheumatic fever | Myosin, glycogen, Vascular cell adhesion molecule 1 (VCAM-1) |
| Rheumatoid arthritis | Rheumatoid factor, Sa, glucose-6-phosphate isomerase, collagen I and II, Hsp65, Bip, a enolase, calpastatin, RA33/hnRNP A2, filaggrin, fibrin, fibrinogen, vimentin |
| Sarcoidosis | Ro, Scl-70, cardiolipin, La |
| Schmidt syndrome | Transglutaminase, 21-hydroxylase, thyroglobulin, thyroperoxidase |
| Scleritis | Laminin, keratin |
| Scleroderma | Sc1-70, U1-RNP, Th/To, RNAP I, II, Ill |
| Sjögren's syndrome | Ro/SSA |
| Sperm & testicular autoimmunity | Hsp70, Hsp70-2, ER60, caspase-3, proteasome complex component 2 and zeta chain, SAGA-1 |
| Stiff person syndrome (SPS) | GAD65, glycine receptor α1, $GABA_A$ receptor associated protein, amphiphysin |

TABLE 2-continued

Autoimmune diseases and associated polypeptides containing antigens that can be expressed by cloaked cells to treat or prevent the autoimmune disease

| Autoimmune disease | Antigen |
|---|---|
| Subacute bacterial endocarditis (SBE) | Proteinase 3, rheumatoid factor |
| Sympathetic ophthalmia (SO) | Retinal soluble antigen, rhodopsin, interphotoreceptor retinoid-binding protein, recoverin |
| Takayasu's arteritis | Ferritin, cardiolipin |
| Tolosa-Hunt syndrome (THS) | Ganglioside GQ1b |
| Transverse myelitis | Aquaporin-4, Ro/SSA |
| Type 1 diabetes | Insulin, Glutamic acid decarboxylase (GAD, e.g., GAD65) |
| Ulcerative colitis (UC) | Tropomyosin (e.g., tropomyosin 5), histone H1, cathepsin G, elastase, β-glucuronidase, lactoferrin, bactericidal permeability increasing (BPI) protein, α-Enolase, high-mobility group (HMG)-1, HMG-2 |
| Undifferentiated connective tissue disease (UCTD) | RNP, Ro/SSA |
| Uveitis | Melanin associated antigen (MAA), retinal arrestin, interphotoreceptor retinoid binding protein (IRBP) |
| Vasculitis | β2 glycoprotein 1 (β2-GPI) |
| Vitiligo | Tyrosinase (Tyr), tyrosinase-related protein 1 (TRP1), tyrosinase-related protein 2 (TRP2), MART-1/Melan A, Pmel17/gp100 |
| Vogt-Koyanagi-Harada Disease | Tyrosinase (Tyr), tyrosinase-related protein 1 (TRP1), tyrosinase-related protein 2 (TRP2), MART-1/Melan A, Pmel17/gp100 |

Treatment of Multiple Sclerosis

In one example, the cloaked cells described herein can be used to treat Multiple Sclerosis (MS). MS is a disease of the brain and spinal cord characterized by immune system-induced damage to the myelin sheath surrounding neurons. T cells in subjects with MS react to MOG, a protein expressed by myelinating oligodendrocytes and Schwann cells. To treat a subject suffering from MS, cloaked cells can be modified to express MOG or a fragment of MOG that induces an inflammatory response (e.g., activation, release of pro-inflammatory cytokines, or cytotoxicity) in T cells isolated from the subject. Cloaked cells can be modified to produce MOG by expression of a transgene encoding MOG operably linked to a constitutive or inducible promoter. Cloaked cells (e.g., stem cells) that express MOG can be directly administered to a subject or differentiated into oligodendrocytes or Schwann cells prior to administration using methods known by those of skill in the art, or isolated oligodendrocytes or Schwann cells (e.g., oligodendrocytes or Schwann cells isolated from a human subject, animal model, or cell line) can be modified to express cloaking transgenes and MOG. Eight hundred million to three billion cloaked cells expressing MOG (e.g., $8\times10^8$, $9\times10^8$, $1\times10^9$, $2\times10^9$, or $3\times10^9$ cloaked stem cells, oligodendrocytes, or Schwann cells) can be injected subcutaneously in a subject to create a cloaked subcutaneous tissue that produces MOG to induce immune tolerance to MOG for the treatment of MS, or $2.5\times10^4$ to $1\times10^5$ cloaked cells expressing MOG (e.g., $2.5\times10^4$, $3\times10^4$, $4\times10^4$, $5\times10^4$, $6\times10^4$, $7\times10^4$, $8\times10^4$, $9\times10^4$, or $1\times10^5$ cloaked cells) can be administered (e.g., injected) to the spinal cord or to a specific brain region to induce immune tolerance to MOG for the treatment of MS. This therapy may lead to the deactivation or death of T cells that react to MOG, preventing further damage to myelinating cells in the subject.

Treatment of Type 1 Diabetes

The cloaked cells described herein can also be used to treat type 1 diabetes. Type 1 diabetes results from immune system-induced damage to the insulin-producing islet beta cells of the pancreas. Subjects with type 1 diabetes often present with auto-antibodies directed against beta cell epitopes, such as GAD65 and insulin. To treat a subject suffering from type 1 diabetes, cloaked cells can be modified to express insulin and/or GAD65, or a fragment thereof that induces an inflammatory response (e.g., activation, release of pro-inflammatory cytokines, or cytotoxicity) in an immune cell isolated from the subject. Cloaked cells can be modified to produce insulin and/or GAD65 by expression of transgenes encoding insulin and/or GAD65 operably linked to a constitutive or inducible promoter. Cloaked cells (e.g., stem cells) that express insulin and/or GAD65 can be differentiated into pancreatic beta cells prior to administration using methods known by those of skill in the art or the cloaked cells can be administered without differentiation. Eight hundred million to three billion cloaked cells (e.g., $8\times10^8$, $9\times10^8$, $1\times10^9$, $2\times10^9$, or $3\times10^9$ cloaked cells) expressing insulin and/or GAD65 to can be injected subcutaneously in a subject to create a cloaked subcutaneous tissue that produces insulin and/or GAD65 for treating type 1 diabetes. This therapy may reduce the autoimmunity to insulin and/or GAD65 in the subject, preventing further damage to pancreatic beta cells and allowing other therapies that restore pancreatic beta cell function to work more effectively.

Methods of Inducing an Immune Response to a Non-Self Antigen

The cloaked cells described herein may also be used in a cell-based method of immunization. The method involves two steps: 1) administering to a subject a cloaked cell (e.g., a cell that the immune system would reject or attack as foreign if not cloaked, e.g., an allogeneic cell) to induce immune tolerance to the cloaked cell, and 2) administering an uncloaked cell of the same type that expresses a polypeptide containing a non-self antigen (e.g., one or more polypeptides containing a non-self antigen, e.g., 1, 2, 3, 4, 5, or more of such polypeptides) that is not endogenous to the uncloaked cell to induce an immune response to the non-self antigen. Administration of the cloaked cell without the non-self antigen tolerizes the subject's immune response to the cell and the proteins and antigens the cell expresses or contains. Upon administration of the uncloaked cell of the same type that is modified to express a polypeptide containing a non-self antigen, the subject's immune system will mount a specific immune response against the non-self antigen that is expressed by the uncloaked cell as the immune system has not previously encountered the non-self antigen. The subject's immune system may proceed to produce antibodies directed to the non-self antigen, creating immunity to the non-self antigen should the subject be exposed to the antigen in the future. This targeted approach allows the immune system to respond specifically to the one or more non-self antigen expressed by the uncloaked cell, a notable improvement over cell-based vaccines, such as cellular cancer vaccines, in which both normal cellular antigens and one or more tumor antigens are presented to the immune system with the potential for the large number of normal cellular immunogens to compete with or dilute out the desired response to the one or more tumor antigens. This method may be used to treat a subject in need of immunity to a non-self antigen (e.g., a cancer antigen, a viral antigen, a bacterial antigen, a parasitic antigen, or a fungal antigen), such as a subject at risk of developing cancer (e.g., a subject at risk of developing cancer due to genetic mutation, family history, or environmental factors), or a subject at risk of viral, bacterial, fungal, or parasitic infection (e.g., at risk due to geographic location or other environmental factors).

The cloaked cell administered to the subject in the initial tolerization phase of the method may be any allogeneic cloaked cell described herein. For example, the cloaked cell may be a stem cell (e.g., an ES cell, an adult stem cell, an iPSC, a tissue-specific stem cell, a hematopoietic stem cell, a mesenchymal stem cell, an endothelial stem cell, an epithelial stem cell, an adipose stem or progenitor cell, a germline stem cell, a lung stem or progenitor cell, a mammary stem cell, an olfactory adult stem cell, a hair follicle stem cell, a multipotent stem cell, an amniotic stem cell, a cord blood stem cell, or a neural stem or progenitor cell), a somatic cell, a cell derived from a cell line, a cell amenable to genome editing, and/or a source of therapeutic cell type (e.g., a cell that can be differentiated into a lineage restricted cell for cell therapy, or a cell of a desired target tissue). In some embodiments, the cell is a skin, heart, brain or spinal cord, liver, lung, kidney, pancreas, bladder, bone marrow, spleen, intestine, or stomach cell. In some embodiments, the cell is a fibroblast, an epithelial cell, or an endothelial cell. The cell may be a vertebrate cell, for example, a mammalian cell, such as a human or mouse cell. The cell may be a cell from a cell line. The cell may be a syngeneic cell. The cell may be cloaked by modifying the cell to express one or more (e.g., two, three, four, five, six, seven, or all eight) of PD-L1, HLA-G (H2-M3), Cd47, Cd200, FASLG (FasL), Ccl21 (Ccl21b), Mfge8, and Serpin B9 (Spi6). In some embodiments, the cloaked cell expresses all eight of PD-L1, HLA-G (H2-M3), Cd47, Cd200, FASLG (FasL), Ccl21 (Ccl21b), Mfge8, and Serpin B9 (Spi6). The cell may be further modified to express one or more of TGF-β, Cd73, Cd39, Lag3, Il1r2, Ackr2, Tnfrsf22, Tnfrs23, Tnfrsf10, Dad1, and IFNγR1 d39. The cell can be modified to express the cloaking transgenes using the methods described herein above (e.g., transfection, viral infection, or gene editing) or using other methods known to those of skill in the art.

The uncloaked cell is a cell of the same type derived from the same source as the cloaked cell, and it can be modified to express a polypeptide containing a non-self antigen (e.g., an antigen that is not endogenous to the subject and that is not expressed by the uncloaked cell) using the methods described herein above (e.g., transfection, viral infection, or gene editing) or using other methods known to those of skill in the art. The non-self antigen provided by the uncloaked cell may be a disease-associated antigen (e.g., a bacterial, viral, parasitic, or fungal protein, such as a bacterial, viral, fungal, or parasitic cell surface protein). The non-self antigen may also be a cancer antigen. Any disease-associated antigen that is functionally inert (e.g., not capable of inducing disease when expressed by the uncloaked cell) may be presented to the immune system of a subject by the methods described herein to promote an immune response in the subject (e.g., to induce the subject's immune system to produce antibodies in response to the non-self antigen).

The uncloaked cell expressing a polypeptide containing a non-self antigen may be administered with an adjuvant, such as alum, AS04, or AS03, to further stimulate the immune response in a subject.

The uncloaked cell may be modified to express the polypeptide containing the antigen at an expression level comparable to the expression level of a housekeeping polypeptide (e.g., β-actin, GAPDH, or Rosa26). Robust expression of the polypeptide can be achieved using strong promoters, such as CAGG or CMV or through the use of a doxycycline inducible system (e.g., a doxycycline inducible TRE).

The cloaked cell can be injected as a circulating cell or injected subcutaneously to produce a cloaked subcutaneous tissue. In some embodiments, one million to one hundred billion cloaked cells (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{16}$, $2\times10^{16}$, $3\times10^{16}$, $4\times10^{10}$, $5\times10^{10}$, $6\times10^{10}$, $7\times10^{10}$, $8\times10^{10}$, $9\times10^{10}$, or $1\times10^{11}$ cloaked cells) are administered to a subject to induce immune tolerance to the cloaked cell. The uncloaked cell expressing the polypeptide containing the non-self antigen can be administered after the immune system of the subject has been tolerized to the cloaked cell. To determine whether the immune system of the subject has been tolerized to the cloaked cell, an immune cell isolated from the subject can be exposed to an uncloaked cell and the response of the immune cell can be measured (e.g., an immune cell, such as a dendritic cell, macrophage, T cell (e.g., a cytotoxic T cell/CD8+ T cell, T helper cell/CD4+ T cell, or regulatory T cell/Treg), B cell, monocyte, granulocyte (e.g., eosinophil, mast cell, neutrophil, or basophil), natural killer (NK) cell, or innate lymphoid cell isolated from the subject can be contacted with the uncloaked cell in vitro, and a response of the immune cell (e.g., immune cell activation, differentiation, polarization, proliferation, migration, pro-inflammatory cytokine production, degranulation, phagocytosis, or cytotoxicity) can be measured). If the immune cell isolated from the subject does not mount an immune response against the uncloaked cell (e.g., if the immune cell does not become more activated or exhibit a cytotoxic, pro-inflammatory, or phagocytic response to the uncloaked cell), the subject's immune system has been successfully tolerized to the cell. The uncloaked cell expressing a polypeptide containing a non-self antigen may be administered to the subject after administration of the cloaked cell (e.g., 1 day, 2 days, 3 days, 4 days, 5 days, 6 days, 1 week, 2 weeks, 3 weeks, 1 month, 2 months, 3 months, 4 months, 5 months, 6 months, 9 months, 1 year or more after the administration of the cloaked cell). The uncloaked cell expressing a polypeptide containing a non-self antigen can be injected as a circulating cell or injected subcutaneously to produce an uncloaked subcutaneous tissue. In some embodiments, one million to one hundred billion uncloaked cells expressing a non-self antigen (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ uncloaked cells expressing a non-self antigen) are administered to a subject to stimulate an immune response to the non-self antigen. A blood sample can be collected from the subject to determine whether the subject's immune system has produced antibodies directed against the non-self antigen.

The cloaked cells can be removed after the subject's immune system has been tolerized to the cloaked cells (e.g., 1 week, 1 month, 2 months, 3 months, 4 months, 5 months, 6 months, 9 months, 1 year, 2 years or more after the subject's immune system has been tolerized to the cloaked cells). The cloaked cells can be removed before or after the administration of the uncloaked cells expressing a polypeptide containing a non-self antigen. The cloaked cells can be removed surgically (e.g., in embodiments in which the cloaked cells formed a tissue, such as a cloaked subcutaneous tissue, the tissue can be surgically removed). In embodiments in which the cloaked cells were modified to contain one or more systems for regulating cell division (e.g., modified to be FAILSAFE™ cells, e.g., by linking the expression of a CDL to an ALINK or EARC), the cloaked cells can be removed by administering an inducer of a negative selectable marker (e.g., the ALINK) or by ceasing to administer an activator of an inducible activator-based gene expression system (e.g., the EARC). The uncloaked cells expressing the polypeptide containing the non-self antigen can be removed after the subject's immune system has generated antibodies directed against the non-self antigen (e.g., 1 week, 1 month, 2 months, 3 months, 4 months, 5 months, 6 months, 9 months, 1 year, 2 years or more after the subject's immune system has generated antibodies directed against the non-self antigen). The uncloaked cells can be removed surgically (e.g., in embodiments in which the uncloaked cells formed a tissue, such as an uncloaked subcutaneous tissue, the tissue can be surgically removed). In embodiments in which the uncloaked cells were modified to contain one or more systems for regulating cell division (e.g., modified to be FAILSAFE™ cells, e.g., by linking the expression of a CDL to an ALINK or EARC), the uncloaked cells can be removed by administering an inducer of a negative selectable marker (e.g., the ALINK) or by ceasing to administer an activator of an inducible activator-based gene expression system (e.g., the EARC).

In some embodiments, the non-self antigen is an antigen of a bacterial pathogen (e.g., an antigen derived from *Acinetobacter* spp. (*Acinetobacter baumanni*), *Bacteroides distasonis, Bacteroides fragilis, Bacteroides ovatus, Bacteroides thetaiotaomicron, Bacteroides uniformis, Bacteroides vulgatus, B. cepacia, Citrobacter freundii, Citrobacter koseri, Clostridium clostridioforme, Clostridium perfringens, C. sordellii, Enterobacter aerogenes, Enterobacter cloacae, Enterococcus faecalis, Enterococcus* spp. (vancomycin susceptible and resistant isolates), *Escherichia coli* (including ESBL and KPC producing isolates), *Eubacterium lentum, Fusobacterium* spp., *Haemophilus influenzae* (including beta-lactamase positive isolates), *Haemophilus parainfluenzae, Klebsiella pneumoniae* (including ESBL and KPC producing isolates), *Klebsiella oxytoca* (including ESBL and KPC producing isolates), *Legionella pneumophilia, Moraxella catarrhalis, Morganella morganii, Mycoplasma* spp., *Peptostreptococcus* spp., *Porphyromonas saccharolytica, Prevotella bivia, Proteus mirabilis, Proteus vulgaris, Providencia rettgeri, Providencia stuartii, Pseudomonas aeruginosa, Serratia marcescens, Streptococcus anginosus, Staphylococcus aureus* (methicillin susceptible and resistant isolates), *Staphylococcus epidermidis* (methicillin susceptible and resistant isolates), *Stenotrophomonas maltophilia, Streptococcus agalactiae, Streptococcus constellatus, Streptococcus pneumoniae* (penicillin susceptible and resistant isolates), *Streptococcus pyogenes*, or *Streptococcus pyogenes*). The bacterial antigen may also be derived from *Mycobacterium tuberculosis, Mycobacterium bovis, Mycobacterium africanum, Mycobacterium microti, Mycobacterium leprae, Salmonella typhimurium, Francisella tularensis, Brucella, Burkholderia mallei, Yersinia pestis, Corynebacterium diphtheria, Neisseria meningitidis, Bordetella pertussis, Clostridium tetani*, or *Bacillus anthracis*. Non-limiting examples of bacterial antigens include 10.4, 85A, 85B, 86C, CFP-10, Rv3871, and ESAT-6 antigens of *Mycobacterium;* 0, H, and K antigens of *E. coli*; and protective antigen (PA) of *Bacillus anthracis.*

The non-self can be a viral antigen, which may be derived from a virus of a viral family selected from the group consisting of Retroviridae, Flaviviridae, Arenaviridae, Bunyaviridae, Filoviridae, Togaviridae, Poxviridae, Herpesviridae, Orthomyxoviridae, Coronaviridae, Rhabdoviridae, Paramyxoviridae, Picornaviridae, Hepadnaviridae, Papillomaviridae, Parvoviridae, Astroviridae, Polyomaviridae, Calciviridae, and Reoviridae. The virus may be, e.g., human immunodeficiency virus (HIV), human papillomavirus (HPV), hepatitis A virus (Hep A), hepatitis B virus (HBV), hepatitis C virus (HCV), *Variola major, Variola minor*, monkeypox virus, measles virus, rubella virus, mumps virus, varicella zoster virus (VZV), poliovirus, rabies virus, Japanese encephalitis virus, herpes simplex virus (HSV), cytomegalovirus (CMV), rotavirus, influenza, Ebola virus, yellow fever virus, Zika virus, or Marburg virus. Non-limiting examples of viral antigens include Gag, Pol, Nef, Tat, Rev, Vif, Vpr, or Vpu of HIV and other retroviruses (see, e.g., U.S. Pub. No. 2012/0076812, incorporated by reference herein); 9D antigen of HSV; Env of all envelope protein-containing viruses. For example, the viral antigen may be an Env protein or a structured protein. In a particular example, the viral antigen may be an HIV or Zika virus Env protein. The viral antigen may also be a Gag, Pol, Env, Nef, Tat, Rev, Vif, Vpr, or Vpu protein.

The non-self antigen can be a parasitic antigen, which may be derived from *Toxoplasma gondii, Plasmodium falciparum, Plasmodium vivax, Plasmodium ovale, Plasmodium malariae, Trypanosoma* spp., or *Legionella* spp. Non-limiting examples of parasitic antigens include circumsporozoite (CS) protein, gamete surface proteins Pfs230 and Pfs48/45, and Liver Specific Antigens 1 or 3 (LSA-1 or LSA-3) of *Plasmodium falciparum.*

In some embodiments, the non-self antigen is an antigen of a fungal pathogen (e.g., an antigen derived from a mold pathogen, such as one from phylum Ascomycota (e.g., *Ajellomyces* spp., *Alternaria* spp., *Aschersonia* spp., *Aspergillus* spp., *Arthroderma* spp., *Ascochyta* spp., *Bipolaris* spp., *Blastomyces* spp., *Botryotinia* spp., *Chaetomium* spp., *Cladosporium* spp., *Coccidioides* spp., *Curvularia* spp., *Emericella* spp., *Emmonsia* spp., *Epicoccum* spp., *Exophiala* spp., *Fusarium* spp., *Geomyces* spp., *Geotrichum* spp., *Gibberella* spp., *Histoplasma* spp., *Magnaporthe* spp., *Metarhizium* spp., *Monascus* spp., *Mycospaerella* spp., *Nectria* spp., *Neosartorya* spp., *Neurospora* spp., *Paecilomyces* spp., *Paracoccidioides* spp., *Penicillium* spp., *Phaeosphaeria* spp., *Phialemonium* spp., *Podospora* spp., *Pyrenophora* spp., *Sclerotinia* spp., *Scopulariopsis* spp., *Sporothrix* spp., *Stachybotrys* spp., *Stemphylium* spp., *Talaromyces* spp., *Trichophyton* spp., *Trichothecium* spp., *Tricoderma* spp., *Tuber* spp., *Uncinocarpus* spp., or *Verticillium* spp.), phylum Basidomycota (e.g., *Moniliophthora* spp., *Sporobolomyces* spp., *Trichosporon* spp., *Ustilago* spp., *Cryptococcus* spp. or *Rhodotorula* spp.), phylum Chytridiomycota, phylum Zygomycota (e.g., *Absidia* spp., *Amylomyces* spp, *Pilaira* spp., *Rhizomucor* spp., *Rhizopus* spp., or *Zygomycetes* spp.), or phylum Oomycota in the Stramenopila kingdom). The fungal antigen may be from *Aspergillus, Blastomyces dermatitidis, Candida, Coccidioides immitis, Cryptococcus neoformans, Histoplasma capsulatum* var. *capsulatum, Paracoccidioides brasiliensis, Sporothrix schenckii, Zygomycetes* spp., *Absidia corymbifera, Rhizomucor pusillus*, or *Rhizopus arrhizus*. Non-limiting examples of fungal antigens include any cell wall mannoprotein (e.g., Afmp1 of *Aspergillus fumigatus*) or surface-expressed glycoprotein (e.g., SOWgp of *Coccidioides immitis*).

The non-self antigen can be a cancer antigen, which may be derived from a carcinoma, lymphoma, blastoma, sarcoma, and leukemia or lymphoid malignancies. For example, the cancer antigen can be derived from a leukemia, lymphoma, liver cancer, bone cancer, lung cancer (such as small-cell lung cancer, non-small-cell lung cancer, adenocarcinoma of the lung, and squamous carcinoma of the lung), brain cancer, bladder cancer (e.g., urothelial bladder cancer (UBC), muscle invasive bladder cancer (MIBC), or BCG-refractory non-muscle invasive bladder cancer (NMIBC)), gastrointestinal cancer (such as non-metastatic or metastatic colorectal cancer, pancreatic cancer, gastric cancer, esophageal cancer, hepatocellular cancer, cholangiocellular cancer, oral cancer, or lip cancer), urogenital cancer (such as hormone sensitive or hormone refractory prostate cancer, renal cell cancer, bladder cancer, or penile cancer), breast cancer (e.g., triple-negative breast cancer, triple-positive breast cancer, HER2-negative breast cancer, HER2-positive breast cancer, estrogen receptor-positive breast cancer, estrogen receptor-negative breast cancer, progesterone receptor-positive breast cancer, progesterone receptor-negative breast cancer, ductal carcinoma in situ (DCIS), invasive ductal carcinoma, invasive lobular carcinoma, inflammatory breast cancer, Paget disease of the nipple, or phyllodes tumor), cardiac cancer, gynecological cancer (such as ovarian cancer, cervical cancer, endometrial cancer), uterine cancer, head and neck cancer (e.g., head and neck squamous cell cancer), gallbladder cancer, laryngeal cancer, lip and oral cavity cancer, ocular cancer, melanoma, pancreatic cancer, prostate cancer (such as castration-resistant prostate cancer (CRPC)), colorectal cancer, testicular cancer, CNS cancer including malignant glioma, astrocytoma, retinoblastoma, and brain metastases, throat cancer, skin cancer (such as malignant melanoma, basal and squamous cell skin cancer, Merkel Cell Carcinoma, lymphoma of the skin, Kaposi Sarcoma), thyroid cancer, bone and soft tissue sarcoma, or hematologic neoplasia (such as multiple myeloma, acute myelogenous leukemia, chronic myelogenous leukemia, myelodysplastic syndrome, acute lymphoblastic leukemia, Hodgkin's lymphoma). The cancer antigen can also be derived from an acute lymphoblastic leukemia (ALL), acute myeloid leukemia (AML), chronic lymphocytic leukemia (CLL), chronic myelogenous leukemia (CML), adrenocortical carcinoma, AIDS-related lymphoma, primary CNS lymphoma, anal cancer, appendix cancer, astrocytoma, atypical teratoid/rhabdoid tumor, basal cell carcinoma, bile duct cancer, extrahepatic cancer, ewing sarcoma family, osteosarcoma and malignant fibrous histiocytoma, central nervous system embryonal tumors, central nervous system germ cell tumors, craniopharyngioma, ependymoma, bronchial tumors, burkitt lymphoma, carcinoid tumor, primary lymphoma, chordoma, chronic myeloproliferative neoplasms, colon cancer, extrahepatic bile duct cancer, ductal carcinoma in situ (DCIS), endometrial cancer, ependymoma, esophageal cancer, esthesioneuroblastoma, extracranial germ cell tumor, extragonadal germ cell tumor, fallopian tube cancer, fibrous histiocytoma of bone, gastrointestinal carcinoid tumor, gastrointestinal stromal tumors (GIST), testicular germ cell tumor, gestational trophoblastic disease, glioma, childhood brain stem glioma, hairy cell leukemia, hepatocellular cancer, langerhans cell histiocytosis, Hodgkin lymphoma, hypopharyngeal cancer, islet cell tumors, pancreatic neuroendocrine tumors, Wilms tumor and other childhood kidney tumors, langerhans cell histiocytosis, small cell lung cancer, cutaneous T cell lymphoma, intraocular melanoma, merkel cell carcinoma, mesothelioma, metastatic squamous neck cancer, midline tract carcinoma, multiple endocrine neoplasia syndromes, multiple myeloma/plasma cell neoplasm, myelodysplastic syndromes, nasal cavity and paranasal sinus cancer, nasopharyngeal cancer, neuroblastoma, non-Hodgkin lymphoma (NHL), non-small cell lung cancer (NSCLC), epithelial ovarian cancer, germ cell ovarian cancer, low malignant potential ovarian cancer, pancreatic neuroendocrine tumors, papillomatosis, paraganglioma, paranasal sinus and nasal cavity cancer, parathyroid cancer, penile cancer, pharyngeal cancer, stomach cancer, renal cancer, pelvic cancer, bronchus cancer, oropharyngeal cancer, larynx cancer, biliary tract cancer, a cancer of the central nervous system, a cancer of the respiratory system, and a cancer of the urinary system, cancer of the peritoneum, hepatocellular cancer, hepatoma, endometrial or uterine carcinoma, salivary gland carcinoma, hepatic carcinoma, anal carcinoma, penile carcinoma, post-transplant lymphoproliferative disorder (PTLD), bladder carcinoma, a pharynx cancer, a tumor of the tongue, a synovial cell sarcoma, a neuroblastoma, pheochromocytoma, pituitary tumor, pleuropulmonary blastoma, primary peritoneal cancer, rectal cancer, retinoblastoma, rhabdomyosarcoma, salivary gland cancer, Kaposi sarcoma, rhabdomyosarcoma, Sézary syndrome, small intestine cancer, soft tissue sarcoma, throat cancer, thymoma and thymic carcinoma, thyroid cancer, transitional cell cancer of the renal pelvis and ureter, urethral cancer, endometrial uterine cancer, uterine sarcoma, vaginal cancer, vulvar cancer, or Waldenström macroglobulinemia. The cancer antigen can also be derived from a leukemia (e.g., B-cell leukemia, T-cell leukemia, acute myeloid leukemia (AML), chronic myeloid leukemia (CML), acute lymphocytic (lymphoblastic) leukemia (ALL), chronic lymphocytic leukemia (CLL), hairy cell leukemia, and erythroleukemia), sarcoma (e.g., angiosarcoma, chondrosarcoma, Ewing's sarcoma, fibrosarcoma, gastrointestinal stromal tumor, leiomyosarcoma, liposarcoma, malignant peripheral nerve sheath tumor, malignant fibrous cytoma, osteosarcoma, pleomorphic sarcoma, rhabdomyosarcoma, synovial sarcoma, vascular sarcoma, Kaposi's sarcoma, dermatofibrosarcoma, epithelioid sarcoma, leyomyosarcoma, and neurofibrosarcoma), carcinoma (e.g., basal cell carcinoma, large cell carcinoma, small cell carcinoma, non-small cell lung carcinoma, renal carcinoma, hepatocarcinoma, gastric carcinoma, choriocarcinoma, adenocarcinoma, hepatocellular carcinoma, giant (or oat) cell carcinoma, squamous cell carcinoma, adenosquamous carcinoma, anaplastic carcinoma, adrenocortical carcinoma, cholangiocarcinoma, Merkel cell carcinoma, ductal carcinoma in situ (DCIS), and invasive ductal carcinoma), blastoma (e.g., hepatoblastoma, medulloblastoma, nephroblastoma, neuroblastoma, pancreatoblastoma, pleuropulmonary blastoma, retinoblastoma, and glioblastoma multiforme), lymphoma (e.g., Hodgkin's lymphoma, non-Hodgkin's lymphoma, low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, Waldenström's Macroglobulinemia, B cell lymphoma, and Burkitt lymphoma), myeloma (e.g., multiple myeloma, plasmacytoma, localized myeloma, and extramedullary myeloma), melanoma (e.g., superficial spreading melanoma, nodular melanoma, lentigno maligna melanoma, acral lentiginous melanoma, and amelanotic melanoma), neuroma (e.g., ganglioneuroma, Pacinian neuroma, and acoustic neuroma), glioma (e.g., astrocytoma, oligoastrocytoma, ependymoma, brainstem glioma, optic nerve glioma, and oligoastrocytoma), pheochromocytoma, meningioma, malignant mesothelioma, or a virally induced cancer.

In some embodiments, the cancer antigen is an ovarian cancer antigen. In some embodiments, the ovarian cancer antigen is Kallikrein 4 (reported immunogenic epitopes include: FLGYLILGV (SEQ ID NO.: 18); SVSESDTIRSISIAS (SEQ ID NO.: 19); LLANGRMPTVLQCVN (SEQ ID NO.: 20); and RMPTVLQCVNVSWS (SEQ ID NO.: 21)); PBF (reported immunogenic epitopes include: CTACRWKKACQR (SEQ ID NO.: 22)); PRAME (reported immunogenic epitopes include: VLDGLDVLL (SEQ ID NO.: 23); SLYSFPEPEA (SEQ ID NO.: 24); ALYVDSLFFL (SEQ ID NO.: 25); SLLQHLIGL (SEQ ID NO.: 26); and LYVDSLFFL (SEQ ID NO.: 27)); WT1 (reported immunogenic epitopes include: TSEKRPFMCAY (SEQ ID NO.: 28); CMTWNQMNL (SEQ ID NO.: 29); LSHLQMHSRKH (SEQ ID NO.: 30); KRYFKLSHLQMHSRKH (SEQ ID NO.: 31); and KRYFKLSHLQMHSRKH (SEQ ID NO.: 31)); HSDL1 (reported immunogenic epitopes include: CYMEAVAL (SEQ ID NO.: 32)); Mesothelin (reported immunogenic epitopes include: SLLFLLFSL (SEQ ID NO.: 33); VLPLTVAEV (SEQ ID NO.: 34); ALQGGGPPY (SEQ ID NO.: 35); LYPKARLAF (SEQ ID NO.: 36); and AFLPWHRLF (SEQ ID NO.: 37)); NY-ESO-1 (reported immunogenic epitopes include: HLA-A2-restricted peptide p157-165 (SLLMWITQC (SEQ ID NO.: 38)); HLA-Cw3-restricted p92-100 (LAMP-FATPM (SEQ ID NO.: 39)); HLA-Cw6-restricted p80-88 (ARGPESRLL (SEQ ID NO.: 40)); SLLMWITQC (SEQ ID NO.: 38); MLMAQEALAFL (SEQ ID NO.: 41); YLAMPFATPME (SEQ ID NO.: 42); ASGPGGGAPR (SEQ ID NO.: 43); LAAQERRVPR (SEQ ID NO.: 44); TVSGNILTIR (SEQ ID NO.: 45); APRGPHGGAASGL (SEQ ID NO.: 46); MPFATPMEAEL (SEQ ID NO.: 47); KEFTVSGNILTI (SEQ ID NO.: 48); MPFATPMEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLLMWITQCFLPVF (SEQ ID NO.: 53); LLEFYLAMPFATPMEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISSCLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFYLAMPFATPM (SEQ ID NO.: 64); and AGATGGRGPRGAGA (SEQ ID NO.: 65)); CEA (reported immunogenic epitopes include: TYYRPGVNLSLSC (SEQ ID NO.: 66); EIIYPNASLLIQN (SEQ ID NO.: 67); YACFVSNLATGRNNS (SEQ ID NO.: 68); LWWVNNQSLPVSP (SEQ ID NO.: 69); LWWVNNQSLPVSP (SEQ ID NO.: 69); LWWVNNQSLPVSP (SEQ ID NO.: 69); EIIYPNASLLIQN (SEQ ID NO.: 67); NSIVKSITVSASG (SEQ ID NO.: 70); KTWGQYWQV (SEQ ID NO.: 71); (A)MLGTHTMEV (SEQ ID NO.: 72); ITDQVPFSV (SEQ ID NO.: 73); YLEPGPVTA (SEQ ID NO.: 74); LLDGTATLRL (SEQ ID NO.: 75); VLYRYGSFSV (SEQ ID NO.: 76); SLADTNSLAV (SEQ ID NO.: 77); RLMKQDFSV (SEQ ID NO.: 78); RLPRIFCSC (SEQ ID NO.: 79); LIYRRRLMK (SEQ ID NO.: 80); ALLAVGATK (SEQ ID NO.: 81); IALNFPGSQK (SEQ ID NO.: 82); and RSYVPLAHR (SEQ ID NO.: 83)); p53 (reported immunogenic epitopes include: VVPCEPPEV (SEQ ID NO.: 84)); Her2/Neu (reported immunogenic epitopes include: HLYQGCQVV (SEQ ID NO.: 85); YLVPQQGFFC (SEQ ID NO.: 86); PLQPEQLQV (SEQ ID NO.: 87); TLEEITGYL (SEQ ID NO.: 88); ALIHHNTHL (SEQ ID NO.: 89); PLTSIISAV (SEQ ID NO.: 90); VLRENTSPK (SEQ ID NO.: 91); and TYLPTNASL (SEQ ID NO.: 92)); EpCAM (reported immunogenic epitopes include: RYQLDPKFI (SEQ ID NO.: 93)); CA125 (reported immunogenic epitopes include: ILFTINFTI (SEQ ID NO.: 94); VLFTINFTI (SEQ ID NO.: 95); TLNFTITNL (SEQ ID NO.: 96); VLQGLLKPL (SEQ ID NO.: 97); VLQGLLRPV (SEQ ID NO.: 98); RLDPKSPGV (SEQ ID NO.: 99); QLYWELSKL (SEQ ID NO.: 100); KLTRGIVEL (SEQ ID NO.: 101); QLTNGITEL (SEQ ID NO.: 102); QLTHNITEL (SEQ ID NO.: 103); and TLDRNSLYV (SEQ ID NO.: 104)); Folate receptor a (reported immunogenic epitopes include: FLLSLALML (SEQ ID NO.: 105); and NLGPWIQQV (SEQ ID NO.: 106)); Sperm protein 17 (reported immunogenic epitopes include: ILDSSEEDK (SEQ ID NO.: 107)); TADG-12 (reported immunogenic epitopes include: YLPKSWTIQV (SEQ ID NO.: 108); and WIHEQMERDLKT (SEQ ID NO.: 109)); MUC-16 (reported immunogenic epitopes include: ILFTINFTI (SEQ ID NO.: 94); VLFTINFTI (SEQ ID NO.: 95); TLNFTITNL (SEQ ID NO.: 96); VLQGLLKPL (SEQ ID NO.: 97); VLQGLLRPV (SEQ ID NO.: 98); RLDPKSPGV (SEQ ID NO.: 99); QLYWELSKL (SEQ ID NO.: 100); KLTRGIVEL (SEQ ID NO.: 101); QLTNGITEL (SEQ ID NO.: 102); QLTHNITEL (SEQ ID NO.: 103); and TLDRNSLYV (SEQ ID NO.: 104); L1CAM (reported immunogenic epitopes include: LLANAYIYV (SEQ ID NO.: 110); YLLCKAFGA (SEQ ID NO.: 111); and KLSPYVHYT (SEQ ID NO.: 112)); Mannan-MUC-1 (reported immunogenic epitopes include: PDTRPAPGSTAPPAHGVTSA (SEQ ID NO.: 113); STAPPVHNV (SEQ ID NO.: 114); LLLLTVLTV (SEQ ID NO.: 115); and PGSTAPPAHGVT (SEQ ID NO.: 116));

HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATGGRGPRGAGA (SEQ ID NO.: 65)); MAGE-A4 (reported immunogenic epitopes include: EVDPASNTY (SEQ ID NO.: 127); GVYDGREHTV (SEQ ID NO.: 128); NYKRCFPVI (SEQ ID NO.: 129); and SESLKMIF (SEQ ID NO.: 130)); SSX-4 (reported immunogenic epitopes include: INKTSGPKRGKHAWTHRLRE (SEQ ID NO.: 131); YFSKKEWEKMKSSEKIVYVY (SEQ ID NO.: 132); MKLNYEVMTKLGFKVTLPPF (SEQ ID NO.: 133); KHAWTHRLRERKQLVVYEEI (SEQ ID NO.: 134); LGFKVTLPPFMRSKRAADFH (SEQ ID NO.: 135); KSSEKIVYVYMKLNYEVMTK (SEQ ID NO.: 136); and KHAWTHRLRERKQLVVYEEI (SEQ ID NO.: 134)); TAG-1 (reported immunogenic epitopes include: SLGWLFLLL (SEQ ID NO.: 137); and LSRLSNRLL (SEQ ID NO.: 138)); or TAG-2 (reported immunogenic epitopes include: LSRLSNRLL (SEQ ID NO.: 138)).

In some embodiments, the cancer antigen is a breast cancer antigen. In some embodiments, the breast cancer antigen is ENAH (hMena) (reported immunogenic epitopes include: TMNGSKSPV (SEQ ID NO.: 139)); mammaglobin-A (reported immunogenic epitopes include: PLLENVISK (SEQ ID NO.: 140)); NY-BR-1 (reported immunogenic epitopes include: SLSKILDTV (SEQ ID NO.: 141)); EpCAM (reported immunogenic epitopes include: RYQLDPKFI (SEQ ID NO.: 93)); NY-ESO-1 (reported immunogenic epitopes include: HLA-A2-restricted peptide p157-165 (SLLMWITQC (SEQ ID NO.: 38)); HLA-Cw3-restricted p92-100 (LAMP-FATPM (SEQ ID NO.: 39)); HLA-Cw6-restricted p80-88 (ARGPESRLL (SEQ ID NO.: 40)); SLLMWITQC (SEQ ID NO.: 38); MLMAQEALAFL (SEQ ID NO.: 41); YLAMPFATPME (SEQ ID NO.: 42); ASGPGGGAPR (SEQ ID NO.: 43); LAAQERRVPR (SEQ ID NO.: 44); TVSGNILTIR (SEQ ID NO.: 45); APRGPHGGAASGL (SEQ ID NO.: 46); MPFATPMEAEL (SEQ ID NO.: 47); KEFTVSGNILTI (SEQ ID NO.: 48); MPFATPMEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLLMWITQCFLPVF (SEQ ID NO.: 53); LLEFYLAMPFATPMEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISSCLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFYLAMPFATPM (SEQ ID NO.: 64); and AGATGGRGPRGAGA (SEQ ID NO.: 65)); BAGE-1 (reported immunogenic epitopes include: AARAVFLAL (SEQ ID NO.: 142)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATGGRGPRGAGA (SEQ ID NO.: 65)); MAGE-A1 (reported immunogenic epitopes include: EADPTGHSY (SEQ ID NO.: 143); KVLEYVIKV (SEQ ID NO.: 144); SLFRAVITK (SEQ ID NO.: 145); EVYDGREHSA (SEQ ID NO.: 146); RVRFFFPSL (SEQ ID NO.: 147); EADPTGHSY (SEQ ID NO.: 143); REPVTKAEML (SEQ ID NO.: 148); KEADPTGHSY (SEQ ID NO.: 149); DPARYEFLW (SEQ ID NO.: 150); ITKKVADLVGF (SEQ ID NO.: 151); SAFPTTINF (SEQ ID NO.: 152); SAYGEPRKL (SEQ ID NO.: 153); RVRFFFPSL (SEQ ID NO.: 147); TSCILESLFRAVITK (SEQ ID NO.: 154); PRALAETSYVKVLEY (SEQ ID NO.: 155); FLLLKYRAREPVTKAE (SEQ ID NO.: 156); and EYVIKVSARVRF (SEQ ID NO.: 157)); MAGE-A2 (reported immunogenic epitopes include: YLQLVFGIEV (SEQ ID NO.: 158); EYLQLVFGI (SEQ ID NO.: 159); REPVTKAEML (SEQ ID NO.: 148); EGDCAPEEK (SEQ ID NO.: 160); and LLKYRAREPVTKAE (SEQ ID NO.: 161)); mucink (reported immunogenic epitopes include: PDTRPAPGSTAPPAHGVTSA (SEQ ID NO.: 113)); Sp17 (reported immunogenic epitopes include: ILDSSEEDK (SEQ ID NO.: 107)); SSX-2 (reported immunogenic epitopes include: KASEKIFYV (SEQ ID NO.: 162); EKIQKAFDDIAKYFSK (SEQ ID NO.: 163); FGRLQGISPKI (SEQ ID NO.: 164); WEKMKASEKIFYVYMKRK (SEQ ID NO.: 165); KIFYVYMKRKYEAMT (SEQ ID NO.: 166); and KIFYVYMKRKYEAM (SEQ ID NO.: 167)); TAG-1 (reported immunogenic epitopes include: SLGWLFLLL (SEQ ID NO.: 137); and LSRLSNRLL (SEQ ID NO.: 138)); TAG-2 (reported immunogenic epitopes include: LSRLSNRLL (SEQ ID NO.: 138)); TRAG-3 (reported immunogenic epitopes include: CEFHACWPAFTVLGE (SEQ ID NO.: 168)); Her2/Neu (reported immunogenic epitopes include: HLYQGCQVV (SEQ ID NO.: 85); YLVPQQGFFC (SEQ ID NO.: 86); PLQPEQLQV (SEQ ID NO.: 87); TLEEITGYL (SEQ ID NO.: 88); ALIHHNTHL (SEQ ID NO.: 89); PLTSIISAV (SEQ ID NO.: 90); VLRENTSPK (SEQ ID NO.: 91); and TYLPTNASL (SEQ ID NO.: 92)); c-myc; cyclin B1; MUC1; p53 (reported immunogenic epitopes include: VVPCEPPEV (SEQ ID NO.: 84)); p62; or Survivin.

In some embodiments, the cancer antigen is a testicular cancer antigen. In some embodiments, the testicular cancer antigen is CD45 (reported immunogenic epitopes include: KFLDALISL (SEQ ID NO.: 169)); DKK1 (reported immunogenic epitopes include: ALGGHPLLGV (SEQ ID NO.: 170)); PRAME (reported immunogenic epitopes include: VLDGLDVLL (SEQ ID NO.: 23); SLYSFPEPEA (SEQ ID NO.: 24); ALYVDSLFFL (SEQ ID NO.: 25); SLLQHLIGL (SEQ ID NO.: 26); and LYVDSLFFL (SEQ ID NO.: 27)); RU2AS (reported immunogenic epitopes include: LPRWPPPQL (SEQ ID NO.: 171)); or Telomerase (reported immunogenic epitopes include: ILAKFLHWL (SEQ ID NO.: 172); RLVDDFLLV (SEQ ID NO.: 173); RPGLLGASVLGLDDI (SEQ ID NO.: 174); and LTDLQPYMRQFVAHL (SEQ ID NO.: 175)).

In some embodiments, the cancer antigen is a pancreatic cancer antigen. In some embodiments, the pancreatic cancer antigen is ENAH (hMena) (reported immunogenic epitopes include: TMNGSKSPV (SEQ ID NO.: 139)); PBF (reported immunogenic epitopes include: CTACRWKKACQR (SEQ ID NO.: 22)); K-ras (reported immunogenic epitopes include: VVVGAVGVG (SEQ ID NO.: 176)); Mesothelin (reported immunogenic epitopes include: SLLFLLFSL (SEQ ID NO.: 33); VLPLTVAEV (SEQ ID NO.: 34); ALQGGGPPY (SEQ ID NO.: 35); LYPKARLAF (SEQ ID NO.: 36); and AFLPWHRLF (SEQ ID NO.: 37)); or mucink (reported immunogenic epitopes include: PDTRPAPGSTAPPAHGVTSA (SEQ ID NO.: 113)).

In some embodiments, the cancer antigen is a liver cancer antigen. In some embodiments, the liver cancer antigen is G250/MN/CAIX (reported immunogenic epitopes include: HLSTAFARV (SEQ ID NO.: 177); KIFGSLAFL (SEQ ID NO.: 178); IISAWGIL (SEQ ID NO.: 179); ALCRWGLLL (SEQ ID NO.: 180); ILHNGAYSL (SEQ ID NO.: 181); RLLQETELV (SEQ ID NO.: 182); WKGWFGI (SEQ ID NO.: 183); and YMIMVKCWMI (SEQ ID NO.: 184)); Hepsin (reported immunogenic epitopes include: SLLSGDWVL (SEQ ID NO.: 185); GLQLGVQAV (SEQ ID NO.: 186); and PLTEYIQPV (SEQ ID NO.: 187)); Intestinal carboxyl esterase (reported immunogenic epitopes include: SPRWWPTCL (SEQ ID NO.: 188)); alpha-foetoprotein (reported immunogenic epitopes include: GVALQTMKQ (SEQ ID NO.: 189); FMNKFIYEI (SEQ ID NO.: 190); and QLAVSVILRV (SEQ ID NO.: 191)); M-CSF (reported immunogenic epitopes include: LPAVVGLSPGEQEY (SEQ ID NO.: 192)); PBF (reported immunogenic epitopes include: CTACRWKKACQR (SEQ ID NO.: 22)); PSMA (reported immunogenic epitopes include: NYARTEDFF (SEQ ID NO.: 193)); NY-ESO-1 (reported immunogenic epitopes include: HLA-A2-restricted peptide p157-165 (SLLMWITQC (SEQ ID NO.: 38)); HLA-Cw3-restricted p92-100 (LAMP-FATPM (SEQ ID NO.: 39)); HLA-Cw6-restricted p80-88 (ARGPESRLL (SEQ ID NO.: 40)); SLLMWITQC (SEQ ID NO.: 38); MLMAQEALAFL (SEQ ID NO.: 41); YLAMPFATPME (SEQ ID NO.: 42); ASGPGGGAPR (SEQ ID NO.: 43); LAAQERRVPR (SEQ ID NO.: 44); TVSGNILTIR (SEQ ID NO.: 45); APRGPHGGAASGL (SEQ ID NO.: 46); MPFATPMEAEL (SEQ ID NO.: 47); KEFTVSGNILTI (SEQ ID NO.: 48); MPFATPMEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLLMWITQCFLPVF (SEQ ID NO.: 53); LLEFYLAMPFATPMEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISSCLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFYLAMPFATPM (SEQ ID NO.: 64); and AGATGGRGPRGAGA (SEQ ID NO.: 65)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATGGRGPRGAGA (SEQ ID NO.: 65)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); Sp17 (reported immunogenic epitopes include: ILDSSEEDK (SEQ ID NO.: 107)); c-myc; cyclin 81; p53 (reported immunogenic epitopes include: VVPCEPPEV (SEQ ID NO.: 84)); p62; or Survivin.

In some embodiments, the cancer antigen is a colorectal cancer antigen. In some embodiments, the colorectal cancer antigen is ENAH (hMena) (reported immunogenic epitopes include: TMNGSKSPV (SEQ ID NO.: 139)); Intestinal carboxyl esterase (reported immunogenic epitopes include: SPRWWPTCL (SEQ ID NO.: 188)); CASP-5 (reported immunogenic epitopes include: FLIIWQNTM (SEQ ID NO.: 194)); COA-1 (reported immunogenic epitopes include: TLYQDDTLTLQAAG (SEQ ID NO.: 195)); OGT (reported immunogenic epitopes include: SLYKFSPFPL (SEQ ID NO.: 196)); OS-9 (reported immunogenic epitopes include: KELEGILLL (SEQ ID NO.: 197)); TGF-betaRII (reported immunogenic epitopes include: RLSSCVPVA (SEQ ID NO.: 198)); NY-ESO-1 (reported immunogenic epitopes include: HLA-A2-restricted peptide p157-165 (SLLMWITQC (SEQ ID NO.: 38)); HLA-Cw3-restricted p92-100 (LAMP-FATPM (SEQ ID NO.: 39)); HLA-Cw6-restricted p80-88 (ARGPESRLL (SEQ ID NO.: 40)); SLLMWITQC (SEQ ID NO.: 38); MLMAQEALAFL (SEQ ID NO.: 41); YLAMPFATPME (SEQ ID NO.: 42); ASGPGGGAPR (SEQ ID NO.: 43); LAAQERRVPR (SEQ ID NO.: 44); TVSGNILTIR (SEQ ID NO.: 45); APRGPHGGAASGL (SEQ ID NO.: 46); MPFATPMEAEL (SEQ ID NO.: 47); KEFTVSGNILTI (SEQ ID NO.: 48); MPFATPMEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLLMWITQCFLPVF (SEQ ID NO.: 53); LLEFYLAMPFATPMEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISSCLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFYLAMPFATPM (SEQ ID NO.: 64); and AGATGGRGPRGAGA (SEQ ID NO.: 65)); CEA (reported immunogenic epitopes include: TYYRPGVNLSLSC (SEQ ID NO.: 66); EIIYPNASLLIQN (SEQ ID NO.: 67); YACFVSNLATGRNNS (SEQ ID NO.: 68); LWWVNNQSLPVSP (SEQ ID NO.: 69); LWWVNNQSLPVSP (SEQ ID NO.: 69); LWWVNNQSLPVSP (SEQ ID NO.: 69); EIIYPNASLLIQN (SEQ ID NO.: 67); NSIVKSITVSASG (SEQ ID NO.: 70); KTWGQYWQV (SEQ ID NO.: 71); (A)MLGTHTMEV (SEQ ID NO.: 72); ITDQVPFSV (SEQ ID NO.: 73); YLEPGPVTA (SEQ ID NO.: 74);

LLDGTATLRL (SEQ ID NO.: 75); VLYRYGSFSV (SEQ ID NO.: 76); SLADTNSLAV (SEQ ID NO.: 77); RLMKQDFSV (SEQ ID NO.: 78); RLPRIFCSC (SEQ ID NO.: 79); LIYRRRLMK (SEQ ID NO.: 80); ALLAVGATK (SEQ ID NO.: 81); IALNFPGSQK (SEQ ID NO.: 82); and RSYVPLAHR (SEQ ID NO.: 83)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATGGRGPRGAGA (SEQ ID NO.: 65)); MAGE-A2 (reported immunogenic epitopes include: YLQLVFGIEV (SEQ ID NO.: 158); EYLQLVFGI (SEQ ID NO.: 159); REPVTKAEML (SEQ ID NO.: 148); EGDCAPEEK (SEQ ID NO.: 160); and LLKYRAREPVTKAE (SEQ ID NO.: 161)); Sp17 (reported immunogenic epitopes include: ILDSSEEDK (SEQ ID NO.: 107)); TAG-1 (reported immunogenic epitopes include: SLGWLFLLL (SEQ ID NO.: 137); and LSRLSNRLL (SEQ ID NO.: 138)); TAG-2 (reported immunogenic epitopes include: LSRLSNRLL (SEQ ID NO.: 138)); c-myc; cyclin B1; MUC1; p53 (reported immunogenic epitopes include: VVPCEPPEV (SEQ ID NO.: 84)); p62; Survivin; or gp70.

In some embodiments, the cancer antigen is a thyroid cancer antigen. In some embodiments, the thyroid cancer antigen is CALCA (reported immunogenic epitopes include: VLLQAGSLHA (SEQ ID NO.: 199)); NY-ESO-1 (reported immunogenic epitopes include: HLA-A2-restricted peptide p157-165 (SLLMWITQC (SEQ ID NO.: 38)); HLA-Cw3-restricted p92-100 (LAMP-FATPM (SEQ ID NO.: 39)); and HLA-Cw6-restricted p80-88 (ARGPESRLL (SEQ ID NO.: 40)); SLLMWITQC (SEQ ID NO.: 38); MLMAQEALAFL (SEQ ID NO.: 41); YLAMPFATPME (SEQ ID NO.: 42); ASGPGGGAPR (SEQ ID NO.: 43); LAAQERRVPR (SEQ ID NO.: 44); TVSGNILTIR (SEQ ID NO.: 45); APRGPHGGAASGL (SEQ ID NO.: 46); MPFATPMEAEL (SEQ ID NO.: 47); KEFTVSGNILTI (SEQ ID NO.: 48); MPFATPMEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLLMWITQCFLPVF (SEQ ID NO.: 53); LLEFYLAMPFATPMEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISSCLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFYLAMPFATPM (SEQ ID NO.: 64); and AGATGGRGPRGAGA (SEQ ID NO.: 65)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATGGRGPRGAGA (SEQ ID NO.: 65)); or Sp17 (ILDSSEEDK (SEQ ID NO.: 107)).

In some embodiments, the cancer antigen is a lung cancer antigen. In some embodiments, the lung cancer antigen is CD274 (reported immunogenic epitopes include: LLNAFTVTV(SEQ ID NO.: 200)); mdm-2 (reported immunogenic epitopes include: VLFYLGQY (SEQ ID NO.: 201)); alpha-actinin-4 (reported immunogenic epitopes include: FIASNGVKLV (SEQ ID NO.: 202)); Elongation factor 2 (squamous cell carcinoma of the lung) (reported immunogenic epitopes include: ETVSEQSNV (SEQ ID NO.: 203)); ME1 (non-small cell lung carcinoma) (reported immunogenic epitopes include: FLDEFMEGV (SEQ ID NO.: 204)); NFYC (squamous cell carcinoma of the lung) (reported immunogenic epitopes include: QQITKTEV (SEQ ID NO.: 205)); NY-ESO-1 (reported immunogenic epitopes include: HLA-A2-restricted peptide p157-165 (SLLMWITQC (SEQ ID NO.: 38)); HLA-Cw3-restricted p92-100 (LAMPFATPM (SEQ ID NO.: 39)); HLA-Cw6-restricted p80-88 (ARGPESRLL (SEQ ID NO.: 40)); SLLMWITQC (SEQ ID NO.: 38); MLMAQEALAFL (SEQ ID NO.: 41); YLAMPFATPME (SEQ ID NO.: 42); ASGPGGGAPR (SEQ ID NO.: 43); LAAQERRVPR (SEQ ID NO.: 44); TVSGNILTIR (SEQ ID NO.: 45); APRGPHGGAASGL (SEQ ID NO.: 46); MPFATPMEAEL (SEQ ID NO.: 47); KEFTVSGNILTI (SEQ ID NO.: 48); MPFATPMEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLLMWITQCFLPVF (SEQ ID NO.: 53); LLEFYLAMPFATPMEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISSCLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFYLAMPFATPM (SEQ ID NO.: 64); and AGATGGRGPRGAGA (SEQ ID NO.: 65)); GAGE-1,2,8 (reported immunogenic epitopes include: YRPRPRRY (SEQ ID NO.: 206)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.:

123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATGGRGPRGAGA (SEQ ID NO.: 65)); MAGE-A2 (reported immunogenic epitopes include: YLQLVFGIEV (SEQ ID NO.: 158); EYLQLVFGI (SEQ ID NO.: 159); REPVTKAEML (SEQ ID NO.: 148); EGDCAPEEK (SEQ ID NO.: 160); and LLKYRAREPVTKAE (SEQ ID NO.: 161)); MAGE-A6 (squamous cell lung carcinoma) (reported immunogenic epitopes include: MVKISGGPR (SEQ ID NO.: 207); EVDPIGHVY (SEQ ID NO.: 208); REPVTKAEML (SEQ ID NO.: 148); EGDCAPEEK (SEQ ID NO.: 160); ISGGPRISY (SEQ ID NO.: 209); and LLKYRAREPVTKAE (SEQ ID NO.: 161)); Sp17 (reported immunogenic epitopes include: ILDSSEEDK (SEQ ID NO.: 107)); TAG-1 (reported immunogenic epitopes include: SLGWLFLLL (SEQ ID NO.: 137); and LSRLSNRLL (SEQ ID NO.: 138)); TAG-2 (reported immunogenic epitopes include: LSRLSNRLL(SEQ ID NO.: 138)); TRAG-3 (reported immunogenic epitopes include: CEFHACWPAFTVLGE (SEQ ID NO.: 168)); XAGE-1b/GAGED2a (non-small cell lung cancer) (reported immunogenic epitopes include: RQKKIRIQL (SEQ ID NO.: 210); HLGSRQKKIRIQLRSQ (SEQ ID NO.: 211); and CATWKVICKSCISQTPG (SEQ ID NO.: 212)); c-myc; cyclin B1; Her2/Neu (reported immunogenic epitopes include: HLYQGCQVV (SEQ ID NO.: 85); YLVPQQGFFC (SEQ ID NO.: 86); PLQPEQLQV (SEQ ID NO.: 87); TLEEITGYL (SEQ ID NO.: 88); ALIHHNTHL (SEQ ID NO.: 89); PLTSIISAV (SEQ ID NO.: 90); VLRENTSPK (SEQ ID NO.: 91); and TYLPTNASL (SEQ ID NO.: 92)); MUC1; p53 (reported immunogenic epitopes include: VVPCEPPEV (SEQ ID NO.: 84)); p62; or Survivin.

In some embodiments, the cancer antigen is a prostate cancer antigen. In some embodiments, the prostate cancer antigen is DKK1 (reported immunogenic epitopes include: ALGGHPLLGV (SEQ ID NO.: 170)); ENAH (hMena) (reported immunogenic epitopes include: TMNGSKSPV (SEQ ID NO.: 139)); Kallikrein 4 (reported immunogenic epitopes include: FLGYLILGV (SEQ ID NO.: 18); SVSESDTIRSISIAS (SEQ ID NO.: 19); LLANGRMPTVLQCVN (SEQ ID NO.: 20); and RMPTVLQCVNVSWS (SEQ ID NO.: 21)); PSMA (reported immunogenic epitopes include: NYARTEDFF(SEQ ID NO.: 193)); STEAPI (reported immunogenic epitopes include: MIAVFLPIV (SEQ ID NO.: 213); and HQQYFYKIPILVINK (SEQ ID NO.: 214)); PAP (reported immunogenic epitopes include: FLFLLFFWL (SEQ ID NO.: 215); TLMSAMTNL (SEQ ID NO.: 216); and ALDVYNGLL (SEQ ID NO.: 217)); PSA (prostate carcinoma) (reported immunogenic epitopes include: FLTPKKLQCV (SEQ ID NO.: 218); and VISNDVCAQV (SEQ ID NO.: 219)); NY-ESO-1 (reported immunogenic epitopes include: HLA-A2-restricted peptide p157-165 (SLLMWITQC (SEQ ID NO.: 38)); HLA-Cw3-restricted p92-100 (LAMP-FATPM (SEQ ID NO.: 39)); HLA-Cw6-restricted p80-88 (ARGPESRLL (SEQ ID NO.: 40)); SLLMWITQC (SEQ ID NO.: 38); MLMAQEALAFL (SEQ ID NO.: 41); YLAMPFATPME (SEQ ID NO.: 42); ASGPGGGAPR (SEQ ID NO.: 43); LAAQERRVPR (SEQ ID NO.: 44); TVSGNILTIR (SEQ ID NO.: 45); APRGPHGGAASGL (SEQ ID NO.: 46); MPFATPMEAEL (SEQ ID NO.: 47); KEFTVSGNILTI (SEQ ID NO.: 48); MPFATPMEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLLMWITQCFLPVF (SEQ ID NO.: 53); LLEFYLAMPFATPMEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISSCLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFYLAMPFATPM (SEQ ID NO.: 64); and AGATGGRGPRGAGA (SEQ ID NO.: 65)); BAGE-1 (reported immunogenic epitopes include: AARAVFLAL (SEQ ID NO.: 142)); GAGE-1,2,8 (reported immunogenic epitopes include: YRPRPRRY (SEQ ID NO.: 206)); GAGE-3,4,5,6,7 (reported immunogenic epitopes include: YYWPRPRRY (SEQ ID NO.: 221)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATGGRGPRGAGA (SEQ ID NO.: 65)); or Sp17 (reported immunogenic epitopes include: ILDSSEEDK (SEQ ID NO.: 107)).

In some embodiments, the cancer antigen is a kidney cancer antigen. In some embodiments, the kidney cancer antigen is FGF5 (reported immunogenic epitopes include: NTYASPRFK (SEQ ID NO.: 222)); Hepsin (reported immunogenic epitopes include: SLLSGDWVL (SEQ ID NO.: 185); GLQLGVQAV (SEQ ID NO.: 186); and PLTEYIQPV (SEQ ID NO.: 187)); Intestinal carboxyl esterase (reported immunogenic epitopes include: SPRWWPTCL (SEQ ID NO.: 188)); M-CSF (reported immunogenic epitopes include: LPAWGLSPGEQEY (SEQ ID NO.: 192)); RU2AS (reported immunogenic epitopes include: LPRWPPPQL (SEQ ID NO.: 171)); hsp70-2 (renal cell carcinoma) (reported immunogenic epitopes include: SLFEGIDIYT (SEQ ID NO.: 223)); Mannan-MUC-1 (renal cell carcinoma) (reported immunogenic epitopes include: PDTRPAPGSTAPPAHGVTSA (SEQ ID NO.: 113); STAPPVHNV (SEQ ID NO.: 114); LLLLTVLTV (SEQ ID NO.: 115); and PGSTAPPAHGVT (SEQ ID NO.: 116)); or MAGE-A9 (renal cell carcinoma) (reported immunogenic epitopes include: ALSVMGVYV (SEQ ID NO.: 224)).

In some embodiments, the cancer antigen is a melanoma cancer antigen. In some embodiments, the melanoma cancer antigen is Hepsin (reported immunogenic epitopes include: SLLSGDWVL (SEQ ID NO.: 185); GLQLGVQA (SEQ ID NO.: 343); and PLTEYIQPV (SEQ ID NO.: 187)); ARTC1 (reported immunogenic epitopes include: YSVYFNLPADTIYTN (SEQ ID NO.: 225)); B-RAF (reported immunogenic epitopes include: EDLTVKIGDFGLATEKSRWSGSHQFEQLS (SEQ ID NO.: 226)); beta-catenin (reported immunogenic epitopes include: SYLDSGIHF (SEQ ID NO.: 227)); Cdc27 (reported immunogenic epitopes include: FSWAMDLDPKGA (SEQ ID NO.: 228)); CDK4 (reported immunogenic epitopes include: ACDPHSGHFV (SEQ ID NO.: 229)); CDK12 (reported immunogenic epitopes include: CILGKLFTK (SEQ ID NO.: 230)); CDKN2A (reported immunogenic epitopes include: AVCPWTWLR (SEQ ID NO.: 231)); CLPP (reported immunogenic epitopes include: ILDKVLVHL (SEQ ID NO.: 232)); CSNKIAI (reported immunogenic epitopes include: GLFGDIYLA (SEQ ID NO.: 233)); FN1 (reported immunogenic epitopes include: MIFEKHGFRRTTPP (SEQ ID NO.: 234)); GAS7 (reported immunogenic epitopes include: SLADEAEVYL (SEQ ID NO.: 235)); GPNMB (reported immunogenic epitopes include: TLDWLLQTPK (SEQ ID NO.: 236)); HAUS3 (reported immunogenic epitopes include: ILNAMIAKI (SEQ ID NO.: 237)); LDLR-fucosyltransferase (reported immunogenic epitopes include: WRRAPAPGA (SEQ ID NO.: 238); and PVTWRRAPA (SEQ ID NO.: 239)); MART2 (reported immunogenic epitopes include: FLEGNEVGKTY (SEQ ID NO.: 240)); MATN (reported immunogenic epitopes include: KTLTSVFQK (SEQ ID NO.: 241)); MUM-1 (reported immunogenic epitopes include: EEKLIWLF (SEQ ID NO.: 242)); MUM-2 (reported immunogenic epitopes include: SELFRSGLDSY (SEQ ID NO.: 243)); and FRSGLDSYV (SEQ ID NO.: 244)); MUM-3 (reported immunogenic epitopes include: EAFIQPITR (SEQ ID NO.: 245)); neo-PAP (reported immunogenic epitopes include: RVIKNSIRLTL (SEQ ID NO.: 246)); Myosin class I (reported immunogenic epitopes include: KINKNPKYK (SEQ ID NO.: 247)); PPPIR3B (reported immunogenic epitopes include: YTDFHCQYV (SEQ ID NO.: 248)); PRDX5 (reported immunogenic epitopes include: LLLDDLLVSI (SEQ ID NO.: 249)); PTPRK (reported immunogenic epitopes include: PYYFAAELPPRNLPEP (SEQ ID NO.: 250)); N-ras (reported immunogenic epitopes include: ILDTAGREEY (SEQ ID NO.: 251)); RBAF600 (reported immunogenic epitopes include: RPHVPESAF (SEQ ID NO.: 252)); SIRT2 (reported immunogenic epitopes include: KIFSEVTLK (SEQ ID NO.: 253)); SNRPD1 (reported immunogenic epitopes include: SHETVIIEL (SEQ ID NO.: 254)); Triosephosphate isomerase (reported immunogenic epitopes include: GELIGILNAAKVPAD (SEQ ID NO.: 255)); OA1 (reported immunogenic epitopes include: LYSACFWWL (SEQ ID NO.: 256)); RAB38/NY-MEL-1 (reported immunogenic epitopes include: VLHWDPETV (SEQ ID NO.: 257)); TRP-1/gp75 (reported immunogenic epitopes include: MSLQRQFLR (SEQ ID NO.: 258); ISPNSVFSQWRWCDSLEDY (SEQ ID NO.: 259); SLPYWNFATG (SEQ ID NO.: 260); and SQWRVVCDSLEDYDT (SEQ ID NO.: 261)); TRP-2 (reported immunogenic epitopes include: SVYDFFVWL (SEQ ID NO.: 262); TLDSQVMSL (SEQ ID NO.: 263); LLGPGRPYR (SEQ ID NO.: 264); ANDPIFWL (SEQ ID NO.: 265); QCTEVRADTRPWSGP (SEQ ID NO.: 266); and ALPYWNFATG (SEQ ID NO.: 267)); tyrosinase (reported immunogenic epitopes include: KCDICTDEY (SEQ ID NO.: 268); SSDYVIPIGTY (SEQ ID NO.: 269); MLLAVLYCL (SEQ ID NO.: 270); CLLWSFQTSA (SEQ ID NO.: 271); YMDGTMSQV (SEQ ID NO.: 272); AFLPWHRLF (SEQ ID NO.: 37); IYMDGTADFSF (SEQ ID NO.: 273); QCSGNFMGF (SEQ ID NO.: 274); TPRLPSSADVEF (SEQ ID NO.: 275); LPSSADVEF (SEQ ID NO.: 276); LHHAFVDSIF (SEQ ID NO.: 277); SEIWRDIDF (SEQ ID NO.: 277); QNILLSNAPLGPQFP (SEQ ID NO.: 278); SYLQDSDPDSFQD (SEQ ID NO.: 279); and FLLHHAFVDSIFEQWLQRHRP (SEQ ID NO.: 280)); Melan-A/MART-1 (reported immunogenic epitopes include: YTTAEEAAGIGILTVILGVLLLIGCWYCRR (SEQ ID NO.: 281)); gp100/Pmel17 (reported immunogenic epitopes include: ALNFPGSQK (SEQ ID NO.: 282); ALNFPGSQK (SEQ ID NO.: 282); VYFFLPDHL (SEQ ID NO.: 283); RTKQLYPEW (SEQ ID NO.: 284); HTMEVTVYHR (SEQ ID NO.: 285); SSPGCQPPA (SEQ ID NO.: 286); VPLDCVLYRY (SEQ ID NO.: 287); LPHSSSHWL (SEQ ID NO.: 288); SNDGPTLI (SEQ ID NO.: 289); GRAMLGTHTMEVTVY (SEQ ID NO.: 290); WNRQLYPEWTEAQRLD (SEQ ID NO.: 291); TTEWVETTARELPIPEPE (SEQ ID NO.: 292); TGRAMLGTHTMEVTVYH (SEQ ID NO.: 293); and GRAMLGTHTMEVTVY (SEQ ID NO.: 290)); NY-ESO-1 (reported immunogenic epitopes include: HLA-A2-restricted peptide p157-165 (SLLMWITQC (SEQ ID NO.: 38)); HLA-Cw3-restricted p92-100 (LAMP-FATPM (SEQ ID NO.: 39)); HLA-Cw6-restricted p80-88 (ARGPESRLL (SEQ ID NO.: 40)); SLLMWITQC (SEQ ID NO.: 38); MLMAQEALAFL (SEQ ID NO.: 41); YLAMPFATPME (SEQ ID NO.: 42); ASGPGGGAPR (SEQ ID NO.: 43); LAAQERRVPR (SEQ ID NO.: 44); TVSGNILTIR (SEQ ID NO.: 45); APRGPHGGAASGL (SEQ ID NO.: 46); MPFATPMEAEL (SEQ ID NO.: 47); KEFTVSGNILTI (SEQ ID NO.: 48); MPFATPMEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLLMWITQCFLPVF (SEQ ID NO.: 53); LLEFYLAMPFATPMEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISSCLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFYLAMPFATPM (SEQ ID NO.: 64); and AGATGGRGPRGAGA (SEQ ID NO.: 65)); BAGE-1 (reported immunogenic epitopes include: AARAVFLAL (SEQ ID NO.: 142)); GAGE-1,2,8 (reported immunogenic epitopes include: YRPRPRRY (SEQ ID NO.: 206)); GAGE-3,4,5,6,7 (cutaneous melanoma) (reported immunogenic epitopes include: YYWPRPRRY (SEQ ID NO.: 221)); GnTVf (reported immunogenic epitopes include: VLPDVFIRC(V) (SEQ ID NO.: 294)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATGGRGPRGAGA (SEQ ID NO.: 65)); LY6K (reported immunogenic epitopes include: RYCNLEGPPI (SEQ ID NO.: 295); KWTEPYCVIAAVKIFPRFFMVAKQ (SEQ ID NO.:

296); and KCCKIRYCNLEGPPINSSVF (SEQ ID NO.: 297)); MAGE-A1 (reported immunogenic epitopes include: EADPTGHSY (SEQ ID NO.: 143); KVLEYVIKV (SEQ ID NO.: 144); SLFRAVITK (SEQ ID NO.: 145); EVYDGREHSA (SEQ ID NO.: 146); RVRFFFPSL (SEQ ID NO.: 147); EADPTGHSY (SEQ ID NO.: 143); REPVTKAEML (SEQ ID NO.: 148); KEADPTGHSY (SEQ ID NO.: 149); DPARYEFLW (SEQ ID NO.: 150); ITKKVADLVGF (SEQ ID NO.: 151); SAFPTTINF (SEQ ID NO.: 152); SAYGEPRKL (SEQ ID NO.: 153); RVRFFFPSL (SEQ ID NO.: 147); TSCILESLFRAVITK (SEQ ID NO.: 154); PRALAETSYVKVLEY (SEQ ID NO.: 155); FLLLKYRAREPVTKAE (SEQ ID NO.: 156); and EYVIKVSARVRF (SEQ ID NO.: 157)); MAGE-A6 (reported immunogenic epitopes include: MVKISGGPR (SEQ ID NO.: 207); EVDPIGHVY (SEQ ID NO.: 208); REPVTKAEML (SEQ ID NO.: 148); EGDCAPEEK (SEQ ID NO.: 160); ISGGPRISY (SEQ ID NO.: 209); and LLKYRAREPVTKAE (SEQ ID NO.: 161)); MAGE-A10 (reported immunogenic epitopes include: GLYDGMEHL (SEQ ID NO.: 297)); and DPARYEFLW (SEQ ID NO.: 150)); MAGE-A12 (reported immunogenic epitopes include: FLWGPRALV (SEQ ID NO.: 298); VRIGHLYIL (SEQ ID NO.: 299); EGDCAPEEK (SEQ ID NO.: 160); REPFTKAEMLGSVIR (SEQ ID NO.: 300); and AELVHFLLLKYRAR (SEQ ID NO.: 301)); MAGE-C2 (reported immunogenic epitopes include: LLFGLALIEV (SEQ ID NO.: 302); ALKDVEERV (SEQ ID NO.: 303); SESIKKKVL (SEQ ID NO.: 304); ASSTLYLVF (SEQ ID NO.: 305); and SSTLYLVFSPSSFST (SEQ ID NO.: 306)); NA88-A (reported immunogenic epitopes include: QGQHFLQKV (SEQ ID NO.: 307)); Sp17 (reported immunogenic epitopes include: ILDSSEEDK (SEQ ID NO.: 107)); SSX-2 (reported immunogenic epitopes include: KASEKIFYV (SEQ ID NO.: 162); EKIQKAFDDIAKYFSK (SEQ ID NO.: 163); FGRLQGISPKI (SEQ ID NO.: 164); WEKMKASEKIFYVYMKRK (SEQ ID NO.: 165); KIFYVYMKRKYEAMT (SEQ ID NO.: 166); and KIFYVYMKRKYEAM (SEQ ID NO.: 167)); SSX-4 (reported immunogenic epitopes include: INKTSGPKRGKHAWTHRLRE (SEQ ID NO.: 131); YFSKKEWEKMKSSEKIVYVY (SEQ ID NO.: 132); MKLNYEVMTKLGFKVTLPPF (SEQ ID NO.: 133); KHAWTHRLRERKQLVVYEEI (SEQ ID NO.: 134); LGFKVTLPPFMRSKRAADFH (SEQ ID NO.: 135); KSSEKIVYVYMKLNYEVMTK (SEQ ID NO.: 136); and KHAWTHRLRERKQLVVYEEI (SEQ ID NO.: 134)); TRAG-3 (reported immunogenic epitopes include: CEFHACWPAFTVLGE (SEQ ID NO.: 168)); TRP2-INT2g (reported immunogenic epitopes include: EVISCKLIKR (SEQ ID NO.: 308)); or pgk.

In some embodiments, the cancer antigen is a squamous cell carcinoma antigen. In some embodiments, the squamous cell carcinoma antigen is CASP-8 (reported immunogenic epitopes include: FPSDSWCYF (SEQ ID NO.: 309)); p53 (reported immunogenic epitopes include: VVPCEPPEV (SEQ ID NO.: 84)); or SAGE (reported immunogenic epitopes include: LYATVIHDI (SEQ ID NO.: 310)).

In some embodiments, the cancer antigen is a chronic myeloid leukemia antigen. In some embodiments, the chronic myeloid leukemia antigen is BCR-ABL (reported immunogenic epitopes include: SSKALQRPV (SEQ ID NO.: 311); GFKQSSKAL (SEQ ID NO.: 312); ATGFKQSSKALQRPVAS (SEQ ID NO.: 313); and ATGFKQSSKALQRPVAS (SEQ ID NO.: 313)); dek-can (reported immunogenic epitopes include: TMKQICKKEIRRLHQY (SEQ ID NO.: 314)); EFTUD2 (reported immunogenic epitopes include: KILDAWAQK (SEQ ID NO.: 315)); or GAGE-3,4,5,6,7 (reported immunogenic epitopes include: YYWPRPRRY (SEQ ID NO.: 221)).

In some embodiments, the cancer antigen is an acute lymphoblastic leukemia antigen. In some embodiments, the acute lymphoblastic leukemia antigen is ETV6-AML1 (reported immunogenic epitopes include: RIAECILGM (SEQ ID NO.: 316); and IGRIAECILGMNPSR (SEQ ID NO.: 317)); or GAGE-3,4,5,6,7 (reported immunogenic epitopes include: YYWPRPRRY (SEQ ID NO.: 221)).

In some embodiments, the cancer antigen is an acute myelogenous leukemia antigen. In some embodiments, the acute myelogenous leukemia antigen is FLT3-ITD (reported immunogenic epitopes include: YVDFREYEYY (SEQ ID NO.: 318)); Cyclin-A1 (reported immunogenic epitopes include: FLDRFLSCM (SEQ ID NO.: 319); and SLIAAAAFCLA (SEQ ID NO.: 320)); or GAGE-3,4,5,6,7 (reported immunogenic epitopes include: YYWPRPRRY (SEQ ID NO.: 221)).

In some embodiments, the cancer antigen is a chronic lymphocytic leukemia antigen. In some embodiments, the chronic lymphocytic leukemia antigen is FNDC3B (reported immunogenic epitopes include: VVMSWAPPV (SEQ ID NO.: 321)); or GAGE-3,4,5,6,7 (reported immunogenic epitopes include: YYWPRPRRY (SEQ ID NO.: 221)).

In some embodiments, the cancer antigen is a promyelocytic leukemia antigen. In some embodiments, the promyelocytic leukemia antigen is pml-RARalpha (reported immunogenic epitopes include: NSNHVASGAGEAAIETQSSSSEEIV (SEQ ID NO.: 322)); or GAGE-3,4,5,6,7 (reported immunogenic epitopes include: YYWPRPRRY (SEQ ID NO.: 221)).

In some embodiments, the cancer antigen is a multiple myeloma antigen. In some embodiments, the multiple myeloma antigen is MAGE-C1 (reported immunogenic epitopes include: ILFGISLREV (SEQ ID NO.: 323); KVVEFLAML (SEQ ID NO.: 324); SSALLSIFQSSPE (SEQ ID NO.: 325); SFSYTLLSL (SEQ ID NO.: 326); and VSSFFSYTL (SEQ ID NO.: 327)); NY-ESO-1 (reported immunogenic epitopes include: HLA-A2-restricted peptide p157-165 (SLLMWITQC (SEQ ID NO.: 38)); HLA-Cw3-restricted p92-100 (LAMP-FATPM (SEQ ID NO.: 39)); HLA-Cw6-restricted p80-88 (ARGPESRLL (SEQ ID NO.: 40)); SLLMWITQC (SEQ ID NO.: 38); MLMAQEALAFL (SEQ ID NO.: 41); YLAMPFATPME (SEQ ID NO.: 42); ASGPGGGAPR (SEQ ID NO.: 43); LAAQERRVPR (SEQ ID NO.: 44); TVSGNILTIR (SEQ ID NO.: 45); APRGPHGGAASGL (SEQ ID NO.: 46); MPFATPMEAEL (SEQ ID NO.: 47); KEFTVSGNILTI (SEQ ID NO.: 48); MPFATPMEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLLMWITQCFLPVF (SEQ ID NO.: 53); LLEFYLAMPFATPMEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISSCLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFYLAMPFATPM (SEQ ID NO.: 64); and AGATGGRGPRGAGA (SEQ ID NO.: 65)); LAGE-1 (reported immunogenic epitopes include: MLMAQEALAFL (SEQ ID NO.:

41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATG-GRGPRGAGA (SEQ ID NO.: 65)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); or Sp17 (reported immunogenic epitopes include: ILDSSEEDK (SEQ ID NO.: 107)).

In some embodiments, the cancer antigen is a B-cell lymphoma antigen. In some embodiments, the B-cell lymphoma antigen is D393-CD20 (reported immunogenic epitopes include: KPLFRRMSSLELVIA (SEQ ID NO.: 328)).

In some embodiments, the cancer antigen is a bladder carcinoma antigen. In some embodiments, the bladder carcinoma antigen is BAGE-1 (reported immunogenic epitopes include: AARAVFLAL (SEQ ID NO.: 142)); GAGE-1,2,8 (reported immunogenic epitopes include: YRPRPRRY (SEQ ID NO.: 206)); GAGE-3,4,5,6,7 (reported immunogenic epitopes include: YYWPRPRRY (SEQ ID NO.: 221)); MAGE-A4 (transitional cell carcinoma of urinary bladder) (reported immunogenic epitopes include: EVDPASNTY (SEQ ID NO.: 127); GVYDGREHTV (SEQ ID NO.: 128); NYKRCFPVI (SEQ ID NO.: 129); and SESLKMIF (SEQ ID NO.: 130)); MAGE-A6 (reported immunogenic epitopes include: MVKISGGPR (SEQ ID NO.: 207); EVDPIGHVY (SEQ ID NO.: 208); REPVTKAEML (SEQ ID NO.: 148); EGDCAPEEK (SEQ ID NO.: 160); ISGGPRISY (SEQ ID NO.: 209); and LLKYRAREPVTKAE (SEQ ID NO.: 161)); SAGE (reported immunogenic epitopes include: LYATVIHDI (SEQ ID NO.: 310)); NY-ESO-1 (reported immunogenic epitopes include: HLA-A2-restricted peptide p157-165 (SLLMWITQC (SEQ ID NO.: 38)); HLA-Cw3-restricted p92-100 (LAMP-FATPM (SEQ ID NO.: 39)); HLA-Cw6-restricted p80-88 (ARGPESRLL (SEQ ID NO.: 40)); SLLMWITQC (SEQ ID NO.: 38); MLMAQEALAFL (SEQ ID NO.: 41); YLAMPFATPME (SEQ ID NO.: 42); ASGPGGGAPR (SEQ ID NO.: 43); LAAQERRVPR (SEQ ID NO.: 44); TVSGNILTIR (SEQ ID NO.: 45); APRGPHG-GAASGL (SEQ ID NO.: 46); MPFATPMEAEL (SEQ ID NO.: 47); KEFTVSGNILTI (SEQ ID NO.: 48); MPFATP-MEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLL-MWITQCFLPVF (SEQ ID NO.: 53); LLEFYLAMPFATP-MEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISS-CLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFY-LAMPFATPM (SEQ ID NO.: 64); and AGATGGRGPR-GAGA (SEQ ID NO.: 65)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATG-GRGPRGAGA (SEQ ID NO.: 65)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); or Sp17 (reported immunogenic epitopes include: ILDSSEEDK (SEQ ID NO.: 107)).

In some embodiments, the cancer antigen is a head and neck cancer antigen. In some embodiments, the head and neck cancer antigen is BAGE-1 (head and neck squamous cell carcinoma) (reported immunogenic epitopes include: AARAVFLAL (SEQ ID NO.: 142)); GAGE-1,2,8 (reported immunogenic epitopes include: YRPRPRRY (SEQ ID NO.: 206)); GAGE-3,4,5,6,7 (reported immunogenic epitopes include: YYWPRPRRY (SEQ ID NO.: 221)); LY6K (reported immunogenic epitopes include: RYCNLEGPPI (SEQ ID NO.: 295; KWTEPYCVIAAVKIFPRFFMVAKQ (SEQ ID NO.: 296); and KCCKIRYCNLEGPPINSSVF (SEQ ID NO.: 297)); MAGE-A3 (head and neck squamous cell carcinoma) (reported immunogenic epitopes include: EVDPIGHLY (SEQ ID NO.: 329); FLWGPRALV (SEQ ID NO.: 298); KVAELVHFL (SEQ ID NO.: 330); TFPDLESEF (SEQ ID NO.: 331); VAELVHFLL (SEQ ID NO.: 332); MEVDPIGHLY (SEQ ID NO.: 333); EVDPIGHLY (SEQ ID NO.: 329); REPVTKAEML (SEQ ID NO.: 148); AEL-VHFLLL (SEQ ID NO.: 342); MEVDPIGHLY (SEQ ID NO.: 333); WQYFFPVIF (SEQ ID NO.: 334); EGDCAP-EEK (SEQ ID NO.: 160); KKLLTQHFVQENYLEY (SEQ ID NO.: 335); RKVAELVHFLLLKYR (SEQ ID NO.: 336); KKLLTQHFVQENYLEY (SEQ ID NO.: 335); ACYE-FLWGPRALVETS (SEQ ID NO.: 337); RKVAEL-VHFLLLKYR (SEQ ID NO.: 336); VIFSKASSSLQL (SEQ ID NO.: 338); VFGIELMEVDPIGHL (SEQ ID NO.: 339); GDNQIMPKAGLLIIV (SEQ ID NO.: 340); TSYVKVLHHMVKISG (SEQ ID NO.: 341); RKVAEL-VHFLLLKYRA (SEQ ID NO.: 336); and FLLLKYRAREPVTKAE (SEQ ID NO.: 156)); MAGE-A6 (reported immunogenic epitopes include: MVKISGGPR (SEQ ID NO.: 207); EVDPIGHVY (SEQ ID NO.: 208); REPVTKAEML (SEQ ID NO.: 148); EGDCAPEEK (SEQ ID NO.: 160); ISGGPRISY (SEQ ID NO.: 209); and LLKYRAREPVTKAE (SEQ ID NO.: 161)); or SAGE (reported immunogenic epitopes include: LYATVIHDI (SEQ ID NO.: 310)).

In some embodiments, the cancer antigen is an esophageal cancer antigen. In some embodiments, the esophageal cancer antigen is GAGE-3,4,5,6,7 (Esophageal squamous cell carcinoma and esophageal adenocarcinoma) (reported immunogenic epitopes include: YYWPRPRRY (SEQ ID NO.: 221)); MAGE-A2 (reported immunogenic epitopes include: YLQLVFGIEV (SEQ ID NO.: 158); EYLQLVFGI (SEQ ID NO.: 159); REPVTKAEML (SEQ ID NO.: 148); EGDCAPEEK (SEQ ID NO.: 160); and LLKYRAREPVT-KAE (SEQ ID NO.: 161)); MAGE-A6 (reported immunogenic epitopes include: MVKISGGPR (SEQ ID NO.: 207); EVDPIGHVY (SEQ ID NO.: 208); REPVTKAEML (SEQ ID NO.: 148); EGDCAPEEK (SEQ ID NO.: 160); ISGG-PRISY (SEQ ID NO.: 209); and LLKYRAREPVTKAE (SEQ ID NO.: 161)); NY-ESO-1 (reported immunogenic epitopes include: HLA-A2-restricted peptide p157-165 (SLLMWITQC (SEQ ID NO.: 38)); HLA-Cw3-restricted p92-100 (LAMP-FATPM (SEQ ID NO.: 39)); HLA-Cw6-restricted p80-88 (ARGPESRLL (SEQ ID NO.: 40)); SLL-MWITQC (SEQ ID NO.: 38); MLMAQEALAFL (SEQ ID NO.: 41); YLAMPFATPME (SEQ ID NO.: 42); ASGPGG-GAPR (SEQ ID NO.: 43); LAAQERRVPR (SEQ ID NO.: 44); TVSGNILTIR (SEQ ID NO.: 45); APRGPHG-GAASGL (SEQ ID NO.: 46); MPFATPMEAEL (SEQ ID NO.: 47); KEFTVSGNILTI (SEQ ID NO.: 48); MPFATP-MEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLL-MWITQCFLPVF (SEQ ID NO.: 53); LLEFYLAMPFATP-MEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISS-CLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFY-LAMPFATPM (SEQ ID NO.: 64); and AGATGGRGPR-GAGA (SEQ ID NO.: 65)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATG-GRGPRGAGA (SEQ ID NO.: 65)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); or Sp17 (reported immunogenic epitopes include: ILDSSEEDK (SEQ ID NO.: 107)).

In some embodiments, the cancer antigen is a brain cancer antigen. In some embodiments, the brain cancer antigen is TAG-1 (reported immunogenic epitopes include: SLGWLFLLL (SEQ ID NO.: 137); and LSRLSNRLL (SEQ ID NO.: 138)); or TAG-2 (reported immunogenic epitopes include: LSRLSNRLL (SEQ ID NO.: 138)).

In some embodiments, the cancer antigen is a pharynx cancer antigen. In some embodiments, the pharynx cancer antigen is TAG-1 (reported immunogenic epitopes include: SLGWLFLLL (SEQ ID NO.: 137); and LSRLSNRLL (SEQ ID NO.: 138)); or TAG-2 (reported immunogenic epitopes include: LSRLSNRLL (SEQ ID NO.: 138)).

In some embodiments, the cancer antigen is a tumor of the tongue antigen. In some embodiments, the tumor of the tongue antigen is TAG-1 (reported immunogenic epitopes include: SLGWLFLLL (SEQ ID NO.: 137); and LSRL-SNRLL (SEQ ID NO.: 138)); or TAG-2 (reported immunogenic epitopes include: LSRLSNRLL (SEQ ID NO.: 138)).

In some embodiments, the cancer antigen is a synovial cell sarcoma antigen. In some embodiments, the synovial cell sarcoma antigen is NY-ESO-1 (reported immunogenic epitopes include: HLA-A2-restricted peptide p157-165 (SLLMWITQC (SEQ ID NO.: 38)); HLA-Cw3-restricted p92-100 (LAMP-FATPM (SEQ ID NO.: 39)); HLA-Cw6-restricted p80-88 (ARGPESRLL (SEQ ID NO.: 40)); SLL-MWITQC (SEQ ID NO.: 38); MLMAQEALAFL (SEQ ID NO.: 41); YLAMPFATPME (SEQ ID NO.: 42); ASGPGG-GAPR (SEQ ID NO.: 43); LAAQERRVPR (SEQ ID NO.: 44); TVSGNILTIR (SEQ ID NO.: 45); APRGPHG-GAASGL (SEQ ID NO.: 46); MPFATPMEAEL (SEQ ID NO.: 47); KEFTVSGNILTI (SEQ ID NO.: 48); MPFATP-MEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLL-MWITQCFLPVF (SEQ ID NO.: 53); LLEFYLAMPFATP-MEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISS-CLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFY-LAMPFATPM (SEQ ID NO.: 64); and AGATGGRGPR-GAGA (SEQ ID NO.: 65)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATG-GRGPRGAGA (SEQ ID NO.: 65)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); or Sp17 (reported immunogenic epitopes include: ILDSSEEDK (SEQ ID NO.: 107)).

In some embodiments, the cancer antigen is a neuroblastoma antigen. In some embodiments, the neuroblastoma antigen is NY-ESO-1 (reported immunogenic epitopes include: HLA-A2-restricted peptide p157-165 (SLL-MWITQC (SEQ ID NO.: 38)); HLA-Cw3-restricted p92-100 (LAMP-FATPM (SEQ ID NO.: 39); HLA-Cw6-restricted p80-88 (ARGPESRLL (SEQ ID NO.: 40)); SLLMWITQC (SEQ ID NO.: 38); MLMAQEALAFL (SEQ ID NO.: 41); YLAMPFATPME (SEQ ID NO.: 42); ASGPGGGAPR (SEQ ID NO.: 43); LAAQERRVPR (SEQ ID NO.: 44); TVSGNILTIR (SEQ ID NO.: 45); APRGPHG-GAASGL (SEQ ID NO.: 46); MPFATPMEAEL (SEQ ID NO.: 47); KEFTVSGNILTI (SEQ ID NO.: 48); MPFATP-MEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLL-MWITQCFLPVF (SEQ ID NO.: 53); LLEFYLAMPFATP-MEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISS- CLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFYLAMPFATPM (SEQ ID NO.: 64); and AGATGGRGPRGAGA (SEQ ID NO.: 65)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATGGRGPRGAGA (SEQ ID NO.: 65)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); or Sp17 (reported immunogenic epitopes include: ILDSSEEDK (SEQ ID NO.: 107)).

In some embodiments, the cancer antigen is a uterine cancer antigen. In some embodiments, the uterine cancer antigen is NY-ESO-1 (reported immunogenic epitopes include: HLA-A2-restricted peptide p157-165 (SLLMWITQC (SEQ ID NO.: 38)); HLA-Cw3-restricted p92-100 (LAMP-FATPM (SEQ ID NO.: 39)); HLA-Cw6-restricted p80-88 (ARGPESRLL (SEQ ID NO.: 40)); SLLMWITQC (SEQ ID NO.: 38); MLMAQEALAFL (SEQ ID NO.: 41); YLAMPFATPME (SEQ ID NO.: 42); ASGPGGGAPR (SEQ ID NO.: 43); LAAQERRVPR (SEQ ID NO.: 44); TVSGNILTIR (SEQ ID NO.: 45); APRGPHGGAASGL (SEQ ID NO.: 46); MPFATPMEAEL (SEQ ID NO.: 47); KEFTVSGNILTI (SEQ ID NO.: 48); MPFATPMEA (SEQ ID NO.: 49); FATPMEAEL (SEQ ID NO.: 50); FATPMEAELAR (SEQ ID NO.: 51); LAMPFATPM (SEQ ID NO.: 52); ARGPESRLL (SEQ ID NO.: 40); SLLMWITQCFLPVF (SEQ ID NO.: 53); LLEFYLAMPFATPMEAELARRSLAQ (SEQ ID NO.: 54); EFYLAMPFATPM (SEQ ID NO.: 55); PGVLLKEFTVSGNILTIRLTAADHR (SEQ ID NO.: 56); RLLEFYLAMPFA (SEQ ID NO.: 57); QGAMLAAQERRVPRAAEVPR (SEQ ID NO.: 58); PFATPMEAELARR (SEQ ID NO.: 59); PGVLLKEFTVSGNILTIRLT (SEQ ID NO.: 60); VLLKEFTVSG (SEQ ID NO.: 61); AADHRQLQLSISSCLQQL (SEQ ID NO.: 62); LKEFTVSGNILTIRL (SEQ ID NO.: 63); PGVLLKEFTVSGNILTIRLTAADHR (SEQ ID NO.: 56); LLEFYLAMPFATPMEAELARRSLAQ (SEQ ID NO.: 54); KEFTVSGNILT (SEQ ID NO.: 220); LLEFYLAMPFATPM (SEQ ID NO.: 64); and AGATGGRGPRGAGA (SEQ ID NO.: 65)); LAGE-1 (reported immunogenic epitopes include: MLMAQEALAFL (SEQ ID NO.: 41); SLLMWITQC (SEQ ID NO.: 38); LAAQERRVPR (SEQ ID NO.: 44); ELVRRILSR (SEQ ID NO.: 122); APRGVRMAV (SEQ ID NO.: 123); SLLMWITQCFLPVF (SEQ ID NO.: 53); QGAMLAAQERRVPRAAEVPR (SEQ ID NO.: 124); AADHRQLQLSISSCLQQL (SEQ ID NO.: 62); CLSRRPWKRSWSAGSCPGMPHL (SEQ ID NO.: 125); ILSRDAAPLPRPG (SEQ ID NO.: 126); and AGATGGRGPRGAGA (SEQ ID NO.: 65)); HERV-K-MEL (reported immunogenic epitopes include: MLAVISCAV (SEQ ID NO.: 117)); KK-LC-1 (reported immunogenic epitopes include: RQKRILVNL (SEQ ID NO.: 118)); KM-HN-1 (reported immunogenic epitopes include: NYNNFYRFL (SEQ ID NO.: 119); EYSKECLKEF (SEQ ID NO.: 120); and EYLSLSDKI (SEQ ID NO.: 121)); or Sp17 (reported immunogenic epitopes include: ILDSSEEDK (SEQ ID NO.: 107)).

Inducible Systems for Expression of Therapeutic Agents

If continuous administration of an antigen (e.g., a donor alloantigen, a self-antigen, or a non-self antigen) expressed by cloaked cells is needed to modulate an immune response, the antigen can be expressed using a constitutive promoter described herein or known by those of skill in the art (e.g., CAG, CMV, or another constitutive promoter). If the antigen is needed intermittently (e.g., needed during a period of relapse or flare up that occurs during a disease or condition, but not needed when a subject is asymptomatic), it can be expressed by an inducible promoter, which provides the capability of expressing the antigen only when it is needed. Antigens that may have potentially adverse effects if administered continuously can also be expressed intermittently using inducible promoters as described herein. Exemplary inducible expression systems are described below.

Tetracycline Response Element

One widely used inducible expression system is based on tetracycline-controlled transcriptional activation. In this system, the antibiotic tetracycline, or one of its derivatives (e.g., doxycycline), is used to reversibly activate or inhibit gene expression. To use this system, a tetracycline response element (TRE) is placed upstream of a gene of interest (e.g., an antigen to be expressed by cloaked cells), typically along with a minimal promoter that has very low basal expression. A protein called rtTA, which also needs to be expressed by the cloaked cells, binds to the TRE and activates transcription in the presence of tetracycline or doxycycline. When tetracycline or doxycycline is removed, rtTA no longer binds to the TRE and the gene of interest is no longer expressed. Advanced versions of this system, Tet-On Advanced transactivator (rtTA2$^{S}$-M2) and Tet-On 3G, may be particularly useful for human therapy as they are human codon optimized and respond to low concentrations of doxycycline, Light Inducible Systems Another method for inducible activation of gene expression involves the use of optogenetics, which uses light sensitive proteins to manipulate gene expression. A recent development in optogenetics that can be used to inducibly express antigens in cloaked cells involves a class of proteins that undergo a conformational change and dimerize in response to blue light. These proteins have been fused to DNA-binding and transcriptional components that have been shown to bind to specific promoter sequences and activate transcription when brought together by exposure to blue light (Wang et al., Nat Methods, 9:266-269, 2012). This method of inducibly activating gene expression could be used to control the production of antigens in cloaked cells that are administered subcutaneously, as blue light can be shone onto the skin near the cloaked subcutaneous tissue to induce production of an antigen by the cloaked cells.

Radiogenetics

A third method of inducibly activating gene expression (e.g., expression of an antigen by cloaked cells) involves the use of radio waves. In one version of a radio wave-inducible expression system, the TRPV1 receptor is fused to a GFP binding domain and co-expressed with a form of ferritin that is linked to GFP (Stanley et al., Nat Med 21:92-98, 2015). The GFP-ferritin binds to the GFP binding domain of the TRPV1 receptor. When a radio wave of a specific frequency is applied to the cell, ferritin interacts with TRPV1 and allows for an influx of calcium, which activates the transcription factor NFAT. Antigens can be inducibly expressed using this system if they are operably linked to an NFAT-sensitive promoter element, such as SRE-CRE-NFATRE, and co-expressed with TRPV1-GFP and GFP-ferritin. Radio wave-induced expression provides the advantage of being able to induce expression in cells that are further from the outside of the body, as radio waves can pass through tissue. For example, radiogenetics could be used to regulate gene expression in the retina. This method could, therefore, be used to inducibly express antigens in cloaked cells with non-invasive and non-harmful radio waves.

Destabilization Domain System

Gene expression can also be regulated using destabilization domain systems. A transgene encoding a protein of interest (e.g., an antigen described herein) can also include destabilizing domains, such that the resulting protein product includes the protein of interest fused to a destabilizing domain. Exemplary destabilizing domains include mutants of the human FK506- and rapamycin-binding protein (FKBP12), which confer instability to the proteins to which they are fused. FKBP12 mutants include N-terminal mutants F15S, V24A, H25R, E60G, and L106P, and C-terminal mutants M66T, R71G, D100G, D100N, E102G, and K1051, as characterized in Banaszynski et al., Cell 126:995 (2006), the disclosure of which is incorporated herein by reference as it pertains to FKBP12 destabilizing domains. Destabilizing domains promote protein degradation. A small molecule synthetic ligand can be used to stabilize the destabilizing domain-containing proteins when expression of the protein of interest (e.g., an antigen) is desired. The small molecule ligand Shield-1 (Shld1) can be used to stabilize FKBP12 mutant-containing proteins by protecting them from degradation. Other destabilizing domains that can be used to regulate expression proteins of interest include mutants of the *E. coli* dihydrofolate reductase (ecDHFR) and mutants of the human estrogen receptor ligand binding domain (ERLBD), which confer instability resulting in degradation when fused to a protein of interest and can be stabilized by small molecule ligand trimethoprim (TMP), or by CMP8 or 4-hydroxytamoxifen (4OHT), respectively, as described in Iwamoto et al., Chem Biol. 17:981 (2010) and Miyazaki et al., J Am Chem Soc., 134:3942 (2012), the disclosures of each of which are incorporated herein by reference as they pertain to destabilization domain systems.

Cumate Switch Inducible System

Another method for inducible activation of gene expression involves the use of the cumate gene-switch system. In the repressor configuration of this system, regulation is mediated by the binding of the repressor (CymR) to the operator site (CuO), placed downstream of a strong constitutive promoter. Addition of cumate, a small molecule, relieves the repression, allowing for expression of the transgene. Alternatively, a reverse-cumate-Trans-Activator (rcTA) may be inserted upstream of a minimal CMV promoter that is operably linked to a transgene encoding an antigen. A 6-times repeat of a Cumate Operator (6×CuO) may be inserted just before the translational start (ATG) of the transgene encoding the antigen. In the absence of cumate, rcTA cannot bind to the 6×CuO, so the transgene encoding the antigen will not be transcribed because the 6×CuO is not active. When cumate is added, it will form a complex with rcTA, which allows for binding to 6×CuO and transcription of the transgene encoding the antigen (Mullick et al., 2006).

Ecdysone Inducible System

Another example of an inducible gene expression system is the ecdysone inducible system, in which a retinoid X receptor (RXR) and an N-terminal truncation of ecdysone receptor (EcR) fused to the activation domain of Vp16 (VpEcR) are inserted in the 5' untranslated region of a gene expressed by the cloaked cell such that they are co-expressed by an endogenous promoter. An ecdysone responsive element (EcRE), with a downstream minimal promoter, can be inserted just upstream of the start codon of the transgene encoding the antigen. Co-expressed RXR and VpEcR can heterodimerize with each other. In the absence of ecdysone or synthetic drug analog muristerone A, dimerized RXR/VpEcR cannot bind to EcRE, so the transgene encoding the antigen is not transcribed. In the presence of ecdysone or muristerone A, dimerized RXR/VpEcR can bind to EcRE, such that the transgene encoding the antigen is transcribed (No et al., 1996). As ecdysone administration has no apparent effect on mammals, its use for regulating genes should be excellent for transient inducible expression of any gene.

Ligand-Reversible Dimerization System

In another example, the transgene encoding an antigen can be modified so that it is functionally divided in to parts/domains, such as a 5' portion and a 3' portion, and an FKBP peptide sequence can be inserted into each domain. An IRES (internal ribosomal entry site) sequence may be placed between the two domains, which allows for simultaneous transcription of the two different domains to generate two separate proteins. In the absence of a dimerization agent, the two separate domains of the antigen will be functionally inactive. Upon introduction of a dimerization agent, such as rapamycin or AP20187, the FKBP peptides will dimerize, bringing together the 5' and 3' domains of the antigen and reconstituting an active protein (Rollins et al., 2000).

Methods of Controlling Division of a Cloaked Cell

In an aspect, a method of controlling proliferation of a cloaked or uncloaked cell expressing a polypeptide containing an antigen is provided (e.g., to reduce the tumorigenic potential of a cloaked cell, to reduce proliferation of a cloaked cell that has become tumorigenic, or to ablate the cloaked or uncloaked cells).

The method comprises: providing a cell (e.g., a cell genetically modified to comprise at least one mechanism for providing antigen-specific immunomodulation when administered to a subject or an uncloaked cell) or a population of such cells; genetically modifying in the cell a cell division locus/loci (CDL), the CDL being one or more loci whose transcription product(s) is expressed by dividing cells (e.g., cells actively undergoing cell division), cells capable of undergoing cell division (e.g., cells that are not currently dividing but that have the capacity to do so), and post-mitotic cells (e.g., neurons), the genetic modification of the CDL containing one or more of: a) an ablation link (ALINK) system, the ALINK system comprising a DNA sequence encoding a negative selectable marker that is transcriptionally linked to a DNA sequence encoding the CDL (e.g., the DNA sequence encoding the negative selectable marker is inserted into the CDL such that expression of the negative selectable marker is linked to expression of the transcription product of the CDL, e.g., such that the negative selectable marker and CDL transcription product are co-expressed); and b) an inducible exogenous activator of regulation of a CDL (EARC) system, the EARC system comprising an inducible activator-based gene expression system that is operably linked to the CDL; permitting proliferation of the genetically modified cell comprising the ALINK system by maintaining the genetically modified cell comprising the ALINK system in the absence of an inducer of the negative selectable marker or ablating and/or inhibiting proliferation of the genetically modified cell comprising the ALINK system by exposing the cell comprising the ALINK system to the inducer of the negative selectable marker; and/or permitting proliferation of the genetically modified cell comprising the EARC system by exposing the genetically modified cell comprising the EARC system to an inducer of the inducible activator-based gene expression system or preventing or inhibiting proliferation of the genetically modified cell comprising the EARC system by maintaining the cell comprising the EARC system in the absence of the inducer of the inducible activator-based gene expression system; and administering the cell or a population of the cells to a subject. This approach can also be used to control cell division after cells containing an ALINK and/or EARC system have been administered to a subject by either administering the inducer (to ablate and/or inhibit proliferation of cells comprising an ALINK system or permit proliferation of cells comprising an EARC system) or withholding the inducer (to permit proliferation of cells comprising an ALINK system or prevent or inhibit proliferation of cells comprising the EARC system). Cells that have been modified to control cell division using one or more ALINK and/or EARC systems in one or more CDLs (e.g., 1, 2, 3, 4, or more CDLs) may be referred to as FAILSAFE™ cells. The number of cells that can be grown from a single FAILSAFE™ cell (clone volume) before the cell loses activity of all of the systems (e.g., ALINKs or EARCs) that control cell division through genetic mutation (e.g., the number of cell divisions it would take for a cell to "escape" from control and exhibit uncontrollable cell proliferation based on mathematical modeling) determines the FAILSAFE™ cell volume. The FAILSAFE™ cell volume will depend on the number of ALINKs and the number of ALINK-targeted CDLs. The fail-safe property is further described in Table 3.

viability or cell proliferation were to lose expression of the CDL (e.g., due to a mutation), the cell would die or stop proliferating, thereby obviating the need for proliferation of the cell to be controlled using the ALINK or EARC system. A cell may be modified to link the transcription of a negative selectable marker (ALINK) or an exogenous inducible transcriptional activator (EARC) to the transcription of a single gene (e.g., a single CDL, such as CDK1), e.g., by insertion of a DNA sequence encoding the negative selectable marker or exogenous inducible transcriptional activator into the gene locus such that the negative selectable marker or exogenous inducible transcriptional activator are co-expressed with the gene product. Alternatively, a cell may be modified to link the transcription of a negative selectable marker (ALINK) or an exogenous inducible transcriptional activator (EARC) to the transcription of more than one gene (e.g., 1, 2, 3, 4, 5, or more CDLs), e.g., by insertion of a DNA sequence encoding the negative selectable marker or exogenous inducible transcriptional activator into each of multiple CDLs (e.g., CDK1 and TOP2A or CDK1 and EEF2). A cell may be modified to include an ALINK system, an EARC system, or both.

In various embodiments, a CDL is a locus identified as an "essential gene" as set forth in Wang et al., 2015, which is incorporated herein by reference as if set forth in its entirety. Essential genes in Wang et al., 2015, were identified by computing a score (i.e., a CRISPR score) for each gene that reflects the fitness cost imposed by inactivation of the gene. In an embodiment, a CDL has a CRISPR score (CS) of less than about −1.0.

In various embodiments, a CDL is a locus/loci that encodes a gene product that is relevant to cell division and/or replication. For example, in various embodiments, a CDL is

TABLE 3

FAILSAFE ™ cell volumes and their relationship to a human body were calculated using mathematical modeling. The model did not take into account an event in which CDL expression was co-lost with the loss of negative selectable marker activity, compromising cell proliferation. Therefore the values are underestimates and were calculated assuming $10^6$ forward mutation rate for the negative selectable marker. The estimated number of cells in a human body as $3.72 \times 10^{13}$ was taken from (Bianconi et al., 2013).

| CDL # | ALINK # | Genotype in CDLs | FAILSAFE ™ cell volume (# cells) | Relative (x) to a human body = $3.72 \times 10^{13}$ cells | Estimated weight of clones |
|---|---|---|---|---|---|
| 1 | 1 | het | 512 | 0.0000000000137 | 1 μg |
| 1 | 2 | hom | 16777216 | 0.000000451 | 31 mg |
| 2 | 3 | het, hom | 1.374E+11 | 0.004 | 0.26 kg |
| 2 | 4 | hom, hom | 1.13E+15 | 30 | 2100 kg |

In some embodiments, the CDL is a gene that is required for cell viability (e.g., the gene is needed for cell survival), such that the absence or loss of CDL expression in a normal, unmodified cell leads to cell death. In other embodiments, the CDL is a gene that is required for cell proliferation, such that the absence or loss of CDL expression in a normal, unmodified cell inhibits or impairs cell proliferation. Linking the expression of a negative selectable marker (ALINK) or exogenous inducible transcriptional activator (EARC) to the transcription of such a gene is desirable because it prevents the cell from "escaping" from control (e.g., the cell cannot divide uncontrollably in the absence of the gene) when linked to expression of the negative selectable marker (ALINK) or exogenous inducible transcriptional activator (EARC)). If a cell modified to co-express a negative selectable marker (ALINK) or exogenous inducible transcriptional activator (EARC) with a CDL required for cell a locus/loci that encodes a gene product that is relevant to one or more of: i) cell cycle; ii) DNA replication; iii) RNA transcription and/or protein translation; and iv) metabolism.

In an embodiment, a CDL is one or more cyclin-dependent kinases that are involved with regulating progression of the cell cycle (e.g., control of G1/S G2/M and metaphase-to-anaphase transition), such as CDK1, CDK2, CDK3, CDK4, CDK5, CDK6, CDK7, CDK8, CDK9 and/or CDK11 (Morgan, 2007). In an embodiment, a CDL is one or more cyclins that are involved with controlling progression of the cell cycle by activating one or more CDK, such as, for example, cyclinB, cyclinE, cyclinA, cyclinC, cyclinD, cyclinH, cyclinC, cyclinT, cyclinL and/or cyclinF (FUNG and POON, 2005). In an embodiment, a CDL is one or more loci involved in the anaphase-promoting complex that controls the progression of metaphase to anaphase transition in the M phase of the cell cycle (Peters, 2002). In an embodiment, a CDL is one or more loci involved with kinetochore components that control the progression of metaphase to anaphase transition in the M phase of the cell cycle (Fukagawa, 2007). In an embodiment, a CDL is one or more loci involved with microtubule components that control microtubule dynamics required for the cell cycle (Cassimeris, 1999).

In various embodiments, a CDL is a locus/loci involved with housekeeping. As used herein, the term "housekeeping gene" or "housekeeping locus" refers to one or more genes that are required for the maintenance of basic cellular function. Housekeeping genes are expressed in all cells of an organism under normal and patho-physiological conditions.

In various embodiments, a CDL is a locus/loci that encodes a gene product that is relevant to cell division and/or proliferation and has a CRISPR score of less than about −1.0. For example, in an embodiment, a CDL is a locus/loci that encodes a gene product that is relevant to one or more of: i) cell cycle; ii) DNA replication; iii) RNA transcription and/or protein translation; and iv) metabolism, and has a CRISPR score of less than about −1.0. In an embodiment, the CDL may also be a housekeeping gene.

In some embodiments, the CDL is Cdk1/CDK1, Top2A/TOP2A, Cenpa/CEPNA, Birc5/BIRC5, or Eef2/EEF2. In some embodiments, the CDL is Cdk1/CDK1. In some embodiments, the CDL is Top2A/TOP2A. In some embodiments, the CDL is Eef2/EEF2. In some embodiments, the CDLs are Cdk1/CDK1 and Top2A/TOP2A or Cdk1/CDK1 and Eef2/EEF2.

In some embodiments, the CDL is one or more (e.g., 1, 2, 3, 4, or more) loci (e.g., genes) selected from the group including (presented in the format: mouse gene name/HUMAN GENE NAME(mouse EntrezGene ID/Human EntrezGene ID)) Actr8/ACTR8(56249/93973); Alg11/ALG11(207958/440138); Anapc11/ANAPC11(66156/51529); Anapc2/ANAPC2(99152/29882); Anapc4/ANAPC4(52206/29945); Anapc5/ANAPC5(59008/51433); Aurka/AURKA(20878/6790); Banf1/BANF1(23825/8815); Birc5/BIRC5(11799/332); Bub3/BUB3(12237/9184); Casc5/CASC5(76464/57082); Ccna2/CCNA2(12428/890); Ccnh/CCNH(66671/902); Cdc123/CDC123(98828/8872); Cdc16/CDC16(69957/8881); Cdc20/CDCl20(107995/991); Cdc23/CDCl23(52563/8697); Cdk1/CDK1(12534/983); Cenpa/CENPA(12615/1058); Cenpm/CENPM(66570/79019); Chek1/CHEK1(12649/1111); Chmp2a/CHMP2A (68953/27243); Ckap5/CKAP5(75786/9793); Cltc/CLTC (67300/1213); Cops5/COPS5(26754/10987); Dctn2/DCTN2(69654/10540); Dctn3/DCTN3(53598/11258); Dhfr/DHFR(13361/1719); Dtl/DTL(76843/51514); Dync1h1/DYNC1H1(13424/1778); Ecd/ECD(70601/11319); Ect2/ECT2(13605/1894); Ep300/EP300(328572/2033); Ercc3/ERCC3(13872/2071); Espl1/ESPL1(105988/9700); Fntb/FNTB(110606/2342); Gadd45gip1/GADD45GIP1(102060/90480); Gins1/GINS1(69270/9837); Gnb2l1/GNB2L1(14694/10399); Gspt1/GSPT1 (14852/2935); Haus1/HAUS1(225745/115106); Haus3/HAUS3(231123/79441); Haus5/HAUS5(71909/23354); Haus8/HAUS8(76478/93323); Hdac3/HDAC3(15183/8841); Kif11/KIF11(16551/3832); Kif23/KIF23(71819/9493); Kpnb1/KPNB1(16211/3837); Mastl/MASTL(67121/84930); Mau2/MAU2(74549/23383); Mcm3/MCM3 (17215/4172); Mcm4/MCM4(17217/4173); Mcm7/MCM7 (17220/4176); Mnat1/MNAT1(17420/4331); Mybbp1a/MYBBP1A(18432/10514); Ncapd2/NCAPD2(68298/9918); Ncaph/NCAPH(215387/23397); Ndc80/NDC80 (67052/10403); Nie1/NLE1(217011/54475); Nsl1/NSL1 (381318/25936); Nudc/NUDC(18221/10726); Nuf2/NUF2 (66977/83540); Nup133/NUP133(234865/55746); Nup160/NUP160(59015/23279); Nup188/NUP188(227699/23511); Nup214/NUP214(227720/8021); n/a/NUP62(n/a/23636); Nup85/NUP85(445007/79902); ORC3/Orc3(50793/23595); Pafah1b1/PAFAH1B1(18472/5048); Pcid2/PCID2(234069/55795); Pfas/PFAS(237823/5198); Phb2/PHB2(12034/11331); Pkmyt1/PKMYT1(268930/9088); Plk1/PLK1 (18817/5347); Pmf1/PMF1(67037/11243); Pole2/POLE2 (18974/5427); Ppat/PPAT(231327/5471); Psma6/PSMA6 (26443/5687); Psma7/PSMA7(26444/5688); Psmb1/PSMB1(19170/5689) Psmb4/PSMB4(19172/5692); Psmd12/PSMD12(66997/5718); Psmd13/PSMD13(23997/5719); Psmd14/PSMD14(59029/10213); Psmd7/PSMD7 (17463/5713); Racgap1/RACGAP1(26934/29127); Rad21/RAD21(19357/5885); Rae1/RAE1(66679/8480); Rcc1/RCC1(100088/1104); Rfc3/RFC3(69263/5983); Rps27a/RPS27A(78294/6233); Rrm2/RRM2(20135/6241); Sae1/SAE1(56459/10055); Sec13/SEC13(110379/6396); Smarcb1/SMARCB1(20587/6598); Smc2/SMC2(14211/10592); Smc4/SMC4(70099/10051); Son/SON(20658/6651); Spc24/SPC24(67629/147841); Spc25/SPC25(66442/57405); Terf2/TERF2(21750/7014); Tpx2/TPX2(72119/22974); Tubg1/TUBG1(103733/7283); Tubgcp2/TUBGCP2(74237/10844); Tubgcp5/TUBGCP5(233276/114791); Tubgcp6/TUBGCP6(328580/85378); Txnl4a/TXNL4A(27366/10907); Usp39/USP39(28035/10713); Wdr43/WDR43(72515/23160); Zfp830/ZNF830(66983/91603); Aatf/AATF(56321/26574); Alyref/ALYREF(21681/10189); Brf2/BRF2(66653/55290); Cdc45/CDCl45(12544/8318); Cdc6/CDCl6(23834/990); Cdt1/CDT1(67177/81620); Cinp/CINP(67236/51550); Cirh1a/CIRH1A(21771/84916); Ddb1/DDB1(13194/1642); (Ercc2/ERCC2(13871/2068); Gabpb1/GABPB1(14391/2553); Gtf2b/GTF2B (229906/2959); Gtf2h4/GTF2H4(14885/2968); Gtf3a/GTF3A(66596/2971); Gtf3c1/GTF3C1(233863/2975); Gtf3c2/GTF3C2(71752/2976); Hinfp/HINFP(102423/25988); n/a/HIST2H2AA3(n/a/8337); Ints3/INTS3(229543/65123); Kin/KIN(16588/22944); Mcm2/MCM2(17216/4171); Mcm6/MCM6(17219/4175); Mcrs1/MCRS1(51812/10445); Med11/MED11(66172/400569); Mtpap/MTPAP (67440/55149); Myc/MYC(17869/4609); Ndnl2/NDNL2 (66647/56160); Nol11/NOL11(68979/25926); Nol8/NOL8 (70930/55035); Pcna/PCNA(18538/5111); Pola1/POLA1 (18968/5422); Pold2/POLD2(18972/5425); Pole/POLE (18973/5426); Polr1a/POLR1A(20019/25885); n/a/POLR2J2(n/a/246721); Polr3a/POLR3A(218832/11128); Polr3c/POLR3C(74414/10623); Polr3h/POLR3H(78929/171568); Prmt1/PRMT1(15469/3276); Prmt5/PRMT5 (27374/10419); Puf60/PUF60 (67959/22827); Rad51/RAD51(19361/5888); Rad51c/RAD51C(114714/5889); Rbx1/RBX1(56438/9978); Rfc2/RFC2(19718/5982); Rfc4/RFC4(106344/5984); Rfc5/RFC5(72151/5985); Rpa1/RPA1(68275/6117); Rps3/RPS3(27050/6188); Rrm1/RRM1(20133/6240); Ruvbl1/RUVBL1(56505/8607); Ruvbl2/RUVBL2(20174/10856); Sap30bp/SAP30BP (57230/29115); Smc1a/SMC1A(24061/8243); Smc3/SMC3 (13006/9126); Snapc4/SNAPC4(227644/6621); Snapc5/SNAPC5(330959/10302); Snip1/SNIP1(76793/79753); Srrt/SRRT(83701/51593); Ssrp1/SSRP1(20833/6749); Taf10/TAF10(24075/6881); Taf1c/TAF1C(21341/9013); Taf6/TAF6(21343/6878); Taf6l/TAF6L(67706/10629); Ticrr/TICRR(77011/90381); Top1/TOP1(21969/7150); Top2a/TOP2A(21973/7153); Trrap/TRRAP(100683/8295); Zbtb11/ZBTB11(271377/27107); Actl6a/ACTL6A(56456/86); Atr/ATR(245000/545); Chd4/CHD4(107932/1108); Ciao1/CIAO1(26371/9391); Ddx21/DDX21(56200/9188); Dnaja3/DNAJA3(83945/9093); Dnmt1/DNMT1(13433/

1786); Gins2/GINS2(272551/51659); Gtf2h3/GTF2H3 (209357/2967); n/a/HIST2H2BF(n/a/440689); Mms22l/MMS22L(212377/253714); Mtor/MTOR(56717/2475); Narfl/NARFL(67563/64428); Ndufa13/NDUFA13(67184/51079); Nol12/NOL12(97961/79159); Nup107/NUP107 (103468/57122); Oraov1/ORAOV1(72284/220064); Pam16/PAM16(66449/51025); Pola2/POLA2(18969/23649); Ppie/PPIE(56031/10450); Prpf19/PRPF19(28000/27339); Psmc5/PSMC5(19184/5705); Rbbp5/RBBP5 (213464/5929); Rbbp6/RBBP6(19647/5930); Rptor/RPTOR(74370/57521); Rrn3/RRN3(106298/54700); Smg1/SMG1(233789/23049); Supt6/SUPT6H(20926/6830); Tada2b/TADA2B(231151/93624); Tfip11/TFIP11(54723/24144); Tonsl/TONSL(66914/4796); Tpt1/TPT1(22070/7178); Uba1/UBA1(22201/7317); Vps25/VPS25(28084/84313); Wbscr22/WBSCR22(66138/114049); Wdr5/WDR5 (140858/11091); Xab2/XAB2(67439/56949); Zmat2/ZMAT2(66492/153527); Zfp335/ZNF335(329559/63925); Acly/ACLY(104112/47); Adsl/ADSL(11564/158); Ahcy/AHCY(269378/191); Arl2/ARL2(56327/402); Chka/CHKA (12660/1119); Coasy/COASY(71743/80347); Cox4i1/COX4I1(12857/1327); n/a/COX7C(n/a/1350); n/a/CTPS1 (n/a/1503); Ddx10/DDX10(77591/1662); Ddx20/DDX20 (53975/11218); Dhdds/DHDDS(67422/79947); Dhx30/DHX30(72831/22907); Dhx8/DHX8(217207/1659); Dhx9/DHX9 (13211/1660); Dlst/DLST(78920/1743); Dpagt1/DPAGT1(13478/1798); Gfpt1/GFPT1(14583/2673); Gmps/GMPS(229363/8833); Gpn1/GPN1(74254/11321); Gpn3/GPN3(68080/51184); Guk1/GUK1 (14923/2987); Hsd17b10/HSD17B10(15108/3028); Lrr1/LRR1(69706/122769); Mtg2/MTG2(52856/26164); Myh9/MYH9 (17886/4627); Nampt/NAMPT(59027/10135); Ncbp1/NCBP1(433702/4686); Nfs1/NFS1(18041/9054); Ppcdc/PPCDC(66812/60490); Qrsl1/QRSL1(76563/55278); Rpp14/RPP14(67053/11102); Smarca4/SMARCA4(20586/6597); Snrnp200/SNRNP200(320632/23020); Srbd1/SRBD1(78586/55133); Srcap/SRCAP(100043597/10847); Ube2i/UBE2I(22196/7329); Ube2m/UBE2M (22192/9040); Vcp/VCP(269523/7415); Aamp/AAMP(227290/14); Acin1/ACIN1(56215/22985); Aco2/ACO2(11429/50); Adss/ADSS(11566/159); Alg2/ALG2(56737/85365); Ap2s1/AP2S1(232910/1175); Arcn1/ARCN1(213827/372); Armc7/ARMC7(276905/79637); Atp2a2/ATP2A2(11938/488); Atp5a1/ATP5A1(11946/498); Atp5d/ATP5D(66043/513); Atp5o/ATP5O(28080/539); Atp6v0b/ATP6V0B (114143/533); Atp6v0c/ATP6VOC(11984/527); Atp6v1a/ATP6V1A(11964/523); Atp6v1b2/ATP6V1B2(11966/526); Atp6v1d/ATP6V1D(73834/51382); Aurkaip1/AURKAIP1 (66077/54998); n/a/C1orf109(n/a/54955); n/a/C21orf59(n/a/56683); Ccdc84/CCDC84(382073/338657); Cct2/CCT2 (12461/10576); Cct3/CCT3(12462/7203); Cct4/CCT4 (12464/10575); Cct5/CCT5(12465/22948); Cct7/CCT7 (12468/10574); Cct8/CCT8(12469/10694); Cdipt/CDIPT (52858/10423); Cenpi/CENPI(102920/2491); Chordc1/CHORDC1(66917/26973); Coa5/COA5(76178/493753); Cog4/COG4(102339/25839); Copa/COPA(12847/1314); Copb1/COPB1(70349/1315); Copb2/COPB2(50797/9276); Cope/COPE(59042/11316); Copz1/COPZ1(56447/22818); Coq4/COQ4(227683/51117); Cox15/COX15(226139/1355); Cox17/COX17(12856/10063); Cse1l/CSE1L (110750/1434); Csnk2b/CSNK2B(13001/1460); Cycs/CYCS(13063/54205); Dad1/DAD1(13135/1603); Dap3/DAP3(65111/7818); Dctn5/DCTN5(59288/84516); Ddost/DDOST(13200/1650); Dgcr8/DGCR8(94223/54487); Dhodh/DHODH(56749/1723); Dnlz/DNLZ(52838/728489); Dnm1l/DNM1L(74006/10059); Dnm2/DNM2 (13430/1785); Dohh/DOHH(102115/83475); Dolk/DOLK (227697/22845); Donson/DONSON(60364/29980); Dph3/DPH3(105638/285381); Dtymk/DTYMK(21915/1841); Eif2b2/EIF2B2(217715/8892); Eif2s2/EIF2S2(67204/8894); Emc1/EMC1(230866/23065); Emc7/EMC7(73024/56851); Eno1/ENO1(13806/2023); Fam50a/FAM50A (108160/9130); Fam96b/FAM96B(68523/51647); Fdps/FDPS(110196/2224); Gapdh/GAPDH(14433/2597); Gart/GART(14450/2618); Gemin4/GEMIN4(276919/50628); Gemin5/GEMIN5(216766/25929); Ggps1/GGPS1(14593/9453); Gmppb/GM PPB(331026/29925); Gnb1l/GNB1L (13972/54584); n/a/GOLGA6L1(n/a/283767); Gosr2/GOSR2(56494/9570); Gpkow/GPKOW(209416/27238); Gpn2/GPN2(100210/54707); Gps1/GPS1(209318/2873); Grpel1/GRPEL1(17713/80273); Grwd1/GRWD1(101612/83743); Hmgcr/HMGCR(15357/3156); Hmgcs1/HMGCS1 (208715/3157); Hspa5/HSPA5(14828/3309); Hspa9/HSPA9 (15526/3313); Hspd1/HSPD1(15510/3329); Hspe1/HSPE1 (15528/3336); Hyou1/HYOU1(12282/10525); Ipo13/IPO13 (230673/9670); Iscu/ISCU (66383/23479); Itpk1/ITPK1 (217837/3705); Kansl2/KANSL2(69612/54934); Kansl3/KANSL3(226976/55683); Kri1/KRI1(215194/65095); Lamtor2/LAMTOR2(83409/28956); Leng8/LENG8 (232798/114823); Ltv1/LTV1(353258/84946); Mak16/MAK16(67920/84549); Mat2a/MAT2A(232087/4144); Mcm3ap/MCM3AP(54387/8888); Mdn1/MDN1(100019/23195); n/a/MFAP1(n/a/4236); Mmgt1/MMGT1(236792/93380); Mrpl16/MRPL16(94063/54948); Mrpl17/MRPL17(27397/63875); Mrpl33/MRPL33(66845/95530); Mrpl38/MRPL38(60441/64978); Mrpl39/MRPL39(27393/54148); Mrpl45/MRPL45(67036/84311); Mrpl46/MRPL46(67308/26589); Mrpl53/MRPL53(68499/116540); Mrps22/MRPS22(64655/56945); Mrps25/MRPS25(64658/64432); Mrps35/MRPS35(232536/60488); Mrps5/MRPS5(77721/64969); Mvd/MVD (192156/4597); Mvk/MVK(17855/4598); Naa25/NAA25(231713/80018); Napa/NAPA(108124/8775); Nat10/NAT10(98956/55226); Ndor1/NDOR1(78797/27158); Ndufab1/NDUFAB1 (70316/4706); Nol10/NOL10(217431/79954); Nop9/NOP9 (67842/161424); Nrde2/NRDE2(217827/55051); Nsf/NSF (18195/4905); Nubp1/NUBP1(26425/4682); Nudcd3/NUDCD3(209586/23386); Nup155/NUP155(170762/9631); Nup93/NUP93(71805/9688); Nus1/NUS1(52014/116150); Nvl/NVL(67459/4931); Ogdh/OGDH (18293/4967); Osbp/OSBP(76303/5007); Pak1ip1/PAK1IP1 (68083/55003); Pfdn2/PFDN2(18637/5202); Pgam1/PGAM1(18648/5223); Pkm/PKM (18746/5315); Pmpcb/PMPCB(73078/9512); Ppil2/PPIL2(66053/23759); Ppp4c/PPP4C(56420/5531); Prelid1/PRELID1(66494/27166); Prpf31/PRPF31(68988/26121); Prpf6/PRPF6(68879/24148); Psma1/PSMA1(26440/5682); Psma2/PSMA2 (19166/5683); Psma3/PSMA3(19167/5684); Psmb2/PSMB2(26445/5690); Psmb3/PSMB3(26446/5691); Psmb5/PSMB5(19173/5693); Psmb6/PSMB6(19175/5694); Psmb7/PSMB7(19177/5695); Psmc2/PSMC2(19181/5701); Psmc3/PSMC3(19182/5702); Psmc4/PSMC4(23996/5704); Psmd1/PSMD1(70247/5707); Psmd2/PSMD2(21762/5708); Psmd3/PSMD3(22123/5709); Psmd4/PSMD4 (19185/5710); Psmd6/PSMD6(66413/9861); Psmg3/PSMG3(66506/84262); Ptpmt1/PTPMT1(66461/114971); Ptpn23/PTPN23(104831/25930); Rabggta/RABGGTA (56187/5875); Rabggtb/RABGGTB(19352/5876); Rbm19/RBM 19(74111/9904); Rfk/RFK(54391/55312); Rheb/RHEB(19744/6009); Riok1/RIOK1(71340/83732); Rpn1/RPN1(103963/6184); Rtfdc1/RTFDC1(66404/51507); Sacm1l/SACM1L(83493/22908); Samm50/SAMM50 (68653/25813); Sco2/SCO2(100126824/9997); Sdha/SDHA(66945/6389); Sdhb/SDHB(67680/6390); Sec61a1/

SEC61A1 (53421/29927); Slc20a1/SLC20A1(20515/6574); Slc7a6os/SLC7A60S(66432/84138); Smn1/SMN1(20595/6606); Smu1/SMU1(74255/55234); Snrpd1/SNRPD1 (20641/6632); Snrpd3/SNRPD3(67332/6634); Snrpe/SNRPE(20643/6635); Spata5/SPATA5(57815/166378); Spata5l1/SPATA5L1(214616/79029); Tango6/TANGO6 (272538/79613); n/a/TBC1D3B (n/a/414059); n/a/TBC1D3C(n/a/414060); Tbcb/TBCB(66411/1155); Tbcc/TBCC(72726/6903); Tbcd/TBCD(108903/6904); Tcp1/TCP1(21454/6950); Telo2/TELO2(71718/9894); Tax10/TEX10(269536/54881); Tfrc/TFRC(22042/7037); Timm10/TIMM10(30059/26519); Timm13/TIMM13(30055/26517); Timm23/TIMM23(53600/100287932); Timm44/TIMM44 (21856/10469); Tmx2/TMX2(66958/51075); Tnpo3/TNPO3(320938/23534); Trmt112/TRMT112(67674/51504); Trnau1ap/TRNAU1AP(71787/54952); Ttc1/TTC1 (66827/7265); Ttc27/TTC27(74196/55622); Tti1/TTI1 (75425/9675); Tti2/TTI2(234138/80185); n/a/TUBB(n/a/203068); Txn2/TXN2(56551/25828); Uqcrc1/UQCRC1 (22273/7384); Uqcrh/UQCRH(66576/7388); Urb2/URB2 (382038/9816); Vmp1/VMP1(75909/81671); n/a/VPS28(n/a/51160); Vps29/VPS29(56433/51699); Vps52/VPS52 (224705/6293); Wars2/WARS2(70560/10352); Wdr7/WDR7(104082/23335); Wdr70/WDR70(545085/55100); Wdr74/WDR74(107071/54663); Wdr77/WDR77(70465/79084); Yae1d1/YAE1D1(67008/57002); Yrdc/YRDC (230734/79693); Znhit2/ZNHIT2(29805/741); Aars/AARS (234734/16); Bms1/BMS1(213895/9790); Bud31/BUD31 (231889/8896); Bysl/BYSL(53414/705); Cars/CARS (27267/833); Cdc5l/CDC5L(71702/988); Cdc73/CDCl73 (214498/79577); Cebpz/CEBPZ(12607/10153); Clasrp/CLASRP(53609/11129); Clp1/CLP1(98985/10978); Cox5b/COX5B(12859/1329); Cpsf1/CPSF1(94230/29894); Cpsf2/CPSF2 (51786/53981); Cpsf3l/CPSF3L(71957/54973); Dars/DARS(226414/1615); Dbr1/DBR1(83703/51163); Ddx18/DDX18(66942/8886); Ddx23/DDX23 (74351/9416); Ddx24/DDX24(27225/57062); Ddx41/DDX41(72935/51428); Ddx46/DDX46(212880/9879); Ddx47/DDX47(67755/51202); Ddx49/DDX49(234374/54555); Ddx54/DDX54(71990/79039); Ddx56/DDX56 (52513/54606); Dgcr14/DGCR14(27886/8220); Dhx15/DHX15(13204/1665); Dhx16/DHX16(69192/8449); Dhx38/DHX38(64340/9785); Diexf/DIEXF(215193/27042); Dimt1/DIMT1(66254/27292); Dis3/DIS3(72662/22894); Dkc1/DKC1(245474/1736); Dnajc17/DNAJC17 (69408/55192); Ears2/EARS2(67417/124454); Ebna1bp2/EBNA1BP2(69072/10969); Eef1a1/EEF1A1(13627/1915); Eef1g/EEF1G(67160/1937); Eef2/EEF2(13629/1938); Eftud2/EFTUD2(20624/9343); Eif1ad/EIF1AD(69860/84285); Eif2b1/EIF2B1(209354/1967); Eif2b3/EIF2B3 (108067/8891); Eif2s1/EIF2S1(13665/1965); Eif3c/EIF3C (56347/8663); n/a/EIF3CL(n/a/728689); Eif3d/EIF3D (55944/8664); Eif3f/EIF3F(66085/8665); Eif3g/EIF3G (53356/8666); Eif3i/EIF3I(54709/8668); Eif3l/EIF3L (223691/51386); Eif4a1/EIF4A1(13681/1973); Eif4a3/EIF4A3(192170/9775); Eif4g1/EIF4G1(208643/1981); Eif5b/EIF5B(226982/9669); Eif6/EIF6(16418/3692); Elac2/ELAC2(68626/60528); Ell/ELL(13716/8178); Etf1/ETF1(225363/2107); Exosc2/EXOSC2(227715/23404); Exosc4/EXOSC4(109075/54512); Exosc5/EXOSC5 (27998/56915); n/a/EXOSC6(n/a/118460); Exosc7/EXOSC7(66446/23016); Exosc8/EXOSC8(69639/11340); Fars2/FARS2(69955/10667); Farsa/FARSA(66590/2193); Farsb/FARSB(23874/10056); Fau/FAU(14109/2197); Fip1l1/FIP1L1(66899/81608); Ftsj3/FTSJ3(56095/117246); Gle1/GLE1(74412/2733); Gnl3l/GNL3L(237107/54552); Gtf2e1/GTF2E1(74197/2960); Gtpbp4/GTPBP4(69237/23560); Hars/HARS(15115/3035); Hars2/HARS2(70791/23438); Heatr1/HEATR1(217995/55127); Hnrnpc/HNRNPC(15381/3183); Hnrnpk/HNRNPK(15387/3190); Hnrnpl/HNRNPL(15388/3191); Hnrnpu/HNRNPU(51810/3192); Iars/IARS(105148/3376); Iars2/IARS2(381314/55699); Imp3/IMP3(102462/55272); Imp4/IMP4(27993/92856); Ints1/INTS1(68510/26173); Ints4/INTS4(101861/92105); Ints5/INTS5(109077/80789); Ints8/INTS8(72656/55656); Ints9/INTS9(210925/55756); Isg2012/ISG20L2 (229504/81875); Kars/KARS(85305/3735); n/a/KIAA0391 (n/a/9692); Lars/LARS(107045/51520); Lars2/LARS2 (102436/23395); Las1l/LAS1L(76130/81887); Lrpprc/LRPPRC(72416/10128); Lsm2/LSM2(27756/57819); Lsm3/LSM3(67678/27258); Lsm7/LSM7(66094/51690); Magoh/MAGOH(17149/4116); Mars/MARS(216443/4141); Mars2/MARS2(212679/92935); Med17/MED17 (234959/9440); Med20/MED20(56771/9477); Med22/MED22(20933/6837); Med27/MED27(68975/9442); Med30/MED30(69790/90390); Med8/MED8(80509/112950); Mepce/MEPCE(231803/56257); Mett116/METTL16(67493/79066); Mphosph10/MPHOSPH10 (67973/10199); Mrp110/MRPL10(107732/124995); Mrp112/MRPL12(56282/6182); Mrp121/MRPL21(353242/219927); Mrp128/MRPL28(68611/10573); Mrpl3/MRPL3 (94062/11222); Mrpl34/MRPL34(94065/64981); Mrpl4/MRPL4(66163/51073); Mrpl41/MRPL41 (107733/64975); Mrpl51/MRPL51 (66493/51258); Mrps14/MRPS14(64659/63931); Mrps15/MRPS15(66407/64960); Mrps 16/MRPS16(66242/51021); Mrps18a/MRPS18A(68565/55168); Mrps2/MRPS2(118451/51116); Mrps21/MRPS21(66292/54460); Mrps24/MRPS24(64660/64951); Mrps6/MRPS6 (121022/64968); Nars/NARS(70223/4677); Nars2/NARS2 (244141/79731); Ncbp2/NCBP2(68092/22916); Nedd8/NEDD8(18002/4738); Ngdn/NGDN(68966/25983): Nhp2/NHP2(52520/55651); Nip7/NIP7(66164/51388); Noc2l/NOC2L(57741/26155); Noc4l/NOC4L(100608/79050); Nol6/NOL6(230082/65083); Nol9/NOL9(74035/79707); Nop16/NOP16(28126/51491); Nop2/NOP2(110109/4839): Nop58/NOP58(55989/51602); Nsa2/NSA2(59050/10412); Nudt21/NUDT21 (68219/11051); Osgep/OSGEP(66246/55644); Pabpn1/PABPN1 (54196/8106); Pdcd11/PDCD11 (18572/22984); Pes1/PES1(64934/23481); Phb/PHB (18673/5245); Phf5a/PHF5A(68479/84844); Pnn/PNN (18949/5411); Polr1b/POLR1 B(20017/84172); Polr1C/POLR10(20016/9533); Polr2a/POLR2A(20020/5430); Polr2b/POLR2B (231329/5431); Polr2c/POLR2C(20021/5432); Polr2d/POLR2D(69241/5433); Polr2f/POLR2F (69833/5435); Polr2g/POLR2G(67710/5436); Polr2h/POLR2H(245841/5437); Polr2i/POLR2l(69920/5438); Polr2j/POLR2J(20022/5439); Polr2l/POLR2L(66491/5441); Polr3e/POLR3E(26939/55718); Pop1/POP1 (67724/10940); Pop4/POP4(66161/10775); Ppa1/PPA1(67895/5464); Ppan/PPAN(235036/56342); Ppp2ca/PPP2CA (19052/5515); Prim1/PRIM1 (19075/5557); Prpf38b/PRPF38B(66921/55119); Prpf4/PRPF4(70052/9128); Prpf8/PRPF8(192159/10594); Ptcd1/PTCD1(71799/26024); Pwp2/PWP2(110816/5822); Qars/QARS(97541/5859); Ran/RAN(19384/5901); Rars/RARS(104458/5917); Rars2/RARS2(109093/57038); Rbm25/RBM25(67039/58517); Rbm8a/RBM8A(60365/9939); Rbmx/RBMX (19655/27316); Rcl/RCL1(59028/10171); Rngtt/RNGTT (24018/8732): Rnmt/RNMT(67897/8731); Rnpc3/RNPC3 (67225/55599); Rpap1/RPAP1 (68925/26015); Rpl10/RPL10(110954/6134); Rpl10a/RPL10A(19896/4736); Rpl11/RPL11(67025/6135); Rpl12/RPL12(269261/6136); Rpl13/RPL13(270106/6137); Rpl14/RPL14(67115/9045); Rpl15/RPL15(66480/6138); Rpl18/RPL18(19899/6141);

Rpl18a/RPL18A(76808/6142); Rpl23/RPL23(65019/9349); n/a/RPL23A(n/a/6147); Rpl24/RPL24(68193/6152); Rpl26/RPL26(19941/6154); Rpl27/RPL27(19942/6155); Rpl27a/RPL27A(26451/6157); Rpl3/RPL3(27367/6122); Rpl30/RPL30(19946/6156); Rpl31/RPL31(114641/6160); Rpl32/RPL32(19951/6161); n/a/RPL34(n/a/6164); Rpl35/RPL35(66489/11224); Rpl35a/RPL35A(57808/6165); Rpl36/RPL36(54217/25873); Rpl37/RPL37(67281/6167); Rpl37a/RPL37A(19981/6168); Rpl38/RPL38(67671/6169); Rpl4/RPL4(67891/6124); Rpl5/RPL5(100503670/6125); Rpl6/RPL6(19988/6128); Rpl7/RPL7(19989/6129); Rpl7a/RPL7A(27176/6130); Rp7l1/RPL7L1(66229/285855); Rpl8/RPL8(26961/6132); Rpl9/RPL9 (20005/6133); Rplp0/RPLP0(11837/6175); Rpp21/RPP21(67676/79897); Rpp30/RPP30(54364/10556); Rps10/RPS10(67097/6204); Rps11/RPS11(27207/6205); Rps12/RPS12(20042/6206); Rps13/RPS13(68052/6207); n/a/RPS14(n/a/6208); Rps15/RPS15(20054/6209); Rps15a/RPS15A(267019/6210); Rps16/RPS16(20055/6217); Rps17/RPS17(20068/6218); Rps19/RPS19(20085/6223); Rps2/RPS2(16898/6187); Rps21/RPS21(66481/6227); Rps23/RPS23(66475/6228); Rps25/RPS25(75617/6230); n/a/RPS3A(n/a/6189); Rps4x/RPS4X(20102/6191); Rps5/RPS5(20103/6193); Rps6/RPS6(20104/6194); Rps7/RPS7(20115/6201); Rps8/RPS8(20116/6202); Rps9/RPS9(76846/6203); Rpsa/RPSA(16785/3921); Rsl24d1/RSL24D1(225215/51187); Sars/SARS(20226/6301); Sars2/SARS2(71984/54938); Sart1/SART1(20227/9092); Sart3/SART3(53890/9733); Sdad1/SDAD1(231452/55153); Sf1/SF1(22668/7536); Sf3a1/SF3A1(67465/10291); Sf3a2/SF3A2(20222/8175); Sf3a3/SF3A3(75062/10946); Sf3b2/SF3B2(319322/10992); Sf3b3/SF3B3(101943/23450); Sf3b4/SF3B4 (107701/10262); Sfpq/SFPQ(71514/6421); Sin3a/SIN3A(20466/25942); Smg5/SMGS(229512/23381); Smg6/SMG6(103677/23293); Snrnp25/SNRNP25(78372/79622); Snrnp27/SNRNP27(66618/11017); Snrpd2/SNRPD2(107686/6633); Snrpf/SNRPF(69878/6636); Srrm1/SRRM1(51796/10250); Srsf1/SRSF1(110809/6426); Srsf2/SRSF2(20382/6427); Srsf3/SRSF3(20383/6428); Srsf7/SRSF7(225027/6432); Ssu72/SSU72(68991/29101); Sugp1/SUGP1(70616/57794); Tars/TARS(110960/6897); Tars2/TARS2(71807/80222); Tb13/TBL3(213773/10607); Thoc2/THOC2(331401/57187); Thoc5/THOC5(107829/8563); Thoc7/THOC7(66231/80145); Timeless/TIMELESS(21853/8914); Tsen2/TSEN2(381802/80746); Tsr1/TSR1(104662/55720); Tsr2/TSR2(69499/90121); Tufm/TUFM(233870/7284); Tut1/TUT1(70044/64852); Twistnb/TWISTNB(28071/221830); U2af1/U2AF1(108121/7307); U2af2/U2AF2(22185/11338); Uba52/UBA52(22186/7311); Ubl5/UBL5(66177/59286); Upf1/UPF1(19704/5976); Upf2/UPF2(326622/26019); Utp15/UTP15(105372/84135); Utp20/UTP20 (70683/27340); Utp23/UTP23(78581/84294); Utp3/UTP3(65961/57050); Utp6/UTP6(216987/55813); Vars/VARS (22321/7407); Wars/WARS(22375/7453); Wdr12/WDR12(57750/55759); Wdr3/WDR3(269470/10885); Wdr33/WDR33(74320/55339); Wdr36/WDR36(225348/134430); Wdr46/WDR46(57315/9277); Wdr61/WDR61 (66317/80349); Wdr75/WDR75(73674/84128); Xpo1/XPO1(103573/7514); Yars/YARS(107271/8565); Yars2/YARS2(70120/51067); Ythdc1/YTHDC1(231386/91746); Zbtb8os/ZBTB8OS(67106/339487); and Zc3h3/ZC3H3(223642/23144). The CDLs are described in more detail in WO 2016141480, which is incorporated herein by reference in its entirety.

A cell can be modified to be a FAILSAFE™ cell by linking the expression of a CDL with that of a DNA sequence encoding a negative selectable marker (e.g., by inserting the DNA sequence encoding the negative selectable marker into a coding or non-coding region of the CDL), thereby allowing drug-induced ablation (e.g., killing) of mitotically active cells expressing both the CDL and the negative selectable marker. Ablation of proliferating cells may be desirable, for example, when cell proliferation is uncontrolled and/or accelerated relative to a cell's normal division rate (e.g., uncontrolled cell division exhibited by cancerous cells), or when therapeutic need for the cells has passed. Ablation of proliferating cells may be achieved via a genetic modification to the cell, referred to herein as an "ablation link" (ALINK), which links the expression of a DNA sequence encoding a negative selectable marker to that of a CDL, thereby allowing elimination or sufficient inhibition of ALINK-modified proliferating cells consequently expressing the CDL locus (sufficient inhibition being inhibition of cell expansion rate to a rate that is too low to contribute to tumor formation). In the presence of a pro-drug or other inducer of the negatively selectable system, cells expressing the negative selectable marker will stop proliferating or die, depending on the mechanism of action of the selectable marker and the identity of the CDL. Cells may be modified to comprise homozygous, heterozygous, hemizygous or compound heterozygous ALINKs. In one embodiment, to improve fidelity of ablation, a negative selectable marker may be introduced into all functional alleles of a CDL. In one preferred embodiment, a negative selectable marker may be introduced into all functional alleles of a CDL. The FAILSAFE™ system can be used to eliminate all of the cloaked cells, if desired.

An ALINK may be inserted in any position of the CDL, which allows co-expression of the CDL and the negative selectable marker.

In some embodiments, the ALINK system comprises a herpes simplex virus-thymidine kinase/ganciclovir system, a cytosine deaminase/5-fluorocytosine system, a carboxyl esterase/irinotecan system or an iCasp9/AP1903 system.

DNA encoding a negatively selectable marker (e.g., HSV-TK), may be inserted into a CDL (e.g., CDK1) in a host cell, such that expression of the negative selectable marker causes host cells expressing the negative selectable marker and, necessarily, the CDL, to be killed in the presence of an inducer (e.g., prodrug) of the negative selectable marker (e.g., ganciclovir (GCV)). In this example, host cells modified with the ALINK will produce thymidine kinase (TK) and the TK protein will convert GCV into GCV monophosphate, which is then converted into GCV triphosphate by cellular kinases. GCV triphosphate incorporates into the replicating DNA during S phase, which leads to the termination of DNA elongation and cell apoptosis (Halloran and Fenton, 1998).

A modified HSV-TK gene (Preuß et al., 2010) is disclosed herein as one example of DNA encoding a negative selectable marker that may be used in an ALINK genetic modification to selectively ablate cells comprising undesirable cell division rate.

It is contemplated herein that alternative and/or additional negative selectable systems could be used in the tools and/or methods provided herein. Various negative selectable marker systems are known in the art (e.g., dCK.DM (Neschadim et al., 2012)).

For example, various negative selectable system having clinical relevance have been under active development in the field of "gene-direct enzyme/prodrug therapy" (GEPT), which aims to improve therapeutic efficacy of conventional cancer therapy with no or minimal side-effects (Hedley et al., 2007; Nawa et al., 2008). Frequently, GEPT involves the use of viral vectors to deliver a gene into cancer cells or into the vicinity of cancer cells in an area of the cancer cells that is not found in mammalian cells and that produces enzymes, which can convert a relatively non-toxic prodrug into a toxic agent.

HSV-TK/GCV, cytosine deaminase/5-fluorocytosine (CD/5-FC), and carboxyl esterase/irinotecan (CE/CPT-11) are examples of negative selectable marker systems being evaluated in GEPT pre- and clinical trials (Danks et al., 2007; Shah, 2012).

To overcome the potential immunogenicity of a Herpes Simplex Virus type 1 thymidine kinase/ganciclovir (TK/GCV) system, a "humanized" suicide system has been developed by engineering the human deoxycytidine kinase enzyme to become thymidine-active and to work as a negative selectable (suicide) system with non-toxic prodrugs: bromovinyl-deoxyuridine (BVdU), L-deoxythymidine (LdT) or L-deoxyuridine (LdU) (Neschadim et al., 2012).

The CD/5-FC negative selectable marker system is a widely used "suicide gene" system. Cytosine deaminase (CD) is a non-mammalian enzyme that may be obtained from bacteria or yeast (e.g., from *Escherichia coli* or *Saccharomyces cerevisiae*, respectively) (Ramnaraine et al., 2003). CD catalyzes conversion of cytosine into uracil and is an important member of the pyrimidine salvage pathway in prokaryotes and fungi, but it does not exist in mammalian cells. 5-fluorocytosine (5-FC) is an antifungal prodrug that causes a low level of cytotoxicity in humans (Denny, 2003). CD catalyzes conversion of 5-FC into the genotoxic agent 5-FU, which has a high level of toxicity in humans (Ireton et al., 2002).

The CE/CPT-11 system is based on the carboxyl esterase enzyme, which is a serine esterase found in a different tissues of mammalian species (Humerickhouse et al., 2000). The anti-cancer agent CPT-11 is a prodrug that is activated by CE to generate an active referred to as 7-ethyl-10-hydroxycamptothecin (SN-38), which is a strong mammalian topoisomerase I inhibitor (Wierdl et al., 2001). SN-38 induces accumulation of double-strand DNA breaks in dividing cells (Kojima et al., 1998).

Another example of a negative selectable marker system is the iCasp9/AP1903 suicide system, which is based on a modified human caspase 9 fused to a human FK506 binding protein (FKBP) to allow chemical dimerization using a small molecule AP1903, which has tested safely in humans. Administration of the dimerizing drug induces apoptosis of cells expressing the engineered caspase 9 components. This system has several advantages, such as, for example, including low potential immunogenicity, since it consists of human gene products, the dimerizer drug only effects the cells expressing the engineered caspase 9 components (Straathof et al., 2005). The iCasp/AP1903 suicide system is being tested in clinical settings (Di Stasi et al., 2011).

It is contemplated herein that the negative selectable marker system of the ALINK system could be replaced with a proliferation antagonist system. The term "proliferation antagonist" as used herein, refers to a natural or engineered compound(s) whose presence inhibits (completely or partially) division of a cell. For example, Omomyc$^{ER}$ is the fusion protein of MYC dominant negative Omomyc with mutant murine estrogen receptor (ER) domain. When induced with tamoxifen (TAM), the fusion protein Omomyc$^{ER}$ localizes to the nucleus, where the dominant negative Omomyc dimerizes with C-Myc, L-Myc and N-Myc, sequestering them in complexes that are unable to bind the Myc DNA binding consensus sequences (Soucek et al., 2002). As a consequence of the lack of Myc activity, cells are unable to divide (Oricchio et al., 2014). Another example of a proliferation antagonist is A-Fos, a dominant negative to activation protein-1 (AP1) (a heterodimer of the oncogenes Fos and Jun) that inhibits DNA binding in an equimolar competition (Olive et al., 1997). A-Fos can also be fused to ER domain, rendering its nuclear localization to be induced by TAM. Omomyc$^{ER}$/tamoxifen or A-Fos$^{ER}$/tamoxifen could be a replacement for TK/GCV to be an ALINK.

A cell can also be modified to be FAILSAFE™ by operably linking the CDL with an EARC, such as an inducible activator-based gene expression system. Under these conditions, the CDL will only be expressed (and the cell can only divide) in the presence of the inducer of the inducible activator-based gene expression system. Under these conditions, EARC-modified cells stop dividing, significantly slow down, or die in the absence of the inducer, depending on the mechanism of action of the inducible activator-based gene expression system and CDL function. Cells may be modified to comprise homozygous or compound heterozygous EARCs or may be altered such that only EARC-modified alleles can produce functional CDLs. In an embodiment, an EARC modification may be introduced into all alleles of a CDL, for example, to provide a mechanism for cell division control.

An EARC may be inserted in any position of CDL that permits co-expression of the CDL and the activator component of the inducible system in the presence of the inducer.

In an embodiment, an "activator" based gene expression system is preferable to a "repressor" based gene expression system. For example, if a repressor is used to suppress a CDL a loss of function mutation of the repressor could release CDL expression, thereby allowing cell proliferation. In a case of an activation-based suppression of cell division, the loss of activator function (mutation) would shut down CDL expression, thereby disallowing cell proliferation.

In some embodiments, the EARC system is a dox-bridge system, a cumate switch inducible system, an ecdysone inducible system, a radio wave inducible system, or a ligand-reversible dimerization system.

A dox-bridge may be inserted into a CDL (e.g., CDK1) in a host cell, such that in the presence of an inducer (e.g., doxycycline or "DOX") the dox-bridge permits CDL expression, thereby allowing cell division and proliferation. Host cells modified with a dox-bridge EARC may comprise a reverse tetracycline Trans-Activator (rtTA) gene (Urlinger et al., 2000) under the transcriptional control of a promoter, which is active in dividing cells (e.g., in the CDL). This targeted insertion makes the CDL promoter no longer available for CDL transcription. To regain CDL transcription, a tetracycline responder element promoter (for example TRE (Agha-Mohammadi et al., 2004)) is inserted in front of the CDL transcript, which will express the CDL gene only in a situation when rtTA is expressed and doxycycline is present. When the only source of CDL expression is dox-bridged alleles, there is no CDL gene expression in the absence of doxycycline. The lack of CDL expression causes the EARC-modified cells to be compromised in their proliferation, either by death, stopping cell division, or by rendering the cell mitotic rate so slow that the EARC-modified cell could not contribute to tumor formation.

The term "dox-bridge" as used herein, refers to a mechanism for separating activity of a promoter from a target transcribed region by expressing rtTA (Gossen et al., 1995) by the endogenous or exogenous promoter and rendering the transcription of target region under the control of TRE. As used herein, "rtTA" refers to the reverse tetracycline trans-activator elements of the tetracycline inducible system (Gossen et al., 1995) and "TRE" refers to a promoter consisting of TetO operator sequences upstream of a minimal promoter. Upon binding of rtTA to the TRE promoter in the presence of doxycycline, transcription of loci downstream of the TRE promoter increases. The rtTA sequence may be inserted in the same transcriptional unit as the CDL or in a different location of the genome, so long as the transcriptional expression's permissive or non-permissive status of the target region is controlled by doxycycline. A dox-bridge is an example of an EARC.

Introduction of an EARC system into the 5' regulatory region of a CDL is also contemplated herein.

It is contemplated herein that alternative and/or additional inducible activator-based gene expression systems could be used in the tools and or methods provided herein to produce EARC modifications. Various inducible activator-based gene expression systems are known in the art.

For example, destabilizing protein domains (Banaszynski et al., 2006) fused with an acting protein product of a coding CDL could be used in conjunction with a small molecule synthetic ligand to stabilize a CDL fusion protein when cell division and/or proliferation is desirable. In the absence of a stabilizer, destabilized-CDL-protein will be degraded by the cell, which in turn would stop proliferation. When the stabilizer compound is added, it would bind to the destabilized-CDL-protein, which would not be degraded, thereby allowing the cell to proliferate.

For example, transcription activator-like effector (TALE) technology (Maeder et al., 2013) could be combined with dimerizer-regulated expression induction (Pollock and Clackson, 2002). The TALE technology could be used to generate a DNA binding domain designed to be specific to a sequence, placed together with a minimal promoter replacing the promoter of a CDL. The TALE DNA binding domain also extended with a drug dimerizing domain. The latter can bind to another engineered protein having corresponding dimerizing domain and a transcriptional activation domain.

For example, a reverse-cumate-Trans-Activator (rcTA) may be inserted in the 5' untranslated region of the CDL, such that it will be expressed by the endogenous CDL promoter. A 6-times repeat of a Cumate Operator (6×CuO) may be inserted just before the translational start (ATG) of CDL. In the absence of cumate in the system, rcTA cannot bind to the 6×CuO, so the CDL will not be transcribed because the 6×CuO is not active. When cumate is added, it will form a complex with rcTA, enabling binding to 6×CuO and enabling CDL transcription (Mullick et al., 2006).

For example, a retinoid X receptor (RXR) and an N-terminal truncation of ecdysone receptor (EcR) fused to the activation domain of Vp16 (VpEcR) may be inserted in the 5' untranslated region of a CDL such that they are co-expressed by an endogenous CDL promoter. Ecdysone responsive element (EcRE), with a downstream minimal promoter, may also be inserted in the CDL, just upstream of the starting codon. Co-expressed RXR and VpEcR can heterodimerize with each other. In the absence of ecdysone or a synthetic drug analog muristerone A, dimerized RXR/VpEcR cannot bind to EcRE, so the CDL is not transcribed. In the presence of ecdysone or muristerone A, dimerized RXR/VpEcR can bind to EcRE, such that the CDL is transcribed (No et al., 1996).

For example, a transient receptor potential vanilloid-1 (TRPV1), together with ferritin, may be inserted in the 5' untranslated region of a CDL and co-expressed by an endogenous CDL promoter. A promoter inducible by NFAT (NFATre) may also be inserted in the CDL, just upstream of the starting codon. In a normal environment, the NFAT promoter is not active. However, upon exposure to low-frequency radio waves, TRPV1 and ferritin create a wave of $Ca^{++}$ entering the cell, which in turn converts cytoplasmatic-NFAT (NFATc) to nuclear-NFAT (NFATn), that ultimately will activate the NFATre and transcribe the CDL (Stanley et al., 2015).

For example, a CDL may be functionally divided in to parts/domains: 5'-CDL and 3'CDL, and a FKBP peptide sequence may be inserted into each domain. An IRES (internal ribosomal entry site) sequence may be placed between the two domains, which will be transcribed simultaneously by a CDL promoter but will generate two separate proteins. Without the presence of an inducer, the two separate CDL domains will be functionally inactive. Upon introduction of a dimerization agent, such as rapamycin or AP20187, the FKBP peptides will dimerize, bringing together the 5' and 3' CDL parts and reconstituting an active protein (Rollins et al., 2000).

Pharmaceutical Compositions

The cloaked and uncloaked cells described herein (e.g., cloaked cells expressing a polypeptide comprising a donor alloantigen, cloaked cells expressing a polypeptide comprising a self-antigen, or uncloaked cells expressing a polypeptide comprising a non-self, disease-associated antigen) may be incorporated into a vehicle for administration into a patient, such as a human patient in need of a tissue or organ transplant or having an autoimmune disease or condition described herein. Pharmaceutical compositions containing cloaked or uncloaked cells can be prepared using methods known in the art. For example, such compositions can be prepared using, e.g., physiologically acceptable carriers, excipients or stabilizers (Remington: The Science and Practice of Pharmacology 22nd edition, Allen, L. Ed. (2013); incorporated herein by reference), and in a desired form, e.g., in the form of aqueous solutions.

The cloaked or uncloaked cells described herein can be administered in any physiologically compatible carrier, such as a buffered saline solution. Pharmaceutically acceptable carriers and diluents include saline, aqueous buffer solutions, solvents and/or dispersion media. The use of such carriers and diluents is well known in the art. Other examples include liquid media, for example, Dulbecco's modified eagle's medium (DMEM), sterile saline, sterile phosphate buffered saline, Leibovitz's medium (L15, Invitrogen, Carlsbad, Calif.), dextrose in sterile water, and any other physiologically acceptable liquid. Dispersions may also be prepared in glycerol, liquid polyethylene glycols, and mixtures thereof and in oils. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. In many cases, it will be preferable to include isotonic agents, for example, sugars or sodium chloride. The solution is preferably sterile and fluid to the extent that easy syringability exists. Preferably, the solution is stable under the conditions of manufacture and storage and preserved against the contaminating action of microorganisms such as bacteria and fungi through the use of, for example, parabens, chlorobutanol, phenol, ascorbic acid, thimerosol, and the like. Solutions of the invention can be prepared by using a pharmaceutically acceptable carrier or diluent and, as required, other ingredients enumerated above, followed by filtered sterilization, and then incorporating the cloaked or uncloaked cells as described herein.

For example, a solution containing a pharmaceutical composition described herein may be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. The person responsible for administration will, in any event, determine the appropriate dose for the individual subject. Moreover, for human administration, preparations may meet sterility, pyrogenicity, general safety, and purity standards as required by FDA Office of Biologics standards.

Pharmaceutical compositions comprising cloaked or uncloaked cells in a semi-solid or solid carrier are typically formulated for surgical implantation at the site of future transplantation or at the affected site of a disease or condition in the subject. It will be appreciated that liquid compositions also may be administered by surgical procedures. In particular embodiments, semi-solid or solid pharmaceutical compositions may comprise semi-permeable gels, matrices, cellular scaffolds and the like, which may be non-biodegradable or biodegradable. For example, in certain embodiments, it may be desirable or appropriate to sequester the cloaked or uncloaked cells from their surroundings, yet enable the cells to secrete and deliver biological molecules (e.g., an antigen listed in Table 2) to surrounding cells.

In other embodiments, different varieties of degradable gels and networks are utilized for the pharmaceutical compositions of the invention. For example, degradable materials include biocompatible polymers, such as poly(lactic acid), poly(lactic acid-co-glycolic acid), methylcellulose, hyaluronic acid, collagen, and the like.

In another embodiment, one or more hydrogels are used for the pharmaceutical compositions. The one or more hydrogels may include collagen, atelocollagen, fibrin constructs, hydrophilic vinyl and acrylic polymers, polysaccharides such as calcium alginate, and poly(ethylene oxide). Further, the hydrogel may be formed of poly(2-hydroxyethyl methacrylate), poly(acrylic acid), self-assembling peptides (e.g., RAD16), poly(methacrylic acid), poly(N-vinyl-2-pyrrolidinone), poly(vinyl alcohol) and their copolymers with each other and with hydrophobic monomers such as methyl methacrylate, vinyl acetate, and the like. Also preferred are hydrophilic polyurethanes containing large poly(ethylene oxide) blocks. Other preferred materials include hydrogels comprising interpenetrating networks of polymers, which may be formed by addition or by condensation polymerization, the components of which may comprise hydrophilic and hydrophobic monomers such as those just enumerated. In situ-forming degradable networks are also suitable for use in the invention (see, e.g., Anseth, K S et al. *J. Controlled Release,* 2002; 78:199-209; Wang, D. et al., *Biomaterials,* 2003; 24:3969-3980; U.S. Patent Publication 2002/0022676). These in situ forming materials are formulated as fluids suitable for injection; then may be induced to form a hydrogel by a variety of means such as change in temperature, pH, and exposure to light in situ or in vivo. In one embodiment, the construct contains fibrin glue containing gels. In another embodiment, the construct contains atelocollagen containing gels.

A polymer used to form a matrix may be in the form of a hydrogel. In general, hydrogels are cross-linked polymeric materials that can absorb more than 20% of their weight in water while maintaining a distinct three-dimensional structure. This definition includes dry cross-linked polymers that will swell in aqueous environments, as well as water-swollen materials. A host of hydrophilic polymers can be cross-linked to produce hydrogels, whether the polymer is of biological origin, semi-synthetic or wholly synthetic. The hydrogel may be produced from a synthetic polymeric material. Such synthetic polymers can be tailored to a range of properties and predictable lot-to-lot uniformity, and represent a reliable source of material that generally is free from concerns of immunogenicity. The matrices may include hydrogels formed from self assembling peptides, such as those discussed in U.S. Pat. Nos. 5,670,483 and 5,955,343, U.S. Patent Application No. 2002/0160471, and PCT Application No. WO 02/062969.

Properties that make hydrogels valuable in drug delivery applications include the equilibrium swelling degree, sorption kinetics, solute permeability, and their in vivo performance characteristics. Permeability to compounds depends, in part, upon the swelling degree or water content and the rate of biodegradation. Since the mechanical strength of a gel may decline in proportion to the swelling degree, it is also well within the contemplation of the present invention that the hydrogel can be attached to a substrate so that the composite system enhances mechanical strength. In some embodiments, the hydrogel can be impregnated within a porous substrate, so as to gain the mechanical strength of the substrate, along with the useful delivery properties of the hydrogel.

In other embodiments, the pharmaceutical composition comprises a biocompatible matrix made of natural, modified natural or synthetic biodegradable polymers, including homopolymers, copolymers and block polymers, as well as combinations thereof.

Examples of suitable biodegradable polymers or polymer classes include any biodegradable polymers discussed within this disclosure, including but not limited to, fibrin, collagen types I, II, III, IV and V, elastin, gelatin, vitronectin, fibronectin, laminin, thrombin, poly(aminoacid), oxidized cellulose, tropoelastin, silk, ribonucleic acids, deoxyribonucleic acids; proteins, polynucleotides, gum arabic, reconstituted basement membrane matrices, starches, dextrans, alginates, hyaluron, chitin, chitosan, agarose, polysaccharides, hyaluronic acid, poly(lactic acid), poly(glycolic acid), polyethylene glycol, decellularized tissue, self-assembling peptides, polypeptides, glycosaminoglycans, their derivatives and mixtures thereof. Suitable polymers also include poly(lactide) (PLA) which can be formed of L(+) and D(−) polymers, polyhydroxybutyrate, polyurethanes, polyphoshazenes, poly(ethylene glycol)-poly(lactide-co-glycolide) co-polymer, degradable polycyanoacrylates and degradable polyurethanes. For both glycolic acid and lactic acid, an intermediate cyclic dimer is may be prepared and purified prior to polymerization. These intermediate dimers are called glycolide and lactide, respectively.

Other useful biodegradable polymers or polymer classes include, without limitation, aliphatic polyesters, poly(alkylene oxalates), tyrosine derived polycarbonates, polyiminocarbonates, polyorthoesters, polyoxaesters, polyamidoesters, polyoxaesters containing amine groups, poly(propylene fumarate), polyfumarates, polydioxanones, polycarbonates, polyoxalates, poly(alpha-hydroxyacids), poly(esters), polyurethane, poly(ester urethane), poly(ether urethane), polyanhydrides, polyacetates, polycaprolactones, poly(orthoesters), polyamino acids, polyamides and blends and copolymers thereof. Additional useful biodegradable polymers include, without limitation stereopolymers of L- and D-lactic acid, copolymers of bis(para-carboxyphenoxy) propane and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of alpha-amino acids, copolymers of alpha-amino acids and caproic acid, copolymers of alpha-benzyl glutamate and polyethylene glycol, copolymers of succinate and poly(glycols), polyphosphazene, poly(hydroxyalkanoates) and mixtures thereof. Binary and ternary systems also are contemplated.

In general, the material used to form a matrix is desirably configured so that it: (1) has mechanical properties that are suitable for the intended application; (2) remains sufficiently intact until tissue has in-grown and healed; (3) does not invoke an inflammatory or toxic response; (4) is metabolized in the body after fulfilling its purpose; (5) is easily processed into the desired final product to be formed; (6) demonstrates acceptable shelf-life; and (7) is easily sterilized.

In another embodiment, the population of cloaked or uncloaked cells can be administered by use of a scaffold. The composition, shape, and porosity of the scaffold may be any described above. Typically, these three-dimensional biomaterials contain the living cells attached to the scaffold, dispersed within the scaffold or incorporated in an extracellular matrix entrapped in the scaffold. Once implanted into the target region of the body, these implants become integrated with the host tissue, wherein the cells gradually become established.

Non-limiting examples of scaffolds that may be used include textile structures, such as weaves, knits, braids, meshes, non-wovens, and warped knits; porous foams, semiporous foams, perforated films or sheets, microparticles, beads, and spheres and composite structures being a combination of the above structures. Nonwoven mats may, for example, be formed using fibers comprised of a synthetic absorbable copolymer of glycolic and lactic acids (PGA/PLA), sold under the tradename VICRYL sutures (Ethicon, Inc., Somerville, N.J.). Foams, composed of, for example, poly(epsilon-caprolactone)/poly(glycolic acid) (PCL/PGA) copolymer, formed by processes such as freeze-drying, or lyophilized, as discussed in U.S. Pat. No. 6,355,699, also may be utilized.

In another embodiment, the framework is a felt, which can be composed of a multifilament yarn made from a bioabsorbable material. The yarn can be made into a felt using standard textile processing techniques consisting of crimping, cutting, carding and needling. In another embodiment, cells are seeded onto foam scaffolds that may be used as composite structures.

The framework may be molded into a useful shape, such as to fill a tissue void. The framework can therefore be shaped to not only provide a channel for neural growth, but also provide a scaffold for the supporting and surrounding tissues, such as vascular tissue, muscle tissue, and the like. Furthermore, it will be appreciated that the population of cells may be cultured on pre-formed, non-degradable surgical or implantable devices.

Pharmaceutical compositions may include preparations made from cloaked or uncloaked cells that are formulated with a pharmaceutically acceptable carrier or medium. Suitable pharmaceutically acceptable carriers include any discussed within this disclosure, including but not limited to, water, salt solution (such as Ringer's solution), alcohols, oils, gelatins, polyvinyl pyrrolidine, carbohydrates such as lactose, amylose, or starch, fatty acid esters, and hydroxymethylcellulose. Such preparations can be sterilized, and if desired, mixed with auxiliary agents such as lubricants, preservatives, stabilizers, wetting agents, emulsifiers, salts for influencing osmotic pressure, buffers, and coloring agents. Pharmaceutical carriers suitable for use in the present invention are known in the art and are described, for example, in Pharmaceutical Sciences ($17^{th}$ Ed., Mack Pub. Co., Easton, Pa.) and WO 96/05309.

Methods of Treatment

The cloaked and uncloaked cells and compositions described herein may be administered to a subject in need thereof (e.g., a subject waiting to receive a tissue or organ transplant, or a subject having or at risk of developing a disease or condition described herein) by a variety of routes, such as local administration to or near the site in need of a transplant, local administration to the site affected by the disease or condition (e.g., injection to or near the pancreas for the treatment of type 1 diabetes, direct administration to the central nervous system (CNS) (e.g., intracerebral, intraventricular, intrathecal, intracisternal, or stereotactic administration) for treating MS), intravenous, parenteral, intradermal, transdermal, intramuscular, intranasal, subcutaneous, percutaneous, intratracheal, intraperitoneal, intraarterial, intravascular, inhalation, perfusion, lavage, and oral administration. The most suitable route for administration in any given case will depend on the particular cells or composition administered, the patient, pharmaceutical formulation methods, administration methods (e.g., administration time and administration route), the patient's age, body weight, sex, severity of the disease being treated, the patient's diet, and the patient's excretion rate. Compositions may be administered once, or more than once (e.g., once annually, twice annually, three times annually, bi-monthly, or monthly). For local administration, the cloaked or uncloaked cells may be administered by any means that places the population of cells in a desired location, including catheter, syringe, shunt, stent, microcatheter, pump, implantation with a device, or implantation with a scaffold.

As described herein, before administration, the population of cells can be incubated in the presence of one or more factors, or under conditions, that stimulate stem cell differentiation into a desired cell type (e.g., a myelinating cell, an insulin producing cell, or other cell types described herein). Such factors are known in the art and the skilled artisan will appreciate that determination of suitable conditions for differentiation can be accomplished with routine experimentation. Such factors include growth or trophic factors, chemokines, cytokines, cellular products, demethylating agents, and other stimuli which are known to stimulate differentiation, for example, of stem cells along glial or islet cell pathways or lineages. Alternatively, the composition administered to the patient includes a population of cloaked cells with one or more factors that stimulate cell differentiation into a desired cell type, where the cell differentiation occurs in vivo at the tissue site.

Subjects that may be treated as described herein are subjects waiting to receive a transplant, subjects having an autoimmune disease or condition described herein (e.g., type 1 diabetes, MS, or a disease or condition listed in Table 2), or subject at risk of developing cancer or a bacterial, viral, fungal, or parasitic infection (e.g., a subject at risk due to family history, genetics, or environmental risk factors). The cells, compositions, and methods described herein can be used to treat a disease or condition in which the subject's immune system aberrantly mounts an immune response against the subject's own cells. The methods described herein may include a step of screening a subject for antigens that induce an immune response (e.g., immune cell activation, proliferation, polarization, differentiation, migration, degranulation, phagocytosis, or cytotoxicity) in immune cells isolated from the subject prior to treatment with or administration of the compositions described herein. The methods described herein may include a step of profiling a cell from an organ or tissue donor to identify donor alloantigens (e.g., donor alloantigens that can be expressed by a cloaked cell described herein to induce immune tolerance prior to a transplant). The methods described herein may also include a step of evaluating the symptoms of the disease or condition in a subject prior to treatment with or administration of the cloaked cells or compositions described herein. The subject can then be evaluated using the same diagnostic tests after administration of the cloaked cells or compositions to determine whether the subject's condition has improved. The compositions and methods described herein may be administered as a preventative treatment to subjects waiting to receive an organ or tissue transplant, to subjects at risk of developing an autoimmune disease or condition, or to subjects at risk of developing cancer or a bacterial, viral, fungal, or parasitic infection.

The cloaked cells, compositions, and methods described herein can be used to specifically modulate the immune response in a subject (e.g., to induce tolerance to a donor alloantigen in a subject prior to a tissue or organ transplant, to induce tolerance to a self-antigen in a subject suffering from an autoimmune disease or condition, or to induce tolerance to a cell before using an uncloaked version of the cell to stimulate an immune response to a non-self antigen in a subject who would benefit from immunization against said non-self antigen). The cloaked cells, compositions, and methods described herein can also be used to induce tolerance to an organ or tissue transplant in advance of a transplant, which may reduce the risk of rejection of the tissue or organ transplant, and reduce, minimize, or eliminate the need for immunosuppressive medications and HLA matching between the donor and recipient. Cloaked cells that express an antigen, such as a self-antigen that is aberrantly targeted by the immune system in a subject with an autoimmune disease or condition, compositions including such cells, or methods of administering such cells, may be used to induce immune tolerance to the antigen in a subject (e.g., an antigen that is associated with an autoimmune disease or condition, e.g., an antigen listed in Table 2). Cloaked cells can also be used to prepare a subject for a second step in a cell-based therapy, such as inducing tolerance to a cloaked cell before administering an uncloaked version of the same cell (e.g., inducing tolerance to a cloaked cell from a donor organ or tissue before a transplant, or inducing tolerance to a cloaked cell before administration of an uncloaked cell of the same type that has been modified to express a non-self antigen to stimulate a specific immune response to the non-self antigen).

Treatment may include administration of cloaked or uncloaked cells or a composition containing cloaked or uncloaked cells in various unit doses. Each unit dose will ordinarily contain a predetermined-quantity of the cloaked cells described herein. The quantity to be administered, and the particular route of administration and formulation, are within the skill of those in the clinical arts. A unit dose need not be administered as a single injection but may comprise continuous infusion over a set period of time. Dosing may be performed using a catheter, syringe, shunt, stent, microcatheter, pump, implantation with a device, or implantation with a scaffold. The number of cells administered may vary depending on whether the cells are administered to a tissue, organ, or body site associated with a disease or injury, or are administered subcutaneously to produce a cloaked or uncloaked subcutaneous tissue. For administration to a tissue, organ, or body site, the cloaked or uncloaked cells may be administered to the patient at a dose of, for example $1\times10^4$ cells to $1\times10^{10}$ cells (e.g., $1\times10^4$, $2\times10^4$, $3\times10^4$, $4\times10^4$, $5\times10^4$, $6\times10^4$, $7\times10^4$, $8\times10^4$, $9\times10^4$, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$ cells). The number of cells administered will depend on the size of the recipient tissue, organ, or body site. For example, $2.5\times10^4$ to $1\times10^5$ cells (e.g., $2.5\times10^4$, $3\times10^4$, $4\times10^4$, $5\times10^4$, $6\times10^4$, $7\times10^4$, $8\times10^4$, $9\times10^4$, or $1\times10^5$ cells) can be administered (e.g., injected) to the subretinal space of the eye or to a specific brain region; $1\times10^6$ to $1\times10^8$ cells (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$ cells) can be administered (e.g., injected) to a joint, with the quantity of cells depending on the size of the joint; and $5\times10^8$ to $5\times10^9$ cells (e.g., $5\times10^8$, $6\times10^8$, $7\times10^8$, $8\times10^8$, $9\times10^8$, $1\times10^9$, $2\times10^9$, $3\times10^9$, $4\times10^9$, or $5\times10^9$ cells) can be administered to the cardiac muscle. For creating cloaked or uncloaked subcutaneous tissue, $8\times10^8$ cells to $3\times10^9$ cells (e.g., $8\times10^8$, $9\times10^8$, $1\times10^9$, $2\times10^9$, $3\times10^9$ cells) can be administered (e.g., injected) subcutaneously. Cloaked or uncloaked cells can be administered in two or more doses (e.g., two, three, four, five, or more different doses) or at the same dose two or more times (e.g., two, three, four, five, six, or more times over the course of an hour, day, week, month, or year). In some embodiments, the cloaked or uncloaked cells described herein are administered as a tissue (e.g., a tissue that has been grown and/or differentiated in vitro from cloaked or uncloaked cells). In some embodiments, the cloaked or uncloaked tissue is administered (e.g., implanted) with a gel, biocompatible matrix, or scaffold.

The compositions described herein are administered in an amount sufficient to prevent or reduce the risk of transplant rejection, to reduce, minimize, or eliminate the need for immunosuppressive drugs, to delay or prevent the onset of an autoimmune disease or condition described herein, to slow the progression of an autoimmune disease or condition described herein, to improve symptoms of an autoimmune disease or condition listed in Table 2 (e.g., to reduce symptoms of osteoarthritis or RA (e.g., reduce inflammation, joint pain, stiffness, or immobility); reduce symptoms of diabetes (e.g., improve insulin levels, reduce the need for regular insulin injections); reduce symptoms of multiple sclerosis (e.g., reduce numbness, weakness, or tingling, reduce tremor, reduce dizziness, improve vision, or improve gait)), or to induce the production of antibodies against a non-self, disease-associated antigen. Transplant rejection may be evaluated using standard methods known by those of skill in the art and may be reduced by 5% or more (e.g., 5%, 10%, 15%, 20%, 30%, 40%, 50%, 60%, 70%, 80%, 90%, 100% or more) compared to rates of transplant rejection typically observed without treatment. In some embodiments, administration of the cloaked cells or compositions described herein results in an equivalent outcome in transplant rejection as that observed in subjects administered immunosuppressive agent(s). Symptoms of diseases and conditions described herein can be evaluated using standard methods known to those of skill in the art and may be reduced (e.g., the subject's condition may be improved) by 5% or more (e.g., 5%, 10%, 15%, 20%, 30%, 40%, 50%, 60%, 70%, 80%, 90%, 100% or more) compared to symptoms prior to administration of the cloaked cells or compositions described herein or compared to outcomes observed in subjects treated with immunosuppressive agents. The production of antibodies directed against a non-self antigen can be measured using a blood sample collected from a subject and may be increased by 5% or more (e.g., 5%, 10%, 15%, 20%, 30%, 40%, 50%, 60%, 70%, 80%, 90%, 100% or more) compared to the amount of the antibody in a blood sample collected from the subject prior to treatment. These effects may occur, for example, within 1 week, 2 weeks, 3 weeks, 4 weeks, 5 weeks, 6 weeks, 7 weeks, 8 weeks, 9 weeks, 10 weeks, 15 weeks, 20 weeks, 25 weeks, or more, following administration of the compositions described herein. The patient may be evaluated 1 month, 2 months, 3 months, 4 months, 5 months, 6 months or more following administration of the cloaked or uncloaked cell or composition depending on the dose and route of administration used for treatment. Depending on the outcome of the evaluation, the patient may receive additional treatments.

In some embodiments, the cloaked or uncloaked cells can be removed after they have elicited the desired therapeutic effect (e.g., after the cloaked cells have induced immune tolerance in the subject, or after the uncloaked cells have promoted the production of antibodies directed against a non-self antigen). The appropriate time for removing the cloaked or uncloaked cells can be determined by assessing an immune response of the subject (e.g., assessing the response of an immune cell isolated from the subject to an antigen to determine whether immune tolerance has been induced, or evaluating a blood sample collected from the subject to determine whether antibodies have been produced in response to a non-self antigen). Cloaked or uncloaked cells can be removed surgically (e.g., if the cells were injected subcutaneously to produce a cloaked or uncloaked subcutaneous tissue, the cloaked or uncloaked subcutaneous tissue can be surgically removed). If the cloaked or uncloaked cells were modified to contain one or more systems for regulating cell division (e.g., modified to be FAILSAFE™ cells, e.g., by linking the expression of a CDL to an ALINK or EARC), the cells can be removed by administering an inducer of a negative selectable marker (e.g., the ALINK) or by ceasing to administer an activator of an inducible activator-based gene expression system (e.g., the EARC).

Combination Therapy

In some embodiments, the cloaked or uncloaked cells described herein are administered in combination with one or more additional therapeutic agents. The additional therapeutic agent(s) can be administered after administration of the cloaked cells or concurrently with administration of the cloaked cells. The cloaked cells and additional therapeutic agents can also be administered simultaneously via co-formulation. The cloaked cells and therapeutic agent(s) can also be administered sequentially, such that the action of the cloaked cells and therapeutic agent(s) overlaps and their combined effect is such that the reduction in a symptom, or other parameter related to the disorder is greater than what would be observed with the cloaked cells or therapeutic agent delivered alone or in the absence of the other. The effect of the cloaked cells and therapeutic agent(s) can be partially additive, wholly additive, or greater than additive (e.g., synergistic). Sequential or substantially simultaneous administration of cloaked cells and therapeutic agent(s) can be effected by any appropriate route including, but not limited to oral routes, intravenous routes, intramuscular routes, local routes, or subcutaneous routes. The cloaked cells and therapeutic agent(s) can be administered by the same route or by different routes. For example, cloaked cells may be administered by subcutaneous injection while the additional therapeutic agent is administered orally. The cloaked cells may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before the additional therapeutic agent.

In one example, the additional therapeutic agent is an immunosuppressive agent(s) commonly given for organ or tissue transplant. The immunosuppressive agent(s) may be administered at a reduced dose relative to the standard dose. The immunosuppressive agent(s) may be an agent that is given immediately after transplantation to prevent acute rejection (e.g., methylprednisolone, atgam, thymoglobulin, OKT3, basiliximab, or daclizumab) or an immunosuppressive agent(s) used for maintenance (e.g., prednisone, a calcineurin inhibitor (e.g., cyclosporine, tacrolimus), Mycophenolate Mofetil, Azathioprine or Rapamycin). Other immunosuppressive agents given after organ transplantation include corticosteroids (e.g., methylprednisolone, dexamethasone, prednisolone), cytotoxic immunosuppressants (e.g., azathioprine, chlorambucil, cyclophosphamide, mercaptopurine, methotrexate), immunosuppressant antibodies (e.g., antithymocyte globulins, basiliximab, infliximab), sirolimus derivatives (e.g., everolimus, sirolimus), and anti-proliferative agents (e.g., mycophenolate mofetil, mycophenolate sodium, and azathioprine). In this case, the cloaked cell(s) is administered to or near the transplant site prior to organ or tissue transplantation to induce immune tolerance, and the immunosuppressive agent(s) is administered as an additional source of immunosuppression, if needed.

For use in treating inflammatory and autoimmune related diseases or conditions, the additional agent may be a disease-modifying anti-rheumatic drug (DMARD), a biologic response modifier (a type of DMARD), a corticosteroid, or a nonsteroidal anti-inflammatory medication (NSAID). In some embodiments, the additional agent is prednisone, prednisolone, methylprednisolone, methotrexate, hydroxychloroquine, sulfasalazine, leflunomide, cyclophosphamide, azathioprine, or a biologic such as tofacitinib, adalimumab, abatacept, anakinra, kineret, certolizumab, etanercept, golimumab, infliximab, rituximab or tocilizumab. In some embodiments, the additional agent is 6-mercaptopurine, 6-thioguanine, abatacept, adalimumab, alemtuzumab (Lemtrada), an aminosalicylate (5-aminoalicylic acid, sulfasalazine, mesalamine, balsalazide, olsalazine), an antibiotic, an anti-histamine, Anti-TNFα (infliximab, adalimumab, certolizumab pegol, natalizumab), azathioprine, belimumab, beta interferon, a calcineurin inhibitor, certolizumab, a corticosteroids, cromolyn, cyclosporin A, cyclosporine, dimethyl fumarate (tecfidera), etanercept, fingolimod (Gilenya), fumaric acid esters, glatiramer acetate (Copaxone), golimumab, hydroxyurea, IFNγ, IL-11, infliximab, leflunomide, leukotriene receptor antagonist, long-acting beta2 agonist, mitoxantrone, mycophenolate mofetil, natalizumab (tysabri), ocrelizumab, pimecrolimus, a probiotic (VSL #3), a retinoid, rituximab, salicylic acid, short-acting beta2 agonist, sulfasalazine, tacrolimus, teriflunomide (Aubagio), theophylline, tocilizumab, ustekinumab (anti-IL-12/IL-23), or vedolizumab (Anti alpha3 beta7 integrin). In this case, the cloaked cell(s) are administered to induce tolerance to an antigen (e.g., a self-antigen) aberrantly targeted by the immune system in connection with the autoimmune disease or condition, and the additional agent could be a compound or general anti-inflammatory agent (e.g., an NSAID or corticosteroid).

For example, if the disease is MS, the additional agent may be one or more of: interferon beta-1a, interferon beta-1b, gliatrimer acetate, daclizumab, teriflunomide, fingolimod, dimethyl fumarate, alemtuzumab, mitoxantrone, ocrelizumab, or natalizumab. The cloaked cell(s) administered could be stem cells or myelin producing cells (e.g., oligodendrocytes or Schwann cells). In some embodiments, the cloaked cell(s) can be modified to produce MOG and can be administered in combination with fingolimod.

For use in treating infectious disease, the additional agent may be an antiviral compound (e.g., vidarabine, acyclovir, gancyclovir, valgancyclovir, nucleoside-analog reverse transcriptase inhibitor (NRTI) (e.g., AZT (Zidovudine), ddl (Didanosine), ddC (Zalcitabine), d4T (Stavudine), or 3TC (Lamivudine)), non-nucleoside reverse transcriptase inhibitor (NNRTI) (e.g., (nevirapine or delavirdine), protease inhibitor (saquinavir, ritonavir, indinavir, or nelfinavir), ribavirin, or interferon); an antibacterial compound; an antifungal compound; an antiparasitic compound. The additional agent can be administered concurrently with or subsequently to uncloaked cell(s) to which the immune system has been tolerized that are modified to express a viral antigen.

For use in treating diabetes, the additional agent may be insulin, a sulfonylurea (e.g., chlorpropamide, glipizide, glyburide, glimepiride), a biguanide (e.g., metformin), a meglitinide (e.g., repaglinide, nateglinide), a thiazolidinedione (e.g., rosiglitazone, pioglitazone), a DPP-4 inhibitor (sitagliptin, saxagliptin, linagliptin, alogliptin), an SGLT2 inhibitor (e.g., canagliflozin, dapagliflozin), an alpha-glucosidase inhibitor (e.g., acarbose, miglitol), a bile acid sequestrant (e.g., colesevelam), aspirin, or a dietary regimen. The cloaked cell(s) administered could be stem cells or pancreatic beta cells that express a transgene encoding insulin and/or GAD65.

For use in treating cancer, the additional agent may be a checkpoint inhibitor, a chemotherapeutic drug, a biologic drug, a non-drug therapy (e.g., radiation therapy, cryotherapy, hyperthermia, or surgical excision or tumor tissue), or an anti-cancer vaccine. The additional agent can be administered concurrently with or subsequently to uncloaked cell(s) to which the immune system has been tolerized that are modified to express a cancer antigen Checkpoint inhibitors can be broken down into at least 4 major categories: i) agents such as antibodies that block an inhibitory pathway directly on T cells or natural killer (NK) cells (e.g., PD-1 targeting antibodies such as nivolumab, pidilizumab/CT-011, and pembrolizumab, antibodies targeting TIM-3, and antibodies targeting LAG-3, 2B4, CD160, A2aR, BTLA, CGEN-15049, or KIR), ii) agents such as antibodies that activate stimulatory pathways directly on T cells or NK cells (e.g., antibodies targeting OX40, GITR, or 4-1BB), iii) agents such as antibodies that block a suppressive pathway on immune cells or rely on antibody-dependent cellular cytotoxicity to deplete suppressive populations of immune cells (e.g., CTLA-4 targeting antibodies such as ipilimumab or tremelimumab, antibodies targeting VISTA, and antibodies targeting PD-L2 (e.g., a PDL2/Ig fusion protein such as AMP 224), Gr1, or Ly6G), and iv) agents such as antibodies or small molecules that block a suppressive pathway directly on cancer cells or that rely on antibody-dependent cellular cytotoxicity to enhance cytotoxicity to cancer cells (e.g., rituximab, antibodies or small molecules targeting PD-L1 (e.g., MPDL3280A/RG7446; MED14736; MSB0010718C; BMS 936559), and antibodies or small molecule inhibitors targeting B7-H3 (e.g., MGA271), B7-H4, Gal-9, or MUC1). In one embodiment, the inhibitor of checkpoint is an inhibitor (e.g., an inhibitory antibody or small molecule inhibitor) of HVEM, CD160, CHK 1, CHK2, B-7 family ligands, or a combination thereof. Such agents described herein can be designed and produced, e.g., by conventional methods known in the art (e.g., Templeton, Gene and Cell Therapy, 2015; Green and Sambrook, Molecular Cloning, 2012). In one embodiment, the inhibitor of checkpoint is an inhibitory antibody (e.g., a monospecific antibody such as a monoclonal antibody). The antibody may be, e.g., humanized or fully human. In other embodiments, the inhibitor of checkpoint is a fusion protein, e.g., an Fc-receptor fusion protein. In some embodiments, the inhibitor of checkpoint is an agent, such as an antibody, that interacts with a checkpoint protein. In other embodiments, the inhibitor of checkpoint is an agent, such as an antibody, that interacts with the ligand of a checkpoint protein.

Chemotherapeutic agents include alkylating agents, antimetabolites, folic acid analogs, pyrimidine analogs, purine analogs and related inhibitors, *vinca* alkaloids, epipodopyyllotoxins, antibiotics, L-asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard;

nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the cloaked cells described herein. Suitable dosing regimens of combination chemotherapies are known in the art.

Anti-cancer biologics include cytokines (e.g., interferon or an interleukin (e.g., IL-2)) used in cancer treatment. In other embodiments the biologic is an anti-angiogenic agent, such as an anti-VEGF agent, e.g., bevacizumab. In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include Rituximab; Daclizumab; Basiliximab; Palivizumab; Infliximab; Trastuzumab; Gemtuzumab ozogamicin; Alemtuzumab; Ibritumomab tiuxetan; Adalimumab; Omalizumab; Tositumomab-I-131; Efalizumab; Cetuximab; Bevacizumab; Natalizumab; Tocilizumab; Panitumumab; Ranibizumab; Eculizumab; Certolizumab pegol; Golimumab; Canakinumab; Ustekinumab; Ofatumumab; Denosumab; Motavizumab; Raxibacumab; Belimumab; Ipilimumab; Brentuximab Vedotin; Pertuzumab; Ado-trastuzumab emtansine; and Obinutuzumab. Also included are antibody-drug conjugates.

Kits

The invention also features a kit containing the cloaked cells described herein (e.g., cloaked cells expressing a set of the cloaking transgenes described herein (e.g., 1, 2, 3, 4, 5, 6, 7, or 8 of PD-L1, H2-M3, Cd47, Cd200, FasL, Ccl21b, Mfge8, and Spi6), optionally further expressing one or more of the following transgenes: TGF-β, Cd73, Cd39, Lag3, Il1r2, Ackr2, Tnfrsf22, Tnfrs23, Tnfrsf10, Dad1, and IFNγR1 d39). In one embodiment of the kit, the cloaked cells are further modified to express a polypeptide comprising an antigen (e.g., a donor alloantigen or a self-antigen associated with an autoimmune disease or condition). In another embodiment of the kit, the kit further includes uncloaked cells of the same type as the cloaked cells that are modified to express a polypeptide comprising a non-self, disease associated antigen (e.g., a cancer antigen, a bacterial antigen, a viral antigen, a fungal antigen, or a parasitic antigen). The cloaked or uncloaked cells may also contain one or more systems for regulating cell division (e.g., an ALINK or EARC system). The cloaked and/or uncloaked cells may be provided in a pharmaceutical composition. The kit may further include a syringe for administration of the cloaked and/or uncloaked cells or pharmaceutical composition and instructions for administering the cloaked cells or pharmaceutical composition for modulating an immune response described herein.

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used.

Figure 1C:
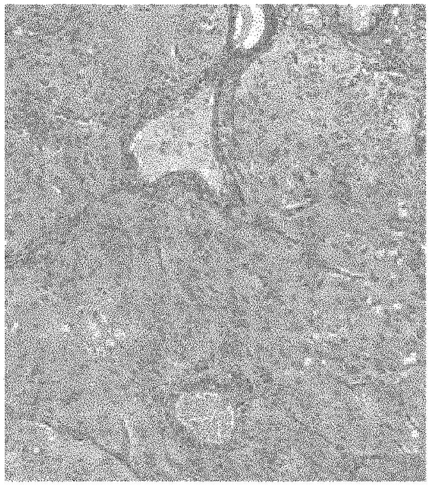
Figure 1A:
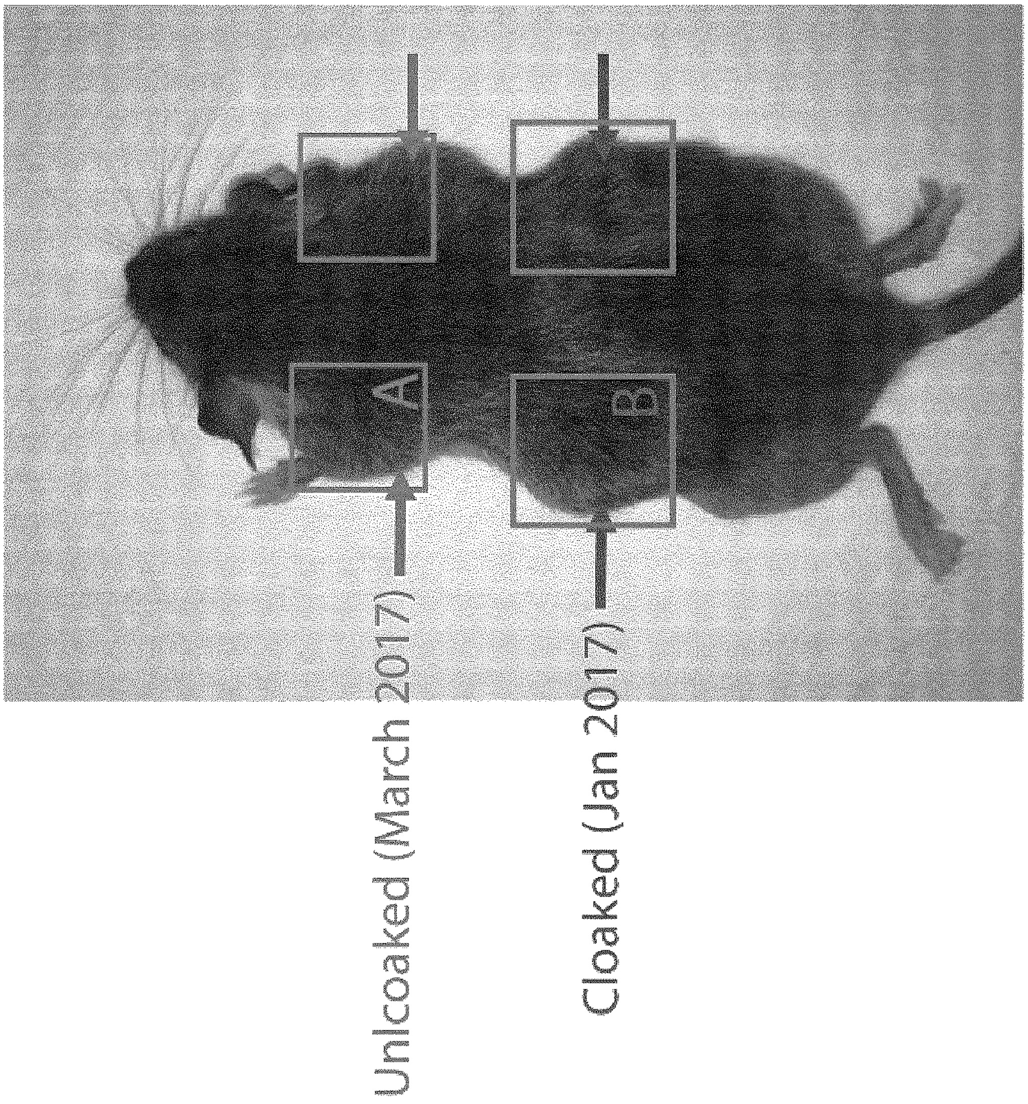

Example 1: Administration of Cloaked Allogenic Cells Promotes Immune Tolerance of Uncloaked Allogenic Cells C3H mice received a subcutaneous injection of allogenic cloaked C57BL/6 embryonic stem cells (ESCs). The cloaked cells expressed all eight cloaking transgenes (Pd-L1, CD200, CD47, H2-M3, Fas-L, Mfge8, Spi6 and Ccl21) and were injected subcutaneously in each flank area. Approximately two months later, the same mice received a subcutaneous injection of uncloaked allogenic cells of the same type (e.g., allogenic cells of the same type from the same source that were not modified to express cloaking transgenes) in the shoulder area. As shown in FIG. 1A, the mouse injected with the cloaked and uncloaked allogenic cells retained both the cloaked cells (boxes labeled "A" near flanks) and the uncloaked cells (boxes labeled "B" near the shoulders). The teratomas formed by both the cloaked (FIG. 1C) and uncloaked (FIG. 1B) allogenic cells showed well differentiated tissues devoid of excessive host-derived lymphocyte infiltration or any sign or necrosis as visualized using H&E staining. These experiments were repeated with FVB/N animals as hosts for C57BL/6 derived ESCs with the same results. These data demonstrate that the initial injection of cloaked allogenic cells induced immune tolerance to the allogenic cells, preventing the immune system from rejecting the subsequently injected uncloaked allogenic cells. Therefore, these findings indicate that cell cloaking technology may be used to induce immune tolerance in a recipient in advance of an organ or tissue transplant.

Example 2: Administration of Cloaked Cells Expressing an Alloantigen to Induce Immune Tolerance Prior to Organ Transplant According to the methods disclosed herein, a physician of skill in the art can treat a subject, such as a human subject in need of an organ transplant (e.g., a kidney transplant), with cloaked cells expressing a polypeptide comprising an alloantigen from an organ donor (e.g., an HLA protein expressed by the kidney cells of the organ donor). To this end, a physician of skill in the art can administer to the human subject cloaked cells (e.g., stem cells or cloaked kidney cells) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG) and an HLA protein expressed by the organ donor under the control of a constitutive promoter (e.g., CMV or CAG). The cloaked cells may be administered to the subject, for example, by local administration near the kidney that will be replaced, or by subcutaneous injection (e.g., to create a cloaked subcutaneous tissue) to induce tolerance in the subject to the alloantigen from the donor providing the kidney. One million to one hundred billion cloaked cells (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ cloaked cells) can be administered near the kidney or injected subcutaneously.

Following administration of the cloaked cells to a patient, a practitioner of skill in the art can evaluate the subject's immune response to the donor alloantigen by a variety of methods. For example, a practitioner can monitor the response of an immune cell from the subject to the donor alloantigen in vitro. A finding that the subject's immune system does not mount an immune response against the donor alloantigen after administration of the cloaked cells indicates that the subject's immune system has been tolerized to the donor alloantigen. The physician may then proceed to transplant the kidney from the organ donor into the subject with the expectation that the subject is at low risk of rejecting the kidney and may not require immunosuppressive medication or may require a reduced dose of immunosuppressive medication relative to the standard dose. A finding of an equivalent outcome in transplant rejection as that observed in subjects administered immunosuppressive agent(s) indicates that the cloaked cell induced immune tolerance to the transplanted organ. Subsequent doses of cloaked cells can be determined and administered as needed.

In some embodiments, the cloaked cells are further modified prior to administration to the subject to allow for control of their proliferation by linking the expression of a CDL to an ALINK or EARC (e.g., a negative selectable marker or an exogenous inducible transcriptional activator). For example, the cloaked cells can be modified to contain homozygous ALINKs (e.g., HSV-TK systems) in two CDL loci (e.g., Cdk1 and Top2A). After subcutaneous injection of the cloaked cells that express a polypeptide comprising a donor alloantigen and contain a mechanism for controlling proliferation, a practitioner of skill in the art can monitor the size of the cloaked subcutaneous tissue. If it appears that the cloaked subcutaneous tissue is becoming tumorigenic, the practitioner can administer ganciclovir to the subject to ablate the proliferating cloaked cells. The mechanism for controlling proliferation can also be used to ablate all of the cloaked cells after immune tolerance has been induced in the subject and the cells are no longer needed.

Example 3: Administration of Cloaked Cells Expressing MOG to a Subject with Multiple Sclerosis According to the methods disclosed herein, a physician of skill in the art can treat a subject, such as a human subject, with MS by inducing tolerance to MOG, an antigen implicated in the T cell damage to oligodendrocytes that occurs during the course of the disease. To this end, a physician of skill in the art can administer to the human subject cloaked cells (e.g., cloaked stem cells, cloaked oligodendrocytes, or cloaked stem cells that have been differentiated into oligodendrocytes) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG) and MOG under the control of a constitutive promoter (e.g., CMV or CAG). The cloaked cells may be administered to the subject, for example, by subcutaneous injection (e.g., to create a cloaked subcutaneous tissue), to treat MS. One million to three billion cloaked cells expressing MOG (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, or $3\times10^9$ cloaked cells) can be administered subcutaneously.

Following administration of the cloaked cells to a subject, a practitioner of skill in the art can monitor the subject's improvement in response to the therapy by a variety of methods. For example, a physician can monitor symptoms of MS (e.g., tremor, coordination, gait, speech, vision, or feelings of numbness or tingling) in a subject with primary-progressive or relapsing-remitting MS, or a physician can monitor the occurrence of relapses in a subject with relapsing-remitting MS. A finding that the subject's symptoms of MS improve or stabilize (e.g., a finding that the symptoms do not worsen or progress), or a finding that the time between relapses increases or the occurrence of relapses decreases compared to measurements taken prior to administration of the cloaked cells indicates that the subject is responding favorably to the treatment. Subsequent doses can be determined and administered as needed.

In some embodiments, the cloaked cells are further modified prior to administration to the subject to allow for control of their proliferation by linking the expression of a CDL to an ALINK or EARC (e.g., a negative selectable marker or an exogenous inducible transcriptional activator). For example, the cloaked cells can be modified to contain homozygous ALINKs (e.g., HSV-TK systems) in two CDL loci (e.g., Cdk1 and Top2A). After subcutaneous injection of the cloaked cells that express MOG and contain a mechanism for controlling proliferation, a practitioner of skill in the art can monitor the size of the cloaked subcutaneous tissue. If it appears that the cloaked subcutaneous tissue is becoming tumorigenic, the practitioner can administer ganciclovir to the subject to ablate the proliferating cloaked cells. The mechanism for controlling proliferation can also be used to ablate all of the cloaked cells after immune tolerance has been induced in the subject and the cells are no longer needed.

Example 4: Administration of Cloaked Cells Expressing Insulin or GAD65 to a Subject with Type 1 Diabetes According to the methods disclosed herein, a physician of skill in the art can treat a subject, such as a human subject, with Type 1 diabetes by inducing immune tolerance to an antigen associated with damage to pancreatic beta cells by immune cells (e.g., insulin and/or GAD65). To this end, a physician of skill in the art can administer to the human subject cloaked cells (e.g., cloaked stem cells, cloaked pancreatic beta cells, or cloaked stem cells that have been differentiated into pancreatic beta cells) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG) and insulin and/or GAD65 under the control of a constitutive promoter (e.g., CMV or CAG). The cloaked cells may be administered to the subject, for example, by subcutaneous injection (e.g., to create a cloaked subcutaneous tissue), to treat Type 1 diabetes. One million to three billion cloaked cells expressing insulin and/or GAD65 (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, or $3\times10^9$ cloaked cells) can be administered subcutaneously or near or to the pancreas.

Following administration of the cloaked cells to a subject, a practitioner of skill in the art can monitor the subject's improvement in response to the therapy by a variety of methods. For example, a physician can monitor insulin levels or symptoms of Type 1 diabetes (e.g., unintended weight loss, fatigue, or blurred vision) using standard approaches. A finding that the subject's insulin levels are increased or the symptoms of Type 1 diabetes are reduced compared to measurements taken prior to administration of the cloaked cells indicates that the subject is responding favorably to the treatment. Subsequent doses can be determined and administered as needed.

In some embodiments, the cloaked cells are further modified prior to administration to the subject to allow for control of their proliferation by linking the expression of a CDL to an ALINK or EARC (e.g., a negative selectable marker or an exogenous inducible transcriptional activator). For example, the cloaked cells can be modified to contain homozygous ALINKs (e.g., HSV-TK systems) in two CDL loci (e.g., Cdk1 and Top2A). After subcutaneous injection of the cloaked cells that express insulin and/or GAD65 and contain a mechanism for controlling proliferation, a practitioner of skill in the art can monitor the size of the cloaked subcutaneous tissue. If it appears that the cloaked subcutaneous tissue is becoming tumorigenic, the practitioner can administer ganciclovir to the subject to ablate the proliferating cloaked cells. The mechanism for controlling proliferation can also be used to ablate all of the cloaked cells after immune tolerance has been induced in the subject and the cells are no longer needed.

Example 5: Administration of Cloaked Cells Followed by Administration of Uncloaked Cells Expressing a Cancer Antigen to Induce Immunity to the Cancer Antigen According to the methods disclosed herein, a physician of skill in the art can treat a subject, such as a human subject, at risk of developing cancer (e.g., breast cancer) by promoting the production of antibodies against a cancer antigen (e.g., a breast cancer antigen) by the immune system of the subject. To this end, a physician of skill in the art can administer to the human subject cloaked cells (e.g., cloaked allogeneic stem cells) that express one or more (e.g., one, two, three, four, five, six, seven, or all eight) of PD-L1, HLA-G (H2-M3), Cd47, Cd200, FASLG (FasL), Ccl21 (Ccl21b), Mfge8, and Serpin B9 (Spi6) under the control of a constitutive promoter (e.g., CMV or CAG). The cloaked cells may be administered to the subject, for example, by subcutaneous injection (e.g., to create a cloaked subcutaneous tissue), to induce immune tolerance to the cloaked cells. One million to three billion cloaked cells (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, or $3\times10^9$ cloaked cells) can be administered subcutaneously.

Following administration of the cloaked cells to a subject, a practitioner of skill in the art can measure an immune response of the subject to an uncloaked cell of the same type (e.g., measure a response of an immune cell isolated from the subject to an uncloaked cell of the same type in vitro). If the subject exhibits immune tolerance to the uncloaked cell (e.g., if the immune cell from the subject does not mount an immune response against the uncloaked cell), an uncloaked cell of the same type that is modified to express a polypeptide containing a cancer antigen (e.g., a breast cancer antigen) under the control of a constitutive promoter (e.g., CMV or CAG) can be administered to the subject. The uncloaked cells expressing a cancer antigen may be administered to the subject, for example, by subcutaneous injection (e.g., to create an uncloaked subcutaneous tissue), to induce an immune response to the cancer antigen (e.g., to promote the production of antibodies directed against the cancer antigen). One million to three billion uncloaked cells (e.g., $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, or $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, or $3\times10^9$ cloaked cells) can be administered subcutaneously or to or near the breast of the subject. A practitioner of skill in the art can determine whether an immune response has been stimulated in the subject by collecting a blood sample from the subject and assaying for the presence of antibodies directed against the cancer antigen. A finding that the blood sample from the subject contains antibodies directed against the cancer antigen indicates that the uncloaked cell has stimulated an immune response to the cancer antigen. Subsequent doses can be determined and administered as needed.

In some embodiments, the cloaked or uncloaked cells are further modified prior to administration to the subject to allow for control of their proliferation by linking the expression of a CDL to an ALINK or EARC (e.g., a negative selectable marker or an exogenous inducible transcriptional activator). For example, the cloaked or uncloaked cells can be modified to contain homozygous ALINKs (e.g., HSV-TK systems) in two CDL loci (e.g., Cdk1 and Top2A). After subcutaneous injection of the cloaked or uncloaked cells that contain a mechanism for controlling proliferation, a practitioner of skill in the art can monitor the size of the cloaked subcutaneous tissue. If it appears that the cloaked or uncloaked subcutaneous tissue is becoming tumorigenic, the practitioner can administer ganciclovir to the subject to ablate the proliferating cloaked or uncloaked cells. The mechanism for controlling proliferation can also be used to ablate all of the cloaked cells after immune tolerance has been induced in the subject and the cells are no longer needed, or to ablate the uncloaked cells after the subject's immune system has produced antibodies directed to the cancer antigen.

Other Embodiments

Although the disclosure has been described with reference to certain specific embodiments, various modifications thereof will be apparent to those skilled in the art. Any examples provided herein are included solely for the purpose of illustrating the disclosure and are not intended to limit the disclosure in any way. Any drawings provided herein are solely for the purpose of illustrating various aspects of the disclosure and are not intended to be drawn to scale or to limit the disclosure in any way. The scope of the claims appended hereto should not be limited by the preferred embodiments set forth in the above description, but should be given the broadest interpretation consistent with the present specification as a whole. The disclosures of all prior art recited herein are incorporated herein by reference in their entirety.

What is claimed is:

1. A eukaryotic cell genetically modified to comprise i) a set of transgenes comprising the following genes: PD-L1, HLA-G or H2-M3, Cd47, Cd200, FASLG or FasL, Ccl21 or Ccl21b, Mfge8, and Serpin B9 or Spi6; and ii) a transgene encoding a polypeptide comprising a self-antigen associated with an autoimmune disease.

2. The eukaryotic cell of claim 1, further comprising one or more of the following transgenes: TGF-β, Cd73, Cd39, Lag3, Il1r2, Ackr2, Tnfrsf22, Tnfrs23, Tnfrsf10, Dad1, and IFNγR1 d39 or a gene encoding a biologic that acts as an agonist of TGF-β, Cd73, Cd39, Lag3, Il1r2, Ackr2, Tnfrsf22, Tnfrs23, Tnfrsf10, Dad1, or IFNγR1 d39.

3. The eukaryotic cell of claim 2, wherein:
(a) the TGF-β or biologic is local acting in the graft environment; or
(b) the IFNγR1 d39 transgene encodes a protein having at least 95% identity to the amino acid sequence of SEQ ID NO: 17.

4. The eukaryotic cell of claim 1, wherein:
(a) the transgene encoding the polypeptide comprising the self-antigen is incorporated into the genome of the cell at a non-endogenous locus;
(b) one or more of PD-L1, HLA-G or H2-M3, Cd47, Cd200, FASLG or FasL, Ccl21 or Ccl21b, Mfge8, and Serpin B9 or Spi6 is expressed at a level that is greater than the expression level of the corresponding endogenous gene in the cell or that is equal to or greater than the expression level of the corresponding endogenous gene in an activated leukocyte;
(c) one or more of PD-L1, HLA-G or H2-M3, Cd47, Cd200, FASLG or FasL, Ccl21 or Ccl21b, Mfge8, and Serpin B9 or Spi6 is expressed at a level that is in the top 5% of gene expression for all genes in the genome of the eukaryotic cell;
(d) the transgenes are operably linked to a constitutive promoter;
(e) the transgene encoding the polypeptide comprising the self-antigen is operably linked to a constitutive promoter; or
(f) the polypeptide comprising the self-antigen is expressed using an inducible expression system selected from the group consisting of a tetracycline response element, a light inducible system, a radiogenetic system, a cumate switch inducible system, an ecdysone inducible system, a destabilization domain system, or a ligand-reversible dimerization system.

5. The eukaryotic cell of claim 4, wherein:
(a) all eight of PD-L1, HLA-G or H2-M3, Cd47, Cd200, FASLG or FasL, Ccl21 or Ccl21b, Mfge8, and Serpin B9 or Spi6 are expressed at a level that is greater than the expression level of the corresponding endogenous gene in the cell or that is equal to or greater than the expression level of the corresponding endogenous gene in an activated leukocyte;
(b) all eight of PD-L1, HLA-G or H2-M3, Cd47, Cd200, FASLG or FasL, Ccl21 or Ccl21b, Mfge8, and Serpin B9 or Spi6 are expressed at a level that is in the top 5% of gene expression for all genes in the genome of the cell; or
(c) the constitutive promoter is selected from the group consisting of the CAG promoter, the cytomegalovirus (CMV) promoter, the EF1a promoter, the PGK promoter, adenovirus late promoter, vaccinia virus 7.5K promoter, SV40 promoter, tk promoter of HSV, mouse mammary tumor virus (MMTV) promoter, LTR promoter of HIV, promoter of moloney virus, Epstein barr virus (EBV) promoter, and the Rous sarcoma virus (RSV) promoter.

6. The eukaryotic cell of claim 1, wherein:
(a) the PD-L1 transgene encodes a protein having at least 95% sequence identity to the amino acid sequence of SEQ ID NO: 11 or SEQ ID NO: 12;
(b) the HLA-G or H2-M3 transgene encodes a protein having at least 95% sequence identity to the amino acid sequence of SEQ ID NO: 16 or SEQ ID NO: 15;
(c) the Cd47 transgene encodes a protein having at least 95% sequence identity to the amino acid sequence of SEQ ID NO: 3 or SEQ ID NO: 4;
(d) the CD200 transgene encodes a protein having at least 95% sequence identity to the amino acid sequence of SEQ ID NO: 5 or SEQ ID NO: 6;
(e) the FASLG or FasL transgene encodes a protein having at least 95% sequence identity to the amino acid sequence of SEQ ID NO: 10 or SEQ ID NO: 9;
(f) the Ccl21 or Ccl21b transgene encodes a protein having at least 95% sequence identity to the amino acid sequence of SEQ ID NO: 2 or SEQ ID NO: 1;
(g) the Mfge8 transgene encodes a protein having at least 95% sequence identity to the amino acid sequence of SEQ ID NO: 13 or SEQ ID NO: 14; and
(h) the Serpin B9 or Spi6 transgene encodes a protein having at least 95% sequence identity to the amino acid sequence of SEQ ID NO: 8 or SEQ ID NO: 7.

7. A population of genetically modified cells, wherein each of the cells is a eukaryotic cell of claim 1.

8. A composition comprising the population of genetically modified cells of claim 7.

9. A composition comprising the eukaryotic cell of claim 1.

10. The composition of claim 9, further comprising a pharmaceutically acceptable excipient.

11. A kit comprising the composition of claim 9.

12. The eukaryotic cell of claim 1, wherein the eukaryotic cell is a stem cell.

13. The eukaryotic cell of claim 12, wherein the stem cell is an embryonic stem cell.

14. The eukaryotic cell of claim 1, wherein the eukaryotic cell is a kidney cell, an oligodendrocyte, or a pancreatic beta cell.

15. The eukaryotic cell of claim 1, wherein the self-antigen comprises a myelin oligodendrocyte glycoprotein (MOG), insulin, or glutamic acid decarboxylase 65 (GAD65).

16. The eukaryotic cell of claim 1, wherein the self-antigen comprises 14-3-3ε, 14-3-3ζ, 14-3-3ζ, 14-3-3η, 17 alpha-Hydroxylase, 21-hydroxylase, 21β-4-hydroxylase, 3-Hydroxy-3-Methylglutaryl-CoA Reductase (HMGCR), trimethylaminobutyraldehyde dehydrogenase, 5'-nucleotidase cytosolic I, 68-kD inner ear protein, actin, ADAM Metallopeptidase with Thrombospondin Type 1 Motif 13 (ADAMTS13), adenine nucleotide translocator, Alpha 3 chain of type IV collagen, Alpha (2)-HSG, alpha-3 chain of type IV collagen, alpha-4 chain of type IV collagen, alpha-5 chain of type IV collagen, Aminoacyl-tRNA synthetase, Aminoacylase 1 (ACY1), AMPA receptors, amphiphysin, amylase-2α, amylase-alpha-2α lactoferrin, amyloid-β, ANNA-1, annexin 5, Annexin A8 Like 1 (ANXA8L1), aquaporin-4, arrestin, Asialoglycoprotein, asialoglycoprotein receptor, AT-Rich Interaction Domain 4B (ARID4B), ATP synthase β chain, ATPase Secretory Pathway Ca2+ Transporting 1 (ATP2C1), B-Cell activating factor, bactericidal permeability increasing (BPI) protein, Basic Leucine Zipper Nuclear Factor 1 (BLZF1), beta actin, beta-2-glycoprotein-1, Bip, BP180, Bruton's tyrosine kinase, bullous pemphigoid antigen 1, Bullous pemphigoid antigen 180 (BP180), bullous pemphigoid antigen 2, bullous pemphigoid antigen 230 (BP230), C1 inhibitor (C1-INH), C1g, C2orf34, C3 convertase, Ca2+/calmodulin-dependent protein kinase II (CamKII), Cadherin 8 (CDH8), Cadherin 9 (CDH9), Calcium/Calmodulin Dependent Protein Kinase IV (CAMK4), calpastatin, calreticulin, carbonic anhydrase, carbonic anhydrase I, Carbonic anhydrase II, carbonic anhydrase IV, carbonic anhydrase-II, carbonic anhydrase-IV, cardiac myosin, cardiolipin, caspase-3, CASPR1, Caspr2, cathepsin G, Cbir1, CD1b Molecule (CD1B), CD33 molecule (CD33), cell-density enhanced protein tyrosine phosphatase-1, CENP-A, CENP-B, CENP-C, CENP-O, Cholinergic Receptor Nicotinic Delta Subunit (CHRND), Cholinergic Receptor Nicotinic Epsilon Subunit (CHRNE), chondromodulin 1, CK10, claudin-1, cluster of differentiation 88 (CD88), cochlin, cold agglutinins, collagen, collagen I, collagen II, collagen III, collagen IV, collagen IX, Collagen Type XXI Alpha 1 Chain (COL21A1), collagen V, collagen VII, collagen XI, complement factor B, complement factor H, connective tissue growth factor, connexion, contactin, Contactin 1 (CNTN1), contactin-1, cornea-associated antigen, CTL2, Cyclin Dependent Kinase Inhibitor 1B (CDKN1B), Cyclin Dependent Kinase Like 1 (CDKL1), Cytochrome B5 Type B (CYB5B), Cytochrome P450 Family 1 Subfamily A Member 2 (CYP1A2), Cytochrome P450 Family 2 Subfamily D Member 6 (CYP2D6), Cytochrome P450 Family 2 Subfamily E Member 1 (CYP2E1), Cytochrome P450 Family 3 Subfamily A Member 4 (CYP3A4), cytokeratin 10, cytokeratin 16, Cytokine Induced Apoptosis Inhibitor 1 (CIAPIN1), Cytosolic 5'-nucleotidase 1A, D2 receptors, DEAD-Box Helicase 17 (DDX17), Delta/Notch Like EGF Repeat Containing (DNER), desmocollin, Desmocollin 1 (DSC1), Desmocollin 3 (DSC3), desmoglein 1, desmoglein 3, DNA topoisomerase II, DNER, Dopamine D2 receptor, DPPX, E (HLA-E), E2 subunit of pyruvate dehydrogenase, ECGF, elastase, Endophilin B1 (SH3GLB1), Enolase, enolase a, Ephrin A3 (EFNA3), epidermal transglutaminase, ER60, erythropoietin, Eukaryotic Translation Initiation Factor 4A2 (EIF4A2), extracellular matrix protein 1, factor VIII, Fc Fragment Of IgG Receptor IIa (CD32), FcγRIIIb, FcεRIa of FCER1, ferritin, FH, fibrillin, fibrin, fibrinogen, filaggrin, FLII actin remodeling protein (FLII), formiminotransferase cyclodeaminase, FSH receptor, GA1, GABAA receptor associated protein, GABAA receptors, GABAB receptors, GAD65, ganglionic acetylcholine receptor (α3-nicotinic AChR), ganglioside GD1a, ganglioside GM1, ganglioside GM1b, Ganglioside GQ1b, ganglioside GT1a, GD1b, GDP Dissociation Inhibitor 2 (GDI2), gliadin, gliomedin, glucose-6-phosphate isomerase, glutamic acid decarboxylase, Glutamic acid decarboxylase (GAD), glutamic acid decarboxylase 65 (GAD65), Glutaminase 2 (GLS2), Gly receptors, glycine receptor a1, glycogen, glycophorin A, Glycoprotein IIb/IIIa (GPIIb/IIIa), glypican 3, glypican 4, GM1, GOR, GP120, GP1BA, gp50-64, gp70-95, GPIb/IX, GSG1 Like (GSG1L), H+/K (+)-ATPase, Heat Shock Protein Family A (Hsp70) Member 8 (HSPA8), helicase/histone deacetylase protein complex, high-mobility group (HMG)-1, histone H1, histone proteins, HLA, HLA-B27, HMG-2, HMGCR, hnRNP H1, Hsp10, Hsp60, Hsp65, Hsp70, Hsp70-2, Hu, Human leukocyte antigen B27 (HLA B27), I antigens of red blood cells, I2, ICQK, IF-R7, IgE, Immunoglobulin Heavy Constant Gamma 1 (IGHG1), insulin, insulinoma antigen 2 protein, Integrin Subunit Alpha L (CD11a), Integrin Subunit Alpha M (CD11b), interleukin 6 (IL-6), interphotoreceptor retinoid binding protein (IRBP), interphotoreceptor retinoid-binding protein, Jo-1, keratin, kinectin, Kpb antigen of Kell blood group system, Ku, Ky1.4 voltage-gated potassium channel, La, La/SSB, LABD97 (97 kDa fragment of bullous pemphigoid antigen 180), lactoferrin, LAD-1 (120 kDa fragment of bullous pemphigoid antigen 180), lamin A, lamin C, laminin, laminin 5, laminin 5 a3 subunit, laminin B receptor, laminin-5, laminin-6, LC1, LDL Receptor Related Protein 4 (LRP4), Leucine Rich Glioma Inactivated 1 (LGI1), LFA-1, LH receptor, LIM And Calponin Homology Domains 1 (LIMCH1), LKM-1, LKM-3, Lyn tyrosine kinase, M1 muscarinic AChR, M2, M2 muscarinic acetylcholine receptor, M2 muscarinic AChR, M3 muscarinic AChR, M4, M8, M9, MAGE Family Member A4 (MAGEA4), Major Histocompatibility Complex Class I, major peripheral myelin protein P0, major zymogen granule membrane glycoprotein 2, MART-1/Melan A, maternal antigen that embryos require (Mater/Nalp5), Matrilin 2 (MATN2), Matrix Gla protein, Matrix metalloproteinase 10 (MMP10), MDA5, Melanin associated antigen (MAA), melanocortin 4 receptor, melanoma differentiation antigen 5, Methyltransferase-like 22, Mg2+/Mn2+ Dependent 1A (PPM1A), mGluR1, Mi-2, Mi2, MJ, MLLT6, muscarinic acetylcholine receptor, Muscarinic Acetylcholine Receptor M3 (CHRM3), muscarinic M2 acetylcholine receptor, muscarinic M3 receptor, Muscle Associated Receptor Tyrosine Kinase (MuSK), mutant transthyretin (V30M), Myelin associated glycoprotein (MAG), Myelin oligodendrocyte glycoprotein, Myelin oligodendrocyte glycoprotein (MOG), myelin peroxidase zero, Myelin Protein Zero (MPZ), myeloperoxidase, Myocyte Enhancer Factor 2D (MEF2D), myofibrillar protein, myosin, NADH: Ubiquinone Oxidoreductase Core Subunit S1 (NDUFS1), NC1 domain of Alpha-3 chain of type IV collagen, NDP52, nebulin-related anchoring protein, Neural Cell Adhesion Molecule 1 (NCAM), Neural Cell Adhesion Molecule 2 (NCAM2), Neurofascin-186, Neurofascin-186 (NF186), neuronal cell adhesion molecule (NrCAM), NF140, NF155, NF186, nicotinic acetylcholine receptor, NIMA Related Kinase 7 (NEK7), NMDA receptors, Nuclear histone 1 of polymorphonuclear leukocytes, nuclear matrix protein 2, NXP-2, NXP2, Ompc, osteoglycin, osteonectin, Outer Dense Fiber of Sperm Tails 2 (ODF-2), P antigens of red blood cells, p155/140, p200, P2RX7, P450scc, p57, P62, pancreas secretory trypsin inhibitor, pancreatic secretory trypsin inhibitor, pancreatic trypsinogen, PCA-1, Peripheral Myelin Protein 2 (PMP2), Peripheral Myelin Protein 22 (PMP22), peroxiredoxin, PHD Finger Containing (MLLT6), phosphatidylserine, phosphatidylserine-prothrombin complex, phosphodiesterase, phosphoglycerate kinase 1, phospholipid cofactor, Plakophilin 3 (PKP3), plasminogen-binding protein, Pm/Scl, Pmel17/gp100, PML, PMP22, PNMA2 (Ma-2/Ta), Poly (ADPRibose) Polymerase Family Member 3 (PARP3), pro-opiomelanocortin-1 (POMC-1), progesterone, proteasome complex component 2 and zeta chain, Protein Kinase D1 (PRKD1), protein phosphatase, protein tyrosine phosphatase, Protein Tyrosine Phosphatase Non-Receptor Type 22 (PTPN22), proteinase 3, Pyruvate Dehydrogenase E1 Alpha 1 Subunit (PDHA1), RA33/hnRNP A2, Raf-1, rapsyn, recoverin, red blood cell antigens, Regulator Of G Protein Signaling 10 (RGS10), retinal arrestin, retinal soluble antigen, rheumatoid factor, rhodopsin, RNAP I, RNAP II, RNAP III, RNP, Ro, Ro/La, Ro/SSA, Ro52, Ryanodine receptor (RyR), Sa, SAE, SAGA-1, Scl-70, Scl70, Serpin family A member 5 (SERPINA5), serum andolase, SH3 Domain Containing GRB2 Like, side-chain cleavage enzyme, signal recognition particle, Sm, Sm/RNP, small ubiquitin-like modifier activating enzyme, SOD2, Solute Carrier Family 36 Member 4 (SLC36A4), SP100, SP140, SPARC Related Modular Calcium Binding 1 (SMOC1), SSA, SSb, sulfoglucuronosyl glycolipids, Superoxide dismutase 2 (SOD2), synapsin synthetase, Th/To, thyroglobulin, thyroid peroxidase, thyroid stimulating hormone, thyroperoxidase, thyrotropin receptor, TIF1-gamma, TIF1-γ, titin, transcriptional intermediary factor 1, transferrin, transglutaminase, Transglutaminase 1 (TGM1), transglutaminase 2, transglutaminase 3, transglutaminase 6, transthyretin, trichohyalin, Tropomyosin, tropomyosin 5, troponin, trypsin, trypsinogen, tubulin-α-1c, tubulointerstitial nephritis antigen, type II collagen, type IX collagen, Tyrosinase (Tyr), tyrosinase 1, tyrosinase 2, tyrosinase-related protein 1 (TRP1), tyrosinase-related protein 2, tyrosinase-related protein 2 (TRP2), tyrosine hydroxylase isoform B1, tyrosine hydroxylase isoform B2, U1 ribonucleoprotein (U1-RNP), U1-RNP, U1A, Ubiquitin Conjugating Enzyme E2 W (UBE2W), UDP-glucuronosyltransferases, UGA-suppressor-tRNA-associated protein, Vascular cell adhesion molecule 1 (VCAM-1), VGCC, vimentin, vinculin, Yo, zinc transporter 8, zonulin, α enolase, a (1) subunits of voltage gated calcium channels, α-Enolase, α-fodrin, a1-adrenaline receptor, α3 chain of type IV collagen, a6-integrin subunit, β(3) subunits of voltage gated calcium channels, β-glucuronidase, B1 adrenergic receptor, β1-adrendergic receptor, β2 glycoprotein 1 (β2-GPI), β2-glycoprotein I, β2-glycoprotein-I, B4-integrin, or β4-integrin subunit.

17. The eukaryotic cell of claim 1, wherein the set of transgenes comprises:

PD-L1, HLA-G, Cd47, Cd200, FASLG, Ccl21, Mfge8, and Serpin B9; or PD-L1, H2-M3, Cd47, Cd200, FasL, Ccl21b, Mfge8, and Spi6.

* * * * *

SEQUENCE LISTING

```
<160> NUMBER OF SEQ ID NOS: 343

<210> SEQ ID NO 1
<211> LENGTH: 133
<212> TYPE: PRT
<213> ORGANISM: Mus musculus

<400> SEQUENCE: 1

Met Ala Gln Met Met Thr Leu Ser Leu Leu Ser Leu Val Leu Ala Leu
1               5                   10                  15

Cys Ile Pro Trp Thr Gln Gly Ser Asp Gly Gly Gly Gln Asp Cys Cys
            20                  25                  30

Leu Lys Tyr Ser Gln Lys Lys Ile Pro Tyr Ser Ile Val Arg Gly Tyr
        35                  40                  45

Arg Lys Gln Glu Pro Ser Leu Gly Cys Pro Ile Pro Ala Ile Leu Phe
    50                  55                  60

Leu Pro Arg Lys His Ser Lys Pro Glu Leu Cys Ala Asn Pro Glu Glu
65                  70                  75                  80

Gly Trp Val Gln Asn Leu Met Arg Arg Leu Asp Gln Pro Pro Ala Pro
                85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
        115                 120                 125

Gln Pro Ser Arg Gly
    130


<210> SEQ ID NO 2
<211> LENGTH: 134
<212> TYPE: PRT
<213> ORGANISM: Homo sapiens

<400> SEQUENCE: 2

Met Ala Gln Ser Leu Ala Leu Ser Leu Leu Ile Leu Val Leu Ala Phe
1               5                   10                  15

Gly Ile Pro Arg Thr Gln Gly Ser Asp Gly Gly Ala Gln Asp Cys Cys
            20                  25                  30

Leu Lys Tyr Ser Gln Arg Lys Ile Pro Ala Lys Val Val Arg Ser Tyr
        35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
```

130

<210> SEQ ID NO 3
<211> LENGTH: 303
<212> TYPE: PRT
<213> ORGANISM: Mus musculus

<400> SEQUENCE: 3

```
Met Trp Pro Leu Ala Ala Ala Leu Leu Leu Gly Ser Cys Cys Cys Gly
1               5                   10                  15

Ser Ala Gln Leu Leu Phe Ser Asn Val Asn Ser Ile Glu Phe Thr Ser
            20                  25                  30

Cys Asn Glu Thr Val Val Ile Pro Cys Ile Val Arg Asn Val Glu Ala
        35                  40                  45

Gln Ser Thr Glu Glu Met Phe Val Lys Trp Lys Leu Asn Lys Ser Tyr
    50                  55                  60

Ile Phe Ile Tyr Asp Gly Asn Lys Asn Ser Thr Thr Thr Asp Gln Asn
65                  70                  75                  80

Phe Thr Ser Ala Lys Ile Ser Val Ser Asp Leu Ile Asn Gly Ile Ala
                85                  90                  95

Ser Leu Lys Met Asp Lys Arg Asp Ala Met Val Gly Asn Tyr Thr Cys
            100                 105                 110

Glu Val Thr Glu Leu Ser Arg Glu Gly Lys Thr Val Ile Glu Leu Lys
        115                 120                 125

Asn Arg Thr Val Ser Trp Phe Ser Pro Asn Glu Lys Ile Leu Ile Val
    130                 135                 140

Ile Phe Pro Ile Leu Ala Ile Leu Leu Phe Trp Gly Lys Phe Gly Ile
145                 150                 155                 160

Leu Thr Leu Lys Tyr Lys Ser Ser His Thr Asn Lys Arg Ile Ile Leu
                165                 170                 175

Leu Leu Val Ala Gly Leu Val Leu Thr Val Ile Val Val Val Gly Ala
            180                 185                 190

Ile Leu Leu Ile Pro Gly Glu Lys Pro Val Lys Asn Ala Ser Gly Leu
        195                 200                 205

Gly Leu Ile Val Ile Ser Thr Gly Ile Leu Ile Leu Leu Gln Tyr Asn
    210                 215                 220

Val Phe Met Thr Ala Phe Gly Met Thr Ser Phe Thr Ile Ala Ile Leu
225                 230                 235                 240

Ile Thr Gln Val Leu Gly Tyr Val Leu Ala Leu Val Gly Leu Cys Leu
                245                 250                 255

Cys Ile Met Ala Cys Glu Pro Val His Gly Pro Leu Leu Ile Ser Gly
            260                 265                 270

Leu Gly Ile Ile Ala Leu Ala Glu Leu Leu Gly Leu Val Tyr Met Lys
        275                 280                 285

Phe Val Ala Ser Asn Gln Arg Thr Ile Gln Pro Pro Arg Asn Arg
    290                 295                 300
```

<210> SEQ ID NO 4
<211> LENGTH: 323
<212> TYPE: PRT
<213> ORGANISM: Homo sapiens

<400> SEQUENCE: 4

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
```

```
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu


<210> SEQ ID NO 5
<211> LENGTH: 278
<212> TYPE: PRT
<213> ORGANISM: Mus musculus

<400> SEQUENCE: 5

Met Gly Ser Leu Val Phe Arg Arg Pro Phe Cys His Leu Ser Thr Tyr
1               5                   10                  15

Ser Leu Ile Trp Gly Met Ala Ala Val Ala Leu Ser Thr Ala Gln Val
            20                  25                  30

Glu Val Val Thr Gln Asp Glu Arg Lys Ala Leu His Thr Thr Ala Ser
        35                  40                  45

Leu Arg Cys Ser Leu Lys Thr Ser Gln Glu Pro Leu Ile Val Thr Trp
    50                  55                  60

Gln Lys Lys Lys Ala Val Ser Pro Glu Asn Met Val Thr Tyr Ser Lys
```

```
65                  70                  75                  80

Thr His Gly Val Val Ile Gln Pro Ala Tyr Lys Asp Arg Ile Asn Val
                85                  90                  95

Thr Glu Leu Gly Leu Trp Asn Ser Ser Ile Thr Phe Trp Asn Thr Thr
            100                 105                 110

Leu Glu Asp Glu Gly Cys Tyr Met Cys Leu Phe Asn Thr Phe Gly Ser
        115                 120                 125

Gln Lys Val Ser Gly Thr Ala Cys Leu Thr Leu Tyr Val Gln Pro Ile
    130                 135                 140

Val His Leu His Tyr Asn Tyr Phe Glu Asp His Leu Asn Ile Thr Cys
145                 150                 155                 160

Ser Ala Thr Ala Arg Pro Ala Pro Ala Ile Ser Trp Lys Gly Thr Gly
                165                 170                 175

Thr Gly Ile Glu Asn Ser Thr Glu Ser His Phe His Ser Asn Gly Thr
            180                 185                 190

Thr Ser Val Thr Ser Ile Leu Arg Val Lys Asp Pro Lys Thr Gln Val
        195                 200                 205

Gly Lys Glu Val Ile Cys Gln Val Leu Tyr Leu Gly Asn Val Ile Asp
    210                 215                 220

Tyr Lys Gln Ser Leu Asp Lys Gly Phe Trp Phe Ser Val Pro Leu Leu
225                 230                 235                 240

Leu Ser Ile Val Ser Leu Val Ile Leu Leu Val Leu Ile Ser Ile Leu
                245                 250                 255

Leu Tyr Trp Lys Arg His Arg Asn Gln Glu Arg Gly Glu Ser Ser Gln
            260                 265                 270

Gly Met Gln Arg Met Lys
        275


<210> SEQ ID NO 6
<211> LENGTH: 278
<212> TYPE: PRT
<213> ORGANISM: Homo sapiens

<400> SEQUENCE: 6

Met Glu Arg Leu Val Ile Arg Met Pro Phe Ser His Leu Ser Thr Tyr
1               5                   10                  15

Ser Leu Val Trp Val Met Ala Ala Val Val Leu Cys Thr Ala Gln Val
            20                  25                  30

Gln Val Val Thr Gln Asp Glu Arg Glu Gln Leu Tyr Thr Pro Ala Ser
        35                  40                  45

Leu Lys Cys Ser Leu Gln Asn Ala Gln Glu Ala Leu Ile Val Thr Trp
    50                  55                  60

Gln Lys Lys Lys Ala Val Ser Pro Glu Asn Met Val Thr Phe Ser Glu
65                  70                  75                  80

Asn His Gly Val Val Ile Gln Pro Ala Tyr Lys Asp Lys Ile Asn Ile
                85                  90                  95

Thr Gln Leu Gly Leu Gln Asn Ser Thr Ile Thr Phe Trp Asn Ile Thr
            100                 105                 110

Leu Glu Asp Glu Gly Cys Tyr Met Cys Leu Phe Asn Thr Phe Gly Phe
        115                 120                 125

Gly Lys Ile Ser Gly Thr Ala Cys Leu Thr Val Tyr Val Gln Pro Ile
    130                 135                 140

Val Ser Leu His Tyr Lys Phe Ser Glu Asp His Leu Asn Ile Thr Cys
145                 150                 155                 160
```

```
Ser Ala Thr Ala Arg Pro Ala Pro Met Val Phe Trp Lys Val Pro Arg
                165                 170                 175

Ser Gly Ile Glu Asn Ser Thr Val Thr Leu Ser His Pro Asn Gly Thr
            180                 185                 190

Thr Ser Val Thr Ser Ile Leu His Ile Lys Asp Pro Lys Asn Gln Val
        195                 200                 205

Gly Lys Glu Val Ile Cys Gln Val Leu His Leu Gly Thr Val Thr Asp
    210                 215                 220

Phe Lys Gln Thr Val Asn Lys Gly Tyr Trp Phe Ser Val Pro Leu Leu
225                 230                 235                 240

Leu Ser Ile Val Ser Leu Val Ile Leu Leu Val Leu Ile Ser Ile Leu
                245                 250                 255

Leu Tyr Trp Lys Arg His Arg Asn Gln Asp Arg Gly Glu Leu Ser Gln
            260                 265                 270

Gly Val Gln Lys Met Thr
        275


<210> SEQ ID NO 7
<211> LENGTH: 374
<212> TYPE: PRT
<213> ORGANISM: Mus musculus

<400> SEQUENCE: 7

Met Asn Thr Leu Ser Glu Gly Asn Gly Thr Phe Ala Ile His Leu Leu
1               5                   10                  15

Lys Met Leu Cys Gln Ser Asn Pro Ser Lys Asn Val Cys Tyr Ser Pro
            20                  25                  30

Ala Ser Ile Ser Ser Ala Leu Ala Met Val Leu Leu Gly Ala Lys Gly
        35                  40                  45

Gln Thr Ala Val Gln Ile Ser Gln Ala Leu Gly Leu Asn Lys Glu Glu
    50                  55                  60

Gly Ile His Gln Gly Phe Gln Leu Leu Leu Arg Lys Leu Asn Lys Pro
65                  70                  75                  80

Asp Arg Lys Tyr Ser Leu Arg Val Ala Asn Arg Leu Phe Ala Asp Lys
                85                  90                  95

Thr Cys Glu Val Leu Gln Thr Phe Lys Glu Ser Ser Leu His Phe Tyr
            100                 105                 110

Asp Ser Glu Met Glu Gln Leu Ser Phe Ala Glu Glu Ala Glu Val Ser
        115                 120                 125

Arg Gln His Ile Asn Thr Trp Val Ser Lys Gln Thr Glu Gly Lys Ile
    130                 135                 140

Pro Glu Leu Leu Ser Gly Gly Ser Val Asp Ser Glu Thr Arg Leu Val
145                 150                 155                 160

Leu Ile Asn Ala Leu Tyr Phe Lys Gly Lys Trp His Gln Pro Phe Asn
                165                 170                 175

Lys Glu Tyr Thr Met Asp Met Pro Phe Lys Ile Asn Lys Asp Glu Lys
            180                 185                 190

Arg Pro Val Gln Met Met Cys Arg Glu Asp Thr Tyr Asn Leu Ala Tyr
        195                 200                 205

Val Lys Glu Val Gln Ala Gln Val Leu Val Met Pro Tyr Glu Gly Met
    210                 215                 220

Glu Leu Ser Leu Val Val Leu Leu Pro Asp Glu Gly Val Asp Leu Ser
225                 230                 235                 240

Lys Val Glu Asn Asn Leu Thr Phe Glu Lys Leu Thr Ala Trp Met Glu
                245                 250                 255
```

```
Ala Asp Phe Met Lys Ser Thr Asp Val Glu Val Phe Leu Pro Lys Phe
            260                 265                 270

Lys Leu Gln Glu Asp Tyr Asp Met Glu Ser Leu Phe Gln Arg Leu Gly
        275                 280                 285

Val Val Asp Val Phe Gln Glu Asp Lys Ala Asp Leu Ser Gly Met Ser
    290                 295                 300

Pro Glu Arg Asn Leu Cys Val Ser Lys Phe Val His Gln Ser Val Val
305                 310                 315                 320

Glu Ile Asn Glu Glu Gly Thr Glu Ala Ala Ala Ala Ser Ala Ile Ile
                325                 330                 335

Glu Phe Cys Cys Ala Ser Ser Val Pro Thr Phe Cys Ala Asp His Pro
            340                 345                 350

Phe Leu Phe Phe Ile Arg His Asn Lys Ala Asn Ser Ile Leu Phe Cys
        355                 360                 365

Gly Arg Phe Ser Ser Pro
    370


<210> SEQ ID NO 8
<211> LENGTH: 376
<212> TYPE: PRT
<213> ORGANISM: Homo sapiens

<400> SEQUENCE: 8

Met Glu Thr Leu Ser Asn Ala Ser Gly Thr Phe Ala Ile Arg Leu Leu
1               5                   10                  15

Lys Ile Leu Cys Gln Asp Asn Pro Ser His Asn Val Phe Cys Ser Pro
            20                  25                  30

Val Ser Ile Ser Ser Ala Leu Ala Met Val Leu Leu Gly Ala Lys Gly
        35                  40                  45

Asn Thr Ala Thr Gln Met Ala Gln Ala Leu Ser Leu Asn Thr Glu Glu
    50                  55                  60

Asp Ile His Arg Ala Phe Gln Ser Leu Leu Thr Glu Val Asn Lys Ala
65                  70                  75                  80

Gly Thr Gln Tyr Leu Leu Arg Thr Ala Asn Arg Leu Phe Gly Glu Lys
                85                  90                  95

Thr Cys Gln Phe Leu Ser Thr Phe Lys Glu Ser Cys Leu Gln Phe Tyr
            100                 105                 110

His Ala Glu Leu Lys Glu Leu Ser Phe Ile Arg Ala Ala Glu Glu Ser
        115                 120                 125

Arg Lys His Ile Asn Thr Trp Val Ser Lys Lys Thr Glu Gly Lys Ile
    130                 135                 140

Glu Glu Leu Leu Pro Gly Ser Ser Ile Asp Ala Glu Thr Arg Leu Val
145                 150                 155                 160

Leu Val Asn Ala Ile Tyr Phe Lys Gly Lys Trp Asn Glu Pro Phe Asp
                165                 170                 175

Glu Thr Tyr Thr Arg Glu Met Pro Phe Lys Ile Asn Gln Glu Glu Gln
            180                 185                 190

Arg Pro Val Gln Met Met Tyr Gln Glu Ala Thr Phe Lys Leu Ala His
        195                 200                 205

Val Gly Glu Val Arg Ala Gln Leu Leu Glu Leu Pro Tyr Ala Arg Lys
    210                 215                 220

Glu Leu Ser Leu Leu Val Leu Leu Pro Asp Asp Gly Val Glu Leu Ser
225                 230                 235                 240

Thr Val Glu Lys Ser Leu Thr Phe Glu Lys Leu Thr Ala Trp Thr Lys
```

```
                245                 250                 255

Pro Asp Cys Met Lys Ser Thr Glu Val Glu Val Leu Leu Pro Lys Phe
            260                 265                 270

Lys Leu Gln Glu Asp Tyr Asp Met Glu Ser Val Leu Arg His Leu Gly
        275                 280                 285

Ile Val Asp Ala Phe Gln Gln Gly Lys Ala Asp Leu Ser Ala Met Ser
    290                 295                 300

Ala Glu Arg Asp Leu Cys Leu Ser Lys Phe Val His Lys Ser Phe Val
305                 310                 315                 320

Glu Val Asn Glu Glu Gly Thr Glu Ala Ala Ala Ala Ser Ser Cys Phe
                325                 330                 335

Val Val Ala Glu Cys Cys Met Glu Ser Gly Pro Arg Phe Cys Ala Asp
            340                 345                 350

His Pro Phe Leu Phe Phe Ile Arg His Asn Arg Ala Asn Ser Ile Leu
        355                 360                 365

Phe Cys Gly Arg Phe Ser Ser Pro
    370                 375


<210> SEQ ID NO 9
<211> LENGTH: 279
<212> TYPE: PRT
<213> ORGANISM: Mus musculus

<400> SEQUENCE: 9

Met Gln Gln Pro Met Asn Tyr Pro Cys Pro Gln Ile Phe Trp Val Asp
1               5                   10                  15

Ser Ser Ala Thr Ser Ser Trp Thr Pro Pro Gly Ser Val Phe Pro Cys
            20                  25                  30

Pro Ser Ser Gly Pro Arg Gly Pro Asp Gln Arg Arg Pro Pro Pro Pro
        35                  40                  45

Pro Pro Pro Val Ser Pro Leu Pro Pro Pro Ser Gln Pro Leu Pro Leu
    50                  55                  60

Pro Pro Leu Thr Pro Leu Lys Lys Lys Asp His Asn Thr Asn Leu Trp
65                  70                  75                  80

Leu Pro Val Val Phe Phe Met Val Leu Val Ala Leu Val Gly Met Gly
                85                  90                  95

Leu Gly Met Tyr Gln Leu Phe His Leu Gln Lys Glu Leu Ala Glu Leu
            100                 105                 110

Arg Glu Phe Thr Asn Gln Ser Leu Lys Val Ser Ser Phe Glu Lys Gln
        115                 120                 125

Ile Ala Asn Pro Ser Thr Pro Ser Glu Lys Lys Glu Leu Arg Ser Val
    130                 135                 140

Ala His Leu Thr Gly Asn Pro His Ser Arg Ser Ile Pro Leu Glu Trp
145                 150                 155                 160

Glu Asp Thr Tyr Gly Thr Ala Leu Ile Ser Gly Val Lys Tyr Lys Lys
                165                 170                 175

Gly Ser Leu Val Ile Asn Glu Ala Gly Leu Tyr Phe Val Tyr Ser Lys
            180                 185                 190

Val Tyr Phe Arg Gly Gln Ser Cys Asn Asn Gln Pro Leu Asn His Lys
        195                 200                 205

Val Tyr Met Arg Asn Ser Lys Tyr Pro Gly Asp Leu Val Leu Met Glu
    210                 215                 220

Glu Lys Arg Leu Asn Tyr Cys Thr Thr Gly Gln Ile Trp Ala His Ser
225                 230                 235                 240
```

```
Ser Tyr Leu Gly Ala Val Phe Asn Leu Thr Ser Ala Asp His Leu Tyr
                245                 250                 255

Val Asn Ile Ser Gln Leu Ser Leu Ile Asn Phe Glu Glu Ser Lys Thr
            260                 265                 270

Phe Phe Gly Leu Tyr Lys Leu
        275


<210> SEQ ID NO 10
<211> LENGTH: 281
<212> TYPE: PRT
<213> ORGANISM: Homo sapiens

<400> SEQUENCE: 10

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
    50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
        115                 120                 125

Lys Gln Ile Gly His Pro Ser Pro Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
        195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280


<210> SEQ ID NO 11
<211> LENGTH: 290
<212> TYPE: PRT
<213> ORGANISM: Mus musculus

<400> SEQUENCE: 11
```

-continued

```
Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95

Ala Ala Leu Gln Ile Thr Asp Val Lys Leu Gln Asp Ala Gly Val Tyr
            100                 105                 110

Cys Cys Ile Ile Ser Tyr Gly Gly Ala Asp Tyr Lys Arg Ile Thr Leu
        115                 120                 125

Lys Val Asn Ala Pro Tyr Arg Lys Ile Asn Gln Arg Ile Ser Val Asp
    130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
            180                 185                 190

Thr Ser Ser Leu Arg Val Asn Ala Thr Ala Asn Asp Val Phe Tyr Cys
        195                 200                 205

Thr Phe Trp Arg Ser Gln Pro Gly Gln Asn His Thr Ala Glu Leu Ile
    210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
            260                 265                 270

Gly Val Glu Asp Thr Ser Ser Lys Asn Arg Asn Asp Thr Gln Phe Glu
        275                 280                 285

Glu Thr
    290


<210> SEQ ID NO 12
<211> LENGTH: 290
<212> TYPE: PRT
<213> ORGANISM: Homo sapiens

<400> SEQUENCE: 12

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80
```

```
Tyr Arg Gln Arg Ala Arg Leu Leu Lys Asp Gln Leu Ser Leu Gly Asn
            85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 13
<211> LENGTH: 463
<212> TYPE: PRT
<213> ORGANISM: Mus musculus

<400> SEQUENCE: 13

Met Gln Val Ser Arg Val Leu Ala Ala Leu Cys Gly Met Leu Leu Cys
1               5                   10                  15

Ala Ser Gly Leu Phe Ala Ala Ser Gly Asp Phe Cys Asp Ser Ser Leu
            20                  25                  30

Cys Leu Asn Gly Gly Thr Cys Leu Thr Gly Gln Asp Asn Asp Ile Tyr
        35                  40                  45

Cys Leu Cys Pro Glu Gly Phe Thr Gly Leu Val Cys Asn Glu Thr Glu
    50                  55                  60

Arg Gly Pro Cys Ser Pro Asn Pro Cys Tyr Asn Asp Ala Lys Cys Leu
65                  70                  75                  80

Val Thr Leu Asp Thr Gln Arg Gly Asp Ile Phe Thr Glu Tyr Ile Cys
                85                  90                  95

Gln Cys Pro Val Gly Tyr Ser Gly Ile His Cys Glu Thr Glu Thr Asn
            100                 105                 110

Tyr Tyr Asn Leu Asp Gly Glu Tyr Met Phe Thr Thr Ala Val Pro Asn
        115                 120                 125

Thr Ala Val Pro Thr Pro Ala Pro Thr Pro Asp Leu Ser Asn Asn Leu
    130                 135                 140

Ala Ser Arg Cys Ser Thr Gln Leu Gly Met Glu Gly Gly Ala Ile Ala
```

```
145                 150                 155                 160

Asp Ser Gln Ile Ser Ala Ser Ser Val Tyr Met Gly Phe Met Gly Leu
                165                 170                 175

Gln Arg Trp Gly Pro Glu Leu Ala Arg Leu Tyr Arg Thr Gly Ile Val
            180                 185                 190

Asn Ala Trp Thr Ala Ser Asn Tyr Asp Ser Lys Pro Trp Ile Gln Val
        195                 200                 205

Asn Leu Leu Arg Lys Met Arg Val Ser Gly Val Met Thr Gln Gly Ala
    210                 215                 220

Ser Arg Ala Gly Arg Ala Glu Tyr Leu Lys Thr Phe Lys Val Ala Tyr
225                 230                 235                 240

Ser Leu Asp Gly Arg Lys Phe Glu Phe Ile Gln Asp Glu Ser Gly Gly
                245                 250                 255

Asp Lys Glu Phe Leu Gly Asn Leu Asp Asn Asn Ser Leu Lys Val Asn
            260                 265                 270

Met Phe Asn Pro Thr Leu Glu Ala Gln Tyr Ile Lys Leu Tyr Pro Val
        275                 280                 285

Ser Cys His Arg Gly Cys Thr Leu Arg Phe Glu Leu Leu Gly Cys Glu
    290                 295                 300

Leu His Gly Cys Ser Glu Pro Leu Gly Leu Lys Asn Asn Thr Ile Pro
305                 310                 315                 320

Asp Ser Gln Met Ser Ala Ser Ser Ser Tyr Lys Thr Trp Asn Leu Arg
                325                 330                 335

Ala Phe Gly Trp Tyr Pro His Leu Gly Arg Leu Asp Asn Gln Gly Lys
            340                 345                 350

Ile Asn Ala Trp Thr Ala Gln Ser Asn Ser Ala Lys Glu Trp Leu Gln
        355                 360                 365

Val Asp Leu Gly Thr Gln Arg Gln Val Thr Gly Ile Ile Thr Gln Gly
    370                 375                 380

Ala Arg Asp Phe Gly His Ile Gln Tyr Val Ala Ser Tyr Lys Val Ala
385                 390                 395                 400

His Ser Asp Asp Gly Val Gln Trp Thr Val Tyr Glu Glu Gln Gly Ser
                405                 410                 415

Ser Lys Val Phe Gln Gly Asn Leu Asp Asn Asn Ser His Lys Lys Asn
            420                 425                 430

Ile Phe Glu Lys Pro Phe Met Ala Arg Tyr Val Arg Val Leu Pro Val
        435                 440                 445

Ser Trp His Asn Arg Ile Thr Leu Arg Leu Glu Leu Leu Gly Cys
    450                 455                 460


<210> SEQ ID NO 14
<211> LENGTH: 387
<212> TYPE: PRT
<213> ORGANISM: Homo sapiens

<400> SEQUENCE: 14

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
        35                  40                  45

Val Phe Pro Ser Tyr Thr Cys Thr Cys Leu Lys Gly Tyr Ala Gly Asn
    50                  55                  60
```

-continued

```
His Cys Glu Thr Lys Cys Val Glu Pro Leu Gly Met Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
    130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
    210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
        275                 280                 285

Leu Gln Val Asp Leu Gly Ser Ser Lys Glu Val Thr Gly Ile Ile Thr
    290                 295                 300

Gln Gly Ala Arg Asn Phe Gly Ser Val Gln Phe Val Ala Ser Tyr Lys
305                 310                 315                 320

Val Ala Tyr Ser Asn Asp Ser Ala Asn Trp Thr Glu Tyr Gln Asp Pro
                325                 330                 335

Arg Thr Gly Ser Ser Lys Ile Phe Pro Gly Asn Trp Asp Asn His Ser
            340                 345                 350

His Lys Lys Asn Leu Phe Glu Thr Pro Ile Leu Ala Arg Tyr Val Arg
        355                 360                 365

Ile Leu Pro Val Ala Trp His Asn Arg Ile Ala Leu Arg Leu Glu Leu
    370                 375                 380

Leu Gly Cys
385
```

<210> SEQ ID NO 15
<211> LENGTH: 249
<212> TYPE: PRT
<213> ORGANISM: Mus musculus

<400> SEQUENCE: 15

```
Ser Ile Glu Glu Ile Pro Arg Met Glu Pro Arg Ala Pro Trp Met Glu
1               5                   10                  15

Lys Glu Arg Pro Glu Tyr Trp Lys Glu Leu Lys Leu Lys Val Lys Asn
            20                  25                  30

Ile Ala Gln Ser Ala Arg Ala Asn Leu Arg Thr Leu Leu Arg Tyr Tyr
        35                  40                  45
```

```
Asn Gln Ser Glu Gly Gly Ser His Ile Leu Gln Trp Met Val Ser Cys
    50                  55                  60

Glu Val Gly Pro Asp Met Arg Leu Leu Gly Ala His Tyr Gln Ala Ala
65                  70                  75                  80

Tyr Asp Gly Ser Asp Tyr Ile Thr Leu Asn Glu Asp Leu Ser Ser Trp
                85                  90                  95

Thr Ala Val Asp Met Val Ser Gln Ile Thr Lys Ser Arg Leu Glu Ser
            100                 105                 110

Ala Gly Thr Ala Glu Tyr Phe Arg Ala Tyr Val Glu Gly Glu Cys Leu
        115                 120                 125

Glu Leu Leu His Arg Phe Leu Arg Asn Gly Lys Glu Ile Leu Gln Arg
    130                 135                 140

Ala Asp Pro Pro Lys Ala His Val Ala His His Pro Arg Pro Lys Gly
145                 150                 155                 160

Asp Val Thr Leu Arg Cys Trp Ala Leu Gly Phe Tyr Pro Ala Asp Ile
                165                 170                 175

Thr Leu Thr Trp Gln Lys Asp Glu Glu Asp Leu Thr Gln Asp Met Glu
            180                 185                 190

Leu Val Glu Thr Arg Pro Ser Gly Asp Gly Thr Phe Gln Lys Trp Ala
        195                 200                 205

Ala Val Val Val Pro Ser Gly Glu Glu Gln Arg Tyr Thr Cys Tyr Val
    210                 215                 220

His His Glu Gly Leu Thr Glu Pro Leu Ala Leu Lys Trp Gly Arg Ser
225                 230                 235                 240

Ser Gln Ser Ser Val Val Ile Met Val
                245


<210> SEQ ID NO 16
<211> LENGTH: 338
<212> TYPE: PRT
<213> ORGANISM: Homo sapiens

<400> SEQUENCE: 16

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
```

```
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Lys Gln Ser Ser Leu Pro
    290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp


<210> SEQ ID NO 17
<211> LENGTH: 439
<212> TYPE: PRT
<213> ORGANISM: Artificial Sequence
<220> FEATURE:
<223> OTHER INFORMATION: Synthetic Construct

<400> SEQUENCE: 17

Met Gly Pro Gln Ala Ala Ala Gly Arg Met Ile Leu Leu Val Val Leu
1               5                   10                  15

Met Leu Ser Ala Lys Val Gly Ser Gly Ala Leu Thr Ser Thr Glu Asp
            20                  25                  30

Pro Glu Pro Pro Ser Val Pro Val Pro Thr Asn Val Leu Ile Lys Ser
        35                  40                  45

Tyr Asn Leu Asn Pro Val Val Cys Trp Glu Tyr Gln Asn Met Ser Gln
    50                  55                  60

Thr Pro Ile Phe Thr Val Gln Val Lys Val Tyr Ser Gly Ser Trp Thr
65                  70                  75                  80

Asp Ser Cys Thr Asn Ile Ser Asp His Cys Cys Asn Ile Tyr Gly Gln
                85                  90                  95

Ile Met Tyr Pro Asp Val Ser Ala Trp Ala Arg Val Lys Ala Lys Val
            100                 105                 110

Gly Gln Lys Glu Ser Asp Tyr Ala Arg Ser Lys Glu Phe Leu Met Cys
        115                 120                 125

Leu Lys Gly Lys Val Gly Pro Pro Gly Leu Glu Ile Arg Arg Lys Lys
    130                 135                 140

Glu Glu Gln Leu Ser Val Leu Val Phe His Pro Glu Val Val Val Asn
145                 150                 155                 160

Gly Glu Ser Gln Gly Thr Met Phe Gly Asp Gly Ser Thr Cys Tyr Thr
                165                 170                 175

Phe Asp Tyr Thr Val Tyr Val Glu His Asn Arg Ser Gly Glu Ile Leu
            180                 185                 190
```

-continued

```
His Thr Lys His Thr Val Glu Lys Glu Glu Cys Asn Glu Thr Leu Cys
        195                 200                 205

Glu Leu Asn Ile Ser Val Ser Thr Leu Asp Ser Arg Tyr Cys Ile Ser
    210                 215                 220

Val Asp Gly Ile Ser Ser Phe Trp Gln Val Arg Thr Glu Lys Ser Lys
225                 230                 235                 240

Asp Val Cys Ile Pro Pro Phe His Asp Asp Arg Lys Asp Ser Ile Trp
                245                 250                 255

Ile Leu Val Val Ala Pro Leu Thr Val Phe Thr Val Val Ile Leu Val
            260                 265                 270

Phe Ala Tyr Trp Tyr Thr Lys Lys Asn Ser Phe Lys Arg Lys Ser Ile
        275                 280                 285

Met Leu Pro Lys Ser Leu Leu Ser Val Val Lys Ser Ala Thr Leu Glu
    290                 295                 300

Thr Lys Pro Glu Ser Lys Tyr Ser Leu Val Thr Pro His Gln Pro Ala
305                 310                 315                 320

Val Leu Glu Ser Glu Thr Val Ile Cys Glu Glu Pro Leu Ser Thr Val
                325                 330                 335

Thr Ala Pro Asp Ser Pro Glu Ala Ala Glu Gln Glu Glu Leu Ser Lys
            340                 345                 350

Glu Thr Lys Ala Leu Glu Ala Gly Gly Ser Thr Ser Ala Met Thr Pro
        355                 360                 365

Asp Ser Pro Pro Thr Pro Thr Gln Arg Arg Ser Phe Ser Leu Leu Ser
    370                 375                 380

Ser Asn Gln Ser Gly Pro Cys Ser Leu Thr Ala Tyr His Ser Arg Asn
385                 390                 395                 400

Gly Ser Asp Ser Gly Leu Val Gly Ser Gly Ser Ser Ile Ser Asp Leu
                405                 410                 415

Glu Ser Leu Pro Asn Asn Asn Ser Glu Thr Lys Met Ala Glu His Asp
            420                 425                 430

Pro Pro Pro Val Arg Lys Ala
        435
```

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

```
Phe Leu Gly Tyr Leu Ile Leu Gly Val
1               5
```

<210> SEQ ID NO 19
<211> LENGTH: 15
<212> TYPE: PRT
<213> ORGANISM: Artificial Sequence
<220> FEATURE:
<223> OTHER INFORMATION: Synthetic Construct

<400> SEQUENCE: 19

```
Ser Val Ser Glu Ser Asp Thr Ile Arg Ser Ile Ser Ile Ala Ser
1               5                   10                  15
```

<210> SEQ ID NO 20
<211> LENGTH: 15
<212> TYPE: PRT

<213> ORGANISM: Artificial Sequence
<220> FEATURE:
<223> OTHER INFORMATION: Synthetic Construct

<400> SEQUENCE: 20

Leu Leu Ala Asn Gly Arg Met Pro Thr Val Leu Gln Cys Val Asn
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Synthetic Construct

<400> SEQUENCE: 21

Arg Met Pro Thr Val Leu Gln Cys Val Asn Val Ser Val Val Ser
1               5                   10                  15

<210> SEQ ID NO 22
<211> LENGTH: 12
<212> TYPE: PRT
<213> ORGANISM: Artificial Sequence
<220> FEATURE:
<223> OTHER INFORMATION: Synthetic Construct

<400> SEQUENCE: 22

Cys Thr Ala Cys Arg Trp Lys Lys Ala Cys Gln Arg
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Val Leu Asp Gly Leu Asp Val Leu Leu
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct

<400> SEQUENCE: 24

Ser Leu Tyr Ser Phe Pro Glu Pro Glu Ala
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

Ala Leu Tyr Val Asp Ser Leu Phe Phe Leu
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Ser Leu Leu Gln His Leu Ile Gly Leu
1 5

<210> SEQ ID NO 27
<211> LENGTH: 9
<212> TYPE: PRT
<213> ORGANISM: Artificial Sequence
<220> FEATURE:
<223> OTHER INFORMATION: Synthetic Construct

<400> SEQUENCE: 27

Leu Tyr Val Asp Ser Leu Phe Phe Leu
1 5

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Thr Ser Glu Lys Arg Pro Phe Met Cys Ala Tyr
1 5 10

<210> SEQ ID NO 29
<211> LENGTH: 9
<212> TYPE: PRT
<213> ORGANISM: Artificial Sequence
<220> FEATURE:
<223> OTHER INFORMATION: Synthetic Construct

<400> SEQUENCE: 29

Cys Met Thr Trp Asn Gln Met Asn Leu
1 5

<210> SEQ ID NO 30
<211> LENGTH: 11
<212> TYPE: PRT
<213> ORGANISM: Artificial Sequence
<220> FEATURE:
<223> OTHER INFORMATION: Synthetic Construct

<400> SEQUENCE: 30

Leu Ser His Leu Gln Met His Ser Arg Lys His
1 5 10

<210> SEQ ID NO 31
<211> LENGTH: 16
<212> TYPE: PRT
<213> ORGANISM: Artificial Sequence
<220> FEATURE:
<223> OTHER INFORMATION: Synthetic Construct

<400> SEQUENCE: 31

Lys Arg Tyr Phe Lys Leu Ser His Leu Gln Met His Ser Arg Lys His
1 5 10 15

<210> SEQ ID NO 32
<211> LENGTH: 8
<212> TYPE: PRT
<213> ORGANISM: Artificial Sequence
<220> FEATURE:

<223> OTHER INFORMATION: Synthetic Construct

<400> SEQUENCE: 32

Cys Tyr Met Glu Ala Val Ala Leu
1 5

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

Ser Leu Leu Phe Leu Leu Phe Ser Leu
1 5

<210> SEQ ID NO 34
<211> LENGTH: 9
<212> TYPE: PRT
<213> ORGANISM: Artificial Sequence
<220> FEATURE:
<223> OTHER INFORMATION: Synthetic Construct

<400> SEQUENCE: 34

Val Leu Pro Leu Thr Val Ala Glu Val
1 5

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

Ala Leu Gln Gly Gly Gly Pro Pro Tyr
1 5

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

Leu Tyr Pro Lys Ala Arg Leu Ala Phe
1 5

<210> SEQ ID NO 37
<211> LENGTH: 9
<212> TYPE: PRT
<213> ORGANISM: Artificial Sequence
<220> FEATURE:
<223> OTHER INFORMATION: Synthetic Construct

<400> SEQUENCE: 37

Ala Phe Leu Pro Trp His Arg Leu Phe
1 5

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

Ser Leu Leu Met Trp Ile Thr Gln Cys
1 5

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

Leu Ala Met Pro Phe Ala Thr Pro Met
1 5

<210> SEQ ID NO 40
<211> LENGTH: 9
<212> TYPE: PRT
<213> ORGANISM: Artificial Sequence
<220> FEATURE:
<223> OTHER INFORMATION: Synthetic Construct

<400> SEQUENCE: 40

Ala Arg Gly Pro Glu Ser Arg Leu Leu
1 5

<210> SEQ ID NO 41
<211> LENGTH: 11
<212> TYPE: PRT
<213> ORGANISM: Artificial Sequence
<220> FEATURE:
<223> OTHER INFORMATION: Synthetic Construct

<400> SEQUENCE: 41

Met Leu Met Ala Gln Glu Ala Leu Ala Phe Leu
1 5 10

<210> SEQ ID NO 42
<211> LENGTH: 11
<212> TYPE: PRT
<213> ORGANISM: Artificial Sequence
<220> FEATURE:
<223> OTHER INFORMATION: Synthetic Construct

<400> SEQUENCE: 42

Tyr Leu Ala Met Pro Phe Ala Thr Pro Met Glu
1 5 10

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Ala Ser Gly Pro Gly Gly Gly Ala Pro Arg
1 5 10

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Leu Ala Ala Gln Glu Arg Arg Val Pro Arg
1 5 10

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Thr Val Ser Gly Asn Ile Leu Thr Ile Arg
1 5 10

<210> SEQ ID NO 46
<211> LENGTH: 13
<212> TYPE: PRT
<213> ORGANISM: Artificial Sequence
<220> FEATURE:
<223> OTHER INFORMATION: Synthetic Construct

<400> SEQUENCE: 46

Ala Pro Arg Gly Pro His Gly Gly Ala Ala Ser Gly Leu
1 5 10

<210> SEQ ID NO 47
<211> LENGTH: 11
<212> TYPE: PRT
<213> ORGANISM: Artificial Sequence
<220> FEATURE:
<223> OTHER INFORMATION: Synthetic Construct

<400> SEQUENCE: 47

Met Pro Phe Ala Thr Pro Met Glu Ala Glu Leu
1 5 10

<210> SEQ ID NO 48
<211> LENGTH: 12
<212> TYPE: PRT
<213> ORGANISM: Artificial Sequence
<220> FEATURE:
<223> OTHER INFORMATION: Synthetic Construct

<400> SEQUENCE: 48

Lys Glu Phe Thr Val Ser Gly Asn Ile Leu Thr Ile
1 5 10

<210> SEQ ID NO 49
<211> LENGTH: 9
<212> TYPE: PRT
<213> ORGANISM: Artificial Sequence
<220> FEATURE:
<223> OTHER INFORMATION: Synthetic Construct

<400> SEQUENCE: 49

Met Pro Phe Ala Thr Pro Met Glu Ala
1 5

<210> SEQ ID NO 50
<211> LENGTH: 9
<212> TYPE: PRT
<213> ORGANISM: Artificial Sequence
<220> FEATURE:
<223> OTHER INFORMATION: Synthetic Construct

<400> SEQUENCE: 50

-continued

```
Phe Ala Thr Pro Met Glu Ala Glu Leu
1               5


<210> SEQ ID NO 51
<211> LENGTH: 11
<212> TYPE: PRT
<213> ORGANISM: Artificial Sequence
<220> FEATURE:
<223> OTHER INFORMATION: Synthetic Construct

<400> SEQUENCE: 51

Phe Ala Thr Pro Met Glu Ala Glu Leu Ala Arg
1               5                   10


<210> SEQ ID NO 52
<211> LENGTH: 9
<212> TYPE: PRT
<213> ORGANISM: Artificial Sequence
<220> FEATURE:
<223> OTHER INFORMATION: Synthetic Construct

<400> SEQUENCE: 52

Leu Ala Met Pro Phe Ala Thr Pro Met
1               5


<210> SEQ ID NO 53
<211> LENGTH: 14
<212> TYPE: PRT
<213> ORGANISM: Artificial Sequence
<220> FEATURE:
<223> OTHER INFORMATION: Synthetic Construct

<400> SEQUENCE: 53

Ser Leu Leu Met Trp Ile Thr Gln Cys Phe Leu Pro Val Phe
1               5                   10


<210> SEQ ID NO 54
<211> LENGTH: 25
<212> TYPE: PRT
<213> ORGANISM: Artificial Sequence
<220> FEATURE:
<223> OTHER INFORMATION: Synthetic Construct

<400> SEQUENCE: 54

Leu Leu Glu Phe Tyr Leu Ala Met Pro Phe Ala Thr Pro Met Glu Ala
1               5                   10                  15

Glu Leu Ala Arg Arg Ser Leu Ala Gln
            20                  25


<210> SEQ ID NO 55
<211> LENGTH: 12
<212> TYPE: PRT
<213> ORGANISM: Artificial Sequence
<220> FEATURE:
<223> OTHER INFORMATION: Synthetic Construct

<400> SEQUENCE: 55

Glu Phe Tyr Leu Ala Met Pro Phe Ala Thr Pro Met
1               5                   10


<210> SEQ ID NO 56
<211> LENGTH: 25
<212> TYPE: PRT
<213> ORGANISM: Artificial Sequence
<220> FEATURE:
<223> OTHER INFORMATION: Synthetic Construct
```

-continued

<400> SEQUENCE: 56

Pro Gly Val Leu Leu Lys Glu Phe Thr Val Ser Gly Asn Ile Leu Thr
1 5 10 15

Ile Arg Leu Thr Ala Ala Asp His Arg
20 25

<210> SEQ ID NO 57
<211> LENGTH: 12
<212> TYPE: PRT
<213> ORGANISM: Artificial Sequence
<220> FEATURE:
<223> OTHER INFORMATION: Synthetic Construct

<400> SEQUENCE: 57

Arg Leu Leu Glu Phe Tyr Leu Ala Met Pro Phe Ala
1 5 10

<210> SEQ ID NO 58
<211> LENGTH: 20
<212> TYPE: PRT
<213> ORGANISM: Artificial Sequence
<220> FEATURE:
<223> OTHER INFORMATION: Synthetic Construct

<400> SEQUENCE: 58

Gln Gly Ala Met Leu Ala Ala Gln Glu Arg Arg Val Pro Arg Ala Ala
1 5 10 15

Glu Val Pro Arg
20

<210> SEQ ID NO 59
<211> LENGTH: 13
<212> TYPE: PRT
<213> ORGANISM: Artificial Sequence
<220> FEATURE:
<223> OTHER INFORMATION: Synthetic Construct

<400> SEQUENCE: 59

Pro Phe Ala Thr Pro Met Glu Ala Glu Leu Ala Arg Arg
1 5 10

<210> SEQ ID NO 60
<211> LENGTH: 20
<212> TYPE: PRT
<213> ORGANISM: Artificial Sequence
<220> FEATURE:
<223> OTHER INFORMATION: Synthetic Construct

<400> SEQUENCE: 60

Pro Gly Val Leu Leu Lys Glu Phe Thr Val Ser Gly Asn Ile Leu Thr
1 5 10 15

Ile Arg Leu Thr
20

<210> SEQ ID NO 61
<211> LENGTH: 10
<212> TYPE: PRT
<213> ORGANISM: Artificial Sequence
<220> FEATURE:
<223> OTHER INFORMATION: Synthetic Construct

<400> SEQUENCE: 61

Val Leu Leu Lys Glu Phe Thr Val Ser Gly
1 5 10

<210> SEQ ID NO 62
<211> LENGTH: 18
<212> TYPE: PRT
<213> ORGANISM: Artificial Sequence
<220> FEATURE:
<223> OTHER INFORMATION: Synthetic Construct

<400> SEQUENCE: 62

```
Ala Ala Asp His Arg Gln Leu Gln Leu Ser Ile Ser Ser Cys Leu Gln
1               5                   10                  15

Gln Leu
```

<210> SEQ ID NO 63
<211> LENGTH: 15
<212> TYPE: PRT
<213> ORGANISM: Artificial Sequence
<220> FEATURE:
<223> OTHER INFORMATION: Synthetic Construct

<400> SEQUENCE: 63

```
Leu Lys Glu Phe Thr Val Ser Gly Asn Ile Leu Thr Ile Arg Leu
1               5                   10                  15
```

<210> SEQ ID NO 64
<211> LENGTH: 14
<212> TYPE: PRT
<213> ORGANISM: Artificial Sequence
<220> FEATURE:
<223> OTHER INFORMATION: Synthetic Construct

<400> SEQUENCE: 64

```
Leu Leu Glu Phe Tyr Leu Ala Met Pro Phe Ala Thr Pro Met
1               5                   10
```

<210> SEQ ID NO 65
<211> LENGTH: 14
<212> TYPE: PRT
<213> ORGANISM: Artificial Sequence
<220> FEATURE:
<223> OTHER INFORMATION: Synthetic Construct

<400> SEQUENCE: 65

```
Ala Gly Ala Thr Gly Gly Arg Gly Pro Arg Gly Ala Gly Ala
1               5                   10
```

<210> SEQ ID NO 66
<211> LENGTH: 13
<212> TYPE: PRT
<213> ORGANISM: Artificial Sequence
<220> FEATURE:
<223> OTHER INFORMATION: Synthetic Construct

<400> SEQUENCE: 66

```
Thr Tyr Tyr Arg Pro Gly Val Asn Leu Ser Leu Ser Cys
1               5                   10
```

<210> SEQ ID NO 67
<211> LENGTH: 13
<212> TYPE: PRT
<213> ORGANISM: Artificial Sequence
<220> FEATURE:
<223> OTHER INFORMATION: Synthetic Construct

<400> SEQUENCE: 67

```
Glu Ile Ile Tyr Pro Asn Ala Ser Leu Leu Ile Gln Asn
```

1 5 10

<210> SEQ ID NO 68
<211> LENGTH: 15
<212> TYPE: PRT
<213> ORGANISM: Artificial Sequence
<220> FEATURE:
<223> OTHER INFORMATION: Synthetic Construct

<400> SEQUENCE: 68

Tyr Ala Cys Phe Val Ser Asn Leu Ala Thr Gly Arg Asn Asn Ser
1 5 10 15

<210> SEQ ID NO 69
<211> LENGTH: 13
<212> TYPE: PRT
<213> ORGANISM: Artificial Sequence
<220> FEATURE:
<223> OTHER INFORMATION: Synthetic Construct

<400> SEQUENCE: 69

Leu Trp Trp Val Asn Asn Gln Ser Leu Pro Val Ser Pro
1 5 10

<210> SEQ ID NO 70
<211> LENGTH: 13
<212> TYPE: PRT
<213> ORGANISM: Artificial Sequence
<220> FEATURE:
<223> OTHER INFORMATION: Synthetic Construct

<400> SEQUENCE: 70

Asn Ser Ile Val Lys Ser Ile Thr Val Ser Ala Ser Gly
1 5 10

<210> SEQ ID NO 71
<211> LENGTH: 9
<212> TYPE: PRT
<213> ORGANISM: Artificial Sequence
<220> FEATURE:
<223> OTHER INFORMATION: Synthetic Construct

<400> SEQUENCE: 71

Lys Thr Trp Gly Gln Tyr Trp Gln Val
1 5

<210> SEQ ID NO 72
<211> LENGTH: 10
<212> TYPE: PRT
<213> ORGANISM: Artificial Sequence
<220> FEATURE:
<223> OTHER INFORMATION: Synthetic Construct

<400> SEQUENCE: 72

Ala Met Leu Gly Thr His Thr Met Glu Val
1 5 10

<210> SEQ ID NO 73
<211> LENGTH: 9
<212> TYPE: PRT
<213> ORGANISM: Artificial Sequence
<220> FEATURE:
<223> OTHER INFORMATION: Synthetic Construct

<400> SEQUENCE: 73

Ile Thr Asp Gln Val Pro Phe Ser Val
1 5

-continued

<210> SEQ ID NO 74
<211> LENGTH: 9
<212> TYPE: PRT
<213> ORGANISM: Artificial Sequence
<220> FEATURE:
<223> OTHER INFORMATION: Synthetic Construct

<400> SEQUENCE: 74

Tyr Leu Glu Pro Gly Pro Val Thr Ala
1               5

<210> SEQ ID NO 75
<211> LENGTH: 10
<212> TYPE: PRT
<213> ORGANISM: Artificial Sequence
<220> FEATURE:
<223> OTHER INFORMATION: Synthetic Construct

<400> SEQUENCE: 75

Leu Leu Asp Gly Thr Ala Thr Leu Arg Leu
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic Construct

<400> SEQUENCE: 76

Val Leu Tyr Arg Tyr Gly Ser Phe Ser Val
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic Construct

<400> SEQUENCE: 77

Ser Leu Ala Asp Thr Asn Ser Leu Ala Val
1               5                   10

<210> SEQ ID NO 78
<211> LENGTH: 9
<212> TYPE: PRT
<213> ORGANISM: Artificial Sequence
<220> FEATURE:
<223> OTHER INFORMATION: Synthetic Construct

<400> SEQUENCE: 78

Arg Leu Met Lys Gln Asp Phe Ser Val
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Construct

<400> SEQUENCE: 79

Arg Leu Pro Arg Ile Phe Cys Ser Cys
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic Construct

<400> SEQUENCE: 80

Leu Ile Tyr Arg Arg Arg Leu Met Lys
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic Construct

<400> SEQUENCE: 81

Ala Leu Leu Ala Val Gly Ala Thr Lys
1               5

<210> SEQ ID NO 82
<211> LENGTH: 10
<212> TYPE: PRT
<213> ORGANISM: Artificial Sequence
<220> FEATURE:
<223> OTHER INFORMATION: Synthetic Construct

<400> SEQUENCE: 82

Ile Ala Leu Asn Phe Pro Gly Ser Gln Lys
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Synthetic Construct

<400> SEQUENCE: 83

Arg Ser Tyr Val Pro Leu Ala His Arg
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Construct

<400> SEQUENCE: 84

Val Val Pro Cys Glu Pro Pro Glu Val
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Construct

<400> SEQUENCE: 85

His Leu Tyr Gln Gly Cys Gln Val Val
1               5

-continued

<210> SEQ ID NO 86
<211> LENGTH: 10
<212> TYPE: PRT
<213> ORGANISM: Artificial Sequence
<220> FEATURE:
<223> OTHER INFORMATION: Synthetic Construct

<400> SEQUENCE: 86

Tyr Leu Val Pro Gln Gln Gly Phe Phe Cys
1               5                   10

<210> SEQ ID NO 87
<211> LENGTH: 9
<212> TYPE: PRT
<213> ORGANISM: Artificial Sequence
<220> FEATURE:
<223> OTHER INFORMATION: Synthetic Construct

<400> SEQUENCE: 87

Pro Leu Gln Pro Glu Gln Leu Gln Val
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic Construct

<400> SEQUENCE: 88

Thr Leu Glu Glu Ile Thr Gly Tyr Leu
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Construct

<400> SEQUENCE: 89

Ala Leu Ile His His Asn Thr His Leu
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic Construct

<400> SEQUENCE: 90

Pro Leu Thr Ser Ile Ile Ser Ala Val
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic Construct

<400> SEQUENCE: 91

Val Leu Arg Glu Asn Thr Ser Pro Lys
1               5

<210> SEQ ID NO 92

<211> LENGTH: 9
<212> TYPE: PRT
<213> ORGANISM: Artificial Sequence
<220> FEATURE:
<223> OTHER INFORMATION: Synthetic Construct

<400> SEQUENCE: 92

Thr Tyr Leu Pro Thr Asn Ala Ser Leu
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic Construct

<400> SEQUENCE: 93

Arg Tyr Gln Leu Asp Pro Lys Phe Ile
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic Construct

<400> SEQUENCE: 94

Ile Leu Phe Thr Ile Asn Phe Thr Ile
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic Construct

<400> SEQUENCE: 95

Val Leu Phe Thr Ile Asn Phe Thr Ile
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Construct

<400> SEQUENCE: 96

Thr Leu Asn Phe Thr Ile Thr Asn Leu
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic Construct

<400> SEQUENCE: 97

Val Leu Gln Gly Leu Leu Lys Pro Leu
1               5

<210> SEQ ID NO 98
<211> LENGTH: 9

-continued

<212> TYPE: PRT
<213> ORGANISM: Artificial Sequence
<220> FEATURE:
<223> OTHER INFORMATION: Synthetic Construct

<400> SEQUENCE: 98

Val Leu Gln Gly Leu Leu Arg Pro Val
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Construct

<400> SEQUENCE: 99

Arg Leu Asp Pro Lys Ser Pro Gly Val
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic Construct

<400> SEQUENCE: 100

Gln Leu Tyr Trp Glu Leu Ser Lys Leu
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic Construct

<400> SEQUENCE: 101

Lys Leu Thr Arg Gly Ile Val Glu Leu
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Construct

<400> SEQUENCE: 102

Gln Leu Thr Asn Gly Ile Thr Glu Leu
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic Construct

<400> SEQUENCE: 103

Gln Leu Thr His Asn Ile Thr Glu Leu
1               5

<210> SEQ ID NO 104
<211> LENGTH: 9
<212> TYPE: PRT

<213> ORGANISM: Artificial Sequence
<220> FEATURE:
<223> OTHER INFORMATION: Synthetic Construct

<400> SEQUENCE: 104

Thr Leu Asp Arg Asn Ser Leu Tyr Val
1 5

<210> SEQ ID NO 105
<211> LENGTH: 9
<212> TYPE: PRT
<213> ORGANISM: Artificial Sequence
<220> FEATURE:
<223> OTHER INFORMATION: Synthetic Construct

<400> SEQUENCE: 105

Phe Leu Leu Ser Leu Ala Leu Met Leu
1 5

<210> SEQ ID NO 106
<211> LENGTH: 9
<212> TYPE: PRT
<213> ORGANISM: Artificial Sequence
<220> FEATURE:
<223> OTHER INFORMATION: Synthetic Construct

<400> SEQUENCE: 106

Asn Leu Gly Pro Trp Ile Gln Gln Val
1 5

<210> SEQ ID NO 107
<211> LENGTH: 9
<212> TYPE: PRT
<213> ORGANISM: Artificial Sequence
<220> FEATURE:
<223> OTHER INFORMATION: Synthetic Construct

<400> SEQUENCE: 107

Ile Leu Asp Ser Ser Glu Glu Asp Lys
1 5

<210> SEQ ID NO 108
<211> LENGTH: 10
<212> TYPE: PRT
<213> ORGANISM: Artificial Sequence
<220> FEATURE:
<223> OTHER INFORMATION: Synthetic Construct

<400> SEQUENCE: 108

Tyr Leu Pro Lys Ser Trp Thr Ile Gln Val
1 5 10

<210> SEQ ID NO 109
<211> LENGTH: 12
<212> TYPE: PRT
<213> ORGANISM: Artificial Sequence
<220> FEATURE:
<223> OTHER INFORMATION: Synthetic Construct

<400> SEQUENCE: 109

Trp Ile His Glu Gln Met Glu Arg Asp Leu Lys Thr
1 5 10

<210> SEQ ID NO 110
<211> LENGTH: 9
<212> TYPE: PRT
<213> ORGANISM: Artificial Sequence
<220> FEATURE:
<223> OTHER INFORMATION: Synthetic Construct

<400> SEQUENCE: 110

Leu Leu Ala Asn Ala Tyr Ile Tyr Val
1 5

<210> SEQ ID NO 111
<211> LENGTH: 9
<212> TYPE: PRT
<213> ORGANISM: Artificial Sequence
<220> FEATURE:
<223> OTHER INFORMATION: Synthetic Construct

<400> SEQUENCE: 111

Tyr Leu Leu Cys Lys Ala Phe Gly Ala
1 5

<210> SEQ ID NO 112
<211> LENGTH: 9
<212> TYPE: PRT
<213> ORGANISM: Artificial Sequence
<220> FEATURE:
<223> OTHER INFORMATION: Synthetic Construct

<400> SEQUENCE: 112

Lys Leu Ser Pro Tyr Val His Tyr Thr
1 5

<210> SEQ ID NO 113
<211> LENGTH: 20
<212> TYPE: PRT
<213> ORGANISM: Artificial Sequence
<220> FEATURE:
<223> OTHER INFORMATION: Synthetic Construct

<400> SEQUENCE: 113

Pro Asp Thr Arg Pro Ala Pro Gly Ser Thr Ala Pro Pro Ala His Gly
1 5 10 15

Val Thr Ser Ala
20

<210> SEQ ID NO 114
<211> LENGTH: 9
<212> TYPE: PRT
<213> ORGANISM: Artificial Sequence
<220> FEATURE:
<223> OTHER INFORMATION: Synthetic Construct

<400> SEQUENCE: 114

Ser Thr Ala Pro Pro Val His Asn Val
1 5

<210> SEQ ID NO 115
<211> LENGTH: 9
<212> TYPE: PRT
<213> ORGANISM: Artificial Sequence
<220> FEATURE:
<223> OTHER INFORMATION: Synthetic Construct

<400> SEQUENCE: 115

Leu Leu Leu Leu Thr Val Leu Thr Val
1 5

<210> SEQ ID NO 116
<211> LENGTH: 12

<212> TYPE: PRT
<213> ORGANISM: Artificial Sequence
<220> FEATURE:
<223> OTHER INFORMATION: Synthetic Construct

<400> SEQUENCE: 116

Pro Gly Ser Thr Ala Pro Pro Ala His Gly Val Thr
1               5                   10

<210> SEQ ID NO 117
<211> LENGTH: 9
<212> TYPE: PRT
<213> ORGANISM: Artificial Sequence
<220> FEATURE:
<223> OTHER INFORMATION: Synthetic Construct

<400> SEQUENCE: 117

Met Leu Ala Val Ile Ser Cys Ala Val
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic Construct

<400> SEQUENCE: 118

Arg Gln Lys Arg Ile Leu Val Asn Leu
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic Construct

<400> SEQUENCE: 119

Asn Tyr Asn Asn Phe Tyr Arg Phe Leu
1               5

<210> SEQ ID NO 120
<211> LENGTH: 10
<212> TYPE: PRT
<213> ORGANISM: Artificial Sequence
<220> FEATURE:
<223> OTHER INFORMATION: Synthetic Construct

<400> SEQUENCE: 120

Glu Tyr Ser Lys Glu Cys Leu Lys Glu Phe
1               5                   10

<210> SEQ ID NO 121
<211> LENGTH: 9
<212> TYPE: PRT
<213> ORGANISM: Artificial Sequence
<220> FEATURE:
<223> OTHER INFORMATION: Synthetic Construct

<400> SEQUENCE: 121

Glu Tyr Leu Ser Leu Ser Asp Lys Ile
1               5

<210> SEQ ID NO 122
<211> LENGTH: 9
<212> TYPE: PRT

<213> ORGANISM: Artificial Sequence
<220> FEATURE:
<223> OTHER INFORMATION: Synthetic Construct

<400> SEQUENCE: 122

Glu Leu Val Arg Arg Ile Leu Ser Arg
1               5

<210> SEQ ID NO 123
<211> LENGTH: 9
<212> TYPE: PRT
<213> ORGANISM: Artificial Sequence
<220> FEATURE:
<223> OTHER INFORMATION: Synthetic Construct

<400> SEQUENCE: 123

Ala Pro Arg Gly Val Arg Met Ala Val
1               5

<210> SEQ ID NO 124
<211> LENGTH: 20
<212> TYPE: PRT
<213> ORGANISM: Artificial Sequence
<220> FEATURE:
<223> OTHER INFORMATION: Synthetic Construct

<400> SEQUENCE: 124

Gln Gly Ala Met Leu Ala Ala Gln Glu Arg Arg Val Pro Arg Ala Ala
1               5                   10                  15

Glu Val Pro Arg
            20

<210> SEQ ID NO 125
<211> LENGTH: 22
<212> TYPE: PRT
<213> ORGANISM: Artificial Sequence
<220> FEATURE:
<223> OTHER INFORMATION: Synthetic Construct

<400> SEQUENCE: 125

Cys Leu Ser Arg Arg Pro Trp Lys Arg Ser Trp Ser Ala Gly Ser Cys
1               5                   10                  15

Pro Gly Met Pro His Leu
            20

<210> SEQ ID NO 126
<211> LENGTH: 13
<212> TYPE: PRT
<213> ORGANISM: Artificial Sequence
<220> FEATURE:
<223> OTHER INFORMATION: Synthetic Construct

<400> SEQUENCE: 126

Ile Leu Ser Arg Asp Ala Ala Pro Leu Pro Arg Pro Gly
1               5                   10

<210> SEQ ID NO 127
<211> LENGTH: 9
<212> TYPE: PRT
<213> ORGANISM: Artificial Sequence
<220> FEATURE:
<223> OTHER INFORMATION: Synthetic Construct

<400> SEQUENCE: 127

Glu Val Asp Pro Ala Ser Asn Thr Tyr
1               5

-continued

<210> SEQ ID NO 128
<211> LENGTH: 10
<212> TYPE: PRT
<213> ORGANISM: Artificial Sequence
<220> FEATURE:
<223> OTHER INFORMATION: Synthetic Construct

<400> SEQUENCE: 128

Gly Val Tyr Asp Gly Arg Glu His Thr Val
1 5 10

<210> SEQ ID NO 129
<211> LENGTH: 9
<212> TYPE: PRT
<213> ORGANISM: Artificial Sequence
<220> FEATURE:
<223> OTHER INFORMATION: Synthetic Construct

<400> SEQUENCE: 129

Asn Tyr Lys Arg Cys Phe Pro Val Ile
1 5

<210> SEQ ID NO 130
<211> LENGTH: 8
<212> TYPE: PRT
<213> ORGANISM: Artificial Sequence
<220> FEATURE:
<223> OTHER INFORMATION: Synthetic Construct

<400> SEQUENCE: 130

Ser Glu Ser Leu Lys Met Ile Phe
1 5

<210> SEQ ID NO 131
<211> LENGTH: 20
<212> TYPE: PRT
<213> ORGANISM: Artificial Sequence
<220> FEATURE:
<223> OTHER INFORMATION: Synthetic Construct

<400> SEQUENCE: 131

Ile Asn Lys Thr Ser Gly Pro Lys Arg Gly Lys His Ala Trp Thr His
1 5 10 15

Arg Leu Arg Glu
20

<210> SEQ ID NO 132
<211> LENGTH: 20
<212> TYPE: PRT
<213> ORGANISM: Artificial Sequence
<220> FEATURE:
<223> OTHER INFORMATION: Synthetic Construct

<400> SEQUENCE: 132

Tyr Phe Ser Lys Lys Glu Trp Glu Lys Met Lys Ser Ser Glu Lys Ile
1 5 10 15

Val Tyr Val Tyr
20

<210> SEQ ID NO 133
<211> LENGTH: 20
<212> TYPE: PRT
<213> ORGANISM: Artificial Sequence
<220> FEATURE:
<223> OTHER INFORMATION: Synthetic Construct -continued

<400> SEQUENCE: 133

Met Lys Leu Asn Tyr Glu Val Met Thr Lys Leu Gly Phe Lys Val Thr
1               5                   10                  15

Leu Pro Pro Phe
            20

<210> SEQ ID NO 134
<211> LENGTH: 20
<212> TYPE: PRT
<213> ORGANISM: Artificial Sequence
<220> FEATURE:
<223> OTHER INFORMATION: Synthetic Construct

<400> SEQUENCE: 134

Lys His Ala Trp Thr His Arg Leu Arg Glu Arg Lys Gln Leu Val Val
1               5                   10                  15

Tyr Glu Glu Ile
            20

<210> SEQ ID NO 135
<211> LENGTH: 20
<212> TYPE: PRT
<213> ORGANISM: Artificial Sequence
<220> FEATURE:
<223> OTHER INFORMATION: Synthetic Construct

<400> SEQUENCE: 135

Leu Gly Phe Lys Val Thr Leu Pro Pro Phe Met Arg Ser Lys Arg Ala
1               5                   10                  15

Ala Asp Phe His
            20

<210> SEQ ID NO 136
<211> LENGTH: 20
<212> TYPE: PRT
<213> ORGANISM: Artificial Sequence
<220> FEATURE:
<223> OTHER INFORMATION: Synthetic Construct

<400> SEQUENCE: 136

Lys Ser Ser Glu Lys Ile Val Tyr Val Tyr Met Lys Leu Asn Tyr Glu
1               5                   10                  15

Val Met Thr Lys
            20

<210> SEQ ID NO 137
<211> LENGTH: 9
<212> TYPE: PRT
<213> ORGANISM: Artificial Sequence
<220> FEATURE:
<223> OTHER INFORMATION: Synthetic Construct

<400> SEQUENCE: 137

Ser Leu Gly Trp Leu Phe Leu Leu Leu
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic Construct

<400> SEQUENCE: 138

Leu Ser Arg Leu Ser Asn Arg Leu Leu
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic Construct

<400> SEQUENCE: 139

Thr Met Asn Gly Ser Lys Ser Pro Val
1               5

<210> SEQ ID NO 140
<211> LENGTH: 9
<212> TYPE: PRT
<213> ORGANISM: Artificial Sequence
<220> FEATURE:
<223> OTHER INFORMATION: Synthetic Construct

<400> SEQUENCE: 140

Pro Leu Leu Glu Asn Val Ile Ser Lys
1               5

<210> SEQ ID NO 141
<211> LENGTH: 9
<212> TYPE: PRT
<213> ORGANISM: Artificial Sequence
<220> FEATURE:
<223> OTHER INFORMATION: Synthetic Construct

<400> SEQUENCE: 141

Ser Leu Ser Lys Ile Leu Asp Thr Val
1               5

<210> SEQ ID NO 142
<211> LENGTH: 9
<212> TYPE: PRT
<213> ORGANISM: Artificial Sequence
<220> FEATURE:
<223> OTHER INFORMATION: Synthetic Construct

<400> SEQUENCE: 142

Ala Ala Arg Ala Val Phe Leu Ala Leu
1               5

<210> SEQ ID NO 143
<211> LENGTH: 9
<212> TYPE: PRT
<213> ORGANISM: Artificial Sequence
<220> FEATURE:
<223> OTHER INFORMATION: Synthetic Construct

<400> SEQUENCE: 143

Glu Ala Asp Pro Thr Gly His Ser Tyr
1               5

<210> SEQ ID NO 144
<211> LENGTH: 9
<212> TYPE: PRT
<213> ORGANISM: Artificial Sequence
<220> FEATURE:
<223> OTHER INFORMATION: Synthetic Construct

<400> SEQUENCE: 144

Lys Val Leu Glu Tyr Val Ile Lys Val
1 5

<210> SEQ ID NO 145
<211> LENGTH: 9
<212> TYPE: PRT
<213> ORGANISM: Artificial Sequence
<220> FEATURE:
<223> OTHER INFORMATION: Synthetic Construct

<400> SEQUENCE: 145

Ser Leu Phe Arg Ala Val Ile Thr Lys
1 5

<210> SEQ ID NO 146
<211> LENGTH: 10
<212> TYPE: PRT
<213> ORGANISM: Artificial Sequence
<220> FEATURE:
<223> OTHER INFORMATION: Synthetic Construct

<400> SEQUENCE: 146

Glu Val Tyr Asp Gly Arg Glu His Ser Ala
1 5 10

<210> SEQ ID NO 147
<211> LENGTH: 9
<212> TYPE: PRT
<213> ORGANISM: Artificial Sequence
<220> FEATURE:
<223> OTHER INFORMATION: Synthetic Construct

<400> SEQUENCE: 147

Arg Val Arg Phe Phe Phe Pro Ser Leu
1 5

<210> SEQ ID NO 148
<211> LENGTH: 10
<212> TYPE: PRT
<213> ORGANISM: Artificial Sequence
<220> FEATURE:
<223> OTHER INFORMATION: Synthetic Construct

<400> SEQUENCE: 148

Arg Glu Pro Val Thr Lys Ala Glu Met Leu
1 5 10

<210> SEQ ID NO 149
<211> LENGTH: 10
<212> TYPE: PRT
<213> ORGANISM: Artificial Sequence
<220> FEATURE:
<223> OTHER INFORMATION: Synthetic Construct

<400> SEQUENCE: 149

Lys Glu Ala Asp Pro Thr Gly His Ser Tyr
1 5 10

<210> SEQ ID NO 150
<211> LENGTH: 9
<212> TYPE: PRT
<213> ORGANISM: Artificial Sequence
<220> FEATURE:
<223> OTHER INFORMATION: Synthetic Construct

<400> SEQUENCE: 150

Asp Pro Ala Arg Tyr Glu Phe Leu Trp 1 5

<210> SEQ ID NO 151
<211> LENGTH: 11
<212> TYPE: PRT
<213> ORGANISM: Artificial Sequence
<220> FEATURE:
<223> OTHER INFORMATION: Synthetic Construct

<400> SEQUENCE: 151

Ile Thr Lys Lys Val Ala Asp Leu Val Gly Phe
1 5 10

<210> SEQ ID NO 152
<211> LENGTH: 9
<212> TYPE: PRT
<213> ORGANISM: Artificial Sequence
<220> FEATURE:
<223> OTHER INFORMATION: Synthetic Construct

<400> SEQUENCE: 152

Ser Ala Phe Pro Thr Thr Ile Asn Phe
1 5

<210> SEQ ID NO 153
<211> LENGTH: 9
<212> TYPE: PRT
<213> ORGANISM: Artificial Sequence
<220> FEATURE:
<223> OTHER INFORMATION: Synthetic Construct

<400> SEQUENCE: 153

Ser Ala Tyr Gly Glu Pro Arg Lys Leu
1 5

<210> SEQ ID NO 154
<211> LENGTH: 15
<212> TYPE: PRT
<213> ORGANISM: Artificial Sequence
<220> FEATURE:
<223> OTHER INFORMATION: Synthetic Construct

<400> SEQUENCE: 154

Thr Ser Cys Ile Leu Glu Ser Leu Phe Arg Ala Val Ile Thr Lys
1 5 10 15

<210> SEQ ID NO 155
<211> LENGTH: 15
<212> TYPE: PRT
<213> ORGANISM: Artificial Sequence
<220> FEATURE:
<223> OTHER INFORMATION: Synthetic Construct

<400> SEQUENCE: 155

Pro Arg Ala Leu Ala Glu Thr Ser Tyr Val Lys Val Leu Glu Tyr
1 5 10 15

<210> SEQ ID NO 156
<211> LENGTH: 16
<212> TYPE: PRT
<213> ORGANISM: Artificial Sequence
<220> FEATURE:
<223> OTHER INFORMATION: Synthetic Construct

<400> SEQUENCE: 156

Phe Leu Leu Leu Lys Tyr Arg Ala Arg Glu Pro Val Thr Lys Ala Glu
1 5 10 15

<210> SEQ ID NO 157
<211> LENGTH: 12
<212> TYPE: PRT
<213> ORGANISM: Artificial Sequence
<220> FEATURE:
<223> OTHER INFORMATION: Synthetic Construct

<400> SEQUENCE: 157

Glu Tyr Val Ile Lys Val Ser Ala Arg Val Arg Phe
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Synthetic Construct

<400> SEQUENCE: 158

Tyr Leu Gln Leu Val Phe Gly Ile Glu Val
1               5                   10

<210> SEQ ID NO 159
<211> LENGTH: 9
<212> TYPE: PRT
<213> ORGANISM: Artificial Sequence
<220> FEATURE:
<223> OTHER INFORMATION: Synthetic Construct

<400> SEQUENCE: 159

Glu Tyr Leu Gln Leu Val Phe Gly Ile
1               5

<210> SEQ ID NO 160
<211> LENGTH: 9
<212> TYPE: PRT
<213> ORGANISM: Artificial Sequence
<220> FEATURE:
<223> OTHER INFORMATION: Synthetic Construct

<400> SEQUENCE: 160

Glu Gly Asp Cys Ala Pro Glu Glu Lys
1               5

<210> SEQ ID NO 161
<211> LENGTH: 14
<212> TYPE: PRT
<213> ORGANISM: Artificial Sequence
<220> FEATURE:
<223> OTHER INFORMATION: Synthetic Construct

<400> SEQUENCE: 161

Leu Leu Lys Tyr Arg Ala Arg Glu Pro Val Thr Lys Ala Glu
1               5                   10

<210> SEQ ID NO 162
<211> LENGTH: 9
<212> TYPE: PRT
<213> ORGANISM: Artificial Sequence
<220> FEATURE:
<223> OTHER INFORMATION: Synthetic Construct

<400> SEQUENCE: 162

Lys Ala Ser Glu Lys Ile Phe Tyr Val
1               5

<210> SEQ ID NO 163
<211> LENGTH: 16
<212> TYPE: PRT
<213> ORGANISM: Artificial Sequence
<220> FEATURE:
<223> OTHER INFORMATION: Synthetic Construct

<400> SEQUENCE: 163

Glu Lys Ile Gln Lys Ala Phe Asp Asp Ile Ala Lys Tyr Phe Ser Lys
1 5 10 15

<210> SEQ ID NO 164
<211> LENGTH: 11
<212> TYPE: PRT
<213> ORGANISM: Artificial Sequence
<220> FEATURE:
<223> OTHER INFORMATION: Synthetic Construct

<400> SEQUENCE: 164

Phe Gly Arg Leu Gln Gly Ile Ser Pro Lys Ile
1 5 10

<210> SEQ ID NO 165
<211> LENGTH: 18
<212> TYPE: PRT
<213> ORGANISM: Artificial Sequence
<220> FEATURE:
<223> OTHER INFORMATION: Synthetic Construct

<400> SEQUENCE: 165

Trp Glu Lys Met Lys Ala Ser Glu Lys Ile Phe Tyr Val Tyr Met Lys
1 5 10 15

Arg Lys

<210> SEQ ID NO 166
<211> LENGTH: 15
<212> TYPE: PRT
<213> ORGANISM: Artificial Sequence
<220> FEATURE:
<223> OTHER INFORMATION: Synthetic Construct

<400> SEQUENCE: 166

Lys Ile Phe Tyr Val Tyr Met Lys Arg Lys Tyr Glu Ala Met Thr
1 5 10 15

<210> SEQ ID NO 167
<211> LENGTH: 14
<212> TYPE: PRT
<213> ORGANISM: Artificial Sequence
<220> FEATURE:
<223> OTHER INFORMATION: Synthetic Construct

<400> SEQUENCE: 167

Lys Ile Phe Tyr Val Tyr Met Lys Arg Lys Tyr Glu Ala Met
1 5 10

<210> SEQ ID NO 168
<211> LENGTH: 15
<212> TYPE: PRT
<213> ORGANISM: Artificial Sequence
<220> FEATURE:
<223> OTHER INFORMATION: Synthetic Construct

<400> SEQUENCE: 168

Cys Glu Phe His Ala Cys Trp Pro Ala Phe Thr Val Leu Gly Glu
1 5 10 15

<210> SEQ ID NO 169
<211> LENGTH: 9
<212> TYPE: PRT
<213> ORGANISM: Artificial Sequence
<220> FEATURE:
<223> OTHER INFORMATION: Synthetic Construct

<400> SEQUENCE: 169

Lys Phe Leu Asp Ala Leu Ile Ser Leu
1 5

<210> SEQ ID NO 170
<211> LENGTH: 10
<212> TYPE: PRT
<213> ORGANISM: Artificial Sequence
<220> FEATURE:
<223> OTHER INFORMATION: Synthetic Construct

<400> SEQUENCE: 170

Ala Leu Gly Gly His Pro Leu Leu Gly Val
1 5 10

<210> SEQ ID NO 171
<211> LENGTH: 9
<212> TYPE: PRT
<213> ORGANISM: Artificial Sequence
<220> FEATURE:
<223> OTHER INFORMATION: Synthetic Construct

<400> SEQUENCE: 171

Leu Pro Arg Trp Pro Pro Pro Gln Leu
1 5

<210> SEQ ID NO 172
<211> LENGTH: 9
<212> TYPE: PRT
<213> ORGANISM: Artificial Sequence
<220> FEATURE:
<223> OTHER INFORMATION: Synthetic Construct

<400> SEQUENCE: 172

Ile Leu Ala Lys Phe Leu His Trp Leu
1 5

<210> SEQ ID NO 173
<211> LENGTH: 9
<212> TYPE: PRT
<213> ORGANISM: Artificial Sequence
<220> FEATURE:
<223> OTHER INFORMATION: Synthetic Construct

<400> SEQUENCE: 173

Arg Leu Val Asp Asp Phe Leu Leu Val
1 5

<210> SEQ ID NO 174
<211> LENGTH: 15
<212> TYPE: PRT
<213> ORGANISM: Artificial Sequence
<220> FEATURE:
<223> OTHER INFORMATION: Synthetic Construct

<400> SEQUENCE: 174

Arg Pro Gly Leu Leu Gly Ala Ser Val Leu Gly Leu Asp Asp Ile
1 5 10 15

-continued

<210> SEQ ID NO 175
<211> LENGTH: 15
<212> TYPE: PRT
<213> ORGANISM: Artificial Sequence
<220> FEATURE:
<223> OTHER INFORMATION: Synthetic Construct

<400> SEQUENCE: 175

Leu Thr Asp Leu Gln Pro Tyr Met Arg Gln Phe Val Ala His Leu
1 5 10 15

<210> SEQ ID NO 176
<211> LENGTH: 9
<212> TYPE: PRT
<213> ORGANISM: Artificial Sequence
<220> FEATURE:
<223> OTHER INFORMATION: Synthetic Construct

<400> SEQUENCE: 176

Val Val Val Gly Ala Val Gly Val Gly
1 5

<210> SEQ ID NO 177
<211> LENGTH: 9
<212> TYPE: PRT
<213> ORGANISM: Artificial Sequence
<220> FEATURE:
<223> OTHER INFORMATION: Synthetic Construct

<400> SEQUENCE: 177

His Leu Ser Thr Ala Phe Ala Arg Val
1 5

<210> SEQ ID NO 178
<211> LENGTH: 9
<212> TYPE: PRT
<213> ORGANISM: Artificial Sequence
<220> FEATURE:
<223> OTHER INFORMATION: Synthetic Construct

<400> SEQUENCE: 178

Lys Ile Phe Gly Ser Leu Ala Phe Leu
1 5

<210> SEQ ID NO 179
<211> LENGTH: 9
<212> TYPE: PRT
<213> ORGANISM: Artificial Sequence
<220> FEATURE:
<223> OTHER INFORMATION: Synthetic Construct

<400> SEQUENCE: 179

Ile Ile Ser Ala Val Val Gly Ile Leu
1 5

<210> SEQ ID NO 180
<211> LENGTH: 9
<212> TYPE: PRT
<213> ORGANISM: Artificial Sequence
<220> FEATURE:
<223> OTHER INFORMATION: Synthetic Construct

<400> SEQUENCE: 180

Ala Leu Cys Arg Trp Gly Leu Leu Leu
1 5

<210> SEQ ID NO 181
<211> LENGTH: 9
<212> TYPE: PRT
<213> ORGANISM: Artificial Sequence
<220> FEATURE:
<223> OTHER INFORMATION: Synthetic Construct

<400> SEQUENCE: 181

Ile Leu His Asn Gly Ala Tyr Ser Leu
1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic Construct

<400> SEQUENCE: 182

Arg Leu Leu Gln Glu Thr Glu Leu Val
1               5

<210> SEQ ID NO 183
<211> LENGTH: 9
<212> TYPE: PRT
<213> ORGANISM: Artificial Sequence
<220> FEATURE:
<223> OTHER INFORMATION: Synthetic Construct

<400> SEQUENCE: 183

Val Val Lys Gly Val Val Phe Gly Ile
1               5

<210> SEQ ID NO 184
<211> LENGTH: 10
<212> TYPE: PRT
<213> ORGANISM: Artificial Sequence
<220> FEATURE:
<223> OTHER INFORMATION: Synthetic Construct

<400> SEQUENCE: 184

Tyr Met Ile Met Val Lys Cys Trp Met Ile
1               5                   10

<210> SEQ ID NO 185
<211> LENGTH: 9
<212> TYPE: PRT
<213> ORGANISM: Artificial Sequence
<220> FEATURE:
<223> OTHER INFORMATION: Synthetic Construct

<400> SEQUENCE: 185

Ser Leu Leu Ser Gly Asp Trp Val Leu
1               5

<210> SEQ ID NO 186
<211> LENGTH: 9
<212> TYPE: PRT
<213> ORGANISM: Artificial Sequence
<220> FEATURE:
<223> OTHER INFORMATION: Synthetic Construct

<400> SEQUENCE: 186

Gly Leu Gln Leu Gly Val Gln Ala Val
1               5

<210> SEQ ID NO 187

<211> LENGTH: 9
<212> TYPE: PRT
<213> ORGANISM: Artificial Sequence
<220> FEATURE:
<223> OTHER INFORMATION: Synthetic Construct

<400> SEQUENCE: 187

Pro Leu Thr Glu Tyr Ile Gln Pro Val
1               5

<210> SEQ ID NO 188
<211> LENGTH: 9
<212> TYPE: PRT
<213> ORGANISM: Artificial Sequence
<220> FEATURE:
<223> OTHER INFORMATION: Synthetic Construct

<400> SEQUENCE: 188

Ser Pro Arg Trp Trp Pro Thr Cys Leu
1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic Construct

<400> SEQUENCE: 189

Gly Val Ala Leu Gln Thr Met Lys Gln
1               5

<210> SEQ ID NO 190
<211> LENGTH: 9
<212> TYPE: PRT
<213> ORGANISM: Artificial Sequence
<220> FEATURE:
<223> OTHER INFORMATION: Synthetic Construct

<400> SEQUENCE: 190

Phe Met Asn Lys Phe Ile Tyr Glu Ile
1               5

<210> SEQ ID NO 191
<211> LENGTH: 10
<212> TYPE: PRT
<213> ORGANISM: Artificial Sequence
<220> FEATURE:
<223> OTHER INFORMATION: Synthetic Construct

<400> SEQUENCE: 191

Gln Leu Ala Val Ser Val Ile Leu Arg Val
1               5                   10

<210> SEQ ID NO 192
<211> LENGTH: 14
<212> TYPE: PRT
<213> ORGANISM: Artificial Sequence
<220> FEATURE:
<223> OTHER INFORMATION: Synthetic Construct

<400> SEQUENCE: 192

Leu Pro Ala Val Val Gly Leu Ser Pro Gly Glu Gln Glu Tyr
1               5                   10

<210> SEQ ID NO 193
<211> LENGTH: 9

<212> TYPE: PRT
<213> ORGANISM: Artificial Sequence
<220> FEATURE:
<223> OTHER INFORMATION: Synthetic Construct

<400> SEQUENCE: 193

Asn Tyr Ala Arg Thr Glu Asp Phe Phe
1 5

<210> SEQ ID NO 194
<211> LENGTH: 9
<212> TYPE: PRT
<213> ORGANISM: Artificial Sequence
<220> FEATURE:
<223> OTHER INFORMATION: Synthetic Construct

<400> SEQUENCE: 194

Phe Leu Ile Ile Trp Gln Asn Thr Met
1 5

<210> SEQ ID NO 195
<211> LENGTH: 14
<212> TYPE: PRT
<213> ORGANISM: Artificial Sequence
<220> FEATURE:
<223> OTHER INFORMATION: Synthetic Construct

<400> SEQUENCE: 195

Thr Leu Tyr Gln Asp Asp Thr Leu Thr Leu Gln Ala Ala Gly
1 5 10

<210> SEQ ID NO 196
<211> LENGTH: 10
<212> TYPE: PRT
<213> ORGANISM: Artificial Sequence
<220> FEATURE:
<223> OTHER INFORMATION: Synthetic Construct

<400> SEQUENCE: 196

Ser Leu Tyr Lys Phe Ser Pro Phe Pro Leu
1 5 10

<210> SEQ ID NO 197
<211> LENGTH: 9
<212> TYPE: PRT
<213> ORGANISM: Artificial Sequence
<220> FEATURE:
<223> OTHER INFORMATION: Synthetic Construct

<400> SEQUENCE: 197

Lys Glu Leu Glu Gly Ile Leu Leu Leu
1 5

<210> SEQ ID NO 198
<211> LENGTH: 9
<212> TYPE: PRT
<213> ORGANISM: Artificial Sequence
<220> FEATURE:
<223> OTHER INFORMATION: Synthetic Construct

<400> SEQUENCE: 198

Arg Leu Ser Ser Cys Val Pro Val Ala
1 5

<210> SEQ ID NO 199
<211> LENGTH: 10
<212> TYPE: PRT

<213> ORGANISM: Artificial Sequence
<220> FEATURE:
<223> OTHER INFORMATION: Synthetic Construct

<400> SEQUENCE: 199

Val Leu Leu Gln Ala Gly Ser Leu His Ala
1               5                   10

<210> SEQ ID NO 200
<211> LENGTH: 9
<212> TYPE: PRT
<213> ORGANISM: Artificial Sequence
<220> FEATURE:
<223> OTHER INFORMATION: Synthetic Construct

<400> SEQUENCE: 200

Leu Leu Asn Ala Phe Thr Val Thr Val
1               5

<210> SEQ ID NO 201
<211> LENGTH: 8
<212> TYPE: PRT
<213> ORGANISM: Artificial Sequence
<220> FEATURE:
<223> OTHER INFORMATION: Synthetic Construct

<400> SEQUENCE: 201

Val Leu Phe Tyr Leu Gly Gln Tyr
1               5

<210> SEQ ID NO 202
<211> LENGTH: 10
<212> TYPE: PRT
<213> ORGANISM: Artificial Sequence
<220> FEATURE:
<223> OTHER INFORMATION: Synthetic Construct

<400> SEQUENCE: 202

Phe Ile Ala Ser Asn Gly Val Lys Leu Val
1               5                   10

<210> SEQ ID NO 203
<211> LENGTH: 9
<212> TYPE: PRT
<213> ORGANISM: Artificial Sequence
<220> FEATURE:
<223> OTHER INFORMATION: Synthetic Construct

<400> SEQUENCE: 203

Glu Thr Val Ser Glu Gln Ser Asn Val
1               5

<210> SEQ ID NO 204
<211> LENGTH: 9
<212> TYPE: PRT
<213> ORGANISM: Artificial Sequence
<220> FEATURE:
<223> OTHER INFORMATION: Synthetic Construct

<400> SEQUENCE: 204

Phe Leu Asp Glu Phe Met Glu Gly Val
1               5

<210> SEQ ID NO 205
<211> LENGTH: 8
<212> TYPE: PRT
<213> ORGANISM: Artificial Sequence
<220> FEATURE:
<223> OTHER INFORMATION: Synthetic Construct

<400> SEQUENCE: 205

Gln Gln Ile Thr Lys Thr Glu Val
1               5

<210> SEQ ID NO 206
<211> LENGTH: 8
<212> TYPE: PRT
<213> ORGANISM: Artificial Sequence
<220> FEATURE:
<223> OTHER INFORMATION: Synthetic Construct

<400> SEQUENCE: 206

Tyr Arg Pro Arg Pro Arg Arg Tyr
1               5

<210> SEQ ID NO 207
<211> LENGTH: 9
<212> TYPE: PRT
<213> ORGANISM: Artificial Sequence
<220> FEATURE:
<223> OTHER INFORMATION: Synthetic Construct

<400> SEQUENCE: 207

Met Val Lys Ile Ser Gly Gly Pro Arg
1               5

<210> SEQ ID NO 208
<211> LENGTH: 9
<212> TYPE: PRT
<213> ORGANISM: Artificial Sequence
<220> FEATURE:
<223> OTHER INFORMATION: Synthetic Construct

<400> SEQUENCE: 208

Glu Val Asp Pro Ile Gly His Val Tyr
1               5

<210> SEQ ID NO 209
<211> LENGTH: 9
<212> TYPE: PRT
<213> ORGANISM: Artificial Sequence
<220> FEATURE:
<223> OTHER INFORMATION: Synthetic Construct

<400> SEQUENCE: 209

Ile Ser Gly Gly Pro Arg Ile Ser Tyr
1               5

<210> SEQ ID NO 210
<211> LENGTH: 9
<212> TYPE: PRT
<213> ORGANISM: Artificial Sequence
<220> FEATURE:
<223> OTHER INFORMATION: Synthetic Construct

<400> SEQUENCE: 210

Arg Gln Lys Lys Ile Arg Ile Gln Leu
1               5

<210> SEQ ID NO 211
<211> LENGTH: 16
<212> TYPE: PRT
<213> ORGANISM: Artificial Sequence
<220> FEATURE:

<223> OTHER INFORMATION: Synthetic Construct

<400> SEQUENCE: 211

His Leu Gly Ser Arg Gln Lys Lys Ile Arg Ile Gln Leu Arg Ser Gln
1 5 10 15

<210> SEQ ID NO 212
<211> LENGTH: 17
<212> TYPE: PRT
<213> ORGANISM: Artificial Sequence
<220> FEATURE:
<223> OTHER INFORMATION: Synthetic Construct

<400> SEQUENCE: 212

Cys Ala Thr Trp Lys Val Ile Cys Lys Ser Cys Ile Ser Gln Thr Pro
1 5 10 15

Gly

<210> SEQ ID NO 213
<211> LENGTH: 9
<212> TYPE: PRT
<213> ORGANISM: Artificial Sequence
<220> FEATURE:
<223> OTHER INFORMATION: Synthetic Construct

<400> SEQUENCE: 213

Met Ile Ala Val Phe Leu Pro Ile Val
1 5

<210> SEQ ID NO 214
<211> LENGTH: 15
<212> TYPE: PRT
<213> ORGANISM: Artificial Sequence
<220> FEATURE:
<223> OTHER INFORMATION: Synthetic Construct

<400> SEQUENCE: 214

His Gln Gln Tyr Phe Tyr Lys Ile Pro Ile Leu Val Ile Asn Lys
1 5 10 15

<210> SEQ ID NO 215
<211> LENGTH: 9
<212> TYPE: PRT
<213> ORGANISM: Artificial Sequence
<220> FEATURE:
<223> OTHER INFORMATION: Synthetic Construct

<400> SEQUENCE: 215

Phe Leu Phe Leu Leu Phe Phe Trp Leu
1 5

<210> SEQ ID NO 216
<211> LENGTH: 9
<212> TYPE: PRT
<213> ORGANISM: Artificial Sequence
<220> FEATURE:
<223> OTHER INFORMATION: Synthetic Construct

<400> SEQUENCE: 216

Thr Leu Met Ser Ala Met Thr Asn Leu
1 5

<210> SEQ ID NO 217
<211> LENGTH: 9
<212> TYPE: PRT
<213> ORGANISM: Artificial Sequence
<220> FEATURE:
<223> OTHER INFORMATION: Synthetic Construct

<400> SEQUENCE: 217

Ala Leu Asp Val Tyr Asn Gly Leu Leu
1 5

<210> SEQ ID NO 218
<211> LENGTH: 10
<212> TYPE: PRT
<213> ORGANISM: Artificial Sequence
<220> FEATURE:
<223> OTHER INFORMATION: Synthetic Construct

<400> SEQUENCE: 218

Phe Leu Thr Pro Lys Lys Leu Gln Cys Val
1 5 10

<210> SEQ ID NO 219
<211> LENGTH: 10
<212> TYPE: PRT
<213> ORGANISM: Artificial Sequence
<220> FEATURE:
<223> OTHER INFORMATION: Synthetic Construct

<400> SEQUENCE: 219

Val Ile Ser Asn Asp Val Cys Ala Gln Val
1 5 10

<210> SEQ ID NO 220
<211> LENGTH: 11
<212> TYPE: PRT
<213> ORGANISM: Artificial Sequence
<220> FEATURE:
<223> OTHER INFORMATION: Synthetic Construct

<400> SEQUENCE: 220

Lys Glu Phe Thr Val Ser Gly Asn Ile Leu Thr
1 5 10

<210> SEQ ID NO 221
<211> LENGTH: 9
<212> TYPE: PRT
<213> ORGANISM: Artificial Sequence
<220> FEATURE:
<223> OTHER INFORMATION: Synthetic Construct

<400> SEQUENCE: 221

Tyr Tyr Trp Pro Arg Pro Arg Arg Tyr
1 5

<210> SEQ ID NO 222
<211> LENGTH: 9
<212> TYPE: PRT
<213> ORGANISM: Artificial Sequence
<220> FEATURE:
<223> OTHER INFORMATION: Synthetic Construct

<400> SEQUENCE: 222

Asn Thr Tyr Ala Ser Pro Arg Phe Lys
1 5

<210> SEQ ID NO 223
<211> LENGTH: 10
<212> TYPE: PRT
<213> ORGANISM: Artificial Sequence
<220> FEATURE:

<223> OTHER INFORMATION: Synthetic Construct

<400> SEQUENCE: 223

Ser Leu Phe Glu Gly Ile Asp Ile Tyr Thr
1 5 10

<210> SEQ ID NO 224
<211> LENGTH: 9
<212> TYPE: PRT
<213> ORGANISM: Artificial Sequence
<220> FEATURE:
<223> OTHER INFORMATION: Synthetic Construct

<400> SEQUENCE: 224

Ala Leu Ser Val Met Gly Val Tyr Val
1 5

<210> SEQ ID NO 225
<211> LENGTH: 15
<212> TYPE: PRT
<213> ORGANISM: Artificial Sequence
<220> FEATURE:
<223> OTHER INFORMATION: Synthetic Construct

<400> SEQUENCE: 225

Tyr Ser Val Tyr Phe Asn Leu Pro Ala Asp Thr Ile Tyr Thr Asn
1 5 10 15

<210> SEQ ID NO 226
<211> LENGTH: 29
<212> TYPE: PRT
<213> ORGANISM: Artificial Sequence
<220> FEATURE:
<223> OTHER INFORMATION: Synthetic Construct

<400> SEQUENCE: 226

Glu Asp Leu Thr Val Lys Ile Gly Asp Phe Gly Leu Ala Thr Glu Lys
1 5 10 15

Ser Arg Trp Ser Gly Ser His Gln Phe Glu Gln Leu Ser
20 25

<210> SEQ ID NO 227
<211> LENGTH: 9
<212> TYPE: PRT
<213> ORGANISM: Artificial Sequence
<220> FEATURE:
<223> OTHER INFORMATION: Synthetic Construct

<400> SEQUENCE: 227

Ser Tyr Leu Asp Ser Gly Ile His Phe
1 5

<210> SEQ ID NO 228
<211> LENGTH: 12
<212> TYPE: PRT
<213> ORGANISM: Artificial Sequence
<220> FEATURE:
<223> OTHER INFORMATION: Synthetic Construct

<400> SEQUENCE: 228

Phe Ser Trp Ala Met Asp Leu Asp Pro Lys Gly Ala
1 5 10

<210> SEQ ID NO 229
<211> LENGTH: 10
<212> TYPE: PRT

<213> ORGANISM: Artificial Sequence
<220> FEATURE:
<223> OTHER INFORMATION: Synthetic Construct

<400> SEQUENCE: 229

Ala Cys Asp Pro His Ser Gly His Phe Val
1               5                   10

<210> SEQ ID NO 230
<211> LENGTH: 9
<212> TYPE: PRT
<213> ORGANISM: Artificial Sequence
<220> FEATURE:
<223> OTHER INFORMATION: Synthetic Construct

<400> SEQUENCE: 230

Cys Ile Leu Gly Lys Leu Phe Thr Lys
1               5

<210> SEQ ID NO 231
<211> LENGTH: 9
<212> TYPE: PRT
<213> ORGANISM: Artificial Sequence
<220> FEATURE:
<223> OTHER INFORMATION: Synthetic Construct

<400> SEQUENCE: 231

Ala Val Cys Pro Trp Thr Trp Leu Arg
1               5

<210> SEQ ID NO 232
<211> LENGTH: 9
<212> TYPE: PRT
<213> ORGANISM: Artificial Sequence
<220> FEATURE:
<223> OTHER INFORMATION: Synthetic Construct

<400> SEQUENCE: 232

Ile Leu Asp Lys Val Leu Val His Leu
1               5

<210> SEQ ID NO 233
<211> LENGTH: 9
<212> TYPE: PRT
<213> ORGANISM: Artificial Sequence
<220> FEATURE:
<223> OTHER INFORMATION: Synthetic Construct

<400> SEQUENCE: 233

Gly Leu Phe Gly Asp Ile Tyr Leu Ala
1               5

<210> SEQ ID NO 234
<211> LENGTH: 14
<212> TYPE: PRT
<213> ORGANISM: Artificial Sequence
<220> FEATURE:
<223> OTHER INFORMATION: Synthetic Construct

<400> SEQUENCE: 234

Met Ile Phe Glu Lys His Gly Phe Arg Arg Thr Thr Pro Pro
1               5                   10

<210> SEQ ID NO 235
<211> LENGTH: 10
<212> TYPE: PRT
<213> ORGANISM: Artificial Sequence
<220> FEATURE:
<223> OTHER INFORMATION: Synthetic Construct

<400> SEQUENCE: 235

Ser Leu Ala Asp Glu Ala Glu Val Tyr Leu
1 5 10

<210> SEQ ID NO 236
<211> LENGTH: 10
<212> TYPE: PRT
<213> ORGANISM: Artificial Sequence
<220> FEATURE:
<223> OTHER INFORMATION: Synthetic Construct

<400> SEQUENCE: 236

Thr Leu Asp Trp Leu Leu Gln Thr Pro Lys
1 5 10

<210> SEQ ID NO 237
<211> LENGTH: 9
<212> TYPE: PRT
<213> ORGANISM: Artificial Sequence
<220> FEATURE:
<223> OTHER INFORMATION: Synthetic Construct

<400> SEQUENCE: 237

Ile Leu Asn Ala Met Ile Ala Lys Ile
1 5

<210> SEQ ID NO 238
<211> LENGTH: 9
<212> TYPE: PRT
<213> ORGANISM: Artificial Sequence
<220> FEATURE:
<223> OTHER INFORMATION: Synthetic Construct

<400> SEQUENCE: 238

Trp Arg Arg Ala Pro Ala Pro Gly Ala
1 5

<210> SEQ ID NO 239
<211> LENGTH: 9
<212> TYPE: PRT
<213> ORGANISM: Artificial Sequence
<220> FEATURE:
<223> OTHER INFORMATION: Synthetic Construct

<400> SEQUENCE: 239

Pro Val Thr Trp Arg Arg Ala Pro Ala
1 5

<210> SEQ ID NO 240
<211> LENGTH: 11
<212> TYPE: PRT
<213> ORGANISM: Artificial Sequence
<220> FEATURE:
<223> OTHER INFORMATION: Synthetic Construct

<400> SEQUENCE: 240

Phe Leu Glu Gly Asn Glu Val Gly Lys Thr Tyr
1 5 10

<210> SEQ ID NO 241
<211> LENGTH: 9
<212> TYPE: PRT
<213> ORGANISM: Artificial Sequence
<220> FEATURE:

<223> OTHER INFORMATION: Synthetic Construct

<400> SEQUENCE: 241

Lys Thr Leu Thr Ser Val Phe Gln Lys
1 5

<210> SEQ ID NO 242
<211> LENGTH: 9
<212> TYPE: PRT
<213> ORGANISM: Artificial Sequence
<220> FEATURE:
<223> OTHER INFORMATION: Synthetic Construct

<400> SEQUENCE: 242

Glu Glu Lys Leu Ile Val Val Leu Phe
1 5

<210> SEQ ID NO 243
<211> LENGTH: 11
<212> TYPE: PRT
<213> ORGANISM: Artificial Sequence
<220> FEATURE:
<223> OTHER INFORMATION: Synthetic Construct

<400> SEQUENCE: 243

Ser Glu Leu Phe Arg Ser Gly Leu Asp Ser Tyr
1 5 10

<210> SEQ ID NO 244
<211> LENGTH: 9
<212> TYPE: PRT
<213> ORGANISM: Artificial Sequence
<220> FEATURE:
<223> OTHER INFORMATION: Synthetic Construct

<400> SEQUENCE: 244

Phe Arg Ser Gly Leu Asp Ser Tyr Val
1 5

<210> SEQ ID NO 245
<211> LENGTH: 9
<212> TYPE: PRT
<213> ORGANISM: Artificial Sequence
<220> FEATURE:
<223> OTHER INFORMATION: Synthetic Construct

<400> SEQUENCE: 245

Glu Ala Phe Ile Gln Pro Ile Thr Arg
1 5

<210> SEQ ID NO 246
<211> LENGTH: 11
<212> TYPE: PRT
<213> ORGANISM: Artificial Sequence
<220> FEATURE:
<223> OTHER INFORMATION: Synthetic Construct

<400> SEQUENCE: 246

Arg Val Ile Lys Asn Ser Ile Arg Leu Thr Leu
1 5 10

<210> SEQ ID NO 247
<211> LENGTH: 9
<212> TYPE: PRT
<213> ORGANISM: Artificial Sequence
<220> FEATURE:
<223> OTHER INFORMATION: Synthetic Construct

<400> SEQUENCE: 247

Lys Ile Asn Lys Asn Pro Lys Tyr Lys
1 5

<210> SEQ ID NO 248
<211> LENGTH: 9
<212> TYPE: PRT
<213> ORGANISM: Artificial Sequence
<220> FEATURE:
<223> OTHER INFORMATION: Synthetic Construct

<400> SEQUENCE: 248

Tyr Thr Asp Phe His Cys Gln Tyr Val
1 5

<210> SEQ ID NO 249
<211> LENGTH: 10
<212> TYPE: PRT
<213> ORGANISM: Artificial Sequence
<220> FEATURE:
<223> OTHER INFORMATION: Synthetic Construct

<400> SEQUENCE: 249

Leu Leu Leu Asp Asp Leu Leu Val Ser Ile
1 5 10

<210> SEQ ID NO 250
<211> LENGTH: 16
<212> TYPE: PRT
<213> ORGANISM: Artificial Sequence
<220> FEATURE:
<223> OTHER INFORMATION: Synthetic Construct

<400> SEQUENCE: 250

Pro Tyr Tyr Phe Ala Ala Glu Leu Pro Pro Arg Asn Leu Pro Glu Pro
1 5 10 15

<210> SEQ ID NO 251
<211> LENGTH: 10
<212> TYPE: PRT
<213> ORGANISM: Artificial Sequence
<220> FEATURE:
<223> OTHER INFORMATION: Synthetic Construct

<400> SEQUENCE: 251

Ile Leu Asp Thr Ala Gly Arg Glu Glu Tyr
1 5 10

<210> SEQ ID NO 252
<211> LENGTH: 9
<212> TYPE: PRT
<213> ORGANISM: Artificial Sequence
<220> FEATURE:
<223> OTHER INFORMATION: Synthetic Construct

<400> SEQUENCE: 252

Arg Pro His Val Pro Glu Ser Ala Phe
1 5

<210> SEQ ID NO 253
<211> LENGTH: 9
<212> TYPE: PRT
<213> ORGANISM: Artificial Sequence
<220> FEATURE:
<223> OTHER INFORMATION: Synthetic Construct

<400> SEQUENCE: 253

Lys Ile Phe Ser Glu Val Thr Leu Lys
1 5

<210> SEQ ID NO 254
<211> LENGTH: 9
<212> TYPE: PRT
<213> ORGANISM: Artificial Sequence
<220> FEATURE:
<223> OTHER INFORMATION: Synthetic Construct

<400> SEQUENCE: 254

Ser His Glu Thr Val Ile Ile Glu Leu
1 5

<210> SEQ ID NO 255
<211> LENGTH: 15
<212> TYPE: PRT
<213> ORGANISM: Artificial Sequence
<220> FEATURE:
<223> OTHER INFORMATION: Synthetic Construct

<400> SEQUENCE: 255

Gly Glu Leu Ile Gly Ile Leu Asn Ala Ala Lys Val Pro Ala Asp
1 5 10 15

<210> SEQ ID NO 256
<211> LENGTH: 9
<212> TYPE: PRT
<213> ORGANISM: Artificial Sequence
<220> FEATURE:
<223> OTHER INFORMATION: Synthetic Construct

<400> SEQUENCE: 256

Leu Tyr Ser Ala Cys Phe Trp Trp Leu
1 5

<210> SEQ ID NO 257
<211> LENGTH: 9
<212> TYPE: PRT
<213> ORGANISM: Artificial Sequence
<220> FEATURE:
<223> OTHER INFORMATION: Synthetic Construct

<400> SEQUENCE: 257

Val Leu His Trp Asp Pro Glu Thr Val
1 5

<210> SEQ ID NO 258
<211> LENGTH: 9
<212> TYPE: PRT
<213> ORGANISM: Artificial Sequence
<220> FEATURE:
<223> OTHER INFORMATION: Synthetic Construct

<400> SEQUENCE: 258

Met Ser Leu Gln Arg Gln Phe Leu Arg
1 5

<210> SEQ ID NO 259
<211> LENGTH: 20
<212> TYPE: PRT
<213> ORGANISM: Artificial Sequence
<220> FEATURE:
<223> OTHER INFORMATION: Synthetic Construct

<400> SEQUENCE: 259

-continued

Ile Ser Pro Asn Ser Val Phe Ser Gln Trp Arg Val Val Cys Asp Ser
1 5 10 15

Leu Glu Asp Tyr
20

<210> SEQ ID NO 260
<211> LENGTH: 10
<212> TYPE: PRT
<213> ORGANISM: Artificial Sequence
<220> FEATURE:
<223> OTHER INFORMATION: Synthetic Construct

<400> SEQUENCE: 260

Ser Leu Pro Tyr Trp Asn Phe Ala Thr Gly
1 5 10

<210> SEQ ID NO 261
<211> LENGTH: 15
<212> TYPE: PRT
<213> ORGANISM: Artificial Sequence
<220> FEATURE:
<223> OTHER INFORMATION: Synthetic Construct

<400> SEQUENCE: 261

Ser Gln Trp Arg Val Val Cys Asp Ser Leu Glu Asp Tyr Asp Thr
1 5 10 15

<210> SEQ ID NO 262
<211> LENGTH: 9
<212> TYPE: PRT
<213> ORGANISM: Artificial Sequence
<220> FEATURE:
<223> OTHER INFORMATION: Synthetic Construct

<400> SEQUENCE: 262

Ser Val Tyr Asp Phe Phe Val Trp Leu
1 5

<210> SEQ ID NO 263
<211> LENGTH: 9
<212> TYPE: PRT
<213> ORGANISM: Artificial Sequence
<220> FEATURE:
<223> OTHER INFORMATION: Synthetic Construct

<400> SEQUENCE: 263

Thr Leu Asp Ser Gln Val Met Ser Leu
1 5

<210> SEQ ID NO 264
<211> LENGTH: 9
<212> TYPE: PRT
<213> ORGANISM: Artificial Sequence
<220> FEATURE:
<223> OTHER INFORMATION: Synthetic Construct

<400> SEQUENCE: 264

Leu Leu Gly Pro Gly Arg Pro Tyr Arg
1 5

<210> SEQ ID NO 265
<211> LENGTH: 9
<212> TYPE: PRT
<213> ORGANISM: Artificial Sequence
<220> FEATURE:
<223> OTHER INFORMATION: Synthetic Construct

<400> SEQUENCE: 265

Ala Asn Asp Pro Ile Phe Val Val Leu
1 5

<210> SEQ ID NO 266
<211> LENGTH: 15
<212> TYPE: PRT
<213> ORGANISM: Artificial Sequence
<220> FEATURE:
<223> OTHER INFORMATION: Synthetic Construct

<400> SEQUENCE: 266

Gln Cys Thr Glu Val Arg Ala Asp Thr Arg Pro Trp Ser Gly Pro
1 5 10 15

<210> SEQ ID NO 267
<211> LENGTH: 10
<212> TYPE: PRT
<213> ORGANISM: Artificial Sequence
<220> FEATURE:
<223> OTHER INFORMATION: Synthetic Construct

<400> SEQUENCE: 267

Ala Leu Pro Tyr Trp Asn Phe Ala Thr Gly
1 5 10

<210> SEQ ID NO 268
<211> LENGTH: 9
<212> TYPE: PRT
<213> ORGANISM: Artificial Sequence
<220> FEATURE:
<223> OTHER INFORMATION: Synthetic Construct

<400> SEQUENCE: 268

Lys Cys Asp Ile Cys Thr Asp Glu Tyr
1 5

<210> SEQ ID NO 269
<211> LENGTH: 11
<212> TYPE: PRT
<213> ORGANISM: Artificial Sequence
<220> FEATURE:
<223> OTHER INFORMATION: Synthetic Construct

<400> SEQUENCE: 269

Ser Ser Asp Tyr Val Ile Pro Ile Gly Thr Tyr
1 5 10

<210> SEQ ID NO 270
<211> LENGTH: 9
<212> TYPE: PRT
<213> ORGANISM: Artificial Sequence
<220> FEATURE:
<223> OTHER INFORMATION: Synthetic Construct

<400> SEQUENCE: 270

Met Leu Leu Ala Val Leu Tyr Cys Leu
1 5

<210> SEQ ID NO 271
<211> LENGTH: 10
<212> TYPE: PRT
<213> ORGANISM: Artificial Sequence
<220> FEATURE:
<223> OTHER INFORMATION: Synthetic Construct -continued

<400> SEQUENCE: 271

Cys Leu Leu Trp Ser Phe Gln Thr Ser Ala
1               5                   10

<210> SEQ ID NO 272
<211> LENGTH: 9
<212> TYPE: PRT
<213> ORGANISM: Artificial Sequence
<220> FEATURE:
<223> OTHER INFORMATION: Synthetic Construct

<400> SEQUENCE: 272

Tyr Met Asp Gly Thr Met Ser Gln Val
1               5

<210> SEQ ID NO 273
<211> LENGTH: 11
<212> TYPE: PRT
<213> ORGANISM: Artificial Sequence
<220> FEATURE:
<223> OTHER INFORMATION: Synthetic Construct

<400> SEQUENCE: 273

Ile Tyr Met Asp Gly Thr Ala Asp Phe Ser Phe
1               5                   10

<210> SEQ ID NO 274
<211> LENGTH: 9
<212> TYPE: PRT
<213> ORGANISM: Artificial Sequence
<220> FEATURE:
<223> OTHER INFORMATION: Synthetic Construct

<400> SEQUENCE: 274

Gln Cys Ser Gly Asn Phe Met Gly Phe
1               5

<210> SEQ ID NO 275
<211> LENGTH: 12
<212> TYPE: PRT
<213> ORGANISM: Artificial Sequence
<220> FEATURE:
<223> OTHER INFORMATION: Synthetic Construct

<400> SEQUENCE: 275

Thr Pro Arg Leu Pro Ser Ser Ala Asp Val Glu Phe
1               5                   10

<210> SEQ ID NO 276
<211> LENGTH: 9
<212> TYPE: PRT
<213> ORGANISM: Artificial Sequence
<220> FEATURE:
<223> OTHER INFORMATION: Synthetic Construct

<400> SEQUENCE: 276

Leu Pro Ser Ser Ala Asp Val Glu Phe
1               5

<210> SEQ ID NO 277
<211> LENGTH: 10
<212> TYPE: PRT
<213> ORGANISM: Artificial Sequence
<220> FEATURE:
<223> OTHER INFORMATION: Synthetic Construct

<400> SEQUENCE: 277

-continued

Leu His His Ala Phe Val Asp Ser Ile Phe
1               5                   10

<210> SEQ ID NO 278
<211> LENGTH: 15
<212> TYPE: PRT
<213> ORGANISM: Artificial Sequence
<220> FEATURE:
<223> OTHER INFORMATION: Synthetic Construct

<400> SEQUENCE: 278

Gln Asn Ile Leu Leu Ser Asn Ala Pro Leu Gly Pro Gln Phe Pro
1               5                   10                  15

<210> SEQ ID NO 279
<211> LENGTH: 13
<212> TYPE: PRT
<213> ORGANISM: Artificial Sequence
<220> FEATURE:
<223> OTHER INFORMATION: Synthetic Construct

<400> SEQUENCE: 279

Ser Tyr Leu Gln Asp Ser Asp Pro Asp Ser Phe Gln Asp
1               5                   10

<210> SEQ ID NO 280
<211> LENGTH: 21
<212> TYPE: PRT
<213> ORGANISM: Artificial Sequence
<220> FEATURE:
<223> OTHER INFORMATION: Synthetic Construct

<400> SEQUENCE: 280

Phe Leu Leu His His Ala Phe Val Asp Ser Ile Phe Glu Gln Trp Leu
1               5                   10                  15

Gln Arg His Arg Pro
            20

<210> SEQ ID NO 281
<211> LENGTH: 30
<212> TYPE: PRT
<213> ORGANISM: Artificial Sequence
<220> FEATURE:
<223> OTHER INFORMATION: Synthetic Construct

<400> SEQUENCE: 281

Tyr Thr Thr Ala Glu Glu Ala Ala Gly Ile Gly Ile Leu Thr Val Ile
1               5                   10                  15

Leu Gly Val Leu Leu Leu Ile Gly Cys Trp Tyr Cys Arg Arg
            20                  25                  30

<210> SEQ ID NO 282
<211> LENGTH: 9
<212> TYPE: PRT
<213> ORGANISM: Artificial Sequence
<220> FEATURE:
<223> OTHER INFORMATION: Synthetic Construct

<400> SEQUENCE: 282

Ala Leu Asn Phe Pro Gly Ser Gln Lys
1               5

<210> SEQ ID NO 283
<211> LENGTH: 9
<212> TYPE: PRT

<213> ORGANISM: Artificial Sequence
<220> FEATURE:
<223> OTHER INFORMATION: Synthetic Construct

<400> SEQUENCE: 283

Val Tyr Phe Phe Leu Pro Asp His Leu
1 5

<210> SEQ ID NO 284
<211> LENGTH: 9
<212> TYPE: PRT
<213> ORGANISM: Artificial Sequence
<220> FEATURE:
<223> OTHER INFORMATION: Synthetic Construct

<400> SEQUENCE: 284

Arg Thr Lys Gln Leu Tyr Pro Glu Trp
1 5

<210> SEQ ID NO 285
<211> LENGTH: 10
<212> TYPE: PRT
<213> ORGANISM: Artificial Sequence
<220> FEATURE:
<223> OTHER INFORMATION: Synthetic Construct

<400> SEQUENCE: 285

His Thr Met Glu Val Thr Val Tyr His Arg
1 5 10

<210> SEQ ID NO 286
<211> LENGTH: 9
<212> TYPE: PRT
<213> ORGANISM: Artificial Sequence
<220> FEATURE:
<223> OTHER INFORMATION: Synthetic Construct

<400> SEQUENCE: 286

Ser Ser Pro Gly Cys Gln Pro Pro Ala
1 5

<210> SEQ ID NO 287
<211> LENGTH: 10
<212> TYPE: PRT
<213> ORGANISM: Artificial Sequence
<220> FEATURE:
<223> OTHER INFORMATION: Synthetic Construct

<400> SEQUENCE: 287

Val Pro Leu Asp Cys Val Leu Tyr Arg Tyr
1 5 10

<210> SEQ ID NO 288
<211> LENGTH: 9
<212> TYPE: PRT
<213> ORGANISM: Artificial Sequence
<220> FEATURE:
<223> OTHER INFORMATION: Synthetic Construct

<400> SEQUENCE: 288

Leu Pro His Ser Ser Ser His Trp Leu
1 5

<210> SEQ ID NO 289
<211> LENGTH: 8
<212> TYPE: PRT
<213> ORGANISM: Artificial Sequence
<220> FEATURE:
<223> OTHER INFORMATION: Synthetic Construct

<400> SEQUENCE: 289

Ser Asn Asp Gly Pro Thr Leu Ile
1 5

<210> SEQ ID NO 290
<211> LENGTH: 15
<212> TYPE: PRT
<213> ORGANISM: Artificial Sequence
<220> FEATURE:
<223> OTHER INFORMATION: Synthetic Construct

<400> SEQUENCE: 290

Gly Arg Ala Met Leu Gly Thr His Thr Met Glu Val Thr Val Tyr
1 5 10 15

<210> SEQ ID NO 291
<211> LENGTH: 16
<212> TYPE: PRT
<213> ORGANISM: Artificial Sequence
<220> FEATURE:
<223> OTHER INFORMATION: Synthetic Construct

<400> SEQUENCE: 291

Trp Asn Arg Gln Leu Tyr Pro Glu Trp Thr Glu Ala Gln Arg Leu Asp
1 5 10 15

<210> SEQ ID NO 292
<211> LENGTH: 18
<212> TYPE: PRT
<213> ORGANISM: Artificial Sequence
<220> FEATURE:
<223> OTHER INFORMATION: Synthetic Construct

<400> SEQUENCE: 292

Thr Thr Glu Trp Val Glu Thr Thr Ala Arg Glu Leu Pro Ile Pro Glu
1 5 10 15

Pro Glu

<210> SEQ ID NO 293
<211> LENGTH: 17
<212> TYPE: PRT
<213> ORGANISM: Artificial Sequence
<220> FEATURE:
<223> OTHER INFORMATION: Synthetic Construct

<400> SEQUENCE: 293

Thr Gly Arg Ala Met Leu Gly Thr His Thr Met Glu Val Thr Val Tyr
1 5 10 15

His

<210> SEQ ID NO 294
<211> LENGTH: 10
<212> TYPE: PRT
<213> ORGANISM: Artificial Sequence
<220> FEATURE:
<223> OTHER INFORMATION: Synthetic Construct

<400> SEQUENCE: 294

Val Leu Pro Asp Val Phe Ile Arg Cys Val
1 5 10

<210> SEQ ID NO 295

<211> LENGTH: 10
<212> TYPE: PRT
<213> ORGANISM: Artificial Sequence
<220> FEATURE:
<223> OTHER INFORMATION: Synthetic Construct

<400> SEQUENCE: 295

Arg Tyr Cys Asn Leu Glu Gly Pro Pro Ile
1               5                   10

<210> SEQ ID NO 296
<211> LENGTH: 24
<212> TYPE: PRT
<213> ORGANISM: Artificial Sequence
<220> FEATURE:
<223> OTHER INFORMATION: Synthetic Construct

<400> SEQUENCE: 296

Lys Trp Thr Glu Pro Tyr Cys Val Ile Ala Ala Val Lys Ile Phe Pro
1               5                   10                  15

Arg Phe Phe Met Val Ala Lys Gln
            20

<210> SEQ ID NO 297
<211> LENGTH: 20
<212> TYPE: PRT
<213> ORGANISM: Artificial Sequence
<220> FEATURE:
<223> OTHER INFORMATION: Synthetic Construct

<400> SEQUENCE: 297

Lys Cys Cys Lys Ile Arg Tyr Cys Asn Leu Glu Gly Pro Pro Ile Asn
1               5                   10                  15

Ser Ser Val Phe
            20

<210> SEQ ID NO 298
<211> LENGTH: 9
<212> TYPE: PRT
<213> ORGANISM: Artificial Sequence
<220> FEATURE:
<223> OTHER INFORMATION: Synthetic Construct

<400> SEQUENCE: 298

Phe Leu Trp Gly Pro Arg Ala Leu Val
1               5

<210> SEQ ID NO 299
<211> LENGTH: 9
<212> TYPE: PRT
<213> ORGANISM: Artificial Sequence
<220> FEATURE:
<223> OTHER INFORMATION: Synthetic Construct

<400> SEQUENCE: 299

Val Arg Ile Gly His Leu Tyr Ile Leu
1               5

<210> SEQ ID NO 300
<211> LENGTH: 15
<212> TYPE: PRT
<213> ORGANISM: Artificial Sequence
<220> FEATURE:
<223> OTHER INFORMATION: Synthetic Construct

<400> SEQUENCE: 300

-continued

Arg Glu Pro Phe Thr Lys Ala Glu Met Leu Gly Ser Val Ile Arg
1 5 10 15

<210> SEQ ID NO 301
<211> LENGTH: 14
<212> TYPE: PRT
<213> ORGANISM: Artificial Sequence
<220> FEATURE:
<223> OTHER INFORMATION: Synthetic Construct

<400> SEQUENCE: 301

Ala Glu Leu Val His Phe Leu Leu Leu Lys Tyr Arg Ala Arg
1 5 10

<210> SEQ ID NO 302
<211> LENGTH: 10
<212> TYPE: PRT
<213> ORGANISM: Artificial Sequence
<220> FEATURE:
<223> OTHER INFORMATION: Synthetic Construct

<400> SEQUENCE: 302

Leu Leu Phe Gly Leu Ala Leu Ile Glu Val
1 5 10

<210> SEQ ID NO 303
<211> LENGTH: 9
<212> TYPE: PRT
<213> ORGANISM: Artificial Sequence
<220> FEATURE:
<223> OTHER INFORMATION: Synthetic Construct

<400> SEQUENCE: 303

Ala Leu Lys Asp Val Glu Glu Arg Val
1 5

<210> SEQ ID NO 304
<211> LENGTH: 9
<212> TYPE: PRT
<213> ORGANISM: Artificial Sequence
<220> FEATURE:
<223> OTHER INFORMATION: Synthetic Construct

<400> SEQUENCE: 304

Ser Glu Ser Ile Lys Lys Lys Val Leu
1 5

<210> SEQ ID NO 305
<211> LENGTH: 9
<212> TYPE: PRT
<213> ORGANISM: Artificial Sequence
<220> FEATURE:
<223> OTHER INFORMATION: Synthetic Construct

<400> SEQUENCE: 305

Ala Ser Ser Thr Leu Tyr Leu Val Phe
1 5

<210> SEQ ID NO 306
<211> LENGTH: 15
<212> TYPE: PRT
<213> ORGANISM: Artificial Sequence
<220> FEATURE:
<223> OTHER INFORMATION: Synthetic Construct

<400> SEQUENCE: 306

Ser Ser Thr Leu Tyr Leu Val Phe Ser Pro Ser Ser Phe Ser Thr

-continued 1 5 10 15

<210> SEQ ID NO 307
<211> LENGTH: 9
<212> TYPE: PRT
<213> ORGANISM: Artificial Sequence
<220> FEATURE:
<223> OTHER INFORMATION: Synthetic Construct

<400> SEQUENCE: 307

Gln Gly Gln His Phe Leu Gln Lys Val
1 5

<210> SEQ ID NO 308
<211> LENGTH: 10
<212> TYPE: PRT
<213> ORGANISM: Artificial Sequence
<220> FEATURE:
<223> OTHER INFORMATION: Synthetic Construct

<400> SEQUENCE: 308

Glu Val Ile Ser Cys Lys Leu Ile Lys Arg
1 5 10

<210> SEQ ID NO 309
<211> LENGTH: 9
<212> TYPE: PRT
<213> ORGANISM: Artificial Sequence
<220> FEATURE:
<223> OTHER INFORMATION: Synthetic Construct

<400> SEQUENCE: 309

Phe Pro Ser Asp Ser Trp Cys Tyr Phe
1 5

<210> SEQ ID NO 310
<211> LENGTH: 9
<212> TYPE: PRT
<213> ORGANISM: Artificial Sequence
<220> FEATURE:
<223> OTHER INFORMATION: Synthetic Construct

<400> SEQUENCE: 310

Leu Tyr Ala Thr Val Ile His Asp Ile
1 5

<210> SEQ ID NO 311
<211> LENGTH: 9
<212> TYPE: PRT
<213> ORGANISM: Artificial Sequence
<220> FEATURE:
<223> OTHER INFORMATION: Synthetic Construct

<400> SEQUENCE: 311

Ser Ser Lys Ala Leu Gln Arg Pro Val
1 5

<210> SEQ ID NO 312
<211> LENGTH: 9
<212> TYPE: PRT
<213> ORGANISM: Artificial Sequence
<220> FEATURE:
<223> OTHER INFORMATION: Synthetic Construct

<400> SEQUENCE: 312

Gly Phe Lys Gln Ser Ser Lys Ala Leu
1 5

<210> SEQ ID NO 313
<211> LENGTH: 17
<212> TYPE: PRT
<213> ORGANISM: Artificial Sequence
<220> FEATURE:
<223> OTHER INFORMATION: Synthetic Construct

<400> SEQUENCE: 313

Ala Thr Gly Phe Lys Gln Ser Ser Lys Ala Leu Gln Arg Pro Val Ala
1 5 10 15

Ser

<210> SEQ ID NO 314
<211> LENGTH: 16
<212> TYPE: PRT
<213> ORGANISM: Artificial Sequence
<220> FEATURE:
<223> OTHER INFORMATION: Synthetic Construct

<400> SEQUENCE: 314

Thr Met Lys Gln Ile Cys Lys Lys Glu Ile Arg Arg Leu His Gln Tyr
1 5 10 15

<210> SEQ ID NO 315
<211> LENGTH: 10
<212> TYPE: PRT
<213> ORGANISM: Artificial Sequence
<220> FEATURE:
<223> OTHER INFORMATION: Synthetic Construct

<400> SEQUENCE: 315

Lys Ile Leu Asp Ala Val Val Ala Gln Lys
1 5 10

<210> SEQ ID NO 316
<211> LENGTH: 9
<212> TYPE: PRT
<213> ORGANISM: Artificial Sequence
<220> FEATURE:
<223> OTHER INFORMATION: Synthetic Construct

<400> SEQUENCE: 316

Arg Ile Ala Glu Cys Ile Leu Gly Met
1 5

<210> SEQ ID NO 317
<211> LENGTH: 15
<212> TYPE: PRT
<213> ORGANISM: Artificial Sequence
<220> FEATURE:
<223> OTHER INFORMATION: Synthetic Construct

<400> SEQUENCE: 317

Ile Gly Arg Ile Ala Glu Cys Ile Leu Gly Met Asn Pro Ser Arg
1 5 10 15

<210> SEQ ID NO 318
<211> LENGTH: 10
<212> TYPE: PRT
<213> ORGANISM: Artificial Sequence
<220> FEATURE:
<223> OTHER INFORMATION: Synthetic Construct

<400> SEQUENCE: 318

Tyr Val Asp Phe Arg Glu Tyr Glu Tyr Tyr 1 5 10

<210> SEQ ID NO 319
<211> LENGTH: 9
<212> TYPE: PRT
<213> ORGANISM: Artificial Sequence
<220> FEATURE:
<223> OTHER INFORMATION: Synthetic Construct

<400> SEQUENCE: 319

Phe Leu Asp Arg Phe Leu Ser Cys Met
1 5

<210> SEQ ID NO 320
<211> LENGTH: 11
<212> TYPE: PRT
<213> ORGANISM: Artificial Sequence
<220> FEATURE:
<223> OTHER INFORMATION: Synthetic Construct

<400> SEQUENCE: 320

Ser Leu Ile Ala Ala Ala Ala Phe Cys Leu Ala
1 5 10

<210> SEQ ID NO 321
<211> LENGTH: 9
<212> TYPE: PRT
<213> ORGANISM: Artificial Sequence
<220> FEATURE:
<223> OTHER INFORMATION: Synthetic Construct

<400> SEQUENCE: 321

Val Val Met Ser Trp Ala Pro Pro Val
1 5

<210> SEQ ID NO 322
<211> LENGTH: 25
<212> TYPE: PRT
<213> ORGANISM: Artificial Sequence
<220> FEATURE:
<223> OTHER INFORMATION: Synthetic Construct

<400> SEQUENCE: 322

Asn Ser Asn His Val Ala Ser Gly Ala Gly Glu Ala Ala Ile Glu Thr
1 5 10 15

Gln Ser Ser Ser Ser Glu Glu Ile Val
20 25

<210> SEQ ID NO 323
<211> LENGTH: 10
<212> TYPE: PRT
<213> ORGANISM: Artificial Sequence
<220> FEATURE:
<223> OTHER INFORMATION: Synthetic Construct

<400> SEQUENCE: 323

Ile Leu Phe Gly Ile Ser Leu Arg Glu Val
1 5 10

<210> SEQ ID NO 324
<211> LENGTH: 9
<212> TYPE: PRT
<213> ORGANISM: Artificial Sequence
<220> FEATURE:
<223> OTHER INFORMATION: Synthetic Construct

<400> SEQUENCE: 324

Lys Val Val Glu Phe Leu Ala Met Leu
1 5

<210> SEQ ID NO 325
<211> LENGTH: 13
<212> TYPE: PRT
<213> ORGANISM: Artificial Sequence
<220> FEATURE:
<223> OTHER INFORMATION: Synthetic Construct

<400> SEQUENCE: 325

Ser Ser Ala Leu Leu Ser Ile Phe Gln Ser Ser Pro Glu
1 5 10

<210> SEQ ID NO 326
<211> LENGTH: 9
<212> TYPE: PRT
<213> ORGANISM: Artificial Sequence
<220> FEATURE:
<223> OTHER INFORMATION: Synthetic Construct

<400> SEQUENCE: 326

Ser Phe Ser Tyr Thr Leu Leu Ser Leu
1 5

<210> SEQ ID NO 327
<211> LENGTH: 9
<212> TYPE: PRT
<213> ORGANISM: Artificial Sequence
<220> FEATURE:
<223> OTHER INFORMATION: Synthetic Construct

<400> SEQUENCE: 327

Val Ser Ser Phe Phe Ser Tyr Thr Leu
1 5

<210> SEQ ID NO 328
<211> LENGTH: 15
<212> TYPE: PRT
<213> ORGANISM: Artificial Sequence
<220> FEATURE:
<223> OTHER INFORMATION: Synthetic Construct

<400> SEQUENCE: 328

Lys Pro Leu Phe Arg Arg Met Ser Ser Leu Glu Leu Val Ile Ala
1 5 10 15

<210> SEQ ID NO 329
<211> LENGTH: 9
<212> TYPE: PRT
<213> ORGANISM: Artificial Sequence
<220> FEATURE:
<223> OTHER INFORMATION: Synthetic Construct

<400> SEQUENCE: 329

Glu Val Asp Pro Ile Gly His Leu Tyr
1 5

<210> SEQ ID NO 330
<211> LENGTH: 9
<212> TYPE: PRT
<213> ORGANISM: Artificial Sequence
<220> FEATURE:
<223> OTHER INFORMATION: Synthetic Construct

<400> SEQUENCE: 330

-continued

Lys Val Ala Glu Leu Val His Phe Leu
1               5

<210> SEQ ID NO 331
<211> LENGTH: 9
<212> TYPE: PRT
<213> ORGANISM: Artificial Sequence
<220> FEATURE:
<223> OTHER INFORMATION: Synthetic Construct

<400> SEQUENCE: 331

Thr Phe Pro Asp Leu Glu Ser Glu Phe
1               5

<210> SEQ ID NO 332
<211> LENGTH: 9
<212> TYPE: PRT
<213> ORGANISM: Artificial Sequence
<220> FEATURE:
<223> OTHER INFORMATION: Synthetic Construct

<400> SEQUENCE: 332

Val Ala Glu Leu Val His Phe Leu Leu
1               5

<210> SEQ ID NO 333
<211> LENGTH: 10
<212> TYPE: PRT
<213> ORGANISM: Artificial Sequence
<220> FEATURE:
<223> OTHER INFORMATION: Synthetic Construct

<400> SEQUENCE: 333

Met Glu Val Asp Pro Ile Gly His Leu Tyr
1               5                   10

<210> SEQ ID NO 334
<211> LENGTH: 9
<212> TYPE: PRT
<213> ORGANISM: Artificial Sequence
<220> FEATURE:
<223> OTHER INFORMATION: Synthetic Construct

<400> SEQUENCE: 334

Trp Gln Tyr Phe Phe Pro Val Ile Phe
1               5

<210> SEQ ID NO 335
<211> LENGTH: 16
<212> TYPE: PRT
<213> ORGANISM: Artificial Sequence
<220> FEATURE:
<223> OTHER INFORMATION: Synthetic Construct

<400> SEQUENCE: 335

Lys Lys Leu Leu Thr Gln His Phe Val Gln Glu Asn Tyr Leu Glu Tyr
1               5                   10                  15

<210> SEQ ID NO 336
<211> LENGTH: 15
<212> TYPE: PRT
<213> ORGANISM: Artificial Sequence
<220> FEATURE:
<223> OTHER INFORMATION: Synthetic Construct

<400> SEQUENCE: 336

Arg Lys Val Ala Glu Leu Val His Phe Leu Leu Leu Lys Tyr Arg 1 5 10 15

<210> SEQ ID NO 337
<211> LENGTH: 16
<212> TYPE: PRT
<213> ORGANISM: Artificial Sequence
<220> FEATURE:
<223> OTHER INFORMATION: Synthetic Construct

<400> SEQUENCE: 337

Ala Cys Tyr Glu Phe Leu Trp Gly Pro Arg Ala Leu Val Glu Thr Ser
1 5 10 15

<210> SEQ ID NO 338
<211> LENGTH: 12
<212> TYPE: PRT
<213> ORGANISM: Artificial Sequence
<220> FEATURE:
<223> OTHER INFORMATION: Synthetic Construct

<400> SEQUENCE: 338

Val Ile Phe Ser Lys Ala Ser Ser Ser Leu Gln Leu
1 5 10

<210> SEQ ID NO 339
<211> LENGTH: 15
<212> TYPE: PRT
<213> ORGANISM: Artificial Sequence
<220> FEATURE:
<223> OTHER INFORMATION: Synthetic Construct

<400> SEQUENCE: 339

Val Phe Gly Ile Glu Leu Met Glu Val Asp Pro Ile Gly His Leu
1 5 10 15

<210> SEQ ID NO 340
<211> LENGTH: 15
<212> TYPE: PRT
<213> ORGANISM: Artificial Sequence
<220> FEATURE:
<223> OTHER INFORMATION: Synthetic Construct

<400> SEQUENCE: 340

Gly Asp Asn Gln Ile Met Pro Lys Ala Gly Leu Leu Ile Ile Val
1 5 10 15

<210> SEQ ID NO 341
<211> LENGTH: 15
<212> TYPE: PRT
<213> ORGANISM: Artificial Sequence
<220> FEATURE:
<223> OTHER INFORMATION: Synthetic Construct

<400> SEQUENCE: 341

Thr Ser Tyr Val Lys Val Leu His His Met Val Lys Ile Ser Gly
1 5 10 15

<210> SEQ ID NO 342
<211> LENGTH: 9
<212> TYPE: PRT
<213> ORGANISM: Artificial Sequence
<220> FEATURE:
<223> OTHER INFORMATION: Synthetic Construct

<400> SEQUENCE: 342

Ala Glu Leu Val His Phe Leu Leu Leu
1 5

-continued

```
<210> SEQ ID NO 343
<211> LENGTH: 8
<212> TYPE: PRT
<213> ORGANISM: Artificial Sequence
<220> FEATURE:
<223> OTHER INFORMATION: Synthetic Construct

<400> SEQUENCE: 343

Gly Leu Gln Leu Gly Val Gln Ala
1               5
```